(12) United States Patent
Ding et al.

(10) Patent No.: US 11,970,689 B2
(45) Date of Patent: *Apr. 30, 2024

(54) CYANOBACTERIAL HOSTS AND METHODS FOR PRODUCING CHEMICALS

(71) Applicant: University of Florida Research Foundation, Incorporated, Gainesville, FL (US)

(72) Inventors: Yousong Ding, Gainesville, FL (US); Guang Yang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 2 days.

This patent is subject to a terminal disclaimer.

(21) Appl. No.: 17/727,934

(22) Filed: Apr. 25, 2022

(65) Prior Publication Data

US 2022/0372427 A1    Nov. 24, 2022

Related U.S. Application Data

(63) Continuation of application No. 16/634,027, filed as application No. PCT/US2018/043993 on Jul. 27, 2018, now Pat. No. 11,352,601.

(Continued)

(51) Int. Cl.
*C07H 21/04* (2006.01)
*C12N 1/12* (2006.01)
(Continued)

(52) U.S. Cl.
CPC .................. *C12N 1/12* (2013.01); *C12N 9/12* (2013.01); *C12N 1/125* (2021.05); *C12R 2001/89* (2021.05)

(58) Field of Classification Search
CPC ..................................................... C07H 21/04
See application file for complete search history.

(56) References Cited

U.S. PATENT DOCUMENTS

| 11,352,601 B2 | 6/2022 | Ding et al. |
| 2007/0220634 A1 | 9/2007 | Metz |
| 2010/0298612 A1 | 11/2010 | Behrouzian et al. |

FOREIGN PATENT DOCUMENTS

WO    WO 2015/200335 A1    12/2015

OTHER PUBLICATIONS

Rastogi et al., "Biotechnological and industrial significance of cyanobacterial secondary metabolites," Biotechnology Advances 27: 521-529, 2009.*

(Continued)

*Primary Examiner* — Rosanne Kosson
(74) *Attorney, Agent, or Firm* — Wolf, Greenfield & Sacks, P.C.

(57) ABSTRACT

The present invention relates to recombinant cyanobacterial cells for the production of a chemical compound of interest. In particular, the present invention relates to genetic modifications that introduce one or more heterologous phosphopantetheinyl transferases (PPTases) into a cyanobacterial cell. These cells can, optionally, further comprise heterologous carrier protein and nucleic acid constructs that provide the cyanobacterial cells with the capability of producing chemicals of interest or compounds of interest, such secondary metabolites polyketides, nonribosomal peptides and their hybrids, the three major families of bioactive natural products, of cyanobacteria and other bacterial phyla, secondary metabolites analogs, and unnatural compounds.

20 Claims, 38 Drawing Sheets

Specification includes a Sequence Listing.

Related U.S. Application Data

(60) Provisional application No. 62/611,634, filed on Dec. 29, 2017, provisional application No. 62/537,516, filed on Jul. 27, 2017.

(51) Int. Cl.
*C12N 9/12* (2006.01)
*C12R 1/89* (2006.01)

(56) References Cited

OTHER PUBLICATIONS

International Search Report and Written Opinion dated Jan. 15, 2019 in connection with PCT/US2018/042993.
International Preliminary Report on Patentability dated Feb. 6, 2020 in connection with PCT/US2018/042993.

\* cited by examiner

|  | FAS | | PKS | | | NRPS | | NRPS/PKS | | | |
|---|---|---|---|---|---|---|---|---|---|---|---|
|  | SFACP | AFACP | APACP | ScACP | SsPCP | FNPCP | FispPcP | MACP | APNPCP | FNsACP | AprACP |
| SPPT | 100.0 | 98.8 | 79.3 | 0.0 | 8.3 | 96.1 | 97.8 | 16.1 | 71.6 | 78.2 | 79.3 |
| MPPT | 94.8 | 99.6 | 84.6 | 18.8 | 24.0 | 96.2 | 97.4 | 100.0 | 83.9 | 93.5 | 93.2 |
| SePPT | 99.5 | 94.9 | 11.9 | 0.0 | 0.0 | 30.5 | 47.3 | 0.0 | 0.0 | 43.6 | 11.9 |
| APPT | 99.1 | 100.0 | 100.0 | 64.9 | 28.8 | 75.4 | 100.0 | 89.7 | 100.0 | 100.0 | 100.0 |
| AvPPT | 98.3 | 96.7 | 22.0 | 28.5 | 32.8 | 81.9 | 93.7 | 88.5 | 96.6 | 94.5 | 93.7 |
| FPPT | 96.1 | 94.5 | 10.1 | 0.0 | 29.0 | 100.0 | 76.5 | 0.0 | 0.0 | 91.0 | 89.9 |
| Sfp | 98.9 | 96.2 | 98.0 | 100.0 | 100.0 | 82.8 | 25.1 | 97.1 | 53.3 | 92.9 | 99.6 |

FIGURE 3

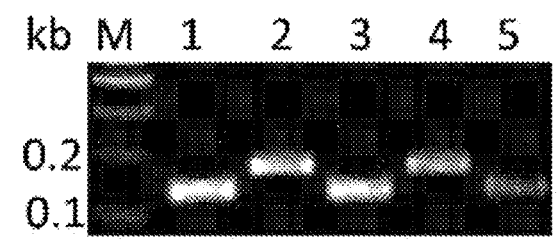
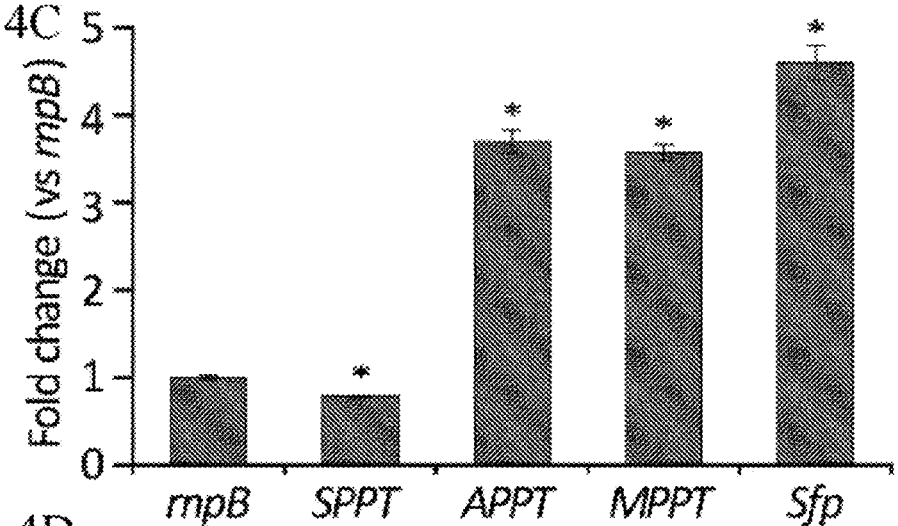
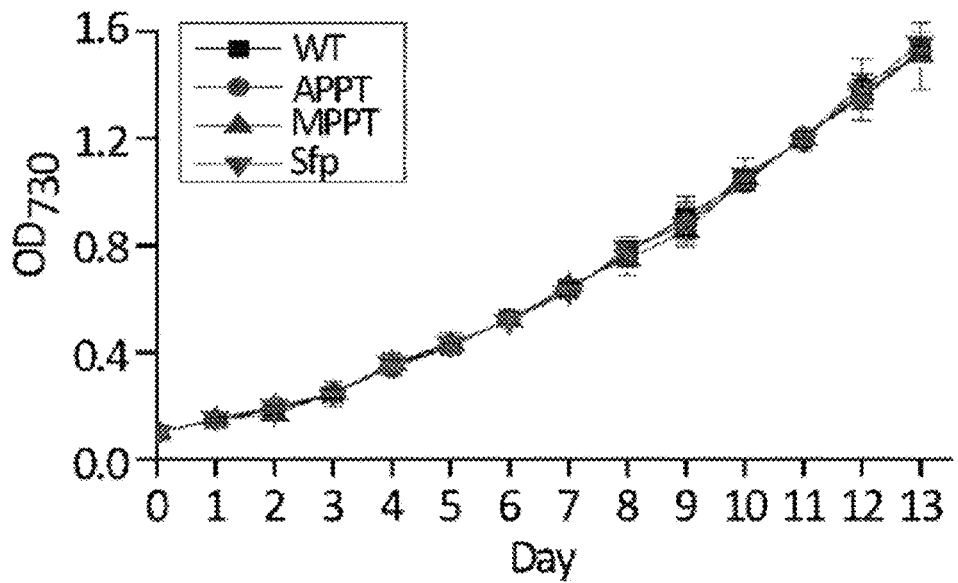
FIGURE 4A
FIGURE 4B
FIGURE 4C
FIGURE 4D

| Accession Number | Gene name/locus tag | Organisms | Length (aa) |
|---|---|---|---|
| ABA22212.1 | PPTase[a] | *Anabaena variabilis ATCC 29413* | 237 |
| WP_044522635.1 | PPTase | *Nostoc sp. PCC 7120* | 237 |
| WP_004163140.1 | PPTase | *Microcystis aeruginosa NIES-843* | 220 |
| ABB57835.1 | HetI protein-like | *Synechococcus elongatus PCC 7942* | 259 |
| WP_012307697.1 | PPTase | *Synechococcus sp. PCC 7902* | 227 |
| WP_010873553.1 | PPTase | *Synechocystis sp. PCC 6803* | 246 |
| WP_017309026.1 | PPTase | *Fischerella sp. PCC 9339* | 240 |
| ACG68433.1 | Sfp | *Bacillus subtilis* | 224 |
| WP_009782852.1 | PPTase | *Lyngbya sp. PCC 8106* | 239 |
| WP_026092908.1 | PPTase | *Calothrix sp. PCC 7103* | 241 |
| WP_016950943.1 | PPTase | *Anabaena sp. PCC 7108* | 240 |
| AAW67221.1 | PPTase | *Nodularia spumigena NSOR10* | 239 |
| WP_015186867.1 | PPTase | *Gloeocapsa sp. PCC 7428* | 253 |
| EHJ11493.1 | PPTase | *Crocosphaera watsonii WH 0003* | 248 |
| WP_006529694.1 | PPTase | *Gloeocapsa sp. PCC 73106* | 242 |
| WP_051044566.1 | hypothetical protein | *Pleurocapsa sp. PCC 7319* | 243 |
| WP_006511535.1 | PPTase | *Stanieria sp. PCC 7305* | 255 |
| BAU60329.1 | PPTase | *Stanieria sp. NIES-3757* | 250 |
| WP_017660318.1 | hypothetical protein | *Geitlerinema sp. PCC 7105* | 226 |
| CUR17315.1 | PPTase | *Planktothrix sp. PCC 11201* | 249 |
| WP_015112227.1 | PPTase | *Nostoc sp. PCC 7107* | 243 |
| SCY12562.1 | PPTase | *Nitrososphaera sp. Nsp13* | 246 |
| WP_017306450.1 | PPTase | *Spirulina subsalsa* | 235 |
| WP_029633554.1 | hypothetical protein | *Scytonema hofmanni UTEX B 1581* | 235 |
| OCQ99688.1 | PPTase | *Oscillatoriales cyanobacterium USR001* | 254 |
| WP_057178475.1 | PPTase | *Cylindrospermopsis sp. CR12* | 240 |
| WP_041933312.1 | PPTase | *Cyanothece sp. PCC 7822* | 240 |
| WP_054469188.1 | hypothetical protein | *Planktothricoides sp. SR001* | 247 |
| WP_059080742.1 | hypothetical protein | *Leptolyngbya sp. NIES-2104* | 235 |
| WP_015127290.1 | PPTase | *Calothrix sp. PCC 7507* | 234 |
| ZP_00107102.1 | PPTase | *Nostoc punctiforme PCC 73102* | 239 |
| ACN96032.1 | holo-acyl-carrier-protein | *Fischerella sp. MP71* | 128 |
| WP_015181769.1 | PPTase | *Microcoleus sp. PCC 7113* | 139 |
| AFY89096.1 | PPTase | *Chroococcidiopsis thermalis PCC 7203* | 137 |
| WP_006519439.1 | holo-ACP synthase | *Leptolyngbya sp. PCC 7375* | 129 |
| NP_926954.1 | ACP synthase | *Gloeobacter violaceus PCC 7421* | 132 |
| AFY65439.1 | holo-acyl-carrier-protein | *Geitlerinema sp. PCC 7407* | 148 |
| WP_006634204.1 | holo-ACP synthase | *Microcoleus vaginatus* | 157 |
| WP_015187908.1 | holo-ACP synthase | *Gloeocapsa sp. PCC 7428* | 129 |
| BAL39319.1 | holo-acyl-carrier-protein | *Escherichia coli str. K-12 substr. MDS42* | 126 |
| AAH75207.1 | MGC84206 protein | *Xenopus laevis* | 302 |
| XP_040785.1 | PPTase | *Homo sapiens* | 309 |
| AGP54231.1 | PPTase | *Streptomyces rapamycinicus NRRL 5491* | 247 |

[a]: PPTase is an abbreviation of 4'-phosphopantetheinyl transferase.

FIGURE 9

| CPs | Strains | Metabolites | Biosynthetic pathway | Apo-form MW | Holo-form MW | | GenBank accession number |
|---|---|---|---|---|---|---|---|
| | | | | | Calculated | Observed | |
| SFACP | Synechocystis sp. PCC6803 | Fatty acid | FAS | 9655.69 | 9995.69 | 9997.78 | sll2084 |
| AFACP | Anabaena sp. PCC7120 | Fatty acid | FAS | 10282.20 | 10622.20 | 10622.65 | WP_010997493.1 |
| APACP | Anabaena sp. PCC7120 | Glycolipid | PKS | 10804.09 | 11144.09 | 11012.84[a] | WP_010993481.1 |
| APNPCP | Anabaena sp. PCC7120 | Unknown | NRPS/PKS | 12115.69 | 12455.69 | 12455.54 | WP_010996791.1 |
| FNPCP | Fischerella sp. PCC9339 | Unknown | NRPS | 10699.21 | 11039.21 | 10808.39[a] | WP_017398667.1 |
| FisPCP | Fischerella sp. PCC9339 | Shinorine | NRPS | 12475.06 | 12815.06 | 12683.15[a] | WP_017332807.1 |
| FNsACP | Fischerella sp. PCC9339 | Unknown[b] | NRPS/PKS | 15215.20 | 15555.20 | 15422.01[a] | WP_017398557.1 |
| ApcACP | Microcystis aeruginosa | Apatoxin | NRPS/PKS | 10693.38 | 11033.38 | 11033.41 | ctg1_8 |
| MACP | Microcystis aeruginosa MIRB845 | Unknown | NRPS/PKS | 11106.54 | 11446.54 | 11314.81[a] | WP_012258828.1 |
| ScACP | Streptomyces coelicolor A3[2] | Concanamycin | PKS | 11186.50 | 11526.50 | 11526.67 | WP_011029786.1 |
| SsPCP | Streptomyces scabies 87.22 | Thaxtomin | PKS | 8240.44 | 8580.44 | 8580.49 | CBG75539.1 |

[a]Values corresponded to the proteins without the N-terminal methionine residue. [b]FNsACP is a homolog of NdaC from Nodularia spumigena NSOR10; [c]gene sequence is provided in the supporting information.

FIGURE 10

| PPTase | CPs | | | | | | | | |
|---|---|---|---|---|---|---|---|---|---|
| | SfACP | AFACP | APNPCP | FNPCP | FhPCP | AprACP | APACP | MACP | FN&ACP | ScACP | SsPCP |
| APPT | 99.1 ± 1.1 | 100 ± 2.0 | 100 ± 1.4 | 75.4 ± 2.9 | 100 ± 1.5 | 100 ± 1.4 | 100 ± 1.6 | 89.7 ± 3.9 | 100 ± 1.4 | 64.9 ± 3.1 | 28.8 ± 3.8 |
| AvPPT | 98.3 ± 2.4 | 98.7 ± 0.6 | 98.6 ± 2.6 | 81.9 ± 1.3 | 93.7 ± 3.2 | 93.7 ± 1.2 | 32 ± 2.3 | 88.5 ± 2.3 | 94.5 ± 0.6 | 28.6 ± 2.1 | 32.8 ± 2.7 |
| MPPT | 94.8 ± 1.3 | 99.6 ± 1.7 | 93.9 ± 1.3 | 98.2 ± 0.6 | 97.4 ± 3.6 | 93.3 ± 1.9 | 83.6 ± 3.8 | 100 ± 2.1 | 93.5 ± 1.3 | 18.8 ± 0.6 | 2.4 ± 2.9 |
| FPPT | 96.1 ± 2.1 | 93.5 ± 0.8 | 0.0 | 100 ± 0.7 | 78.5 ± 3.1 | 89.9 ± 2.1 | 10.1 ± 1.0 | 0.0 | 91.0 ± 2.4 | 0.0 | 2.9 ± 3.2 |
| SaPPT | 99.5 ± 0.8 | 94.9 ± 2.2 | 0.0 | 30.5 ± 2.7 | 47.3 ± 2.8 | 11.9 ± 1.1 | 11.9 ± 0.8 | 0.0 | 43.6 ± 3.3 | 0.0 | 0.0 |
| SfPPT | 100 ± 1.6 | 95.8 ± 3.1 | 71.6 ± 2.3 | 96.1 ± 1.5 | 87.8 ± 1.3 | 79.3 ± 2.7 | 79.3 ± 4.1 | 16.1 ± 1.7 | 79.2 ± 3.2 | 0.0 | 8.3 ± 0.8 |
| Sfp | 98.6 ± 1.7 | 96.2 ± 1.3 | 35.3 ± 3.8 | 82.8 ± 1.9 | 25.1 ± 1.5 | 99.6 ± 2.2 | 98 ± 3.3 | 97.1 ± 2.9 | 97.9 ± 2.0 | 100 ± 1.7 | 100 ± 1.0 |

The data represented mean ± SD of three independent experiments.

FIGURE 11

| | Sequence 5'-3' | Function |
|---|---|---|
| Sfp-Fw | CATGCCATGGAAATTTATGGGATTTAC | Sfp expression |
| Sfp-Rv | CCGCTCGAGCTACAACAGTTCTTCATAG | Sfp expression |
| MPPT-Fw | CATGCCATGGTTATATCTACCGATGA | MPPT expression |
| MPPT-Rv | CCGCTCGAGTAGATCAGAAAGGCCA | MPPT expression |
| SPPT-Fw | CATGCCATGGTCCCCAGCCCCAAAT | SPPT expression |
| SPPT-Rv | CCGCTCGAGGGGCAATGAATCAAGG | SPPT expression |
| SePPT-Fw | CATGCCATGGAACGCCCCAACCCTAG | SePPT expression |
| SePPT-Rv | CCGCTCGAGATGATTTTCCGGATTATG | SePPT expression |
| APPT-Fw | CATGCCATGGTGCAGCATACTTGGC | APPT expression |
| APPT-Rv | CCGCTCGAGATAATGCCAGAATTTTG | APPT expression |
| AvPPT-Fw | CATGCCATGGTGCAGCATACTTGGCTAC | AvPPT expression |
| AvPPT-Rv | CCGCTCGAGATACTGCCAGAATTTTGGC | AvPPT expression |
| FPPT-Fw | CATGCCATGGGGTCTGAGACTAATCA | FPPT expression |
| FPPT-Rv | CCGCTCGAGATACTGCCAGTACTTTAA | FPPT expression |
| SFACP-Fw | CATGCCATGGATCAGGAAATTTTTGA | SFACP expression |
| SFACP-Rv | CCGCTCGAGTTTACTTTCGATATGCTC | SFACP expression |
| AFACP-Fw | GGAATTCCATATGAGCCAATCAG | AFACP expression |
| AFACP-Rv | CCGCTCGAGAGCTGATGCGGCAACTTG | AFACP expression |
| APACP-Fw | CATGCCATGGGTCTAAAACAAAATTATAG | APACP expression |
| APACP-Rv | CCGCTCGAGAGATTGTTCTTCCAATTCTTC | SFACP expression |
| APNPCP-Fw | CATGCCATGGAACAATCTACAACTAATC | APNPCP expression |
| APNPCP-Rv | CCGCTCGAGATCAGTAATAGGCGATTG | APNPCP expression |
| FNPCP-Fw | CATGCCATGGCCCAACGCCCTATCATTATC | FNPCP expression |
| FNPCP-Rv | CCGCTCGAGTTCAACTTCATCACTATC | FNPCP expression |
| FisPCP-Fw | CATGCCATGGGATCGCTTCCCAAACCTG | FisPCP expression |
| FisPCP-Rv | CCGCTCGAGTGAATTGGGAAAAACATC | FisPCP expression |
| FNsACP-Fw | CATGCCATGGCTTTTCTAGAAGATGTC | FNsACP expression |
| FNsACP-Rv | CCGCTCGAGGGAATTACCTAGAAAAGC | FNsACP expression |
| AprACP-Fw | CATGCCATGGAAATTTTGAACAGGAAT | AprACP expression |
| AprACP-Rv | CCGCTCGAGACTAAAATTAATATCTTC | AprACP expression |
| MACP-Fw | CATGCCATGGTGACAACTGTTCAATC | MACP expression |
| MACP-Rv | CCGCTCGAGAAGATATAATTCCCCT | MACP expression |
| ScACP-Fw | CATGCCATGGAGCAGCGGCTGGCTC | ScACP expression |
| ScACP-Rv | CCGCTCGAGCTCCTGCTCGCCGAAC | ScACP expression |
| SSPCP-Fw | CATGCCATGGAGGAGATCCTCGCC | SSPCP expression |
| SSPCP-Rv | CCGCTCGAGGGTACGCCCGGCCAGGC | SSPCP expression |
| Pirc-F | GGATCCATTCTGAAATGAGCTGTTGAC | Shinorine Cloning |
| SHI-F | CTCGAGATGGGTACACCTCACGCTAC | Shinorine Cloning |
| SHI-R | AGATCTTCAGCACAAACATTTCTG | Shinorine Cloning |
| PRNPB-F | AGATCTTTCAATGCGGTCCAATAC | PPT cloning |
| PRNPB-R | GTTGATGCCTACCATCATATGTTTTTCTAGTGTGCCATTG | PPT cloning |
| FPPT-F | TGGCACACTAGAAAACATATGATGGTAGGCATCAACTAT | FPPT cloning |
| FPPT-R | GAGCTCTCACTCTGGCCACCGCCAAC | FPPT cloning |
| APPT-F | TGGCACACTAGAAAACATATGATGTTGCAGCATACTTGG | APPT cloning |
| APPT-R | GAGCTCATAATGCCAGAATTTTGGCTG | APPT cloning |
| SPPT-Up-F | CCAAGCTT CCTGGCAGTAGTGTTGGTG | Integration vector |
| SPPT-Up-R | GGTAACGAAAACTAGTCGTACGAGGTCAGTTTAAACAGCG | Integration vector |
| SPPT-Dn-F | AAACTGACCTCGTACG ACTAGTTTTCGTTACCTTGGGCCG | Integration vector |
| SPPT-Dn-R | GTGAATTC GGGCTACACCGTCGCTAC | Integration vector |
| Syn-APPT-F | TAAAGAGGTATATATTAATGTTGCAGCATACTTGG | Integration vector |
| Syn-APPT-R | CATAGCTGTTTCCTGTGTCAAAAAACCCCTCAAGACCCGTTTAG AGGCCCCAAGGGGTTATGCTAGTCAATAATGCCAGAATTTTG | Colony PCR |

FIGURE 12

| Primer | Sequence 5'-3' | Function |
|---|---|---|
| Syn-MPPT-F | TAAAGAGGTATATATTAATGTTTATATCTACCGATG | Colony PCR |
| Syn-MPPT-R | CATAGCTGTTTCCTGTGTCAAAAAACCCCTCAAGACCCGTTTAGA GGCCCCAAGGGGTTATGCTAGTCATAGATCAGAAAGGCC | Colony PCR |
| Syn-SFP-F | TAAAGAGGTATATATTAATGAAAATTTATGGGATTTAC | Colony PCR |
| Syn-SFP-R | CATAGCTGTTTCCTGTGTCAAAAAACCCCTCAAGACCCGTTTAGA GGCCCCAAGGGGTTATGCTAGCTACAACAGTTCTTCATAG | Colony PCR |
| Ptrc-F | CTCGTACGATTCTGAAATGAGCTGTTG | Colony PCR |
| Ptrc-APPT-R | CCAAGTATGCTGCAACATTAATATATACCTCTTTA | Colony PCR |
| Ptrc-MPPT-R | CATCGGTAGATATAAACATTAATATATACCTCTTTA | Colony PCR |
| Ptrc-SFP-R | GTAAATCCCATAAATTTTCATTAATATATACCTCTTTA | Colony PCR |
| Kana-F | GTCTTGAGGGGTTTTTTG ACACAGGAAACAGCTATG | Colony PCR |
| Kana-R | AAACTAGTAAACGACGGCCAGTGAAT | Colony PCR |
| RT-rnpB-F | CGTGAGGACAGTGCCACAG | RT-PCR |
| RT-rnpB-R | CGCTCTTACCGCACCTTTG | RT-PCR |
| RT-SPPT-F | TTTGATTGGCTTAAGTAC | RT-PCR |
| RT-SPPT-R | AATGCTTCCTTCGCTGTC | RT-PCR |
| RT-APPT-F | ATCTAGTGACGAATTAGC | RT-PCR |
| RT-APPT-R | AATAAACCACTCTCGGC | RT-PCR |
| RT-MPPT-F | GTATTAACTATCAATTGC | RT-PCR |
| RT-MPPT-R | AAGCTATCTAAATCTTTC | RT-PCR |
| RT-Sfp-F | TAGTCATTCTGGTCGCTG | RT-PCR |
| RT-Sfp-R | ATAAATCAGAGTATTCGG | RT-PCR |

*SFACP*

ATGGATCAGGAAATTTTTGAAAAAGTAAAAAAAATCGTCGTGGAACAGTTGGAAGTGGATCCTGAC
AAAGTGACCCCCGATGCCACCTTTGCCGAAGATTTAGGGGCTGATTCCCTCGATACAGTGGAATTGG
TCATGGCCCTGGAAGAAGAGTTTGATATTGAAATTCCCGATGAAGTGGCGGAAACCATTGATACCGT
GGGCAAAGCCGTTGAGCATATCGAAAGTAAA

*AFACP*

ATGGGCCAATCAGAAACTTTTGAAAAAGTCAAAAAAATTGTTATCGAACAACTAAGTGTGGAGAAC
CCTGACACAGTAACTCCAGAAGCTAGTTTTGCCAACGATTTACAGGCTGATTCCCTCGATACAGTAG
AACTAGTAATGGCTTTGGAAGAAGAATTTGATATCGAAATTCCCGATGAAGCCGCAGAGAAAATTA
CCACTGTTCAAGAAGCGGTGGATTACATCAATAACCAAGTTGCCGCATCAGCT

*APACP*

ATGGGTCTAAAACAAAATTATAGTGCAGCAGATATTCAAGCTTGGATGATATCTAATCTAGCTGAAT
TGTTGGGAGTAGATGGTGATGAAATCGATGCTACTGTCAATTTAGAAAGCTATGGTTTGGATTCGGC
ACAGGCAATGGTACTAGTTAGTAAACTAGAGCAATTGTTGGGATTTCAACCATCACCTTTGTTGTTGT
GGCATTACCCCACTATTGAATCGTTGTCTGAACGTTTAGCTGAAGAATTGGAAGAACAATCT

*APNPCP*

ATGGAACAATCTACAACTAATCACGCCCGCCCCCAAATTACCGCTACCTACCTTCCCCCCAGCAATG
AAATTGAAGCCAGAGTCACCCAAGTAATGGAGAGTTTATTGGGAATCGCTCCTATTGGGGTTAATGA
TAACTTCTTTGAGTTAGGAGGACATTCCCTGTTAGCAATTCAAGCAGTTTCACAGCTACGGGAAGAA
TTTCAAGTAGAATTACCCATGCGACAATTTTTATTTGAGTCACCCACAATTGGGGGGATAGCCAAAA
TTATCATTGAAAATCAATCGCCTATTACTGAT

*FNPCP*

ATGGCCCAACGCCCTATCATTATCCCTCGTACAAATACTGAACAGCGAATAGGCGAGATTTGGAAGA
AGGCGATGAAGTGGGATTCTGTCTCGATATGTGATGATTTCTTTGAATCTGGCGGAAATTCACTTATT
GCTGTGAGAATAATCAACGCTATCAACAAAGAATTTCATTGTGCCTTGCCTTTACATGCTCTTTTTGA
AGCTCCAAGCATTGAAAAGCTCGCTCATAAGGTTGATAGTGATGAAGTTGAA

*FNsACP*

ATGGCTTTTCTAGAAGATGTCCCTCCAACAGAACGTCGAGAACACTTATTAGAATATCTTGGAAAA
GAAGTAGCAAAAATCTTAGGAATAAAACATATACCCGACCCAGAACAAGGATTTATAGAAATGGG
AATTGACTCTTTGCTTTCCATTGAATTCAAAAATCGTTTAGAAAAAGGATTAGAAATTGCTTTACC
ATCTACTTTAATATTTGATTTTCCGAATATTAGCAAATTAAATAATTATCTATTTGAGCAAATTTAT
GGTTGGGAAGTAAATACTACCGTGGAGACAACTGTTGATATTGTAGAAGTTAATGAAGATTTAATT
TTGCAAGAACTGGCAGATTTAGAAGCTTTTCTAGGTAATTCC

FIGURE 15

*FisPCP*

ATGGGATCGCTTCCCAAACCTGATTTTTCTAACTTAATCACTCATGAAGATTTTACGCCTGCACGCAA
TGATTTAGAGAGAAAAATCGCGCAGATTTGGTCAGAAATTTTACAGATTTCGGAAATTGATATTAGA
GATAACTTTTTTGAAGTTGGTGGTAATTCCCTTTTAGCATTACATTTAATGAATGCCATCGAACAAAA
ATTTGGTCGAGAGTTAGCACTGTCAACTTTACTTACTAATAACTCAATTGAAAAACTAGCAGAAATT
CTGCAAAACCCCACAGATGTTTTTCCCAATTCA

*AprACP*

ATGGAAATTTTTGAACAGGAATGTCGAAAATTATTAAAATCTCTACTGGGTGTTCAACGTATGGAGA
GATTGCCTGGTGACACACCACTAATGGAGTCAGGAATGGATTCACTGGAGTTGTTAGAATTTCGTGC
TCTTATAGAAAGAAAGTTTGGGATTAAGTTAAAGTCTACCTTCTTTTTTAGTTACAAAACTCTTATAG
CGGTAGCAGAGTATCTTTCAGAACGGGAAGATATTAATTTTAGT

*MACP*

ATGGTGACAACTGTTCAATCTCCTTGTACCGTTGAAGACATTCAAAACTGGCTCGTTGATCAGTTTGC
TCAACAACTCGATGTTGACCTTGATGACATTGATATTGAAGAACCTTTTGATAATTATGAACTCGACT
CACGAAAAGCGTTAGTTTTATTAGGACGCTTAGAAAAATGGCTCGGAAAGGAATTAAATCCTGTGGT
CATTTTTAACTATCCCACCATTGCTGAATTAGCAACCCGATTAGGGGAATTATATCTT

*ScACP*

ATGGAGCAGCGGCTGGCTCCGCTGTCCGCGGCCGAGCGCGAGCGGGCACTCACGGATCTCGTGCGC
GTCCAGGTCGCGGCGGTGCTCGGGCACTCTGACCCCGGCGCGATCGAGTCCGGCCGGGCCTTCCAGG
AGCTGGGCTTCGACTCACTGACAGCCGTCGAACTTCGCAACCAGCTGAGCACCGCGAGCGGACTGCG
CCTGCCCACCACCCTCGTCTTCGACCACCCCTCCCCCGCCGCTCTCGCCGCCCACCTCTCGGCGGAGC
TGTTCGGCGAGCAGGAG

*SsPCP*

ATGGCCCGCCGGCTCGAACCGTTGGACGAACCCGCGCGACGCCGTCTGCTGCTCGACCTGGTGTGCG
ACCACGCGGCCGCGGTCCTCGGCCACACCGGCCGCCAGGCCGTCCCGGCCGACCAGGCGTTCTCCGC
CGTCGGGTTCGACTCGATGCTCGCCGTGTCCTTCCGTAACCGGCTGCGCACCGCGACCGGCGTCCCC
GTCGCCGCGACGGTGGTGTTCGACCATCCCACCCCCGCCGCCCTCGCCGACCACCTGTACGACGGGT
TGAGCGCCCGTCCCGGACCGGCCGTT

**Codon optimized *Sfp***

ATGAAAATTTATGGGATTTACATGGATAGACCCCTGAGCCAAGAAGAAAACGAACGCTTTATGACCT
TTATTAGCCCTGAAAAACGGGAAAAATGTCGCCGTTTTTATCATAAAGAAGATGCCCATCGTACCTT
ATTGGGTGATGTGTTGGTTCGGAGTGTGATTTCTCGCCAATACCAATTGGATAAAAGTGATATTCGGT
TTTCTACTCAAGAATATGGTAAACCCTGTATTCCCGATTTGCCCGATGCCCATTTTAATATTAGTCAT
TCTGGTCGCTGGGTTATTGGTGCTTTTGATAGTCAACCCATTGGTATTGATATTGAAAAAACCAAACC
CATTTCTTTGGAAATTGCCAAACGCTTTTTCAGTAAAACCGAATACTCTGATTTATTGGCTAAAGATA
AAGATGAACAAACTGATTACTTTTACCATTTGTGGAGTATGAAAGAATCTTTTATTAAACAAGAAGG
TAAAGGTTTAAGTTTGCCCTTAGATAGTTTTTCTGTGCGGTTGCATCAAGATGGTCAAGTTAGTATTG
AATTACCCGATAGTCATTCTCCCTGTTACATTAAAACTTATGAAGTTGATCCCGGTTATAAAATGGCT
GTTTGTGCAGCACACCCCGATTTTCCAGAAGATATTACTATGGTTTCCTATGAAGAACTGTTGTAG

FIGURE 15 (continued)

```
BBa_J23119  ttgacagctagctcagtcctaggtataatgctagc
BBa_J23100  ttgacggctagctcagtcctaggtacagtgctagc
BBa_J23101  tttacagctagctcagtcctaggtattatgctagc
BBa_J23102  ttgacagctagctcagtcctaggtactgtgctagc
BBa_J23103  ctgatagctagctcagtcctaggyattatgctagc
BBa_J23104  ttgacagctagctcagtcctaggtattgtgctagc
BBa_J23105  tttacggctagctcagtcctaggtactatgctagc
BBa_J23106  tttacggctagctcagtcctaggtatagtgctagc
BBa_J23107  tttacggctagctcagcctaggtattatgctagc
BBa_J23108  ctgacagctagctcagtcctaggtataatgctagc
BBa_J23109  tttacagctagctcagtcctaggyactgtgctagc
BBa_J23110  tttacggctagctcagtcctaggtacaatgctagc
BBa_J23111  ttgacggctagctcagtcctaggtatagtgctagc
BBa_J23112  ctgatagctagctcagtcctaggyattatgctagc
BBa_J23113  ctgatggctagctcagtcctaggyattatgctagc
BBa_J23114  tttatggctagctcagtcctaggtacaatgctagc
BBa_J23115  tttatagctagctcagcccttggtacaatgctagc
BBa_J23116  ttgacagctagctcagtcctaggyactatgctagc
BBa_J23117  ttgacagctagctcagtcctaggyattgtgctagc
BBa_J23118  ttgacggctagctcagtcctaggtattgtgctagc
```

FIGURE 19

CYANOBACTERIAL HOSTS AND METHODS FOR PRODUCING CHEMICALS

CROSS-REFERENCE TO RELATED APPLICATIONS

This application is a continuation application of U.S. application Ser. No. 16/634,027, filed Jan. 24, 2020, which is a National Stage filing under 35 U.S.C. § 371 of International Patent Application No. PCT/US2018/043993, filed Jul. 27, 2018, which claims priority to U.S. Provisional Application No. 62/537,516, filed Jul. 27, 2017 and U.S. Provisional Application No. 62/611,634, filed Dec. 29, 2017. The entire content of each of the foregoing applications is expressly incorporated by reference herein.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 8, 2022, is named U119570139US03-SEQ-KZM and is 207 bytes in size.

FIELD OF INVENTION

The present invention relates to recombinant cyanobacterial cells for the production of chemical compounds of interest. In particular, the present invention relates to genetic modifications that introduce one or more heterologous phosphopantetheinyl transferases (PPTases) into the cyanobacterial cells. These cells can, optionally, further comprise heterologous carrier protein and nucleic acid constructs which provide the cyanobacterial cells with the capability of producing chemicals of interest or compounds of interest, such as secondary metabolites polyketides, nonribosomal peptides and their hybrids, the three major families of bioactive natural products, of cyanobacteria and other bacterial phyla, secondary metabolites analogs, and unnatural compounds. The nucleic acid constructs can be chromosomally integrated or present in self-replicating plasmids.

BACKGROUND OF THE INVENTION

Cyanobacteria produce structurally and functionally diverse secondary metabolites polyketides, nonribosomal peptides and their hybrids. Sfp-like phosphopantetheinyl transferases (PPTases) are essential to the modular biosynthesis of these compounds via functionalizing carrier proteins (CPs) of megaenzymes. However, cyanobacterial Sfp-like PPTases remain poorly characterized, posing a significant barrier to the exploitation of cyanobacteria for biotechnological and biomedical applications.

Herein, we describe the characterization of multiple cyanobacterial Sfp-like PPTases. Biochemical characterization and kinetic analysis of these enzymes along with the prototypic enzyme Sfp from *Bacillus subtilis* demonstrated their varying specificities toward recombinant CPs from different types of biosynthetic pathways in cyanobacterial and *Streptomyces* strains. Moreover, two selected cyanobacterial PPTases along with Sfp were transiently expressed in one PPTase-deficient mutant of model cyanobacterium *Synechocystis* sp. PCC6803 and supported its growth comparable to the wild type. These enzymes in the cyanobacterial cell lysates also functionalized selected CPs in vitro.

The subject application provides new tools to synthesize cyanobacterial natural products using in vitro and in vivo synthetic biology approaches. In one embodiment, cyanobacterial cells can be engineered to express heterologous proteins or chemicals/compounds of interest (such as cyanobacterial secondary metabolites polyketides, nonribosomal peptides and their hybrids, the three major families of bioactive natural products). In one embodiment, *Synechocystis* sp. PCC6803 can be engineered for the heterologous expression of a shinorine gene cluster from the cyanobacterium *Fischerella* sp. PCC9339. After optimization, the yield of shinorine in the engineered *Synechocystis* sp. PCC6803 was higher than any known cyanobacterial producers in nature. This work demonstrates the feasibility of the *Synechocystis* sp. PCC6803 to produce cyanobacterial secondary metabolites polyketides, nonribosomal peptides and their hybrids, the three major families of bioactive natural products.

BRIEF SUMMARY OF THE INVENTION

This invention provides a recombinant, i.e. non-naturally occurring, cyanobacterial cell for the production of chemical compounds of interest. The cyanobacterial cell comprises an inactivated endogenous phosphopantetheinyl transferase(s) (PPTase(s)) and expresses one or more heterologous PPTases. These engineered cells can further comprise exogenous expression genetic constructs that permit the expression of heterologous proteins or chemicals/compounds of interest (such as cyanobacterial secondary metabolites polyketides, nonribosomal peptides and their hybrids, the three major families of bioactive natural products). The genetically engineered cells can further comprise one or more heterologous carrier proteins (CPs) activated by the heterologous PPTases.

The invention also provides a method for producing the above-mentioned cyanobacterial cell. The method comprises inactivating endogenous PPTases within a cyanobacterial cell, providing at least one transformable nucleic acid construct for the genetic modification said cyanobacterial cell that encodes a heterologous PPTase and, optionally, providing at least one transformable nucleic acid construct encoding a heterologous protein or a compound/chemical of interest. The transformable nucleic acid constructs can be transformed into a cyanobacterial cell to obtain the recombinant cyanobacterial cell of the present invention. The transformable nucleic acid constructs can be transformed into a cyanobacterial cell and then integrated into the chromosomal DNA to obtain the recombinant cyanobacterial cell of the present invention. Alternatively, the transformable nucleic acid constructs can be present within the recombinant cyanobacterial cell in the form of self-replicating plasmids or modules (see, for example, Taton, Arnaud et al. "Broad-Host-Range Vector System for Synthetic Biology and Biotechnology in Cyanobacteria." *Nucleic Acids Research* 42.17 (2014): e136. *PMC*. Web. 26 July 2017. the disclosure of which is hereby incorporated by reference in its entirety).

BRIEF DESCRIPTION OF THE DRAWINGS

FIG. 3. Relative activity of seven PPTases on 11 CP substrates. For any CP, the activity of the most active PPTase was set as 100%, and those of other PPTases were normalized as shown in the heatmap. The data represent the mean of three independent experiments. Red to white color indicates the high to low relative activity of PPTases. CPs are grouped according to the biosynthetic pathways while cyanobacterial PPTases are organized by the subsections of sources.

FIGS. 4A-4D. The in vivo activity of APPT, MPPT and Sfp in *Synechocystis*. (A) The APPT, MPPT and Sfp genes chromosomally replaced the SPPT gene in *Synechocystis* mutants. The PCR diagnosis detected the SPPT in the wild type (lane 1) but not in three mutants (lanes 2 to 4). The APPT, MPPT and Sfp genes were found in three mutants, respectively (lanes 2 to 4). (B) RT-PCR analysis of the transcription of SPPT, APPT, MPPT and Sfp genes in wild type *Synechocystis* and mutants (lanes 2 to 5). The rnpB gene encoding the RNA subunit of RNase P was used as a positive control (lane 1). (C) Quantitative analysis of transcriptional levels of SPPT, APPT, MPPT and Sfp genes. The signals were normalized with that of rnpB gene. The asterisk (*) indicates significance of the changes (≥95%). (D) Growth curve of wild type *Synechocystis* and mutants. OD730 was continuously monitored for 13 days.

FIG. 9. PPTases used in the phylogenetic analysis. The sequences of the PPTases can be obtained from GenBank or EMBL using the accession numbers listed in the table and these sequences are hereby incorporated by reference in their entireties.

FIG. 10. CPs used to characterize PPTases. The sequences of the CPs can be obtained from GenBank or EMBL using the accession numbers listed in the table and these sequences are hereby incorporated by reference in their entireties.

FIG. 11. Relative Activity of select PPTases in activating CPs.

FIG. 12. Oligos used in the Examples (SEQ ID NOs: 89-159).

FIG. 14. Multiple-sequence alignment of characterized cyanobacterial PPTases and Sfp. The completely conserved residues are shaded in gray. The proposed magnesium binding residues are indicated with asterisks (*). Boxed region indicates the conserved W/KEA motif. Sfp, SEQ ID NO: 7; SePPT, SEQ ID NO: 5; SPPT, SEQ ID NO: 6; MPPT, SEQ ID NO: 3; FPPT, SEQ ID NO: 4; AvPPT, SEQ ID NO: 2; and APPT, SEQ ID NO: 1.

FIG. 15. Sequences of selected CP genes and codon optimized Sfp gene. SFACP (SEQ ID NOs: 8 and 9); AFACP (SEQ ID NOs: 10 and 11); APACP (SEQ ID NOs: 12 and 13); APNPCP (SEQ ID NOs: 14 and 15); FNPCP (SEQ ID NOs: 16 and 17); FNsACP (SEQ ID NOs: 18 and 19); FisPCP (SEQ ID NOs: 20 and 21); AprACP (SEQ ID NOs: 22 and 23); MACP (SEQ ID NOs: 24 and 25); ScACP (SEQ ID NOs: 26 and 27); SsPCP (SEQ ID NOs: 28 and 29); and Codon optimized Sfp (SEQ ID NOs: 30 and 31).

FIG. 19. Exemplary promoters in the J23 library (SEQ ID NOs: 160-179).

DETAILED DISCLOSURE OF THE INVENTION

Figure 1:
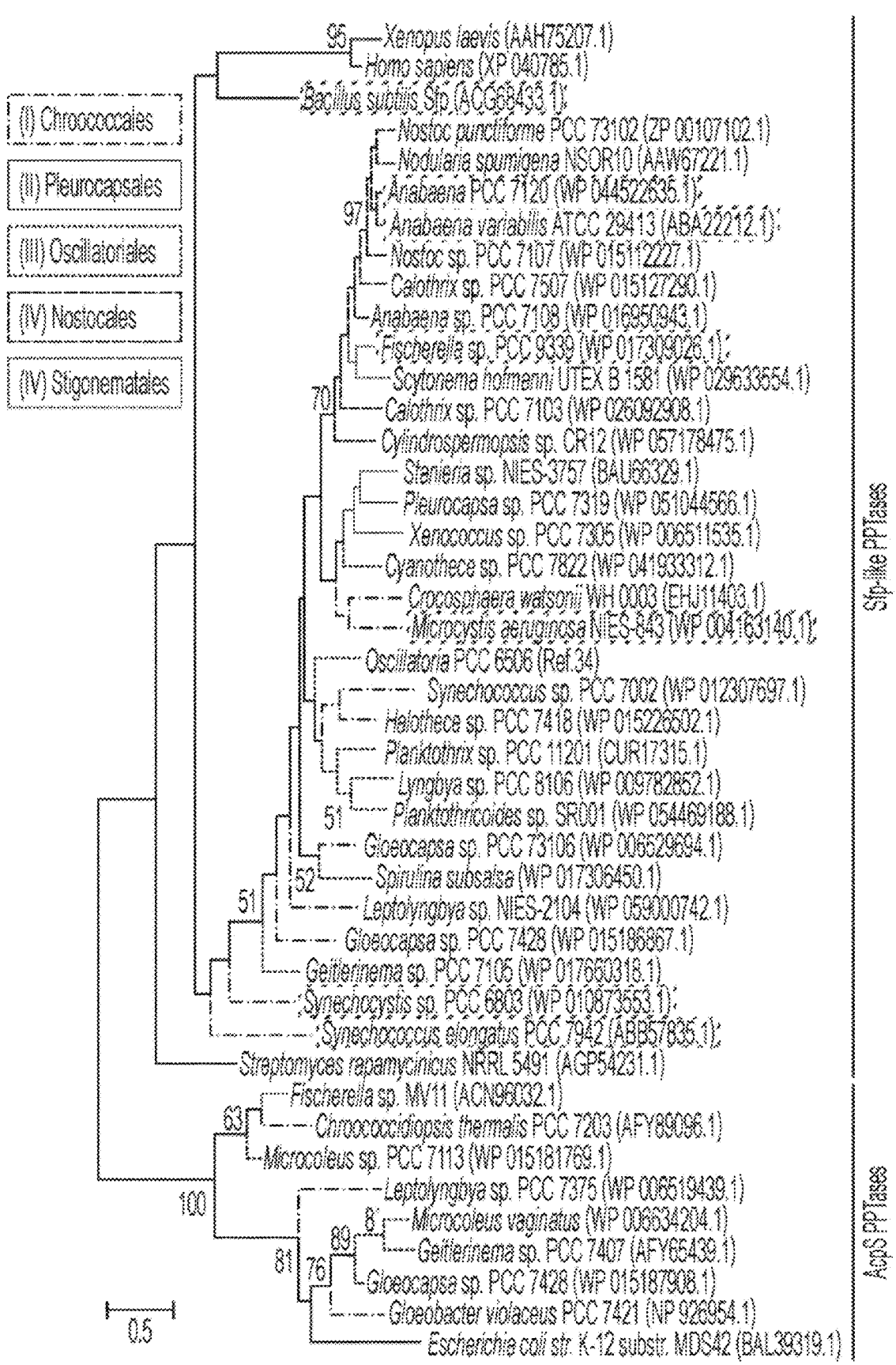
FIG. 1. A maximum-likelihood phylogeny based on selected cyanobacterial PPTases. A phylogenetic tree was generated using MEGA7 maximum-likelihood method. Enzymes are shown as the names of corresponding strains with NCBI accession numbers given in parenthesis. The *E. coli* AcpS was chosen as an outgroup for the AcpS-like PPTase clade, while the PPTases from *Streptomyces rapamycinicus* NRRL5491, *Xenopus laevis* and *Homo sapiens* were outgroups for the Sfp-like PPTase clade. Branches are color-coded according to morphological subsections of cyanobacteria. Branch length is proportional to the amount of genetic change. Significant bootstrap values (over 500 of 1,000 repeats) are shown. PPTases with shaded taxa names were selected for the characterization in this study.

In a first aspect, the subject invention provides a recombinant, i.e. non-naturally occurring, cyanobacterial cell for the production of a chemical compound of interest. The cyanobacterial cell comprises an inactivated endogenous phosphopantetheinyl transferase(s) (PPTase(s)) and expresses one or more heterologous PPTases. These engineered cells can further comprise exogenous expression cassettes or nucleic acid constructs that permit the expression of heterologous proteins or chemicals/compounds of interest (such as cyanobacterial secondary metabolites polyketides, nonribosomal peptides and their hybrids, the three major families of bioactive natural products). The genetically engineered cells can further comprise one or more heterologous carrier proteins (CPs) activated by the heterologous PPTases.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 10% (i.e., ±10%).

The term "Cyanobacterium" refers to a member from the group of photoautotrophic prokaryotic microorganisms which can utilize solar energy and fix carbon dioxide. Cyanobacteria are also referred to as blue-green algae. Exemplary cyanobacteria include, but are not limited to, *Synechocystis* sp. The cyanobacterial cell of the present invention can be selected from the group consisting of *Synechocystis, Synechococcus, Anabaena, Chroococcidiopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena, Cyanobacterium, Geitlerinema, Euhalothece, Calothrix,* and *Scytonema*. Particularly preferred is *Synechocystis* PCC6803.

The terms "host cell" and "recombinant host cell" are intended to include a cell suitable for genetic manipulation, e.g., which can incorporate heterologous polynucleotide sequences, e.g., which can be transformed. The term is intended to include progeny of the cell originally transformed. In particular embodiments, the cell is a prokaryotic cell, e.g., a cyanobacterial cell. The term "recombinant host cell" is intended to include a cell that has already been selected or engineered to have certain desirable properties and to be suitable for further genetic enhancement.

"Competent to express" refers to a host cell that provides a sufficient cellular environment for expression of endogenous and/or heterologous polynucleotides.

The terms "polynucleotide" and "nucleic acid" also refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be an endogenous or heterologous gene that is recombinantly introduced into the host cell.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994, Nucleic Acids Research 22: 4673-4680). A nucleotide sequence or an amino acid sequence can also be used as a so-called "query sequence" to perform a search against public nucleic acid or protein sequence databases in order, for example, to identify PPTases within microorganisms, which can also be used in various embodiments of this invention for either transformation of a microorganism or inactivation of an endogenous PPTase within a microorganism.

In addition, any nucleic acid sequences or protein sequences disclosed in this patent application can also be used as a "query sequence" in order to identify yet unknown sequences in public databases, which can encode PPTases or CPs which could be useful in this invention. Such searches can be performed using the algorithm of Karlin and Altschul (1990, Proceedings of the National Academy of Sciences U.S.A. 87: 2,264 to 2,268), modified as in Karlin and Altschul (1993, Proceedings of the National Academy of Sciences U.S.A. 90: 5,873 to 5,877). Such an algorithm is incorporated in the NBLAST and XBLAST programs of Altschul et al. (1990, Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997, Nucleic Acids Research, 25: 3,389 to 3,402).

As used herein, the term "genetically modified" refers to any change in the endogenous genome of a wild type cell or to the addition of non-endogenous (heterologous) genetic code to a wild type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

The term "recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacterium." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at any of a large number of genomic locations.

The term "expressed endogenously" refers to polynucleotides that are native to the host cell and are naturally expressed in the host cell. The term "operably linked" refers to a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a native or a heterologous polynucleotide), where the expression control sequence directs transcription of the polynucleotide.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors"). Thus, transformable nucleic acid constructs can be transformed into a cyanobacterial cell and then integrated into the chromosomal to obtain the recombinant cyanobacterial cell of the present invention. Alternatively, the transformable nucleic acid constructs can be present within the recombinant cyanobacterial cell in the form of self-replicating plasmids or modules (see, for example, Taton, Arnaud et al. "Broad-Host-Range, Vector System for Synthetic Biology and Biotechnology in Cyanobacteria."*Nucleic Acids Research* 42.17 (2014): e136. PMC, Web. 26 July 2017, the disclosure of which is hereby incorporated by reference in its entirety). A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription. The term "promoter" is intended to include a polynucleotide segment that can transcriptionally control a gene of interest, e.g., a PPTase gene that it does or does not transcriptionally control in nature. In one embodiment, the transcriptional control of a promoter results in an increase in expression of the gene of interest. In an embodiment, a promoter is placed 5' to the gene of interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., chemicals, nutrient starvation, heat shock, mechanical stress, metal ions, light exposure, etc.) will induce the promoter leading to the transcription of the gene. In certain embodiments, constitutive promoters, such as ptrc, can be used to express heterologous PPTases within a recombinant cell. Other constitutive promoters that can be used in the context of this invention include Pcpc560, Ptrc, Ptrc2O-2, PAllacO-1, L03, PnrsB, PpsbA2, PpsbA, the plastocyanin promoter and the promoters provided in the J23 library (a synthetic library of minimal and constitutive $\sigma^{70}$ promoters, examples of which are provided in FIG. 19). These and other promoters, such as inducible promoters, are disclosed in "Engineered transcriptional systems for cyanobacterial biotechnology", Camsund and Lindblad, *Frontiers in Bioengineering and Biotechnology*, 2014, 2:40, which is hereby incorporated by reference in its entirety. Endogenous and exogenous promoters can also be identified using a bioinformatics algorithm, such as bTSSfinder: a novel tool for the prediction of promoters in cyanobacteria and Escherichia coli, Bioinformatics. 2017; 33(3): 334-340.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). The recombinant nucleic acid molecule (e.g., a recombinant DNA molecule) also includes an isolated nucleic acid molecule or gene of the present invention.

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. In particular embodiments, the subject invention provides genes encoding PPTases disclosed herein and, optionally, CPs as disclosed herein.

The term "endogenous gene" refers to a native gene in its natural location in the genome of an organism. The terms "endogenous" and "native" can be used interchangeably within this application. A "foreign" gene, "exogenous gene" or "heterologous" gene refers to a gene not normally found in the host organism, but that is introduced into the host organism by gene transfer or transformation of the microorganism. Foreign genes can comprise native genes inserted into a non-native organism, or chimeric genes. A "transgene" is a gene that has been introduced into the genome by a transformation procedure. A "foreign gene" can also comprise an endogenous gene that is introduced into another location in the genome of an organism (i.e., moved from its natural location within the genome of the organism) which is operably linked to its naturally occurring promoter or to a heterologous promoter. A heterologous gene can also include a native gene of a microorganism that is found in its native location but which has had its native promoter substituted with a heterologous (non-native) promoter, such as the constitutive or inducible promoters discussed within this application. The terms "heterologous", "exogenous", and "foreign" can be used interchangeably within this application.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6, 50, 100, 200, 500, 1,000, to about 1,500 or more consecutive nucleotides of a polynucleotide according to the invention.

The term "open reading frame," abbreviated as "ORF," refers to a length of nucleic acid sequence, either DNA, cDNA or RNA that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments. The terms "homology" and "identity" can be used interchangeably within the subject application.

As used herein, "substantially similar" refers to nucleic acid fragments wherein changes in one or more nucleotide bases results in substitution of one or more amino acids, but do not affect the functional properties of the protein encoded by the DNA sequence.

The term "substantially similar" also refers to modifications of the nucleic acid fragments of the instant invention such as deletion or insertion of one or more nucleotide bases that do not substantially affect the functional properties of the resulting transcript.

The term "expression", as used herein, refers to the transcription and stable accumulation mRNA derived from a nucleic acid or polynucleotide. Expression may also refer to translation of mRNA into a protein or polypeptide.

An "expression cassette" or "nucleic acid construct" or "genetic construct" refers to a series of polynucleotide elements that permit transcription of a gene in a host cell. Typically, the expression cassette or nucleic acid construct includes a promoter (native or heterologous) and a heterologous or native polynucleotide sequence that is transcribed. Expression cassettes or constructs may also include, e.g., transcription termination signals, polyadenylation signals, and enhancer elements.

The term "codon" refers to a triplet of nucleotides coding for a single amino acid.

The term "codon bias" refers to the fact that different organisms use different codon frequencies.

The term "codon optimization" refers to the modification of at least some of the codons present in a heterologous gene sequence from a triplet code that is not generally used in the host organism to a triplet code that is more common in the particular host organism. This can result in a higher expression level of the gene of interest.

The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "knockout" generally refers to a partial or complete suppression of the expression of at least a portion of a protein encoded by an endogenous DNA sequence in a cell. As used herein, the "knockout" relates to the deletion of a target gene, such as an endogenous PPTase or CP.

The term "knockout construct" refers to a nucleic acid sequence that is designed to decrease or suppress expression of a protein encoded by endogenous DNA sequence in a cell. The knockout construct is inserted into a cell, and integrates with the genomic DNA of the cell in such a position so as to prevent or interrupt transcription of the native DNA sequence. Such insertion usually occurs by homologous recombination. The knockout construct nucleic acid sequence may comprise (1) a full or partial sequence of the gene to be suppressed, (2) a full or partial promoter sequence of the gene to be suppressed, or (3) combinations thereof. Typically, the knockout construct is inserted into a cyanobacterial host cell and is integrated into the cell genomic DNA to delete a target gene, such as an endogenous PPTase and/or CP, usually by the process of homologous recombination.

The phrases "disruption of the gene" and "gene disruption" refer to the deletion or insertion of a nucleic acid sequence into one region of the native DNA sequence and/or the promoter region of a gene so as to decrease or prevent expression of that gene in the cell as compared to the wild-type or naturally occurring sequence of the gene.

The term "plurality" means more than one.

The terms "chemical compound of interest" or "product of interest" refer to a product produced by the modified cyanobacteria. In one embodiment, the product is shinorine. In other embodiments, the product can be cyanobacterial secondary metabolites, polyketides, or non-ribosomal peptides and their hybrids. In other embodiments, the product can be analogs of cyanobacterial secondary metabolites, polyketides, or non-ribosomal peptides and their hybrids. In other embodiments, the product can be unnatural compounds of polyketides, or non-ribosomal peptides and their hybrids. In other embodiments, the product can be secondary metabolites, polyketides, or non-ribosomal peptides and their hybrids of bacterial species that do not belong to the cyanobacterium phylum.

Non-limiting examples of PPTases that can be used in the context of this invention for transformation into recombinant cells are identified in the following table. Other PPTases suitable for use in the context of the subject application can be found in FIG. 9. The sequences for these PPTases can be found, by their accession number, in various databases such as GenBank and EMBL.

| PPTases | Accession No. | SEQ ID NO: |
|---------|---------------|------------|
| APPT    | WP_044522635.1 | 1 |
| AvPPT   | ABA22212.1    | 2 |
| MPPT    | WP_004163140.1 | 3 |
| FPPT    | WP_017309026.1 | 4 |
| SePPT   | ABB57835.1    | 5 |
| SPPT    | WP_010873553.1 | 6 |
| Sfp     | ACG68433.1    | 7 |

APPT
(SEQ ID NO: 1)
```
  1  mlqhtwlpkp pnltllsdev hlwripldqp esqlqdlaat lssdelaran rfyfpehrrr
 61  ftagrgilrs ilggylgvep gqvkfdyesr gkpilgdrfa esgllfnlsh sqnlalcavn
121  ytrqigidle ylrptsdles lakrfflpre yellrslpde qkqkiffryw tckeaylkat
181  gdgiakleei eialtptepa klqtapawsl lelvpddncv aavavagfgw qpkfwhy
```

AvPPT
(SEQ ID NO: 2)
```
  1  mlqhtwlpkp pnltllsdev hlwripldrp esqlqhlaat lssdelaran rfyfpehrqr
 61  ftagrgilrs ilglylgvep kqvkfeyesr gkpvlgdrfa dsgllfnlsh sqnlglcavn
121  ytrqigidle ylrptsdles lakrfflpre yellrslpde qkqkiffryw tckeaylkat
181  gdgiakleei eialtptepa klqttpawsl lelvpddncv aavavagfgw qpkfwqy
```

MPPT
(SEQ ID NO: 3)
```
  1  mfistdevhl yfisldpsgd rletlaslls edeiiranry hfpehkrrfl vargclreil
 61  gsylaispek iefiysergk psinyqlqfn lshseemaic gltltarigv dlekmrqmkd
121  ldsltkrffc arehelveks aekeklffql wtakeaylka vgtgisggld rvevglnplk
181  ldnvagewql wtaaigdnyr atvviegsdr viktfglsdl
```

FPPT
(SEQ ID NO: 4)
```
  1  mgsetnhlwl taptnltllp ddvhvwrisl drpeselqal qttlssdeia raqrfyfeqh
 61  rqrfvagrgi lrtilgrylg vepqavefty elrgkpllad rfadsgvsfn lshsqdlalc
121  gvsrnrkigi dveymrsvsd vealaerffa preyevvrsl psnqqqqvff rywtckeayl
181  kaigvgivql ekveisltle qpaklitdee wslielvpgd hylgavaiag qnldlkywqy
```

SePPT
(SEQ ID NO: 5)
```
  1  mqrpnpsdav pvpsipscdr gpipnpvtwr tspeplflsa qtvhlwrcsl trslssaeqa
 61  ivaadcdraq aygsnrrhqf lcgrwwlrql lslylpeepa dfrfqlsptg kpelpqsnlc
121  fnlshsgstl liaiawqpvg vdveqprsrs wlalarryfp saelaamqqs tdcdrwglas
181  wvckeawika qgrtlanslr hlqcawtang qprlsglgse esqvqllqvd pqeqlwaaia
241  mpagwnyqtw taaiirknh
```

SPPT
(SEQ ID NO: 6)
```
  1  mlpqpqiwlc ptdrplipgy qallsseema rgeryqrpqd kqrfltmrla lrillarqld
 61  clpqqlqfty gpqgkpelvd rerrspwfnv ahsgnyglig lstegeigvd lqimlpkphy
121  lklakrffap qevqqlesle gekrtklfyq lwtakeaflk atgkgisggl nqvipdenla
181  kyqylpdsgd tnhwrlssqp lladqgsndn ywmaiawctn evnqvesnyl pniqpfqwpr
241  nldslp
```

Sfp
(SEQ ID NO: 7)
```
  1  mkiygiymdr plsqeenerf mtfispekre kcrrfyhked ahrtllgdvl vrsvisrqyq
 61  ldksdirfst qeygkpcipd lpdahfnish sgrwvigafd sqpigidiek tkpisleiak
121  rffskteysd llakdkdeqt dyfyhlwsmk esfikqegkg lslpldsfsv rlhqdgqvsi
181  elpdshspcy iktyevdpgy kmavcaahpd fpeditmvsy eell
```

Non-limiting examples of carrier proteins (Cps) that can be used in the context of the subject application include: ACPs of *Synechocystis* (SFACP) and *Anabaena* (AFACP), the ACP of the glycolipid PKS in *Anabaena* (APACP), the ACP of the apratoxin (PK/NRP) gene cluster in *Lyngbya* sp. (AprACP), the PCP of the shinorine gene cluster from *Fischerella* (FisPCP), CPs from *Fischerella* (FNPCP, an NRP pathway), *Anabaena* (APNPCP, an NRP/PK pathway) and *M. aeruginosa* NIES843 (MACP, an NRP/PK pathway), $ArCP_{Np}$ from *Fischerella* (FNsACP), one ACP of a putative concanamycin gene cluster from *Streptomyces coelicolor* A(3)2 (ScACP) and one PCP of a thaxtomin cluster from plant pathogen *Streptomyces scabiei* 87.22 (SsPCP).

```
SFACP
                                              (SEQ ID NOs: 8 and 9)
ATGGATCAGGAAATTTTTGAAAAAGTAAAAAAAATCGTCGTGGAACAGTTGGAAGTGGATCCTGAC

AAAGTGACCCCCGATGCCACCTTTGCCGAAGATTTAGGGGCTGATTCCCTCGATACAGTGGAATTGG

TCATGGCCCTGGAAGAAGAGTTTGATATTGAAATTCCCGATGAAGTGGCGGAAACCATTGATACCGT

GGGCAAAGCCGTTGAGCATATCGAAAGTAAA

AFACP
                                             (SEQ ID NOs: 10 and 11)
ATGGGCCAATCAGAAACTTTTGAAAAAGTCAAAAAAATTGTTATCGAACAACTAAGTGTGGAGAAC

CCTGACACAGTAACTCCAGAAGCTAGTTTTGCCAACGATTTACAGGCTGATTCCCTCGATACAGTAG

AACTAGTAATGGCTTTGGAAGAAGAATTTGATATCGAAATTCCCGATGAAGCCGCAGAGAAAATTA

CCACTGTTCAAGAAGCGGTGGATTACATCAATAACCAAGTTGCCGCATCAGCT

APACP
                                             (SEQ ID NOs: 12 and 13)
ATGGGTCTAAAACAAAATTATAGTGCAGCAGATATTCAAGCTTGGATGATATCTAATCTAGCTGAAT

TGTTGGGAGTAGATGGTGATGAAATCGATGCTACTGTCAATTTAGAAAGCTATGGTTTGGATTCGGC

ACAGGCAATGGTACTAGTTAGTAAACTAGAGCAATTGTTGGGATTTCAACCATCACCTTTGTTGTTGT

GGCATTACCCCACTATTGAATCGTTGTCTGAACGTTTAGCTGAAGAATTGGAAGAACAATCT

APNPCP
                                             (SEQ ID NOs: 14 and 15)
ATGGAACAATCTACAACTAAFCACGCCCGCCCCCAAATTACCGCTACCTACCTTCCCCCCAGCAATG

AAATTGAAGCCAGAGTCACCCAAGTAATGGAGAGTTTATTGGGAATCGCTCCTATTGGGGTTAATGA

TAACTTCTTTGAGTTAGGAGGACATTCCCTGTTAGCAATTCAAGCAGTTTCACAGCTACGGGAAGAA

TTTCAAGTAGAATTACCCATGCGACAATTTTTATTTGAGTCACCCACAATTGGGGGGATAGCCAAAA

TTATCATTGAAAATCAATCGCCTATTACTGAT

FNPCP
                                             (SEQ ID NOs: 16 and 17)
ATGGCCCAACGCCCTATCATTATCCCTCGTACAAATACTGAACAGCGAATAGGCGAGATTTGGAAGA

AGGCGATGAAGTGGGATTCTGTCTCGATATGTGATGATTTCTTTGAATCTGGCGGAAATTCACTTATT

GCTGTGAGAATAATCAACGCTATCAACAAAGAATTTCATTGTGCCTTGCCTTTACATGCTCTTTTGA

AGCTCCAAGCATTGAAAAGCTCGCTCATAAGGTTGATAGTGATGAAGTTGAA

FNsACP
                                             (SEQ ID NOs: 18 and 19)
ATGGCTTTTCTAGAAGATGTCCCTCCAACAGAACGTCGAGAACACTTATTAGAATATCTTGGAAAAG

AAGTAGCAAAAATCTTAGGAATAAAACATATACCCGACCCAGAACAAGGATTTATAGAAATGGGAA

TTGACTCTTTGCTTTCCATTGAATTCAAAAATCGTTTAGAAAAAGGATTAGAAATTGCTTTACCATCT

ACTTTAATATTTGATTTTCCGAATATTAGCAAATTAAATAATTATCTATTTGAGCAAATTTATGGTTG

GGAAGTAAATACTACCGTGGAGACAACTGTTGATATTGTAGAAGTTAATGAAGATTTAATTTTGCAA

GAACTGGCAGATTTAGAAGCTTTTCTAGGTAATTCC

FisPCP
                                             (SEQ ID NOs: 20 and 21)
ATGGGATCGCTTCCCAAACCTGATTTTTCTAACTTAATCACTCATGAAGATTTTACGCCTGCACGCAA

TGATTTAGAGAGAAAAATCGCGCAGATTTGGTCAGAAATTTTACAGATTTCGGAAATTGATATTAGA
```

```
-continued
GATAACTTTTTTGAAGTTGGTGGTAATTCCCTTTTAGCATTACATTTAATGAATGCCATCGAACAAAA

ATTTGGTCGAGAGTTAGCACTGTCAACTTTACTTACTAATAACTCAATTGAAAAACTAGCAGAAATT

CTGCAAAACCCCACAGATGTTTTTCCCAATTCA

AprACP
                                                 (SEQ ID NOs: 22 and 23)
ATGGAAATTTTTGAACAGGAATGTCGAAAATTATTAAAATCTCTACTGGGTGTTCAACGTATGGAGA

GATTGCCTGGTGACACACCACTAATGGAGTCAGGAATGGATTCACTGGAGTTGTTAGAATTTCGTGC

TCTTATAGAAAGAAAGTTTGGGATTAAGTTAAAGTCTACCTTCTTTTTTAGTTACAAAACTCTTATAG

CGGTAGCAGAGTATCTTTCAGAACGGGAAGATATTAATTTTAGT

MACP
                                                 (SEQ ID NOs: 24 and 25)
ATGGTGACAACTGTTCAATCTCCTTGTACCGTTGAAGACATTCAAAACTGGCTCGTTGATCAGTTTGC

TCAACAACTCGATGTTGACCTTGATGACATTGATATTGAAGAACCTTTTGATAATTATGAACTCGACT

CACGAAAAGCGTTAGTTTTATTAGGACGCTTAGAAAAATGGCTCGGAAAGGAATTAAATCCTGTGGT

CATTTTTAACTATCCCACCATTGCTGAATTAGCAACCCGATTAGGGGAATTATATCTT

ScACP
                                                 (SEQ ID NOs: 26 and 27)
ATGGAGCAGCGGCTGGCTCCGCTGTCCGCGGCCGAGCGCGAGCGGGCACTCACGGATCTCGTGCGC

GTCCAGGTCGCGGCGGTGCTCGGGCACTCTGACCCCGGCGCGATCGAGTCCGGCCGGGCCTTCCAGG

AGCTGGGCTTCGACTCACTGACAGCCGTCGAACTTCGCAACCAGCTGAGCACCGCGAGCGGACTGCG

CCTGCCCACCACCCTCGTCTTCGACCACCCCTCCCCCGCCGCTCTCGCCGCCCACCTCTCGGCGGAGC

TGTTCGGCGAGCAGGAG

SsPCP
                                                 (SEQ ID NOs: 28 and 29)
ATGGCCCGCCGGCTCGAACCGTTGGACGAACCCGCGCGACGCCGTCTGCTGCTCGACCTGGTGTGCG

ACCACGCGGCCGCGGTCCTCGGCCACACCGGCCGCCAGGCCGTCCCGGCCGACCAGGCGTTCTCCGC

CGTCGGGTTCGACTCGATGCTCGCCGTGTCCTTCCGTAACCGGCTGCGCACCGCGACCGGCGTCCCC

GTCGCCGCGACGGTGGTGTTCGACCATCCCACCCCCGCCGCCCTCGCCGACCACCTGTACGACGGGT

TGAGCGCCCGTCCCGGACCGGCCGTT
```

The subject invention also provides a codon optimized Sfp gene:

```
Codon optimized Sfp
                                                 (SEQ ID NOs: 30 and 31)
ATGAAAATTTATGGGATTTACATGGATAGACCCCTGAGCCAAGAAGAA

ACGAACGCTTTATGACCTTTATTAGCCCTGAAAAACGGGAAAAATGTCG

CCGTTTTTATCATAAAGAAGATGCCCATCGTACCTTATTGGGTGATGTG

TTGGTTCGGAGTGTGATTTCTCGCCAATACCAATTGGATAAAAGTGATA

TTCGGTTTTCTACTCAAGAATATGGTAAACCCTGTATTCCCGATTTGCC

CGATGCCCATTTTAATATTAGTCATTCTGGTCGCTGGGTTATTGGTGCT

TTTGATAGTCAACCCATTGGTATTGATATTGAAAAAACCAAACCCATTT

CTTTGGAAATTGCCAAACGCTTTTTCAGTAAAACCGAATACTCTGATTT

ATTGGCTAAAGATAAAGATGAACAAACTGATTACTTTTACCATTTGTGG

AGTATGAAAGAATCTTTTATTAAACAAGAAGGTAAAGGTTTAAGTTTGC

CCTTAGATAGTTTTTCTGTGCGGTTGCATCAAGATGGTCAAGTTAGTAT

TGAATTACCCGATAGTCATTCTCCCTGTTACATTAAAACTTATGAAGTT
```

-continued
```
GATCCCGGTTATAAAATGGCTGTTTGTGCAGCACACCCCGATTTTCCAG

AAGATATTACTATGGTTTCCTATGAAGAACTGTTGTAG
```

In one embodiment of the subject invention, a recombinant host cell comprising inactivated endogenous PPTase(s) and genetically modified to contain one or more exogenous PPTase. Such cells may, optionally, also be genetically modified to contain one or more exogenous CP (with or without inactivation of endogenous CPs within the recombinant host cell. Other embodiments provide for recombinant host cells that have been genetically modified to substitute a constitutive promoter for the endogenous promoter. For example, it is possible that the genetic modification causes a constitutive expression of the endogenous and/or exogenous PPTase. These cells may further comprise additional nucleic acid constructs that permit the expression of a chemical or other compound of interest.

Certain embodiments of the invention demonstrate the ability of production of a compound of interest (shinorine) by the recombinant host cells disclosed herein.

As discussed above, the invention provides for the genetic modification of a recombinant host cell in a manner that decreases or eliminates the expression of endogenous PPTases. One possibility is that the genetic modification comprises a heterologous nucleic acid sequence encoding a knockdown component that reduces or eliminates the expression of the endogenous PPTase and/or CP. As used herein, the term "heterologous" refers to an element such as a gene, part of a gene or protein in a cyanobacterium which does not naturally have this element. For example, a "heterologous nucleic acid sequence" has been inserted into the host organism by recombinant DNA technology. The term "heterologous" also means a DNA sequence which appears endogenously in the cyanobacterium but is additionally present in a non-native form, for instance by forming part of a synthetic plasmid or by artificially controlling expression of the DNA sequence by a promoter which is not naturally controlling the sequence in the cyanobacterium. The knockdown component can comprise RNA transcribed from the heterologous nucleic acid that is at least partially complementary to mRNA transcribed from a PPTase and/or CP gene for binding to the mRNA and initiating degradation and/or inhibiting translation of at least part thereof. For example, the heterologous nucleic acid can encode a small RNA (sRNA) or an antisense RNA (asRNA) to silence the expression of the PPTase gene and/or the CP gene.

The expression of the knockdown component is preferably controlled by a constitutive promoter or, as the case may be, a promoter that is at least constitutive under typical cyanobacterial culturing conditions. Suitable constitutive promoters for the various aspects of the present invention include, but are not limited to, Pcpc560, Ptrc, Ptrc2O-2, PAllacO-1, L03, PnrsB, PpsbA2, PpsbA, the plastocyanin promoter and the promoters provided in the J23 library.

Alternatively, the genetic modification can comprise at least partial disruption or complete removal of an endogenous PPTase and/or CP gene. In this way, the gene may be translated into a protein which has an altered or reduced function or is non-functional. Preferably, the gene is not translated at all. It is possible that the genome of the cyanobacterial cell harbors more than one copy of the endogenous PPTase and/or CP gene. In such a case, it is further preferred that all copies of the gene comprise the at least partial disruption or, more preferably, have been completely removed in order to deprive the cyanobacterium of the possibility utilizing the endogenous PPTase and/or CP.

In a second aspect, this invention provides a method for producing a chemical or compound of interest with the recombinant cyanobacterial cell. The method comprises culturing the cyanobacterial cell under conditions that permit the expression of the chemical or compound of interest, thereby producing the chemical compound of interest. Typically, the cyanobacterium is exposed to light and $CO_2$ during the method steps.

In the following, certain embodiments of the invention will be explained in more detail with reference to figures and experimental data. The figures and examples are not intended to be limiting with respect to specific details.

EXAMPLES

Example 1

Methods

Reagents and Chemicals

Restriction enzymes, Taq DNA polymerase and Phusion DNA polymerase were purchased from Thermo Scientific. Chemicals and solvents were from Sigma Aldrich, Fisher Scientific or RPI Corp (USA). The GeneJET Plasmid Miniprep Kit, PCR Purification Kit and Gel Extraction Kit were from Thermo Scientific. Oligonucleotide primers were synthesized by Sigma Aldrich, while codon-optimized Sfp gene was obtained from GenScript. DNA sequencing was performed at Eurofins.

Strains and Culture Conditions

*Escherichia coli* DH5a and BL21-CodonPlus (DE3) RIPL were used for routine molecular biology studies and protein expression, respectively, and were grown in Luria-Bertani broth or Terrific broth. *Synechocystis* sp. PCC6803, *Anabaena* sp. PCC7120, *Anabaena variabilis* ATCC29413, *Fischerella* sp. PCC9339, *Microcystis aeruginosa* NIES-843, and *Synechococcus* sp. PCC7942 were purchased from UTEX or NIES (Japan) and cultured in BG11 medium with $CO_2$ bubbling. All cyanobacterial cultures were performed at 26° C. with 16 h/8 h light/dark cycle using 2000-2500 lux during lighting period. BG-11 medium supplemented with 1.0% (wt/vol) agar and 0.3% (wt/vol) sodium thiosulfate was used to grow cyanobacterial strains on the plate.

Construction of Plasmids

Figure 18:
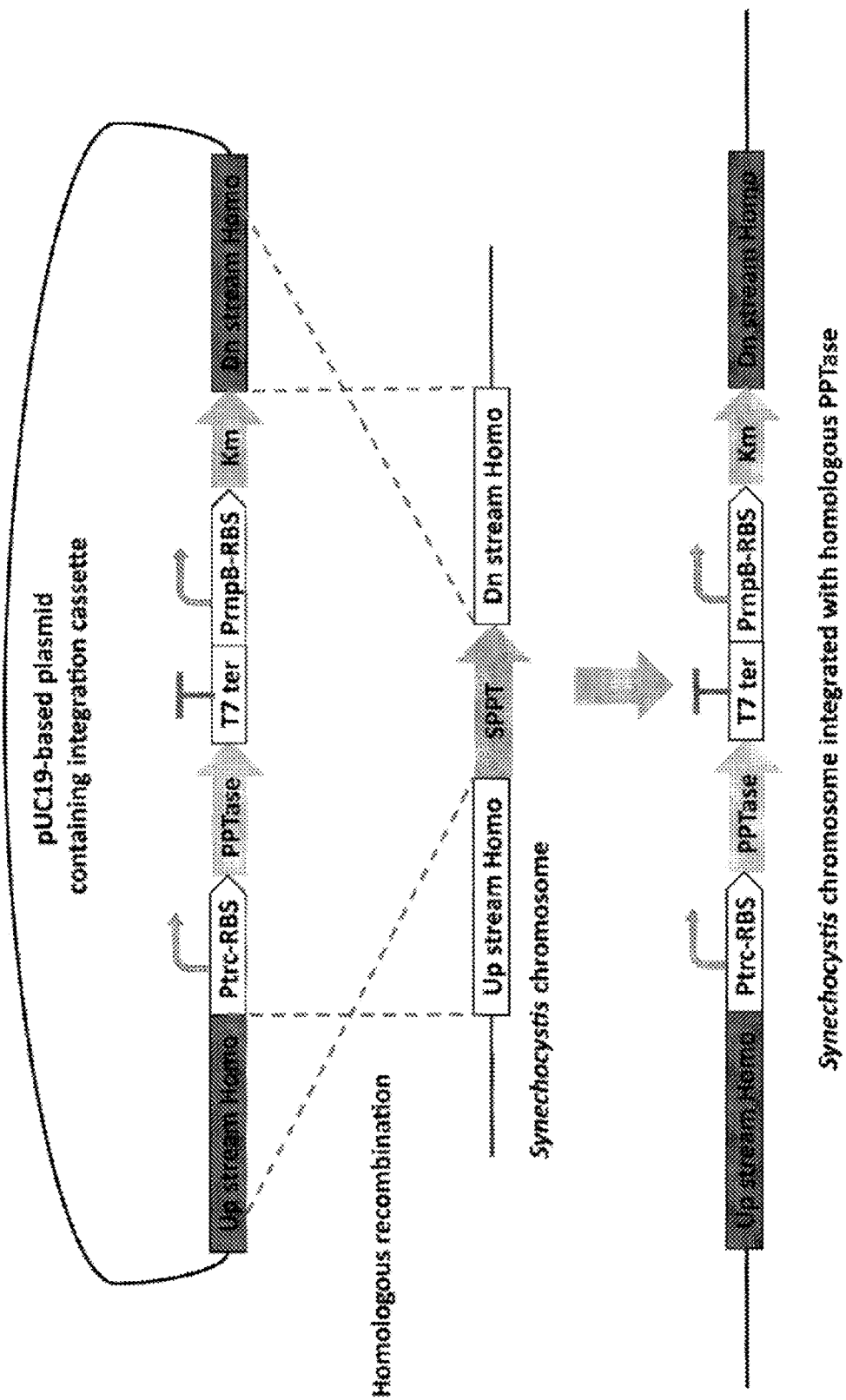
FIG. 18. Schematic representation of homologous replacement of the SPPT gene with foreign PPTase genes in *Synechocystis* sp. PCC6803.

All oligonucleotide primers used in this work were listed in FIG. 12. The PPTase and CP genes were PCR amplified and cloned into pET28b (Novagen) to generate the expression plasmids. The inserts in the integration plasmids were sequentially constructed in the PCR reactions as shown in FIG. 18. The details were included in the supporting information. Briefly, a T7 terminator fragment was first introduced to the 3'-end of APPT, MPPT and Sfp genes by the PCR reactions. The resulted amplicons were fused to the 3'-end of Ptrc promoter-ribosomal binding site (Ptrc-RBS) in the overlapping PCR reaction. Next, a kanamycin resistance cassette amplified from pUC4K (Pharmacia) was fused to the 3'-end of the above amplicons to generate the final insert products. The final products were cloned into the integration vector pUC19int. To generate the pUC19int, the upstream and downstream regions (~1 kb) of the SPPT gene in *Synechocystis* were amplified and fused in the PCR reactions. The fusion product was then digested by HindIII and EcoRI and cloned into pUC19 to create pUC19int. All constructed plasmids were sequenced to eliminate potential errors in the inserts.

Protein Expression and Purification

Recombinant proteins with a His-tag were expressed in *E. coli* BL21-CodonPlus (DE3) RIPL. Cells were grown at 37° C. to an OD600=0.5-0.6, and then cooled to 18° C. prior to the addition of 0.1-0.5 mM isopropyl-β-D-galactopyranoside (IPTG). The cultures were grown at 18° C. for another 18-20 h before harvesting. *E. coli* cells were collected after centrifugation at 4° C., 4,000×g for 15 min, and frozen at −80° C. until the use. Pellets were thawed on ice, resuspended in a suitable volume of lysis buffer (50 mM Tris-HCl buffer, pH 8.0, 300 mM NaCl, 3 mM BME, 10 mM imidazole, 10% glycerol; wt/vol=1:4), and subjected to sonication on ice with 2-s pulses. The soluble fractions were collected after centrifugation at 4° C., 25,000×g for 30 min, and incubated with Ni-NTA agarose resin (Thermo Fisher) at 4° C. for 1 h. The resin was then washed successively with ~10 column volumes of the lysis buffer containing 30 mM imidazole. Recombinant proteins were eluted with 50-300 mM imidazole in the lysis buffer. After SDS-PAGE analysis, elution fractions containing the targeted proteins were combined. The purified proteins were then exchanged into a storage buffer (50 mM Tris-HCl buffer, pH 8, 100 mM NaCl, 10% glycerol) using PD-10 column according to the manufacture's protocol (GE), aliquoted and stored at −80° C. until the use. The concentrations of recombinant proteins were determined by Nanodrop and/or Bradford assay.

HPLC and LC-MS Analysis

A Shimadzu Prominence UHPLC system (Kyoto, Japan) fitted with a Vydac 218TP54-C18 (5 µm, 4.6 mm×250 mm) column was used for HPLC analysis. Solvent A was $H_2O$ with 0.1% TFA and solvent B was $CH_3CN$ with 0.1% TFA. The column was equilibrated with 10% solvent B for 2 min and then protein sample was eluted with a linear gradient of 10-70% in 30 min, followed by another linear gradient of 70-98% solvent B in 1 min. The column was further cleaned with 98% solvent B for 5 min and then re-equilibrated with 10% solvent B for 2 min. The flow rate was set as 0.8 mL/min, and the product was detected at 220 nm with a PDA detector. Apo- and holo-proteins were further analyzed in LC-MS analysis. MS spectra were acquired by using an API Qstar Pulsar i hybrid tandem mass spectrometer (Applied Biosystems) as previously described. An Agilent Eclipse Plus C18, (3.5 um, 2.1×100 mm) was used. In LC-MS analysis, solvent A was $H_2O$ with 0.1% FA and solvent B was $CH_3CN$ with 0.1% FA. The protein samples were eluted with a linear gradient of 10-90% in 15 min at a flow rate of 0.3 mL/min. HRMS data were obtained using a Thermo Fisher Q Exactive Focus mass spectrometer equipped with electrospray probe on Universal Ion Max API source. The LC conditions were the same as those for the LC-MS analysis.

Phylogenetic Analysis of Cyanobacterial PPTases

*E. coli* AcpS and Sfp were used as two queries to mine the current available cyanobacterial genomes in NCBI database (up to Nov 1st, 2016) in BLAST analysis. The output data of BLAST were carefully analyzed to identify the sequences with comparatively high similarity (with e-values≤$10^{-5}$) and to eliminate redundant sequences from taxonomically close species. The selected cyanobacterial PPTase sequences along with those from *Streptomyces rapamycinicus* NRRL5491, *Xenopus laevis* and *Homo sapiens* were aligned by Clustal Omega and then analyzed by MEGA7 to construct a phylogenetic tree.

Biochemical Characterization of PPTase Activity

The enzyme reaction solutions (100 µl) typically contained 50 mM Tris-Cl, pH 8.0, 12.5 mM $MgCl_2$, 0.5 mM coenzyme A, 5 mM dithiothreitol (DTT) and 50 µM CPs. The reactions were initiated by adding 0.3 µM (final concentration) of PPTases and incubated at 37° C. After 20 min, the reactions were terminated by mixing with 100 µl of 10% formic acid. To quantitatively determine the relative activity of the enzymes, the reactions may be incubated for up to 40 min before the quenching. The quenched solutions were centrifuged at 4° C., 16,000×g for 15 min and clear supernatants were collected and subjected to HPLC and LCMS analysis with details shown in the supporting information. All experiments were repeated in triplicate. For kinetic studies, the reactions were set up as described above except that the concentrations of CPs were varied from 1 to 100 µM. The reactions were performed at 37° C. for 5-10 min to ensure that ≤10% of substrates were converted. To determine the concentrations of holo-CPs, 0.2 to 50 µM of apo-proteins were fully converted in the enzyme reactions and then quantitated in HPLC analysis to establish standard curves of holo-CPs. The concentrations of existing holo-CPs in the substrate solutions were subtracted in the data analysis. Data were fit into the Michaelis-Menten equation to determine kinetic parameters using GraphPad Prism 4.0. All experiments were independently repeated three times.

Genetic Engineering of *Synechocystis*

*Synechocystis* cells (about $1×10^8$ cells/ml) in the exponential phase were collected after centrifugation at 8,000 rpm for 15 min and resuspended in fresh BG11 medium at a density of $1×10^9$ cells/ml. Integration constructs at a final concentration of 10 µg/ml were then incubated with the cell solution at room temperature. After 5 h, the mixtures were spread onto BG11 agar plates supplemented with 5 µg/ml kanamycin. The segregation of wild type with the desirable mutants was achieved by iteratively streaking the colonies onto plates with progressively increased kanamycin (up to 50 m/ml). The final stable mutants were genotyped by the colony PCR using the primers listed in FIG. 12. Growth curves of the wild type and three mutant strains were determined by daily record of the $OD_{730}$ of the liquid cultures over the period of 13 days.

Quantitative RT-PCR Analysis of the Integrated Exogenous PPTase Genes

Total RNA samples were isolated from *Synechocystis* and its mutants using ZR Fungal/Bacterial RNA MiniPrep kit (Zymo Research). The quantity and quality of the isolated RNAs were determined using Nanodrop. Synthesis of cDNAs was performed with random primers following the manufacturer's protocol (Thermo Scientific). The synthesized cDNAs were used as templates for qPCR to detect the transcription of the integrated PPTase genes, while the isolated RNA samples themselves were used as the templates of PCR reactions to detect any residual genomic DNAs using primers listed in FIG. 12. The student's t-test analysis was applied to determine significance difference between the samples, and a P-value<0.05 was considered to be significant.

Preparation of Cell Lysates of *Synechocystis* Mutants for PPTase Activity Test

Cells of the wild type and three *Synechocystis* mutants were harvested from 0.8 to 1.0 L culture after centrifugation at 4° C., 4,000×g for 15 min. Cell pellets were washed with fresh BG11 medium and then resuspended in 4 ml of lysis buffer (50 mM MES, pH 7.0, 10 mM $MgCl_2$, 5 mM $CaCl_2$, 1 mM phenylmethylsulfonyl fluoride and 10% glycerol). The solutions were frozen at −80° C. and thawed at room temperature once prior to the sonication on ice with 2-s pulses. Cell homogenates were centrifuged at 4° C., 25,000×g for 30 min to collect clear cell lysates. The enzyme reaction mixtures were set up as described above but contained 70 µl of cell lysates. The reactions were incubated at 37° C. for 16 h, and the holo-products were detected in LCMS analysis as described above. The reactions were performed in triplicate.

DNA Manipulation and Plasmid Construction for Cloning of Shinorine Gene Cluster

Genomic DNA was extracted from *Synechocystis* using a modification of the method described by Murray and Thompson. In brief, a 2 ml aliquot of late-logarithmic-phase cells was pelleted by centrifugation at 15,000 rpm for 5 min, the medium was decanted, and the pellet was resuspended in 567 µl of TE. Cells were lysed by the addition of 30 µl of 10% (wt/vol) SDS and 3.0 µl of 20 mg of proteinase K per ml to give final concentrations of 100 µg of proteinase K per ml and 0.5% (wt/vol) SDS. The solution was mixed thoroughly and incubated at 60° C. for 4 h before the addition of 100 µl of 5M NaCl and 80 µl of 10% (wt/vol) CTAB in 0.7% (wt/vol) NaCl. The CTAB-NaCl solution was prepared by slow addition of CTAB (10 g) to 100 ml of 0.7 M NaCl while heating and stirring. Samples were mixed thoroughly and incubated at 65° C. for 10 min. CTAB complexes were extracted with 1 volume of chloroform-isoamyl alcohol (24:1 [vol/vol]) and centrifugation at 15,000 rpm for 5 min, and the supernatant was transferred to a fresh tube. Any CTAB complexes remaining in the supernatant were extracted with 1 volume of phenol-chloroform-isoamyl alcohol (25:24:1 [vol/vol/vol]) and centrifugation at 15,000 rpm for 5 min. The supernatant was transferred to a fresh tube, and nucleic acids were precipitated by the addition of 0.6 volume of isopropanol. After the contents of the tubes were mixed by gentle inversion, the nucleic acids were collected by spooling on a glass rod and washed successively in 50, 70, and 100% (vol/vol) ethanol. Spooled and washed DNA was transferred to a fresh tube, dried briefly in vacuo, and resuspended in deionized water.

Genomic DNA was extracted from *Fischerella* by using a modification of the method described by Fiore et al. In brief, an aliquot of cultured cells (5 ml) were harvested in mid to late exponential phase (10-25 days) by centrifugation (15,000 rpm for 5 min at 25° C.) in a sterile 1.5 ml microcentrifuge tube. Cells were resuspended in 500 µl TE Buffer (10 mM Tris, 1 mM EDTA, pH 8.0) and subjected to sonic shock for 10 min. This treatment allowed cell separation and filament breakage. Cells that still presented aggregated colonies were dispersed by repeated pipetting with a 1.0-ml micropipette prior to the final centrifugation. Pelleted cells were washed in 1.0 ml of a solution containing 50 mM Tris-HCl, pH 8.0, 5 mM EDTA and 50 mM NaCl to reduce extracellular polysaccharides. Cell pellets were resuspended in a 200 µl solution of 50 mM Tris-HCl, pH 8.0, and 50 mM EDTA. Subsequently, 600 µl of prewarmed (55° C.) extraction buffer (3%, w/v, CTAB, 20 mM EDTA, 1.4 M NaCl, 0.1 M Tris-HCl, pH 8.0, 1% v/v, 2-mercaptoethanol, freshly prepared) were added and incubated at 55° C. in a water bath for 30 min with mixing by gentle inversion every 5-10 min. The mixture was allowed to cool for 30 s before adding 800 µl of chloroform:isoamyl alcohol (24:1, v/v) and mixed by gentle inversion (30 times) until an emulsion was formed. After centrifugation (15,000 rpm for 5 min at 25° C.), the supernatant (500 µl) was transferred to a sterile microcentrifuge tube and gently mixed with 0.6 volume of isopropanol until DNA precipitated. The DNA pellets were recovered by centrifugation, (10 min, 4° C., 15,000 rpm) and washed with 1 ml of ice-cold 70% ethanol to remove any residual salt. After a final centrifugation (5 min, 4° C., 15,000 rpm), the supernatant was discarded, and the pellets were dried before being resuspended in 100 µl TE Buffer (10 mM Tris, 1 mM EDTA, pH 8.0). The samples were treated with 1 µl of RNAse (10 mg/ml) for 1 h at 37° C.

For genomic DNA extraction from *Anabaena* 7120, cells were resuspended into 0.5 ml of 0.15 M NaCl and 0.1 M EDTA, and poured into 2 ml cryogenic vials. Three freeze-thawing cycles, alternating freezing in liquid nitrogen and thawing at 37° C. in a water bath, were used to damage the cell walls and render the cells more susceptible to further enzymatic lysis. The cells were then collected by centrifugation (10 min, 8000 rpm), resuspended in 0.5 ml TE Buffer (10 mM Tris, 1 mM EDTA, pH 8.0) and transferred to fresh 2 ml tubes for enzymatic cell wall lysis with 100 µl of 50 mg/ml lysozyme for 30 min at 37° C. Subsequently, proteins were degraded with 5 µl of 50 mg/ml proteinase K and in 2% SDS final concentration, for 1 h at 37° C. Polysaccharides, proteins and cell wall debris were thereafter removed by selective precipitation with CTAB in presence of NaCl: 150 µl of 5 M NaCl was added to the tubes, followed by 0.1 volume of a 10% CTAB stock solution. The samples were gently mixed by inversion, then further incubated at 65° C. for 10 min to optimize the formation of CTAB-protein and -polysaccharides complexes. Nucleic acids purification was achieved by extraction in 1 volume of chloroform:isoamyl alcohol (24:1). The tubes were placed on ice for 30 min to allow precipitation of CTAB complexes, before being centrifuged (10 min, 8000 rpm). The supernatant was transferred to a fresh tube, gently mixed with 0.6 volume of isopropanol until DNA precipitated. The DNA pellets were recovered by centrifugation, (10 min, 4° C., 15,000 rpm) and washed with 1 ml of ice-cold 70% ethanol to remove any residual salt. After a final centrifugation (5 min, 4° C., 15,000 rpm), the supernatant was discarded, and the pellets were dried before being resuspended in 100 µl TE Buffer (10 mM Tris, 1 mM EDTA, pH 8.0). The samples were treated with 1 µl of RNAse (10 mg/ml) for 1 h at 37° C.

PCR amplification of shinorine gene cluster was carried out by using the primers shown in table 1. The PCR-amplified products were subjected to the assembly of plasmid pSL1211-shinorine by enzyme digestion and ligation method. After sequencing confirmation of the correct construction of pSL1211-shinorine, shinorine gene cluster with the Ptrc promoter was amplified again and inserted into pRL1383a vector to construct plasmid pRL1383-Ptrc-shi. On the other hand, the *Fischerella* PPTase (Fppt) and *Anabaena* PPTase (Appt) were amplified from *Fischerella* and *Anabaena* genomic DNA, respectively. Also, the promoter PrnpB was amplified from *Synechocystis* genomic DNA. PCR fusion was performed to link PrnpB and Fppt/Appt. The fused genes were cloned into pRL1383-Ptrc-shi to construct the shinorine expression plasmids pRL1383-Ptrc-shi-PrnpB-Fppt and pRL1383-Ptrc-shi-PrnpB-Appt.

Conjugation Transfer of Shinorine Gene Cluster Containing Plasmid into *Synechocystis*

Triparental mating was used to transfer the expression plasmid pRL1383-shinorine. In brief, both conjugal and cargo *E. coli* strains were grown in LB medium plus the appropriate antibiotics overnight at 37° C. For spot matings, 0.75 ml of each culture was transferred to 1.5 ml Eppendorf tube and centrifuged to collect the cells. Cell pellet was washed once with LB medium and resuspended in 0.75 ml LB medium without antibiotics. Two tubes of cells were then mixed and centrifuged again to collect cells. Cell pellet was then resuspended into 60 µl of fresh LB medium without antibiotics. On the other hand, 1 ml *Synechocystis* culture was centrifuged and cell pellet was washed once with fresh BG11 medium. The cell pellet was resuspended into 100 µl of BG11 medium. Following 5 µl of mixed *E. coli* culture and 5 µl of *Synechocystis* culture were mixed and 2 µl of the mixture was transferred on to a BG11-agar plate containing no antibiotics. The conjugation was conducted under normal growth conditions for *Synechocystis* for 24 h. Then, cells from the spot were spread on a BG11 plate with 20 µl/ml gentamycin. After single colonies are developed and visible, colonies were selected and transferred to tube and bottle culture.

Extraction of Shinorine from *Synechocystis*

The *Synechocystis* transformants were grown in the 300 ml BG11 medium at 26° C. with air bubbling. After incubation at 26° C. for 14 days with air bubbling the whole culture was mixed with an equal volume of methanol and the mixture was subjected to a vigorous vortex procedure. The supernatant was collected by centrifugation at 3,000 rpm for 10min, and a 20 µl portion of the supernatant was directly analyzed by high-performance liquid chromatography (HPLC). On the other hand, the supernatant was evaporated to remove methanol and redissolved in 1 ml water for HPLC analysis. Authentic samples of shinorine were prepared from Helioguard 365.

Results and Discussion

Phylogenetic analysis of cyanobacterial Sfp-like PPTases. To gain an understanding of the evolutionary relationship of cyanobacterial PPTases, we mined all cyanobacterial genomes available in NCBI database using *E. coli* AcpS and Sfp as queries. We then selected and retrieved 39 sequences from strains covering all five subsections of cyanobacteria (FIG. 9). These sequences were phylogenetically analyzed along with AcpS, Sfp and enzymes from *Streptomyces rapamycinicus* NRRL5491, *Xenopus laevis* and *Homo sapiens* as outgroups. The constructed phylogenetic tree comprised an AcpS-like clade with AcpS and eight cyanobacterial PPTases and a Sfp-like clade containing all other enzymes (FIG. 1). Three outgroups along with Sfp were separated from cyanobacterial Sfp-like PPTases in the Sfp-like clade. This analysis further revealed that the PPTases from the heterocystous cyanobacteria (subsections IV and V) formed a separate sub-clade. The relationship of enzymes from the sections I-III was not obvious. For example, the PPTase from the subsection I *Gloeocapsa* sp. PCC73106 was in the same group as the one from *Spirulina subsalsa* (subsection III) (FIG. 1). These results indicate that cyanobacterial Sfp-like PPTases share a common ancestor and have acquired different traits over the course of evolution.

Figure 14:
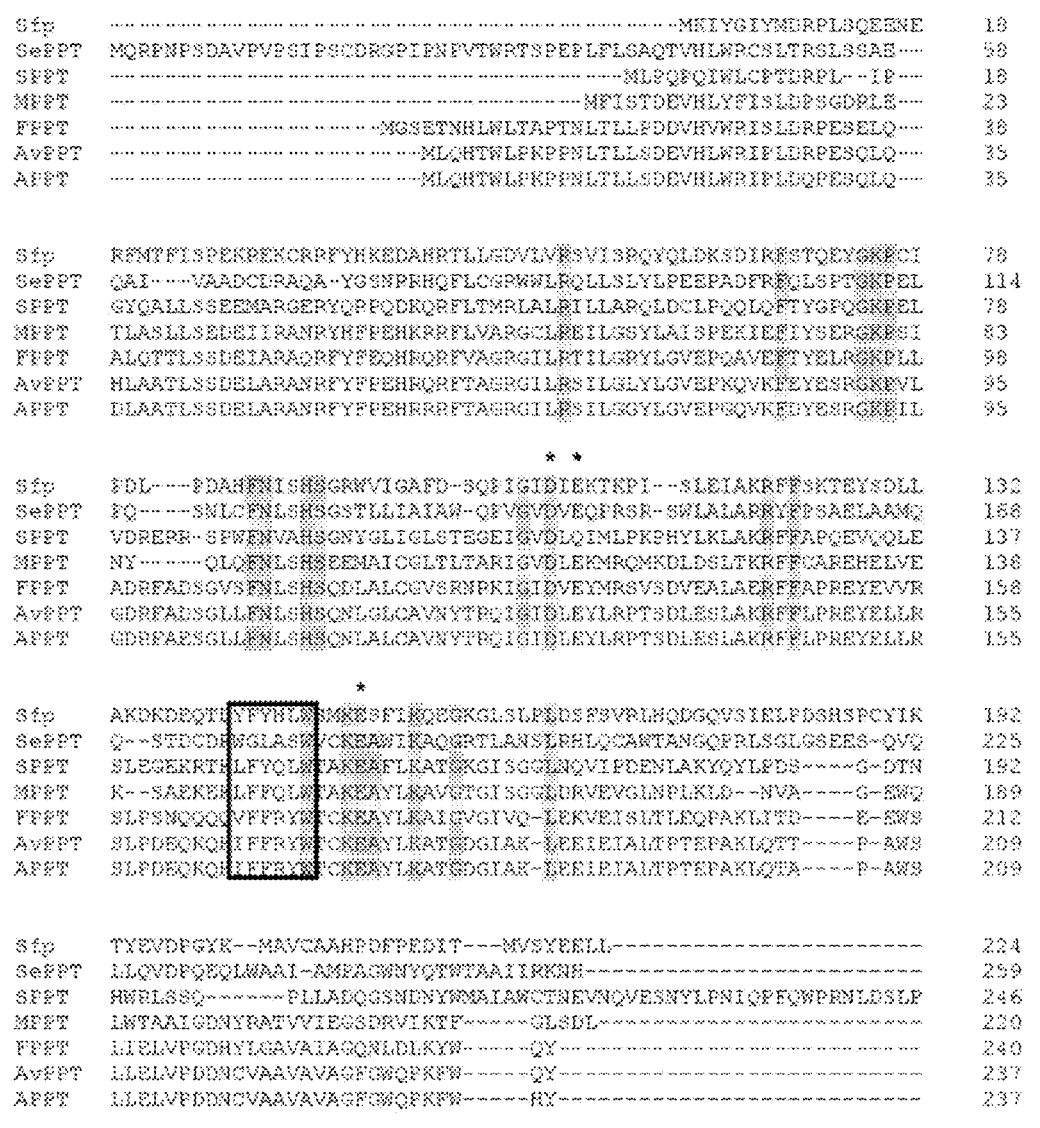

Selection of cyanobacterial Sfp-like PPTases and CP substrates. To biochemically characterize cyanobacterial Sfp-like PPTases, we next selected representative enzymes based on the result of phylogenetic analysis (FIG. 1) and predicted biosynthetic potential of cyanobacterial strains. The subsection V heterocystous cyanobacterium *Fischerella* sp. PCC9339 (referred to as *Fischerella*) possesses >10 NRP and/or PK gene clusters and its PPTase (FPPT) was therefore included in this work due to its potential substrate promiscuity. With the same rationale, we selected the PPTases from the subsection IV *Anabaena* sp. PCC7120 (hereafter referred to as *Anabaena*, APPT) and its close species *A. variabilis* ATCC29413 (AvPPT). In the constructed phylogenetic tree, FPPT and APPT/AvPPT belong to two distantly related groups in the same subclade and can potentially represent the enzymes from a variety of heterocystous cyanobacteria (FIG. 1). We also selected the PPTase from the subsection I *Microcystis aeruginosa* NIES843 (MPPT) that carries >10 NRP and/or PK gene clusters. On the other hand, although *Synechococcus elongatus* PCC7942 encodes no NRP or PK cluster, its PPTase (SePPT) becomes a separate leaf in the phylogenetic tree (FIG. 1) and was thus selected. Furthermore, we included SPPT as a control in this work due to its demonstrated incompetency in activating noncognate cyanobacterial CPs. Finally, the paucity of biochemical characterization of Sfp in activating cyanobacterial CPs led to its selection. These six selected cyanobacterial PPTases and Sfp contain the featured W/KEA motif (FIG. 14) and together cover the broad space of the constructed phylogenetic tree (FIG. 1).

We further chose 11 CPs from multiple biosynthetic pathways of different species for biochemical characterization of the selected PPTases (FIG. 10 and FIG. 15). They included two ACPs of FASs from *Synechocystis* (SFACP) and *Anabaena* (AFACP), the ACP of the glycolipid PKS in *Anabaena* (APACP), the ACP of the apratoxin (PK/NRP) gene cluster in *Lyngbya* sp. (AprACP), and the PCP of the shinorine gene cluster from *Fischerella*. In addition, we included three CPs of uncharacterized gene clusters from *Fischerella* (FNPCP, an NRP pathway), *Anabaena* (APNPCP, an NRP/PK pathway) and *M. aeruginosa* NIES843 (MACP, an NRP/PK pathway) and one homolog of previously characterized ArCP$_{Np}$ from *Fischerella* (FNsACP). To thoroughly examine the versatility of selected PPTases, we also included the ACP of a putative concanamycin gene cluster from *Streptomyces coelicolor* A(3)2 (ScACP) and the PCP of a thaxtomin cluster from plant pathogen *S. scabiei* 87.22 (SsPCP).

Figures 2A, 2B:
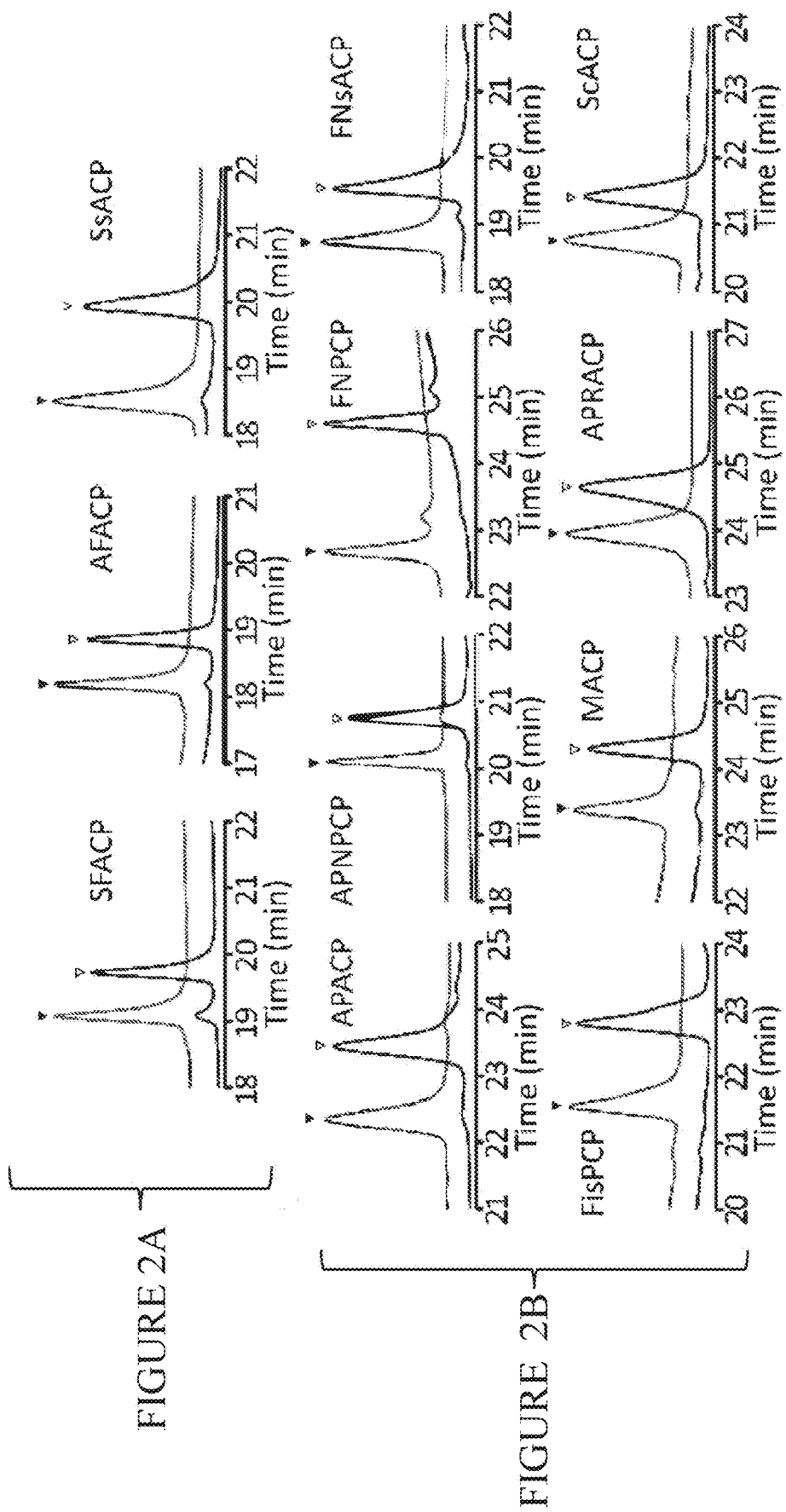
FIGS. 2A-2B. HPLC traces of selected PPTase reactions. (A) SFACP, AFACP and SsPCP substrates were partially phosphopantetheinylated over the course of overexpression in *E. coli*. They were fully-converted in some of PPTase reactions. (B) All other CPs were completely functionalized by some PPTases. Red traces represent the enzyme reactions and black ones show the substrates. ▼ indicates the holo-CP, while ▽ represents the apo-CPs. The minor peaks in APACP, APNPCP, and MACP substrates showed similar retention times to the corresponding holo-proteins but had different molecular weights in the MS analysis.
Figure 16A:
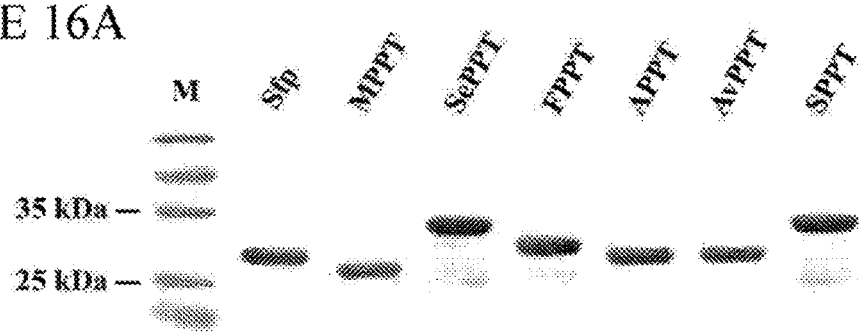
FIGS. 16A-16B. SDS-PAGE analysis of the purified PPTases and CP proteins. All proteins showed expected molecular weights and CPs were validated in LC-MS analysis.
Figure 16B:
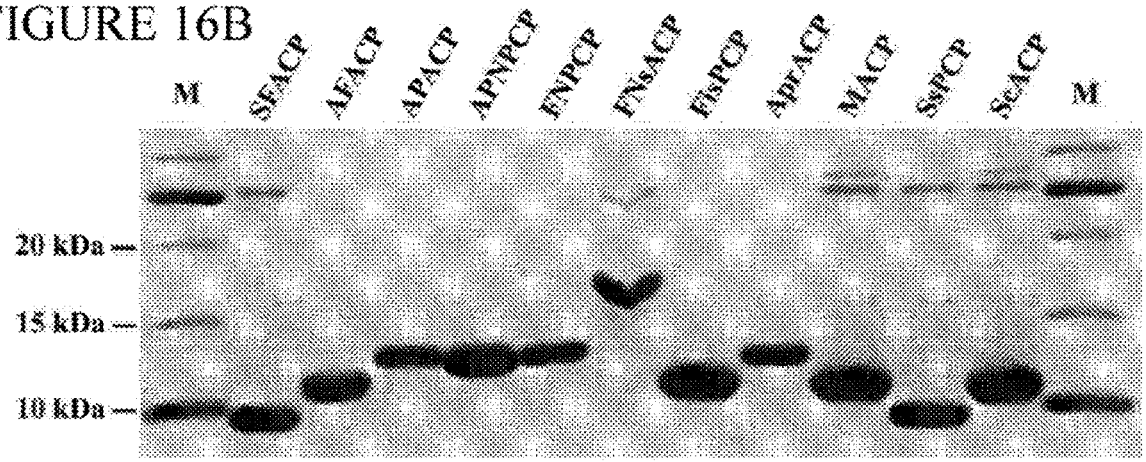
Figure 17:
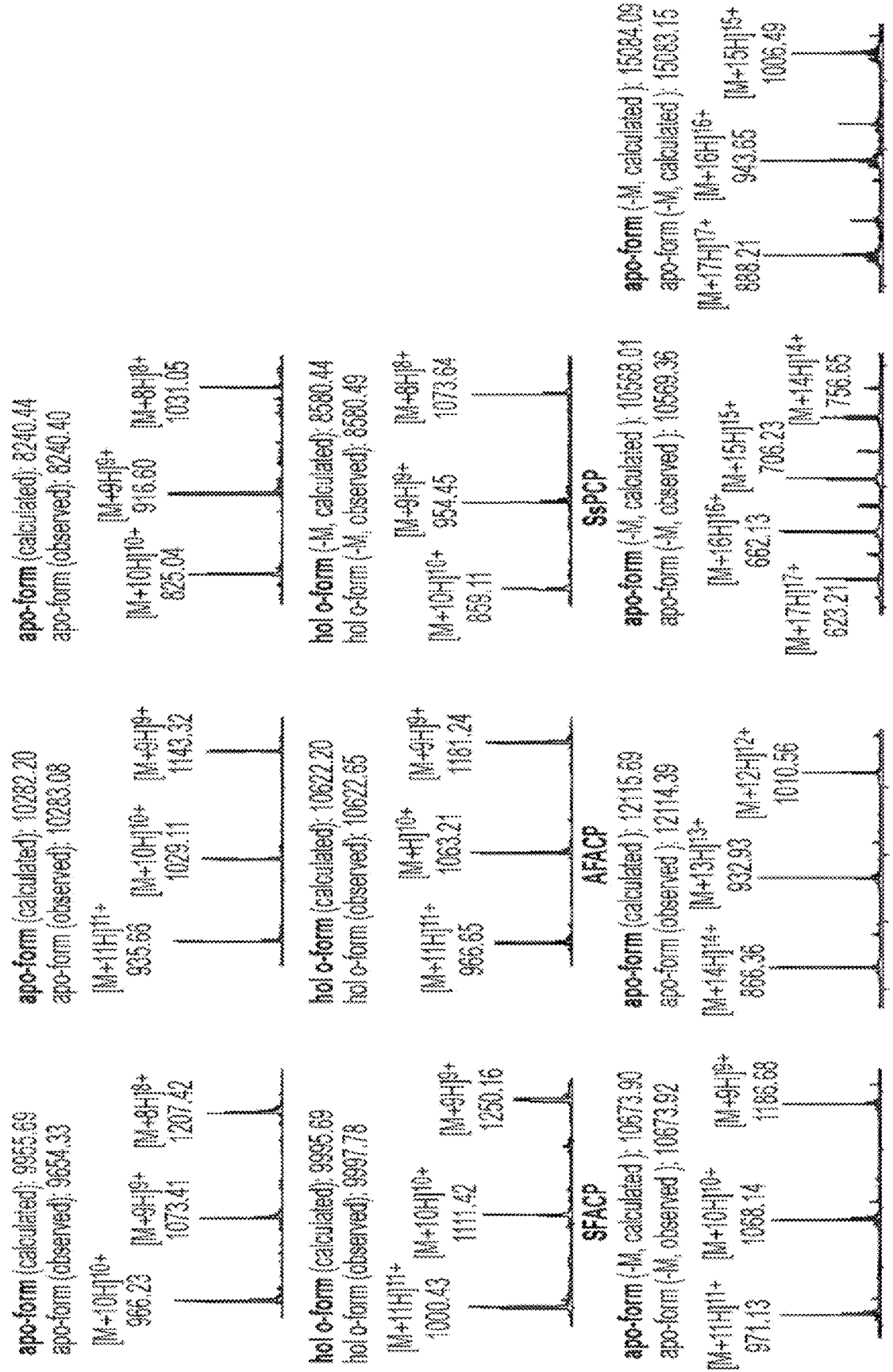
FIG. 17. HR-MS spectra of apo- and holo-CPs. The charge status, m/z value, and calculated and observed molecular weights of CPs were shown.
Figure 17:
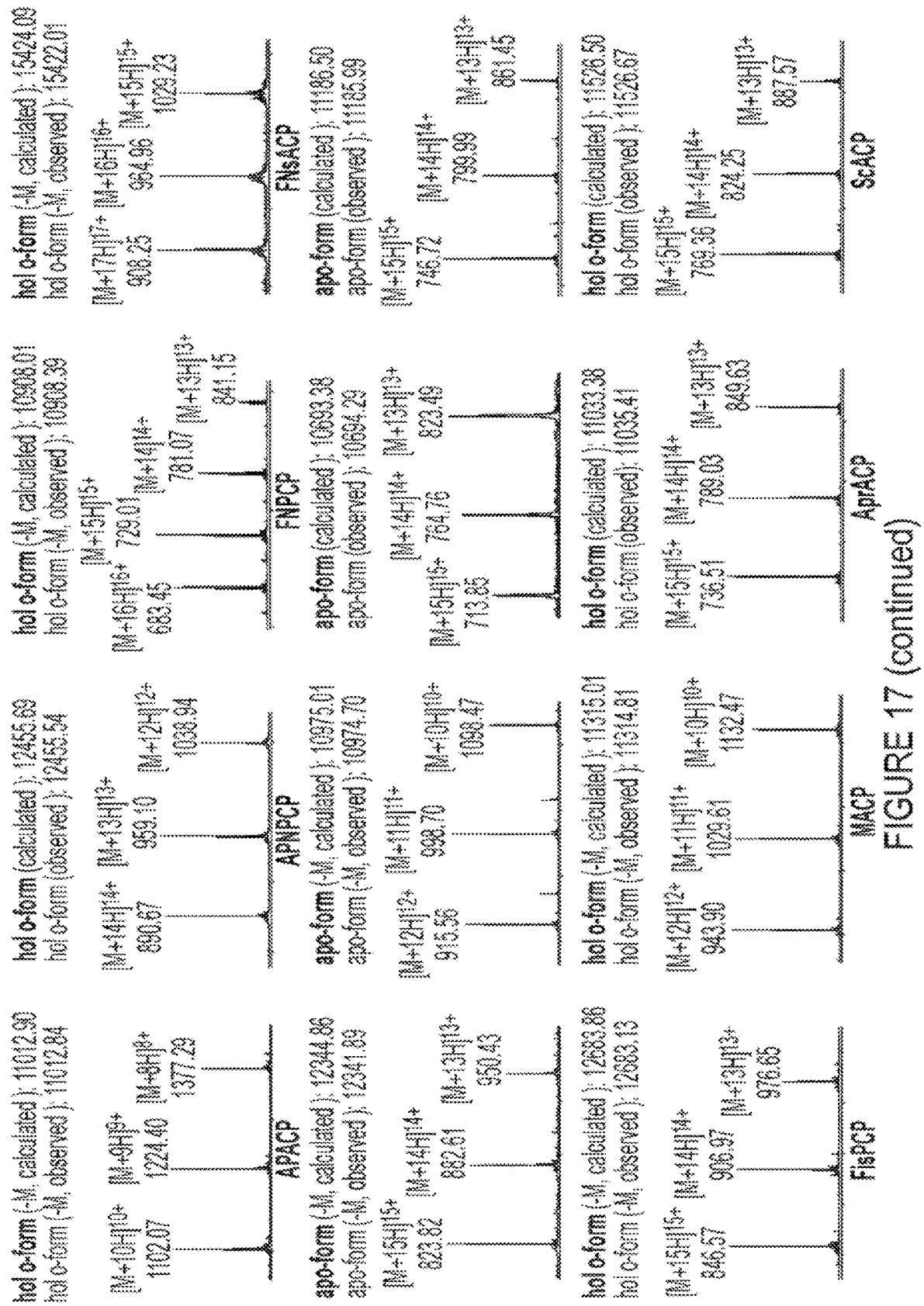

In vitro phosphopantetheinylation of cognate and noncognate CPs by selected PPTases. All selected genes were amplified from bacterial genomic DNAs or commercially synthesized (FIG. 15) and then expressed in *E. coli* BL21-CodonPlus (DE3) RIPL. Recombinant proteins were purified by a single step Ni-NTA affinity chromatography to achieve the high purity (FIG. 15). All purified proteins showed expected molecular weights in SDS-PAGE analysis (FIGS. 16A and 16B) and were further confirmed via LC-MS. SFACP, AFACP and SsPCP gave rise to two peaks in their HPLC traces (FIG. 2A). The MS analysis revealed the smaller peaks as the halo-proteins and the major peaks as the apo substrates (FIG. 10 and FIG. 17). The remaining eight CP substrates adapted the apo-form (FIG. 2B). This result suggests that *E. coli* AcpS activates noncognate ACPs of FASs to a low level and shows a limited promiscuity toward CPs of NPRSs and PKSs.

We next examined the catalytic activity of each PPTase toward all 11 recombinant CPs. The LC-MS analysis revealed the full conversion of the substrates to the holo-products in 69 out of 77 reactions (FIG. 2 and FIG. 3). In particular, APPT, AvPPT, MPPT and Sfp functionalized all substrates (FIG. 3 and FIG. 10). Unexpectedly, SPPT also phosphopantetheinylated all CP substrates except ScACP (FIG. 3 and FIG. 11), a strikingly different outcome compared with its narrow substrate specificity in an early report. On the other hand, we observed the relatively narrow substrate scope of SePPT and FPPT (FIG. 3 and FIG. 11). SePPT showed no activity toward APNPCP, MACP, ScACP, and
SsPCP, while FPPT shared the same substrate scope as SePPT with the exception of its low activity toward SsPCP.

To quantitate the enzyme performance, we performed the reactions to phosphopantetheinylate <95% of a CP substrate. The activity of the most active enzyme was set as 100% to normalize the activities of the other PPTases toward the same substrate (FIG. 3 and FIG. 11). This analysis further confirmed the versatility and activity of APPT, AvPPT, MPPT, and SPPT. APPT showed the highest conversion rate toward seven cyanobacterial CPs from the fatty acid, PK, NRP, and PK/NRP biosynthetic pathways (FIG. 3 and FIG. 11). It also activated ScACP and SsPCP from *Streptomyces* species to a modest-to-significant extent. In line with this result, APPT functionalized the ACP of microalgal polyunsaturated fatty acid synthase in canola and allowed the heterologous production of lyngbyatoxin A in *Anabaena*. AvPPT possessed a similar substrate scope and comparable activities to the majority of substrates as APPT (FIG. 3 and FIG. 11). Addition to the two enzymes from the subsection IV, MPPT showed >84% relative activity toward all nine cyanobacterial CPs including the highest activity on MACP (FIG. 3 and FIG. 11). This enzyme also displayed a modest relative activity toward ScACP and SsPCP. Similarly, SPPT promoted >71% relative conversion of eight cyanobacterial CPs (FIG. 3 and FIG. 11). Despite the low or no activity toward MACP, SsPCP and ScACP, these data clearly highlighted the significant catalytic activity of SPPT in functionalizing noncognate cyanobacterial CPs of both primary and secondary metabolism. By contrast, both SePPT and FPPT showed a relatively narrow substrate scope (FIG. 3 and FIG. 11). SePPT demonstrated strong activity toward two ACPs of FASs but no others, while FPPT was not competent to activate SsPCP, APACP, APNPCP, MACP, and ScACP. We also quantitated the in vitro catalytic activity of Sfp. This enzyme functionalized seven cyanobacterial CPs to comparable levels of APPT and activated APNPCP and FisPCP to a modest-to-good level (FIG. 3 and FIG. 11). Among all PPTases, Sfp showed the highest relative activity toward ScACP and SsPCP. Collectively, these results provide the first comprehensive evaluation of cyanobacterial PPTases in terms of enzymatic activity and substrate scope, and suggest the potential applications of APPT, AvPPT, MPPT, SPPT and Sfp in synthesizing cyanobacterial natural products.

Kinetics analysis of APPT, MPPT, SPPT and Sfp. To further assess the catalytic performance of selected PPTases, we kinetically analyzed APPT, MPPT, SPPT and Sfp in activating all 11 substrates. This analysis determined the highest catalytic efficiency at $2.1\pm0.2$ $\mu M^{-1}$ $min^{-1}$ when Sfp converted SsPCP into the holo form (Table 1). Sfp also demonstrated a high $k_{cat}/K_m$ value in activating ScACP ($1.8\pm0.1$ $\mu M^{-1}$ $min^{-1}$), consistent with its overall kinetic performance toward CPs of actinomycetes. We further observed the varied catalytic efficiencies of Sfp toward cyanobacterial CPs (Table 1). Among them, APACP was the best substrate of Sfp ($k_{cat}/K_m=1.5\pm0.3$ $\mu M^{-1}$ $min^{-1}$), while the FisPCP was the least ($0.1\pm0.02$ $\mu M^{-1}$ $min^{-1}$). To our knowledge, AnaD, a standalone PCP, from *Oscillatoria* PCC6506 was the only cyanobacterial CP that has been kinetically evaluated in the studies of Sfp. This work adds new, useful information about this versatile enzyme and suggests its broad use in cyanobacterial natural products research.

Among all selected enzymes, APPT demonstrated the highest catalytic efficiencies toward AprACP, AFACP and APACP (1.6 to 1.8 $\mu M^{-1}$ $min^{-1}$) (Table 1). These three substrates were also favored by MPPT and SPPT ($k_{cat}/K_m \geq 1.0$ $\mu M^{-1}$ $min^{-1}$) (Table 1). By contrast, neither FisPCP nor FNsACP were kinetically preferred by the selected cyanobacterial PPTases ($k_{cat}/K_m=0.3$ $\mu M^{-1}$ $min^{-1}$) and Sfp (Table 1). The $k_{cat}/K_m$ values of APPT, MPPT and SPPT toward four other cyanobacterial CP substrates varied from $0.1\pm0.02$ to $1.4\pm0.2$ $\mu M^{-1}$ $min^{-1}$. None of the selected PPTases showed a preference to substrates from any specific pathways or sources. Interestingly, the kinetic studies revealed overall high catalytic efficiency of cognate CP/PPTase pairs ($k_{cat}/K_m \geq 0.9$ $\mu M^{-1}$ $min^{-1}$, e.g., MACP/MPPT, SFACP/SPPT and APNPCP/APPT), indicating the potential co-evolution of biosynthetic enzymes.

The $K_m$ values of four PPTases toward 11 CPs were in the $\mu M$ range (Table 1). SFACP showed relatively tight interactions with all PPTases ($K_m=1.5\pm0.2$ to $3.2\pm0.2$ $\mu M$), while overall relatively weak interactions were observed between all PPTases and APACP ($K_m=10.0\pm0.9$ $\mu M$ to $26.5\pm5.2$ $\mu M$). Conversely, these PPTases showed high activity toward APACP ($k_{cat} \geq 14.6\pm1.3$ $min^{-1}$) and low activity toward SFACP ($k_{cat} < 2.2\pm0.1$ $min^{-1}$). Furthermore, CP substrates demonstrated the lowest $K_m$ values with their cognate PPTases in comparison with other enzymes (Table 1), potentially indicating co-evolution. In this regard, SPPT showed higher $K_m$ values toward the majority of noncognate CPs in comparison with APPT and MPPT (Table 1), presumably because of the lack of any PK or NRP cluster in *Synechocystis*. Similarly, the relatively weak interactions of Sfp with the majority of cyanobacterial CPs may also support the biosynthetic co-evolution.

Figure 5:
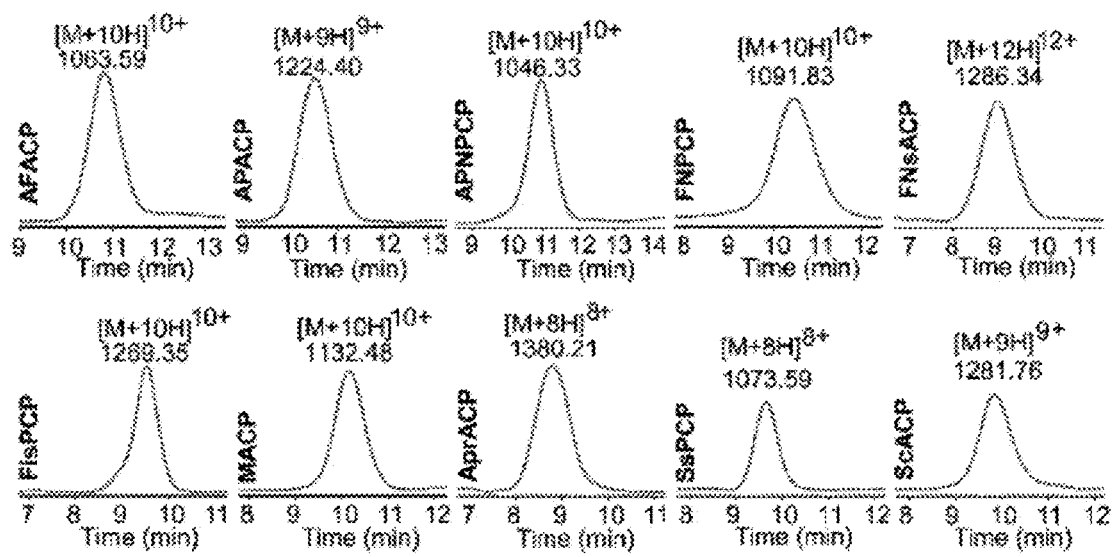
FIG. 5. Extracted ion chromatograms of holo-form of 10 CPs produced in the reactions of cell lysate of *Synechocystis* APPT mutant. The products showed the expected molecular weights. The similar traces were observed in the reactions of cell lysates of two other mutants.

In vivo and in vitro activity of transiently expressed APPT, MPPT and Sfp in *Synechocystis*. To further explore the in vivo catalytic performance of APPT, MPPT and Sfp, we chromosomally integrated their genes to replace the essential SPPT gene of *Synechocystis* (FIG. 4A and FIG. 18). The expression of the integrated PPTase genes was controlled by a constitutive strong promoter Ptrc. After homologous recombination and multiple rounds of segregation, three stable *Synechocystis* mutants were confirmed as the loss of the SPPT gene and the presence of foreign PPTase gene in the PCR diagnosis (FIG. 4A). The transcription levels of these PPTase genes in the mutants were five to six times higher than that of SPPT in the wild type in the quantitative reverse transcription PCR (RT-PCR) analysis (FIGS. 4B and 4C). Importantly, the growth curve of the three mutant strains closely resembled the wild type over the entire 13-day culturing period (FIG. 4D). This data suggested the successful expression of APPT, MPPT and Sfp in *Synechocystis* and demonstrated their in vivo function as activating SFACP for the synthesis of essential fatty acids. To evaluate the catalytic performance of these enzymes toward additional substrates, we prepared and employed the soluble cell lysates of three *Synechocystis* mutants to functionalize the selected 10 CPs except SFACP. LC-MS analysis detected holo-products from all 30 reactions after the incubation for 16 hours (FIG. 5), revealing the broad substrate scope of the transiently expressed APPT, MPPT, and Sfp in *Synechocystis*. The relatively long reaction time is likely caused by the low concentrations of recombinant proteins in the cyanobacterial expression system. A high-copy self-replicating vector can potentially alleviate this issue. The three *Synechocystis* mutants can find broad applications in the heterologous production of cyanobacterial PKs, NRPs, and their hybrids.

Figure 6:
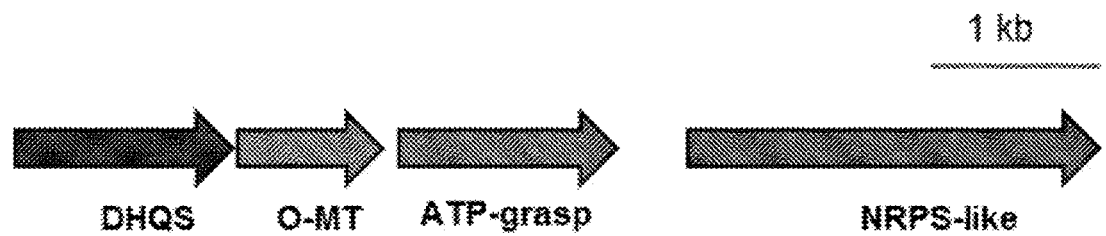
FIG. 6. *Fischerella* shinorine biosynthesis gene cluster.

Bioinformatics analysis of shinorine gene cluster in *Fischerella*. A homology search for a gene cluster for shinorine biosynthesis of *A. variabilis* ATCC29413 against public databases identified a similar gene cluster in the cyanobacterium *Fischerella*. The biosynthetic gene cluster in *Fischerella* is composed of four genes encoding putative dimethyl 4-deoxygadusol (DDG) synthase, O-methyltransferase (O-MT), ATP-grasp family protein and a NRPS-like protein (FIG. 6). The putative protein sequences encoded by these genes shared high similarity to the proteins encoded by Ava_3858-Ava_3855 of *A. variabilis* ATCC29413 (Table 2).

Figure 7A:
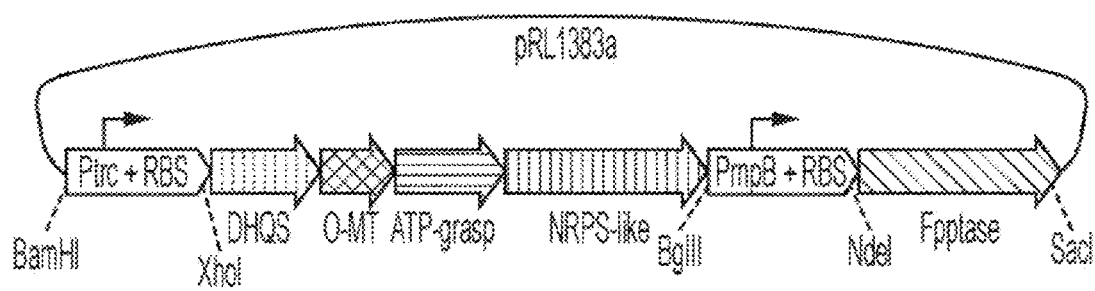
FIGS. 7A-7B. Plasmids for the expression of shinorine in *Synechocystis*. A and B. plasmids for *Synechocystis* expression of shinorine.
Figure 7B:
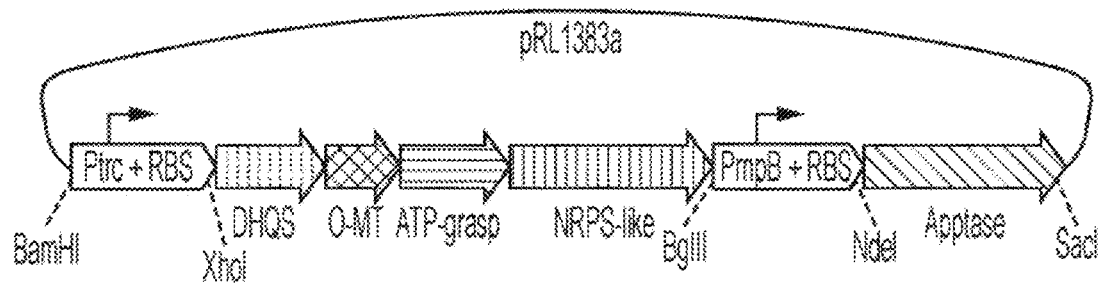

Cloning of shinorine gene cluster. PCR amplifications of shinorine gene cluster from *Fischerella* result into a 6.6 kb DNA fragments. Shinorine gene cluster amplified by using the primers pair Shino-BamHI-Fw and Shina-Xba-Xho-Rv was digested with BamHI and XhoI restriction enzymes and cloned into pET28b which was previously digested with the same pair of enzymes to construct the E. coli expression plasmid pET28b-shinorine (FIG. 7A). To facilitate the Synechocystis expression of shinorine, pRL1383a vector was used as backbone to clone the gene cluster (FIG. 7B). In this construct, Ptrc promoter was cloned in the upstream of the gene cluster to drive the expression of the genes. As a proper functional phosphopantetheinyl transferase (PPTase) is needed for cross-species modification of carrier proteins embedded in NRPS modules in the NRPS-like protein in the gene cluster, we cloned the PPTase from Fischerella or Anabaena into the plasmid. The transcription of PPTases in the plasmid will be driven by the inserted PrnpB promoter in the upstream of the PPTases (FIGS. 7A and 7B).

Figure 8:
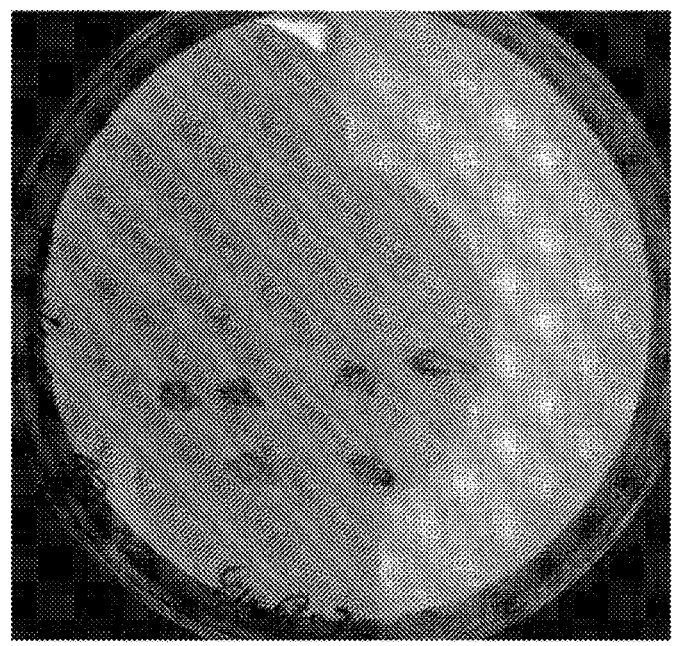
FIG. 8. Triparental mating conjugal transfer of shinorine expression plasmids into *Synechocystis*.
Figure 13:
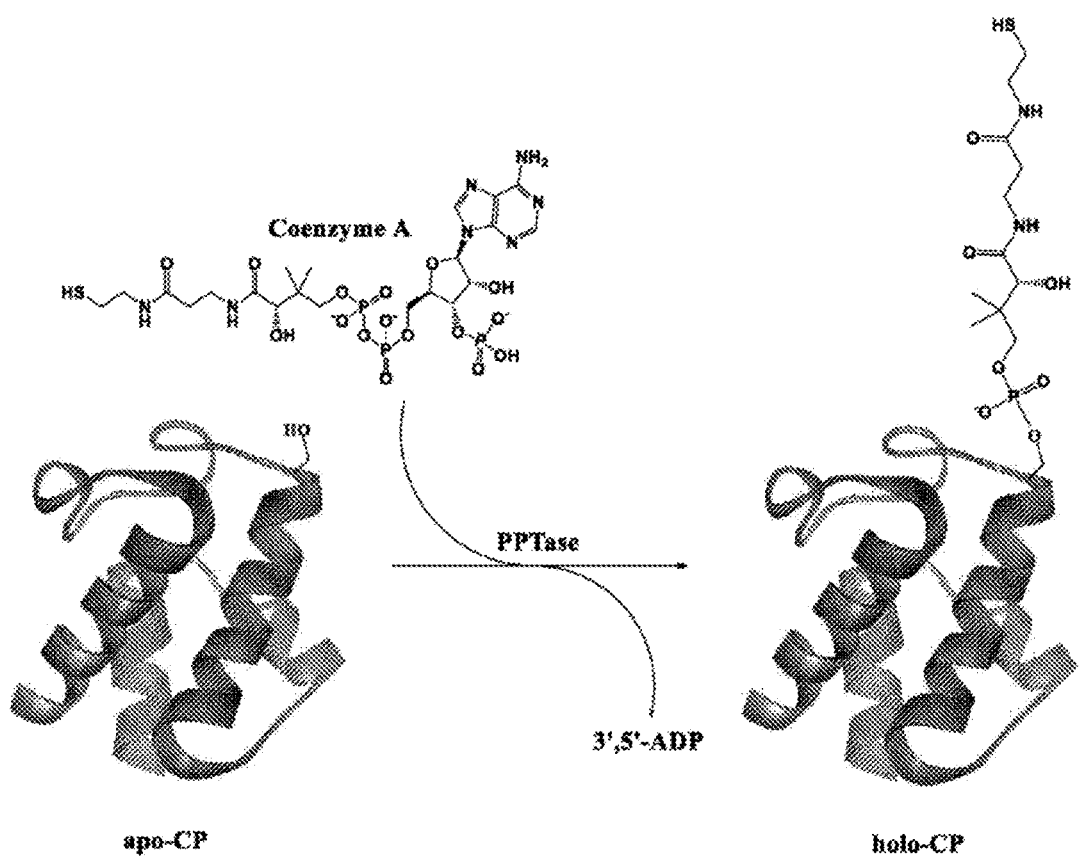
FIG. 13. Schematic representation of post-translational phosphopantetheinylation of a CP domain by a PPTase. The modification leads to a mass increase of 340 Dalton.

Triparental mating of Synechocystis for conjugal transfer of 1383a-SHI-APPT and 1383a-SHI-FPPT. For the Synechocystis expression of shinorine, the constructed plasmids 1383a-SHI-APPT and 1383a-SHI-FPPT were transferred into Synechocystis by using triparental mating method. As shown in FIG. 8, the conjugated Synechocystis showed growth on BG11-Agar plates with antibiotics. The colonies will be subjected to the following liquid culture and shinorine expression test.

HPLC and LCMS analysis of shinorine produced by Fischerella and Synechocystis. To investigate the production of shinorine in Fischerella and Synechocystis, these strains cultured in liquid BG11 medium were subjected to a natural product isolation approach described below. HPLC and LCMS analysis of the cell extract indicated the presence of a tiny amount of MAA-like compound from Fischerella and about 10-fold amount of MA that exhibited absorbance spectra characteristic for MAAs and whose retention time was identical to that of shinorine standard. The amount of MAA-like compound extracted from Synechocystis was about 10-fold to that from Fischerella.

Conclusions

PPTases are essential enzymes of all three domains of life as they functionalize CPs of FASs, PKSs, and NRPSs. The past two decades have witnessed significant advances of PPTase research, particularly about structure-function-relationship, the development of enzyme inhibitors, and biotechnological and biomedical applications. Here, we analyzed the phylogenetic relationships of cyanobacterial PPTases and rationally selected six cyanobacterial enzymes along with Sfp to characterize their substrate scope and catalytic activity toward 11 CPs of FASs, PKSs, and NRPSs from cyanobacteria and Streptomyces strains. Compared with Sfp, APPT and MPPT demonstrated higher or similar catalytic activity and kinetic performance toward the majority of cyanobacterial CPs. They can be useful plug-and-play tools to produce primary and secondary metabolites of cyanobacteria and potentially of strains from other phyla. In this regard, the validated in vivo and in vitro functions of transiently expressed APPT, MPPT and Sfp in the Synechocystis mutants indicate the availability of the novel, capable cyanobacterial synthetic biology chassis. Further studies will include the expression and optimization of selected cyanobacterial gene clusters in these chassis and develop additional cyanobacterial synthetic biology tools.

We have further identified the shinorine gene cluster in Fischerella. The gene cluster was cloned into different plasmid for Synechocystis expression of shinorine. With the HPLC and LC-MS results, we understand that the engineered Synechosytis strain produces shinorine with about 10-fold higher in yield compared with that produced by the native producer Fischerella.

TABLE 1

Kinetics parameters of four selected PPTases toward 11 CPs[a]

| Substrate | APPT | | | MPPT | | |
|---|---|---|---|---|---|---|
| | $K_m^b$ | $k_{cat}^b$ | $k_{cat}/K_m^b$ | $K_m$ | $k_{cat}$ | $k_{cat}/K_m$ |
| SFACP | 2.8 ± 0.2 | 1.6 ± 0.09 | 0.6 ± 0.07 | 3.2 ± 0.2 | 1.2 ± 0.1 | 0.4 ± 0.07 |
| AFACP | 6.8 ± 0.5 | 11.7 ± 0.5 | 1.7 ± 0.2 | 6.9 ± 0.4 | 8.4 ± 0.2 | 1.2 ± 0.1 |
| APACP | 10.0 ± 0.9 | 17.0 ± 0.6 | 1.6 ± 0.2 | 23.1 ± 4.1 | 21.2 ± 1.6 | 0.9 ± 0.2 |
| ScACP | 14.1 ± 1.6 | 5.4 ± 0.3 | 0.4 ± 0.07 | 12.4 ± 1.5 | 2.6 ± 0.1 | 0.2 ± 0.04 |
| SsPCP | 7.4 ± 0.5 | 7.6 ± 0.2 | 1.0 ± 0.09 | 9.1 ± 0.3 | 7.1 ± 0.1 | 0.7 ± 0.04 |
| FNPCP | 12.1 ± 0.5 | 12.2 ± 0.3 | 1.0 ± 0.07 | 7.2 ± 0.7 | 9.6 ± 0.4 | 1.3 ± 0.2 |
| FisPCP | 7.1 ± 0.5 | 2.3 ± 0.06 | 0.3 ± 0.03 | 7.2 ± 0.3 | 1.9 ± 0.03 | 0.3 ± 0.02 |
| MACP | 7.9 ± 0.9 | 3.7 ± 0.2 | 0.5 ± 0.08 | 4.9 ± 0.3 | 4.2 ± 0.1 | 0.9 ± 0.07 |
| APNPCP | 1.6 ± 0.1 | 1.0 ± 0.05 | 0.6 ± 0.09 | 9.5 ± 0.4 | 1.9 ± 0.1 | 0.2 ± 0.02 |
| FNsACP | 8.4 ± 0.8 | 2.2 ± 0.08 | 0.3 ± 0.03 | 8.3 ± 0.8 | 2.1 ± 0.4 | 0.3 ± 0.07 |
| AprACP | 7.8 ± 0.8 | 14.3 ± 0.8 | 1.8 ± 0.3 | 9.1 ± 1.4 | 10.4 ± 0.8 | 1.1 ± 0.3 |

| Substrate | SPPT | | | Sfp | | |
|---|---|---|---|---|---|---|
| | $K_m$ | $k_{cat}$ | $k_{cat}/K_m$ | $K_m$ | $k_{cat}$ | $k_{cat}/K_m$ |
| SFACP | 1.5 ± 0.2 | 1.4 ± 0.1 | 0.9 ± 0.2 | 2.5 ± 0.3 | 2.2 ± 0.1 | 0.9 ± 0.2 |
| AFACP | 13.3 ± 1.6 | 14.7 ± 1.1 | 1.1 ± 0.2 | 11.6 ± 0.6 | 9.8 ± 0.3 | 0.8 ± 0.07 |
| APACP | 26.5 ± 5.2 | 14.6 ± 1.3 | 0.5 ± 0.1 | 15.3 ± 2.1 | 22.1 ± 1.4 | 1.5 ± 0.3 |
| ScACP | N/A[c] | N/A[c] | N/A[c] | 8.3 ± 0.5 | 15.2 ± 0.5 | 1.8 ± 0.1 |
| SsPCP | 14.3 ± 1.1 | 1.0 ± 0.04 | 0.06 ± 0.008 | 7.9 ± 0.7 | 16.7 ± 0.7 | 2.1 ± 0.2 |
| FNPCP | 7.0 ± 0.6 | 10.1 ± 0.4 | 1.4 ± 0.2 | 11.7 ± 0.8 | 14.5 ± 0.6 | 1.2 ± 0.1 |
| FisPCP | 10.0 ± 0.5 | 2.5 ± 0.05 | 0.3 ± 0.02 | 14.0 ± 1.2 | 1.7 ± 0.07 | 0.1 ± 0.02 |
| MACP | 22.0 ± 1.6 | 4.3 ± 1.1 | 0.2 ± 0.06 | 6.7 ± 0.7 | 5.1 ± 0.2 | 0.8 ± 0.1 |
| APNPCP | 17.0 ± 1.3 | 2.3 ± 0.2 | 0.1 ± 0.02 | 12.0 ± 0.9 | 2.2 ± 0.2 | 0.2 ± 0.02 |
| FNsACP | 14.1 ± 1.4 | 1.5 ± 0.07 | 0.1 ± 0.02 | 10.9 ± 0.5 | 2.4 ± 0.05 | 0.2 ± 0.01 |
| AprACP | 12.9 ± 2.1 | 13.1 ± 1.2 | 1.0 ± 0.2 | 9.0 ± 1.0 | 2.9 ± 0.1 | 0.3 ± 0.05 |

[a]The data represent mean ± SD of three independent experiments;
[b]Units of $K_m$, $k_{cat}$, and $k_{cat}/K_m$ are μM, min$^{-1}$, μM$^{-1}$ min$^{-1}$, respectively;
[c]No detectable activity.

TABLE 2

Deduced functions of ORFs in the biosynthetic gene cluster for shinorine of *Anabaena variabilis* ATCC 29413 and *Fischerella* PCC 9339

| *Anabaena variabilis* ATCC 29413 ORF | aaa | *Fischerella* 9339 ORF | aaa | Identity/similarity (%) | Predicted function |
|---|---|---|---|---|---|
| ava_3858 | 410 | PCC9339_RS0123055 | 409 | 72/85 | Dimethyl 4-deoxygadusol (DDG) synthase |
| ava_3857 | 279 | PCC9339_RS0123056 | 276 | 64/77 | O-Methyltransferase (O-MT) |
| ava_3856 | 458 | PCC9339_RS0123057 | 459 | 75/84 | ATP-grasp family protein |
| ava_3855 | 888 | PCC9339_RS0123058 | 913 | 68/81 | NRPS-like protein |

Example 2

Mycosporine-like amino acids (MAAs) are water-soluble secondary metabolites produced by a variety of marine organisms including cyanobacteria and macroalgae. These compounds have strong ultraviolet (UV) absorption maxima between 310 and 362 nm and are biological sunscreens for counteracting the damaging effects of UV radiation. Shinorine is one MAA analog and is the key active ingredient of sunscreen creams. Commercially used shinorine is isolated from a red algae that is harvested from the wild. *Synechocystis* sp. PCC6803 as a novel host for the heterologous production of shinorine is described. A shinorine gene cluster was mined from the filamentous cyanobacterium *Fischerella* sp. PCC 9339. When expressing the cluster in *Synechocystis* sp. PCC6803, LC-MS analysis detected the production of shinorine but its productivity was three times lower than the native producer. Integrated transcriptional and metabolic profiling identified multiple rate-limiting steps in the heterologous production of shinorine. The use of multiple promoters led to a 10-fold increase of shinorine yield to 2.37±0.21 mg/g dry biomass weight, comparable to commercially used shinorine producer. The UV protection of shinorine was further confirmed using the engineered *Synechocystis* sp. PCC6803. As such, photosynthetic overproduction of MAA is demonstrated. These results suggest that *Synechocystis* sp. PCC6803 can have broad applications as the synthetic biology chassis to produce other cyanobacterial natural products, expediting the translation of genomes into chemicals.

Both ultraviolet (UV)-A (315-400 nm) and UV-B (280-315 nm) can induce DNA damages and generate reactive oxygen species, being harmful to humans. Recent depletion of stratospheric ozone layer has resulted in the increase of UV intensity reaching on earth. Sunscreens comprising different types of synthetic organic and/or inorganic compounds filter a broad spectrum of solar UV rays and prevent the UV-induced damages to humans when applied to the skin. However, multiple negative effects of these manmade UV radiation filters on aquatic ecosystems have become increasingly apparent and gradually shifted the trends of customers toward the use of more environmentally compatible products.

Figure 20:
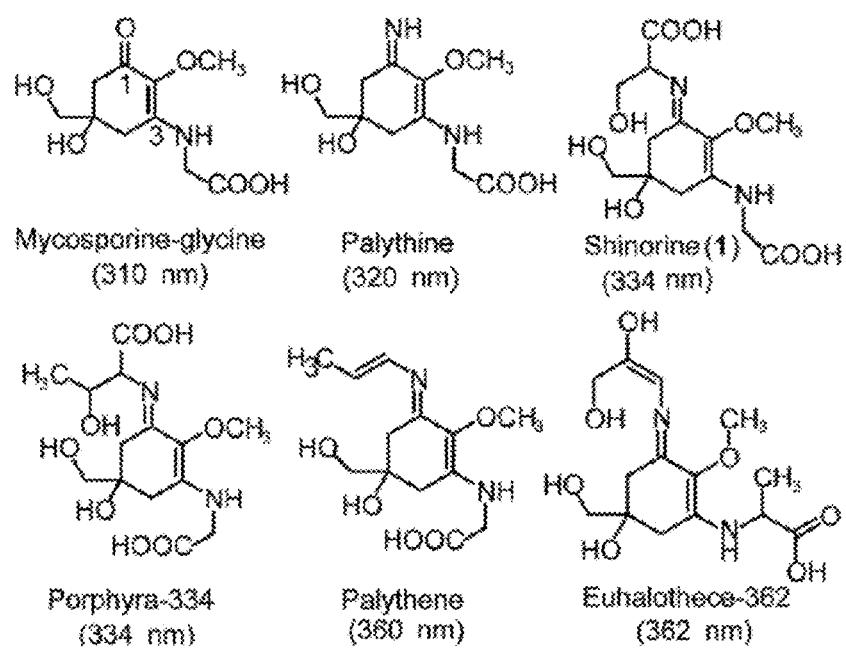
FIG. 20. Chemical structures and absorption maxima of selected cyanobacterial mycosporine-like amino acids.

Mycosporine-like amino acids (MAAs) are a family of over 30 known water-soluble secondary metabolites produced by a variety of taxonomically diverse aquatic organisms (e.g., cyanobacteria and macroalgae) that are frequently exposed to high levels of UV radiation. These compounds share a 4-deoxygadusol (4-DG) core and possess various decorations, e.g., C1oxo or imino group and C3-glycine, that influence their maximal absorbance wavelengths between 310 and 362 nm ($\varepsilon$=28,100-50,000 M$^{-1}$ cm$^{-1}$) (FIG. 20). MAAs promptly convert the absorbed energy to heat without the formation of free oxygen species (FIG. 20), making them biodegradable sunscreens. Indeed, shinorine (1), one MAA commonly produced by marine cyanobacteria and algae, is an important active ingredient of two commercial sunscreen products (Helioguard 365 and Helionori®). The commercially used shinorine is isolated from the red alga *Porphyra umbilicalis* with a yield of 3.27 mg/g dry biomass weight (DW). *P. umbilicalis* is often harvested from the wild and its MAA contents can seasonally and geographically vary. On the other hand, cultivation of *P. umbilicalis* is less economical because of its long doubling time even under the optimal culture conditions.

The biosynthesis of MAAs has been elucidated well in many organisms. 4-Deoxygadusol (4-DG) is the first key biosynthetic intermediate that is produced from the shikimate pathway by a dehydroquinate synthase (DHQS) (FIG. 21). Next, an ATP-grasp ligase conjugates glycine to the C3 of 4-DG to produce mycosporine-glycine (MG) that is then converted to shinorine (1) and other MAAs by a nonribosomal peptide synthetase (NRPS) or a d-Ala-d-Ala ligase-like protein (FIG. 21). Recently, an alternative route to 4-DG was discovered in cyanobacterial species, and requires both demethyl 4-deoxygadusol synthase (DDGS) and O-methyltransferase (O-MT) to produce 4-DG from sedoheptulose-7-phosphate (SH-7P) of the pentose phosphate pathway (FIG. 21). This four-gene cluster of shinorine is conserved among a number of cyanobacterial species, e.g., ava_3855 to ava_3858 in the filamentous cyanobacterium *Anabaena variabilis* ATCC29413.

Heterologous expression has proven to be a useful strategy for the production of natural products of diverse origins. Commonly used hosts in these studies include *Escherichia coli*, *Streptomyces* strains and yeast. However, these hosts have demonstrated limited successes in heterologous production of cyanobacterial natural products. Thus far, only several families of ribosomally synthesized and post-translationally modified peptides, lyngbyatoxin and microcystins have achieved successful production in *E. coli*, while 4-O-demethylbarbamide is the only cyanobacterial secondary metabolite produced in *Streptomyces* species (<1 µg/L). Shinorine (1) was also produced in *E. coli* expressing the cluster from *Anabaena* but its low yield of 145 µg/L and the significant accumulation of 4-DG indicate the inefficient and unbalanced production. Indeed, genetic backgrounds between cyanobacteria and *E. coli* are notably different (e.g., GC content and transcriptional elements), which might result in the no-to-low production of expressed cyanobacterial natural products. On the other hand, filamentous cyanobacterium *Anabaena* sp. PCC7120 was used to produce lyngbyatoxin A with the highest yield of 2.3 µµg/g DW (Videau et al.). Videau et al. demonstrated the potential of cyanobacterial chassis in producing cyanobacterial natural products. However, the five NRPS/polyketide synthase (PKS) gene clusters in *Anabaena* sp. PCC7120 could compete with the expression of foreign clusters and complicate the identification and isolation of expressed natural products.

The unicellular cyanobacterium *Synechocystis* sp. PCC6803 has been used to produce biofuels, commodity chemicals and biomaterials. *Synechocystis* can be a suitable host for photosynthetically producing cyanobacterial natural products because (1) it has a short doubling time (5 to 10 h) compared with other cyanobacteria; (2) it is amenable to genetic modifications with a variety of available tools; and (3) it contains no NRPS/PKS cluster, avoiding inherent competition of biosynthetic building blocks and simplifying the isolation and identification of expressed products. The use of *Synechocystis* is provided as a heterologous host to express a shinorine gene cluster from the filamentous cyanobacterium *Fischerella* sp. PCC9339 (hereafter *Fischerella*). Combining transcriptional and metabolic profiling, the gene cluster was engineered to improve the productivity of shinorine close to the commercially used red algae and avoid the accumulation of biosynthetic intermediates. Furthermore, the UV protection effect of shinorine expressed in *Synechocystis* was confirmed.

This Example provides *Synechocystis* in expressing the secondary metabolite gene cluster and suggests the broad uses of this new synthetic biology chassis to produce multiple families of cyanobacterial natural products.

The Shinorine Biosynthesis in *Fischerella*

Cyanobacteria can be classified into five subsections, and the subsection V strains are particularly rich of structurally diverse natural products in their genomes. When mining the genomes of all 18 subsection V cyanobacteria available in the NCBI Genbank database (as of July 2017), the MAA gene cluster from 10 strains (Table 3) were identified.

TABLE 3

Putative MAA gene clusters in *Anabaena* and subsection V cyanobacteria.

| Cyanobacterial strain/Genome accession code | Genes involved in the biosynthesis of MAAs* | | | |
|---|---|---|---|---|
| | DDGS homologue | O-Methyltransferase | ATP-grasp homologue | NRP synthetase |
| *Anabaena variabilis* ATCC 29413/ NC_007413.1 | ava_3858 | ava_3857 | ava_3856 | ava_3855 |
| *Fischerella* sp. PCC 9339/ NZ_ALVS00000000.1 | PCC9339_RS0129530 (84.7%) | PCC9339_RS0129525 (77.1%) | PCC9339_RS0129520 (85.0%) | PCC9339_RS0129515 (77.8%) |
| *Fischerella* sp. PCC 9431/NZ_ALVS00000000.1 | FIS9431_RS0125705 (84.7%) | FIS9431_RS0125700 (77.8%) | FIS9431_RS0125700 (85.2%) | FIS9431_RS0125695 (79.2%) |
| *Fischerella muscicola* SAG 1427-1/ NZ_ALVX00000000.1 | UYG_RS0121930 (84.9%) | UYG_RS0121925 (77.4%) | UYG_RS0121920 (85.2%) | UYG_RS0121915 (77.1%) |
| *Mastigocoleus testarum* BC008/ NZ_AJLJ00000000.1 | BC008_38355 (89.1%) | BC008_38350 (77.4%) | BC008_38345 (83.5%) | BC008_38340 (53.6%) |
| *Chlorogloeopsis* PCC 9212/NZ_AJLM00000000.1 | UYE_RS0123135 (91.3%) | UYE_RS0123130 (83.5%) | UYE_RS0123125 (86.5%) | UYE_RS0123120 (57.1%) |
| *Chlorogloeopsis fritschii* PCC 6912/NZ_AJLM00000000.1 | UYC_RS0133575 (91.3%) | UYC_RS0133570 (83.5%) | UYC_RS0133565 (86.5%) | UYC_RS0133560 (57.1%) |
| *Hapalosiphon* sp. MRB220/NZ_AJLN00000000. 1 | AMR41_RS24135 (84.7%) | AMR41_RS24130 (77.8%) | AMR41_RS24125 (85.8%) | AMR41_RS25775 (77.6%) |
| *Mastigocladus laminosus* UU774/NZ_JXU00000000.1 | SP67_25945 (48.0%) | SP67_25950 (35.1%) | SP67_25955 (85.2%) | SP67_25960 (75.4%) |
| *Westiella intricata* UH HT-29-1**/Reference 4 | + | + | + | + |
| *Hapalosiphon welwitschii* UH IC-52-3**/Reference 4 | + | + | + | + |

*The NCBI accession numbers of the genes are shown. The numbers in the parentheses indicate the percentage similarities of the genes compared to their homologs in *Anabaena variabilis* ATCC 29413.
**Genomes of *Westiella intricata* UH HT-29-1 and *Hapalosiphon welwitschii* UH IC-52-3 are not publically available, but the MAA biosynthetic gene clusters have been described in the reference Micallef et al.

Figure 22:
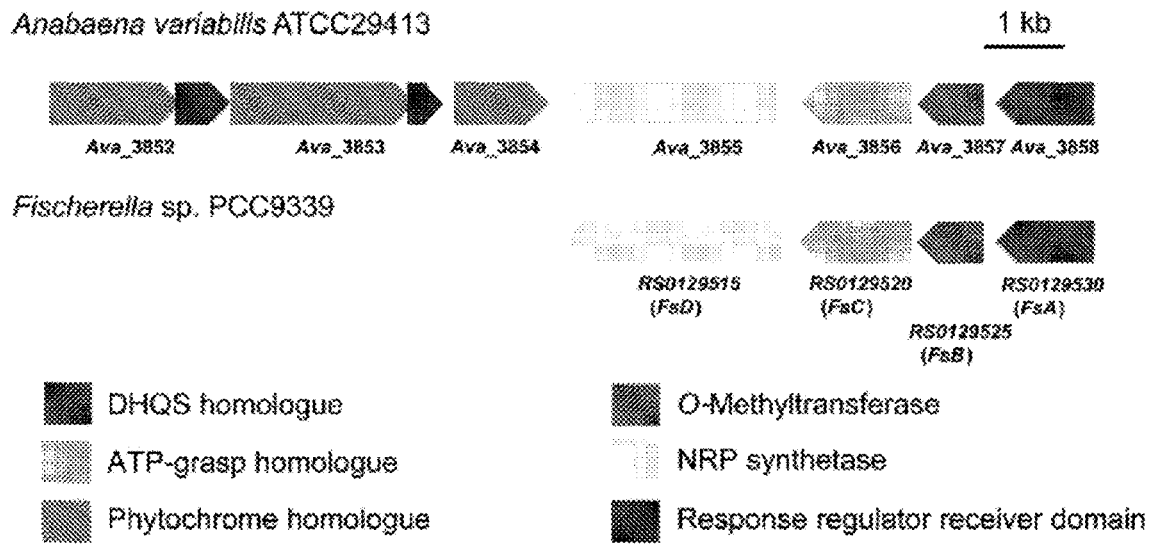
FIG. 22. The shinorine gene clusters in *Anabaena* and *Fischerella* share over 77% amino acid similarities. The shinorine gene cluster in *Anabaena* is flanked by five genes/domains encoding phytochrome-like sensor kinases and response regulators. These regulatory factors are not found in the surrounding regions of the gene cluster in *Fischerella*.
Figure 23:
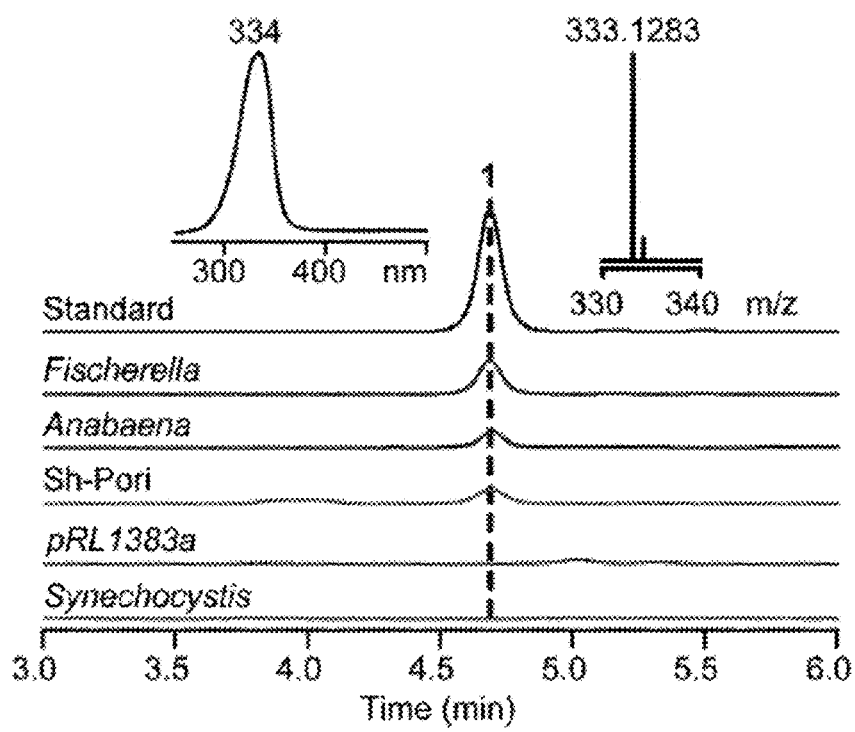
FIG. 23. HPLC and LC-MS analyses revealed the production of shinorine (1) by *Fischerella, Anabaena*, and Sh-Pori. Shinorine in the methanolic extracts of cyanobacterial cell biomass had the identical retention time as the standard, possessed the featured absorption spectrum (left-top) and showed the expected m/z value of its molecular ion (right-top). Wild type (WT) *Synechocystis* and the strain containing pRL1383a did not produce shinorine.
Figure 24:
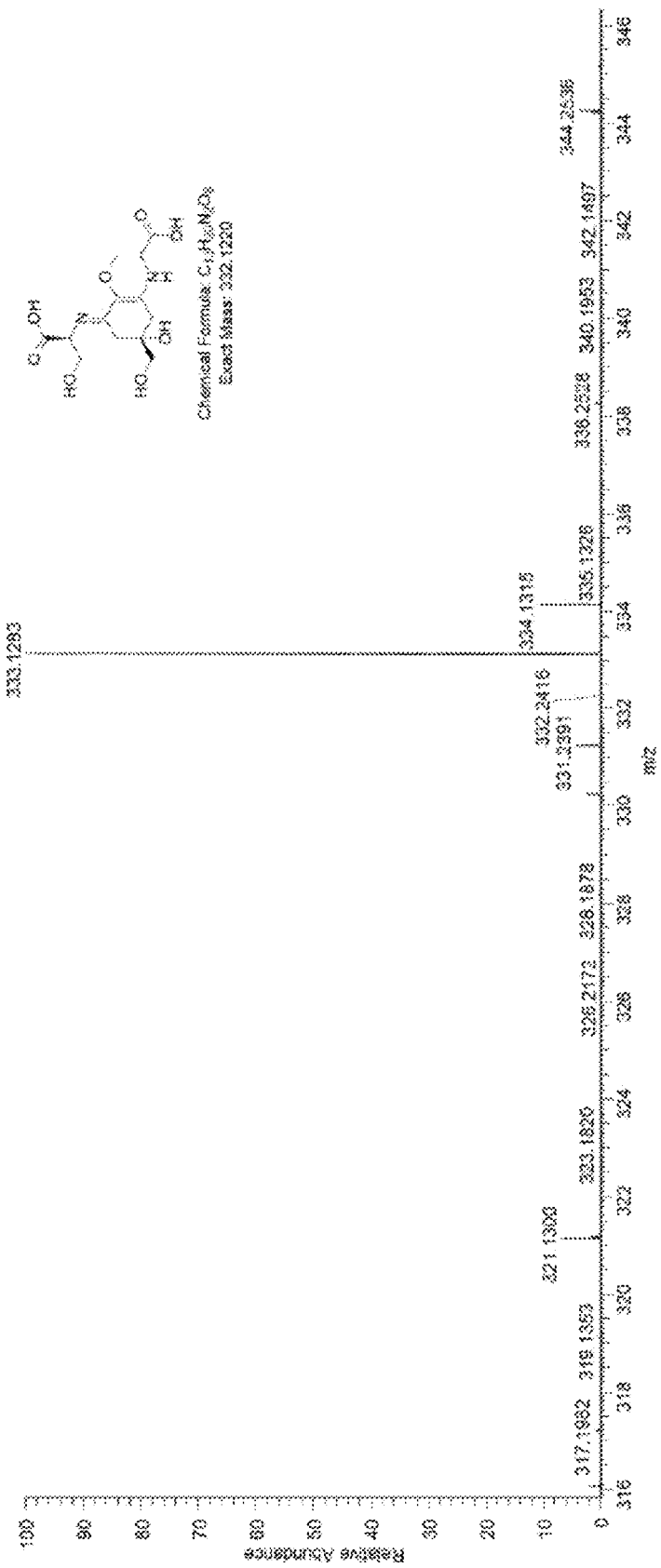
FIG. 24. HR-MS (top) and MS/MS (bottom) spectra of expressed shinorine in *Synechosystis*.
Figure 24:
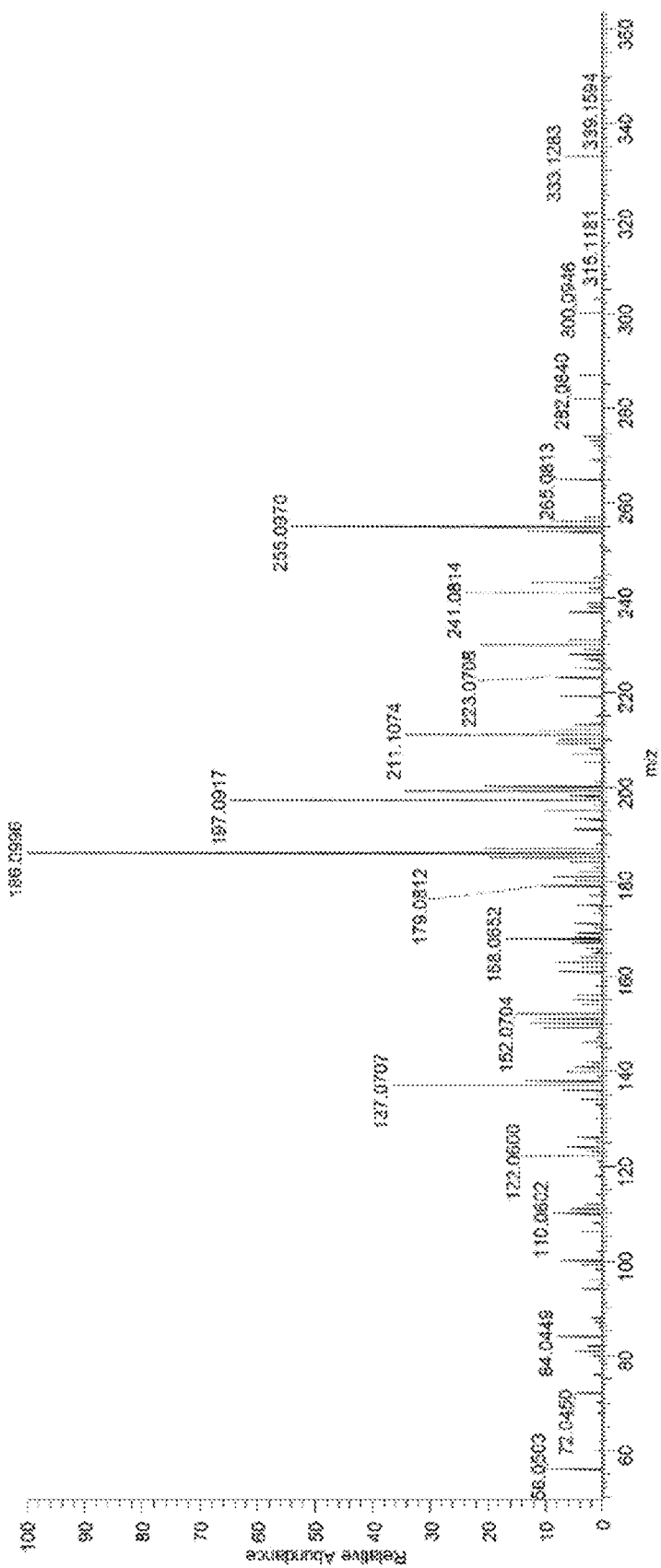

The *Fischerella* genome contains 40 natural product gene clusters including a putative shinorine cluster (NCBI Genbank: PCC9339_RS0129515-PCC9339_RS0129530, named as FsD-A) that shows over 77% amino acid similarities to the one in *Anabaena* (FIG. 22). To probe the function of this cluster, *Fischerella* and *Anabaena* were cultured in BG-11 medium at 26° C. for 21 days. HPLC analysis of methanolic extracts of pelleted *Fischerella* and *Anabaena* cells identified a peak with the diagnostic maximal absorbance wavelength at 334 nm and the identical retention time (4.7 min) to the shinorine standard (FIG. 23). The peak content showed an expected m/z value of 333.1283 (calculated [M+H]$^+$: 333.1220) in the high resolution (HR) MS analysis (FIG. 23). Furthermore, its fragmentation pattern agreed with the previous report (FIG. 24). Collectively, these results suggested a functional shinorine cluster in *Fischerella*. Indeed, *Fischerella* produced 2.5-fold more shinorine (1) than *Anabaena* under the same culture conditions (0.76±0.05 mg/g DW vs. 0.32±0.03 mg/g DW, Table 4). In this regard, *Fischerella* produced a comparable amount of shinorine (1) to other known cyanobacterial producers, such as *Aulosira fertilissima* (0.5 mg/g DW) and *Anabaena variabilis* PCC7937 (0.97 mg/g DW), although it is four times lower than the commercially used red algae *P. umbilicalis* (3.27 mg/g DW).

TABLE 4

Titers of shinorine in *Anabaena, Fischerella* and engineered *Synechocystis* strains.

| Strain | Shinorine (mg/g DW)* |
|---|---|
| *Anabaena* | 0.32 ± 0.03 |
| *Fischerella* | 0.76 ± 0.05 |
| Sh-Pori | 0.23 ± 0.08 |
| Sh-PrnpB | 0.82 ± 0.04 |
| Sh-Ptrc | 1.12 ± 0.05 |
| Sh-P560 | 1.67 ± 0.06 |
| Sh-DP560 | 1.93 ± 0.09 |
| Sh-TP560 | 2.37 ± 0.21 |
| Sh-TP560/Ser | 2.28 ± 0.27 |
| Sh-TP560/UV-A | 2.21 ± 0.37 |
| Sh-TP560/UV-B | 2.15 ± 0.34 |

*Data represent mean ± standard deviation (n = 3).

Heterologous Production of Shinorine in *Synechocystis*

Figure 25A:
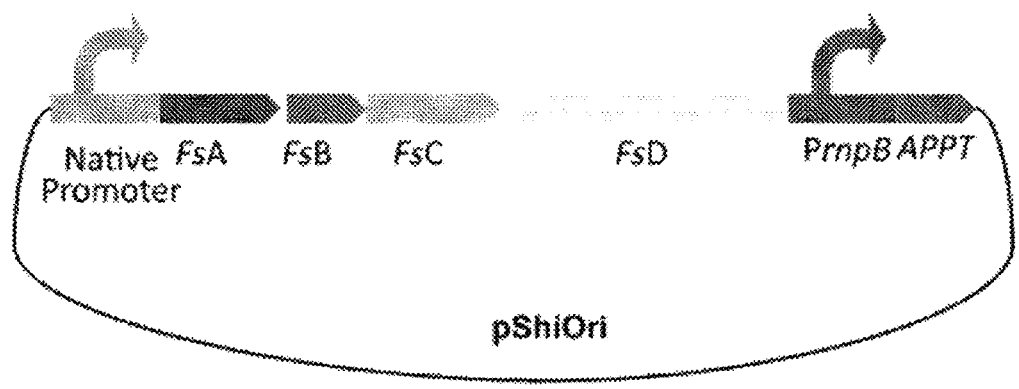
FIGS. 25A-25B. (A). Schematic representation of the construction of pShiOri (SEQ ID NO: 83). (B) Triparental mating of *Synechocystis* for the conjugation of the shinorine expression plasmid.
Figure 25B:
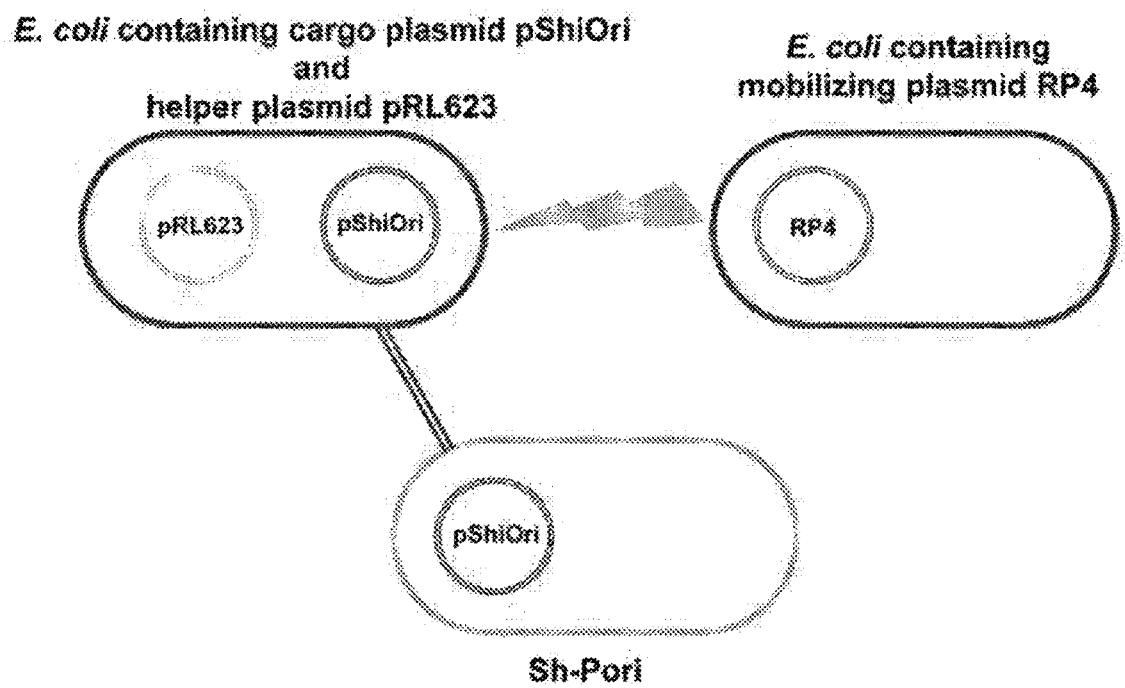
Figure 26A:
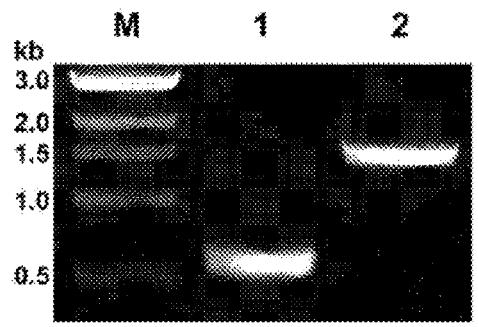
FIGS. 26A-26B. PCR analysis of the shinorine gene cluster in Sh-Pori. (A) Colony PCR diagnosis of Sh-Pori. M: NEB 1 kb DNA Ladder, lane 1: PCR amplicons by using primers Pori-FsA-F and Pori-FsA-R, lane 2: PCR amplicons by using primers FsD-APPT-F and FsD-APPT-R. (B) Reverse transcription PCR (RT-PCR) analysis detected the proper transcription of each cluster gene in Sh-Pori. M: NEB 100 bp DNA Ladder, lane 1-4: RT-PCR amplicons of FsA-D, respectively.
Figure 26B:
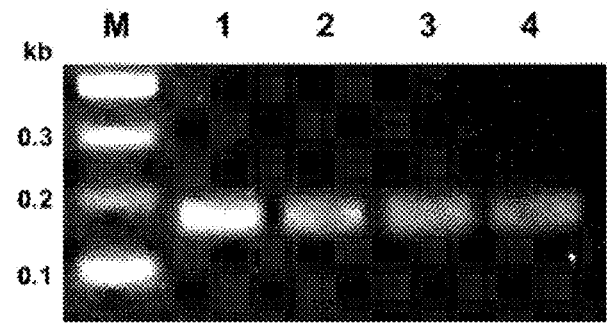

The red algae *P. umbilicalis* is used to commercially supply shinorine but has a long generation time that varies from 2 to 6 days under optimized laboratory conditions to at least 64 days in the wild. To access shinorine in a fast and reliable manner, its cluster from *Fischerella* in *Synechocystis* were heterologously expressed. As shown in FIG. 21, the final step of shinorine biosynthesis is catalyzed by the pathway-specific NRPS enzyme FsD. The proper function of FsD requires a posttranslational modification on its peptidyl carrier protein (PCP) domain, which is promoted by a phosphopantetheinyl transferase (PPT). *Synechocystis* carries one PPT gene (SPPT) but an early report indicated the catalytic incompetence of SPPT in activating foreign carrier protein domains including PCPs. By contrast, SPPT successfully modified multiple cyanobacterial carrier protein domains, including the one of FsD. Its in vitro catalytic efficiency ($k_{cat}/K_m$=0.3±0.02 $\mu M^{-1}$ $min^{-1}$) toward this substrate is three times higher than the canonical PPT Sfp from *Bacillus subtilis* and is at the same level as the PPT from *Anabaena* sp. PCC7120 (APPT), although APPT possesses a broader substrate scope. To ensure the successful production of shinorine, a self-replicative vector pRL1383a was used to co-express the APPT gene and the shinorine gene cluster including its native promoters (FIG. 25). The expression of APPT was under the control of PrnpB, a strong constitutive promoter of *Synechocysti*. The resultant construct was conjugated into *Synechocystis* via triparental mating to generate the production strain Sh-Pori. PCR-based diagnosis validated the presence of the shinorine cluster in Sh-Pori cells, and the proper transcription of each gene was observed by the reverse transcription PCR (RT-PCR) analysis (FIG. 26). Sh-Pori along with wild type (WT) *Synechocystis* and the engineered strain carrying pRL1383a (*Synechocystis*-pRL1383a) as two controls were cultured in BG-11 medium for 13 days. HPLC analysis of the methanolic extract of Sh-Pori biomass identified a new peak that was missing in the extracts of two controls (FIG. 23). The peak content was determined as shinorine by comparing its retention time with the authentic standard and analyzing its MS and MS/MS spectra (FIG. 24). The titer of shinorine was further determined to be 0.23±0.08 mg/g DW, about three times lower than its native producer *Fischerella* cultured for 21 days (Table 4). This study represents the first heterologous production of any MAA in a photosynthetic host. Heterologous expression of the shinorine cluster in *E. coli* leads to a low yield (~0.1 mg/L) and a high amount of 4-DG byproduct. In contrast, *Synechocystis* achieves a complete conversion of all biosynthetic intermediates, and is thus a superior host for expression of shinorine. *Synechocystis* does not encode any shinorine biosynthetic gene.

Production Improvement of Shinorine Using Different Promoters

Figure 27A:
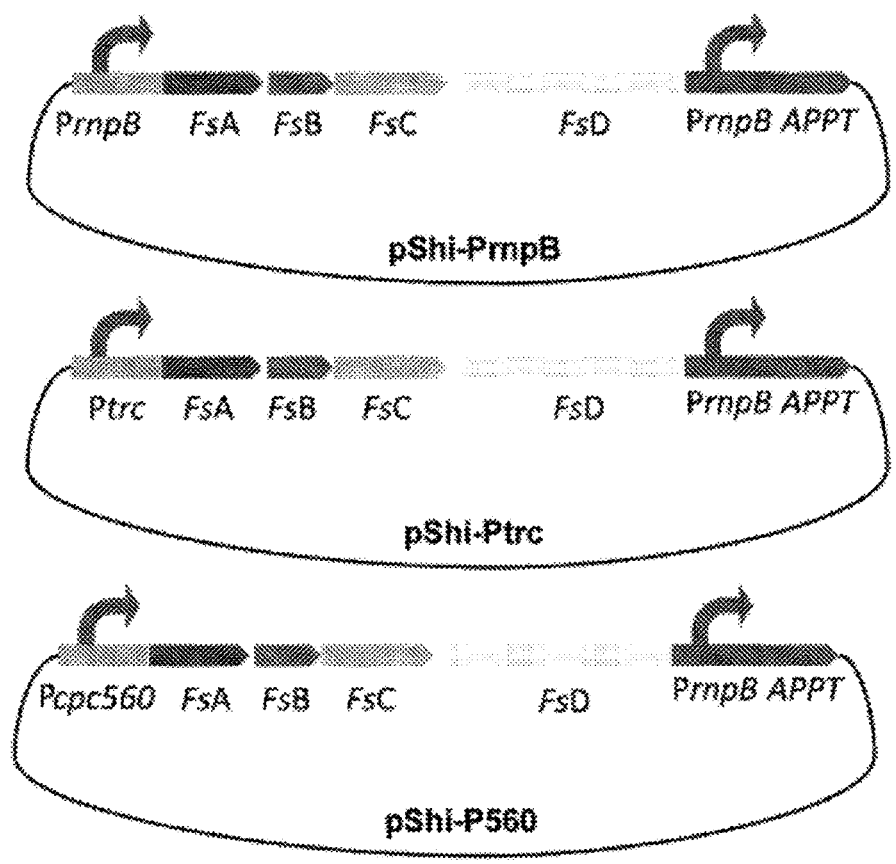
FIGS. 27A-27B. Expression of the shinorine gene clusters under the control of different promoters. (A) Schematic representation of the plasmids containing the shinorine gene cluster under the control of PrnpB (SEQ ID NO: 80), Ptrc (SEQ ID NO: 81) and Pcpc560 (SEQ ID NO: 82) promoters. (B) Colony PCR analysis of Sh-PrnpB, Sh-Ptrc and Sh-P560. M: NEB 1 kb DNA Ladder, lane 1-3: PCR amplicons of the shinorine gene cluster in Sh-PrnpB (containing plasmid pSh-PrnpB (SEQ ID NO: 84)), Sh-Ptrc (containing plasmid pSh-Ptrc (SEQ ID NO: 85) and Sh-P560 (containing plasmid pSh-P560 SEQ ID NO: 86), respectively.
Figure 27B:
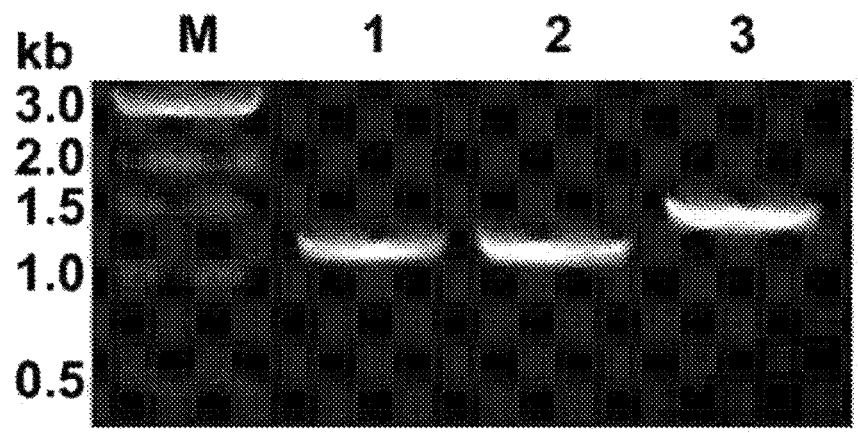
Figure 28A:
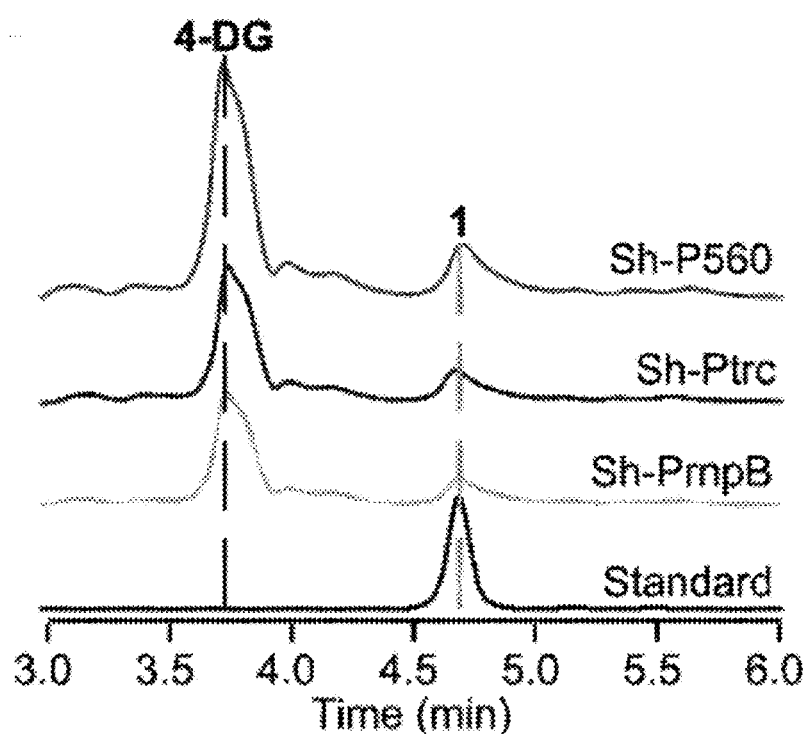
FIGS. 28A-28B. Enhanced production of shinorine in *Synechocystis* using different promoters. (A) HPLC analysis identified shinorine (1) and 4-DG in the extracts of Sh-Ptrc, Sh-PrnpB and Sh-P560. Biosynthetic intermediate 4-DG was the dominant product. (B) qRT-PCR analysis revealed that different promoters affected the transcription of shinorine biosynthetic genes to varying degrees. The rnpB gene was included as the positive control, and its transcription level was used to normalize the signals of the biosynthetic genes of the same strain. Data represent mean±standard deviation (n=3). * indicates statistically significant difference (P<0.05, Student's t-test) of the transcription levels of the same gene in two different strains.
Figure 29:
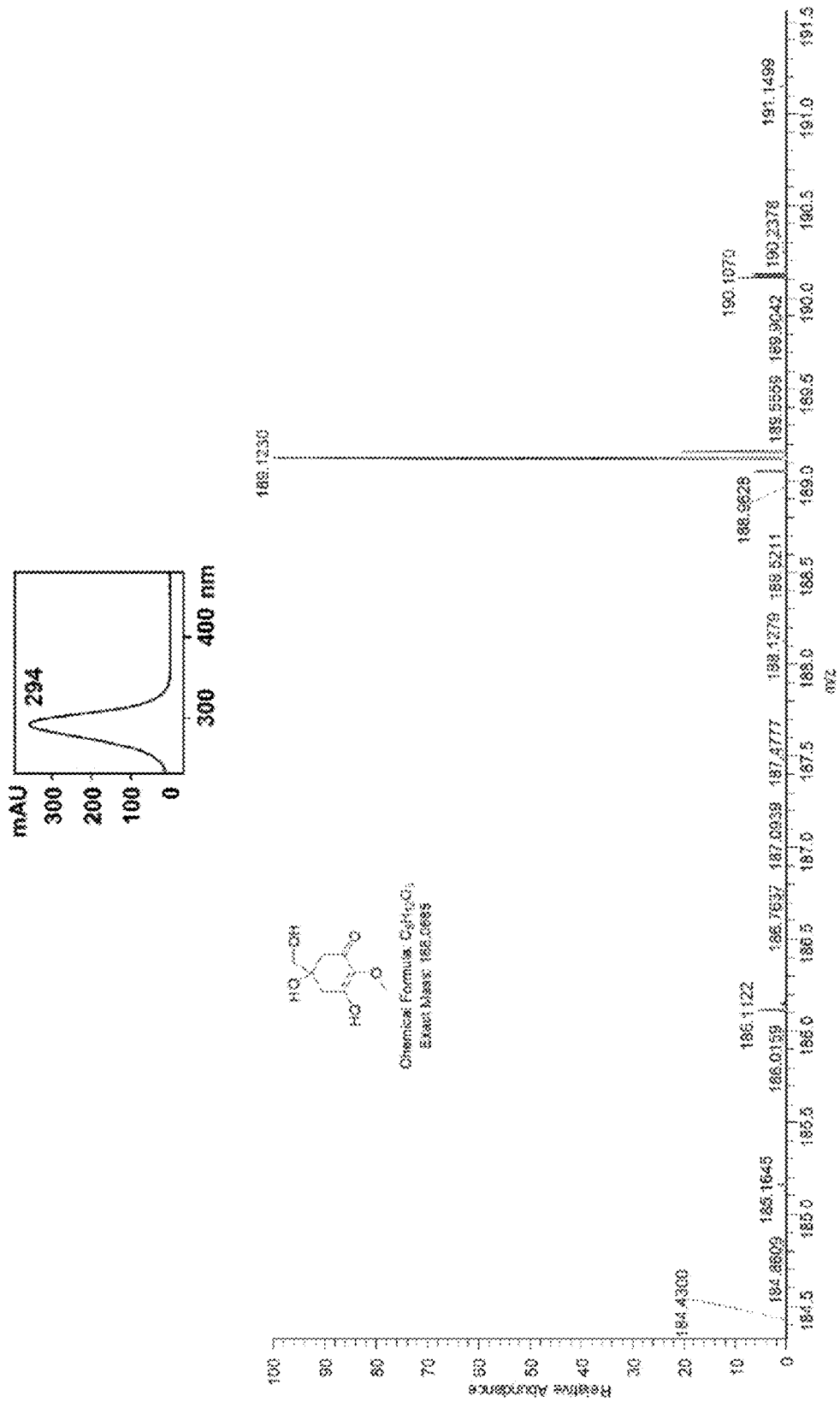
FIG. 29. The absorption (top), HRMS (middle) and MS/MS (bottom) spectra of expressed 4-DG in *Synechosystis*.
Figure 29:
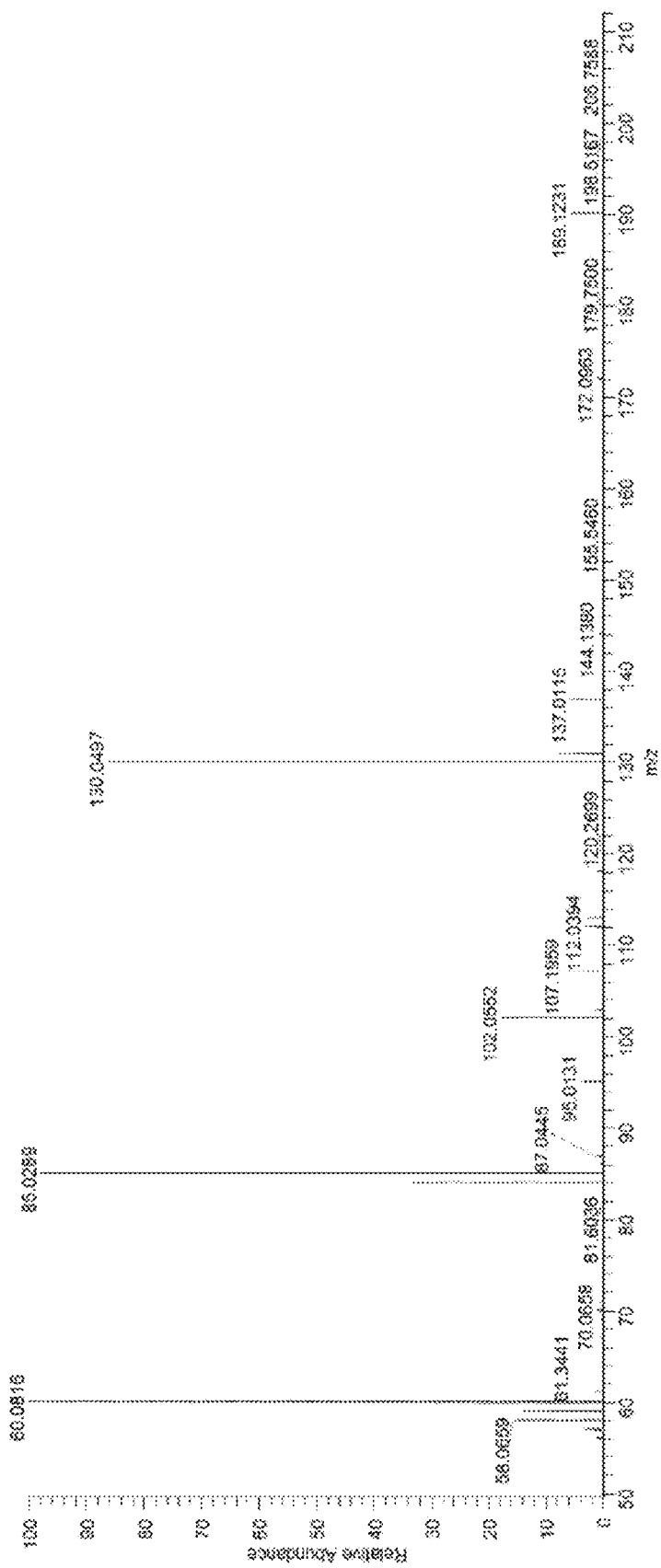
Figure 30A:
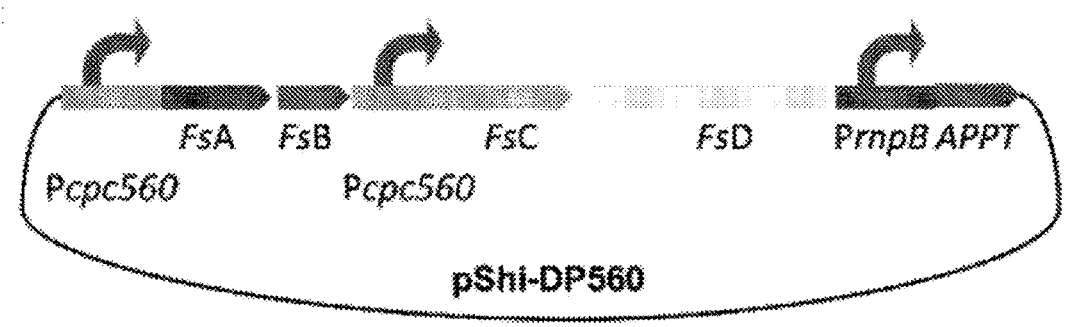
FIGS. 30A-30C. Expression of the shinorine gene clusters under the control of two Pcpc560 promoters. (A) Schematic representation of the plasmid containing the shinorine gene cluster under the control of two Pcpc560 promoters. (B) Colony PCR analysis of strain Sh-DP560 (containing plasmid pSh-DP560 having the sequence of SEQ ID NO: 87). M: NEB 1 kb DNA Ladder, lane 1: PCR amplicons using primers P560-FsA-F and FsA-R, lane 2: PCR amplicons using primers DP560-FsC-F and DP560-FsC-R. Expected sizes were found. (C) RT-PCR analysis demonstrated the proper transcription of the individual genes in Sh-DP560. M: NEB 100 bp DNA Ladder, lane 1-4: RT-PCR amplicons of FsA-D, respectively.
Figure 30B:
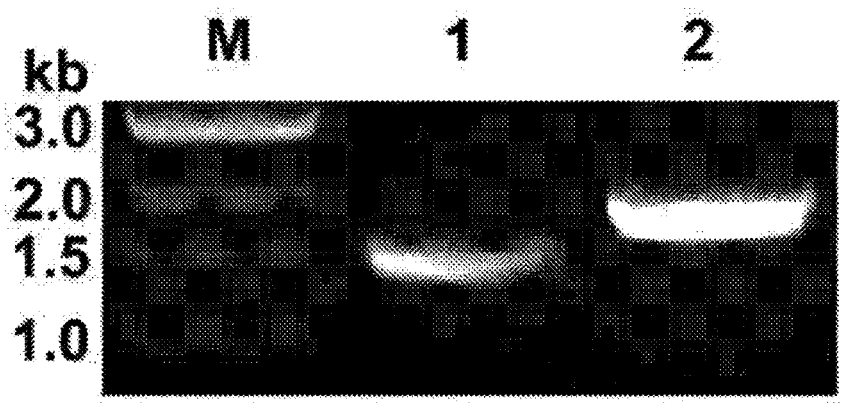
Figure 30C:
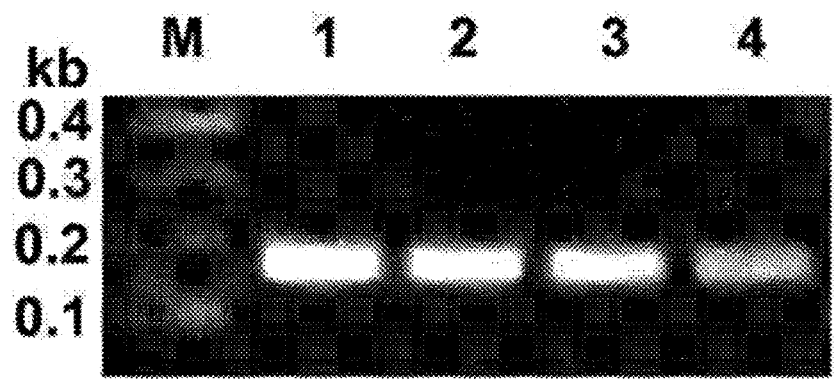

Transcriptional elements are known to control the productivity of expressed compounds in *Synechocystis*, but their functions vary among different cyanobacterial hosts. To overproduce shinorine in *Synechocystis*, the expression of its cluster was optimized using three promoters with varied strengths, including one synthetic promoter Ptrc and two promoters of *Synechocystis* PrnpB and Pcpc560. All three promoters have previously been used in *Synechocystis*. Since FsA-D have the same gene orientation, the replacement of the original promoter in the upstream of FsA with these new promoters can influence the expression of all four genes (FIG. 27A). Three new expression vectors were thus constructed and transformed into *Synechocystis* to create the production strains Sh-Ptrc, Sh-PrnpB, and Sh-P560, which were further validated in the PCR diagnosis (FIG. 27B). The yield of shinorine was quantitated in the strains that were cultured under the same conditions as Sh-Pori. Remarkably, the promoter engineering improved the titers of shinorine in Sh-PrnpB (0.82±0.04 mg/g DW), Sh-Ptrc (1.12±0.05 mg/g DW) and Sh-P560 (1.67±0.06 mg/g DW) by about 4, 5, and 8 times, respectively, compared with Sh-Pori (FIG. 28A, Table 4). Of note, both Sh-Ptrc and Sh-P560 produced more shinorine than any known cyanobacterial species. In addition to shinorine, these new strains produced a new compound that was shown as a dominant peak in the HPLC traces and was missing in the extract of Sh-Pori (FIG. 23, FIG. 28A). The peak content was determined to be 4-DG based on its absorbance maximum at 294 nm and its HRMS and MS/MS spectra (FIG. 29), which agreed well with the reported data of 4-DG. Among three strains, Sh-P560 accumulated the highest amount of 4-DG, while Sh-PrnpB had the least (FIG. 28A).

Figure 28B:
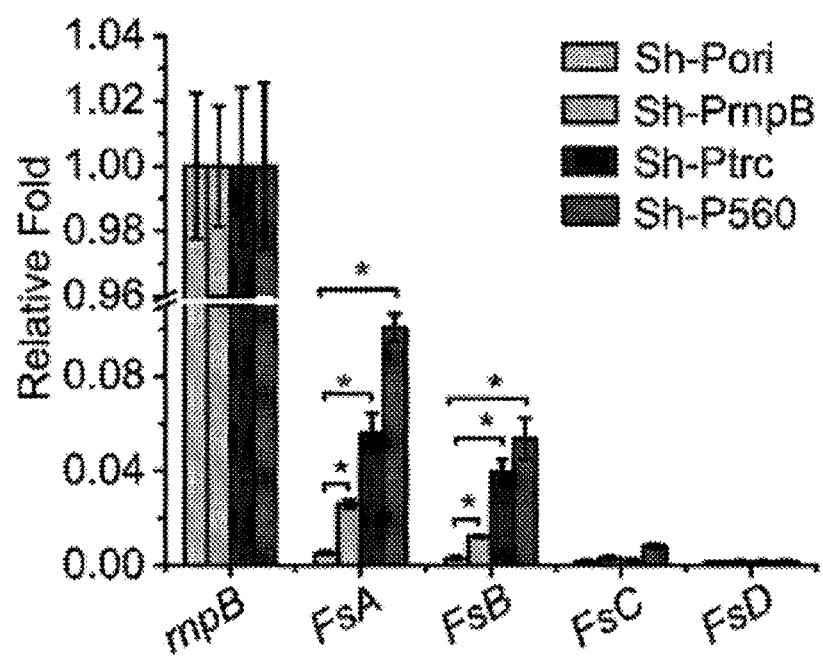

The accumulation of 4-DG likely indicated the imbalanced expression of shinorine biosynthetic genes in three new strains. To quantitate the effects of these promoters on the transcription of shinorine cluster, quantitative RT-PCR (qRT-PCR) analysis was performed. The transcription level of the conserved gene rnpB in each strain was set as 1 and then used to normalize other signals. This analysis revealed that the transcription level of FsA in Sh-Pori was about 2, 3, and 3 times higher than FsB, FsC, and FsD, respectively (FIG. 28B, Table 5). Compared with the original promoter, Ptrc, PrnpB and Pcpc560 statistically significantly enhanced the transcription levels of FsA and FsB by about 10, 5 and 19 folds, respectively, agreeing with the improved production of shinorine in the three new strains (FIG. 28A). By contrast, the transcription levels of FsC were enhanced to a modest extent, while the new promoters did not upregulate the expression of FsD (FIG. 28B, Table 5). Therefore, the transcriptional analysis indicated that the accumulation of 4-DG is caused by the relatively low expression of FsC whose encoded enzyme converts 4-DG into MG (FIG. 22). In line with this observation, the transcription level of FsC in Sh-P560 was 2-4 folds higher than Sh-Ptrc and Sh-PrnpB, likely leading to 1.5-2 times more shinorine in Sh-P560 (FIG. 28B, Table 4).

TABLE 5 qRT-PCR analysis of the shinorine biosynthetic genes in *Synechocystis* mutants.

| | *Synechocystis* mutants | | | | | |
|---|---|---|---|---|---|---|
| Gene | Sh-Pori | Sh-PrnpB | Sh-Ptrc | Sh-P560 | Sh-DP560 | Sh-TP560 |
| rnpB | 1 ± 0.0224 | 1 ± 0.0186 | 1 ± 0.0241 | 1 ± 0.0258 | 1 ± 0.0128 | 1 ± 0.0163 |
| FsA | 0.0053 ± 0.0007 | 0.0259 ± 0.0021 | 0.0558 ± 0.0085 | 0.1006 ± 0.0057 | 0.1042 ± 0.0120 | 0.1037 ± 0.0186 |
| FsB | 0.0031 ± 0.0008 | 0.0123 ± 0.0005 | 0.0393 ± 0.0055 | 0.0537 ± 0.0087 | 0.0576 ± 0.0108 | 0.0556 ± 0.0080 |
| FsC | 0.0018 ± 0.0005 | 0.0032 ± 0.0006 | 0.0022 ± 0.0007 | 0.0082 ± 0.0007 | 0.0349 ± 0.0008 | 0.0361 ± 0.0018 |
| FsD | 0.0016 ± 0.0004 | 0.0019 ± 0.0002 | 0.0018 ± 0.0003 | 0.0019 ± 0.0004 | 0.0154 ± 0.0029 | 0.0683 ± 0.0109 |

Overproduction of Shinorine by Tuning the Expression of Individual Genes

Figure 31:
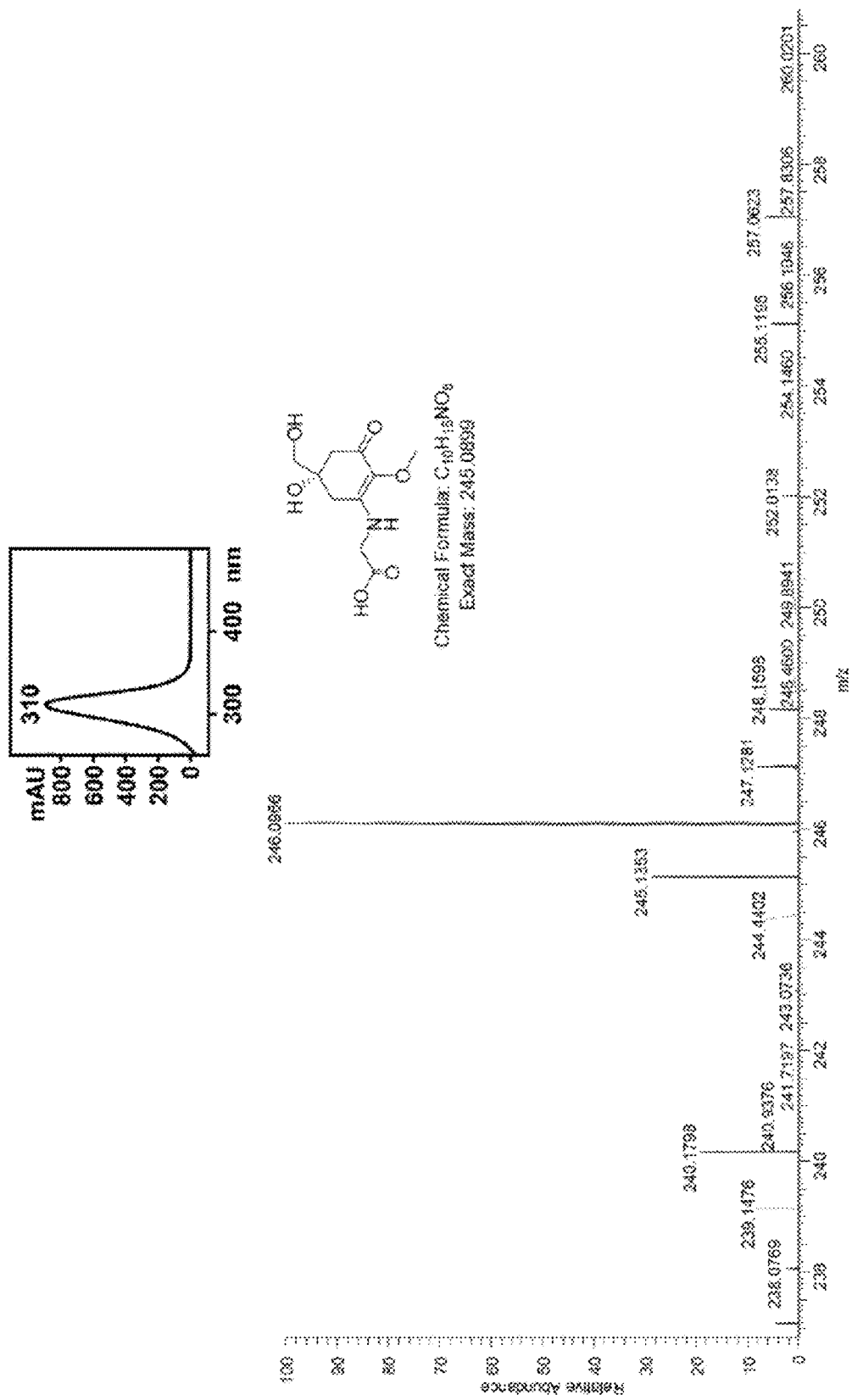
FIG. 31. The absorption (top), HRMS (middle) and MS/MS (bottom) spectra of expressed MG in Sh-DP560.
Figure 31:
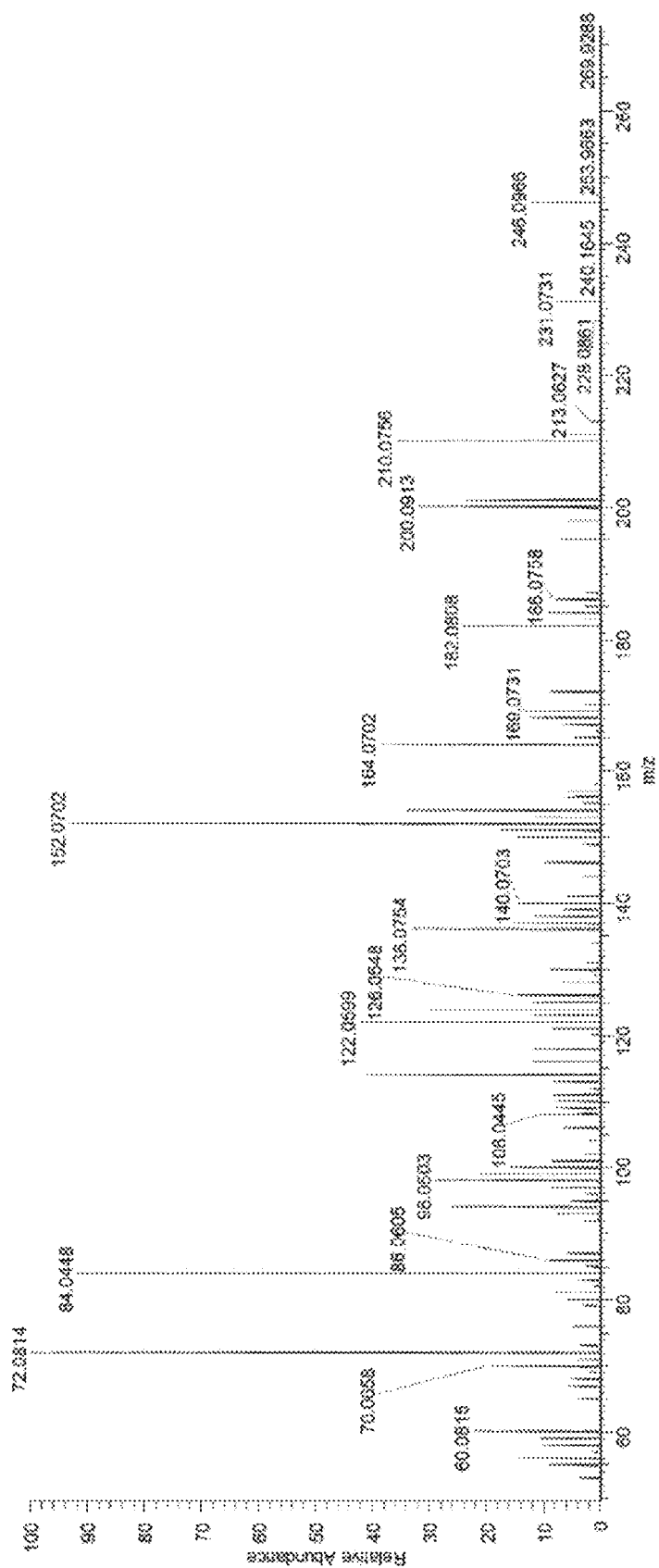
Figure 32A:
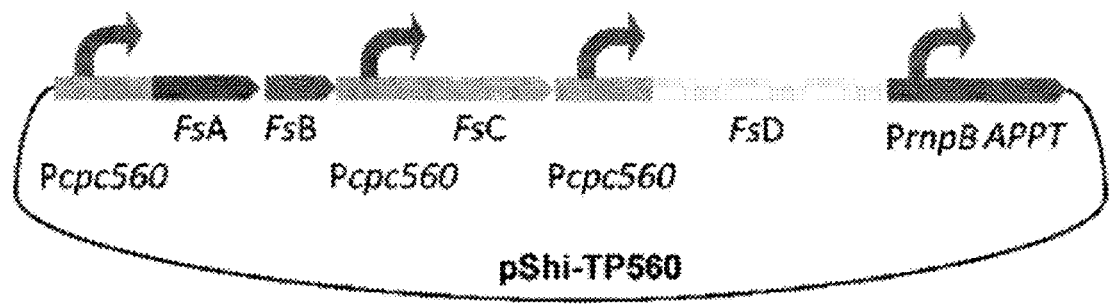
FIGS. 32A-32C. Expression of the shinorine gene clusters under the control of three Pcpc560 promoters (containing plasmid pSh-TP560 having the sequence of SEQ ID NO: 88). (A) Schematic representation of the plasmid containing the shinorine gene cluster under the control of three Pcpc560 promoters. (B) Colony PCR analysis of Sh-TP560. M: NEB 1 kb DNA Ladder, lane 1: PCR amplicons using primers P560-FsA-F and FsA-R, lane 2: PCR amplicons using primers DP560-FsC-F and DP560-FsC-R, lane 3: PCR amplicons using primers TP560-FsD-F and TP560-FsD-R. Expected sizes were found. (C) RT-PCR analysis demonstrated the proper transcription of the individual genes in Sh-TP560. M: NEB 100 bp DNA Ladder, lane 1-4: RT-PCR amplicons of FsA-D, respectively.
Figure 32B:
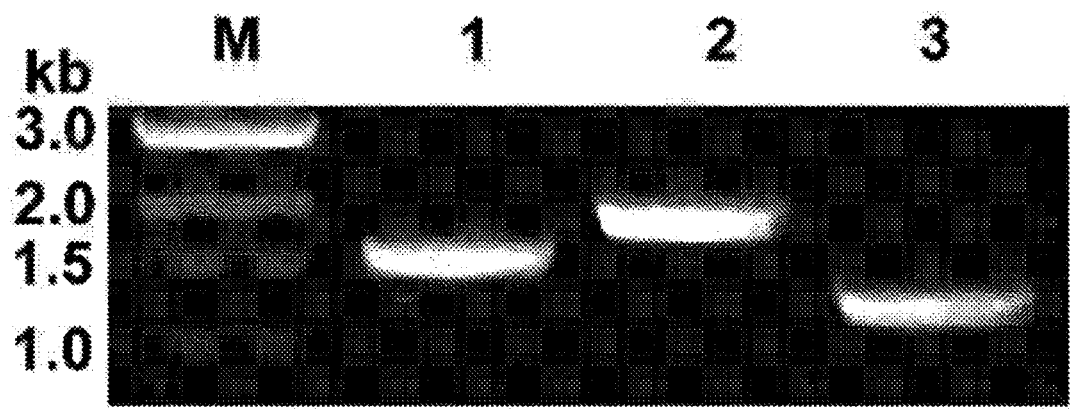
Figure 32C:
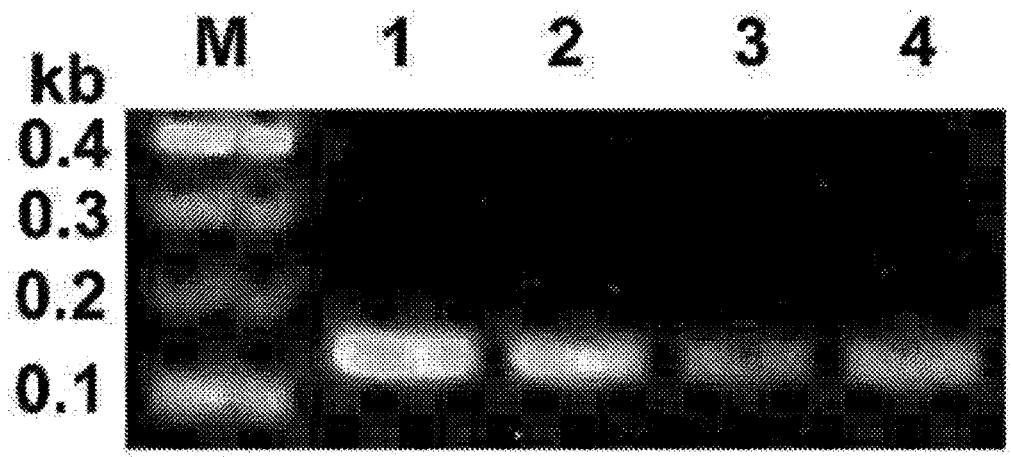
Figure 33A:
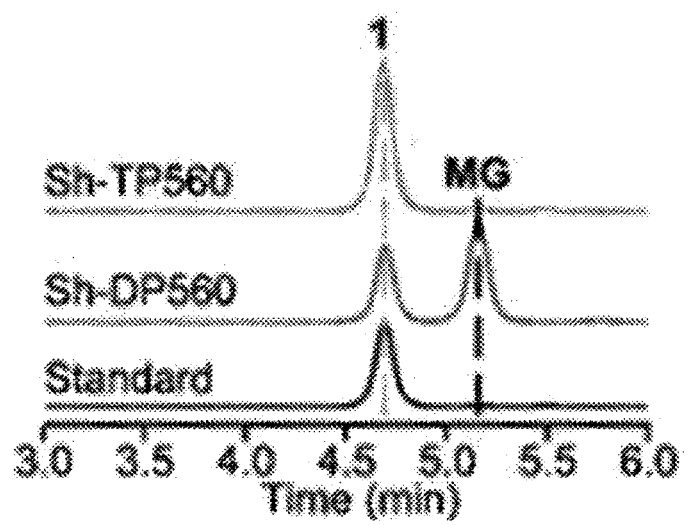
FIGS. 33A-33B. Overproduction of shinorine in *Synechocystis* by tuning the expression of individual genes. (A) HPLC analysis of the metabolic profiles of Sh-DP560 and Sh-Tp560. MG was produced in Sh-DP560 and completely converted into shinorine (1) in Sh-TP560. (B) qRT-PCR analysis of the transcription levels of FsC and FsD in Sh-P560, Sh-DP560 and Sh-TP560. The transcription level of rnpB gene in each strain was quantitated for normalizing the signals of these genes in the same strain. Data represent mean±standard deviation (n=3). * indicates statistically significant difference (p<0.05, Student's t-test).
Figure 33B:
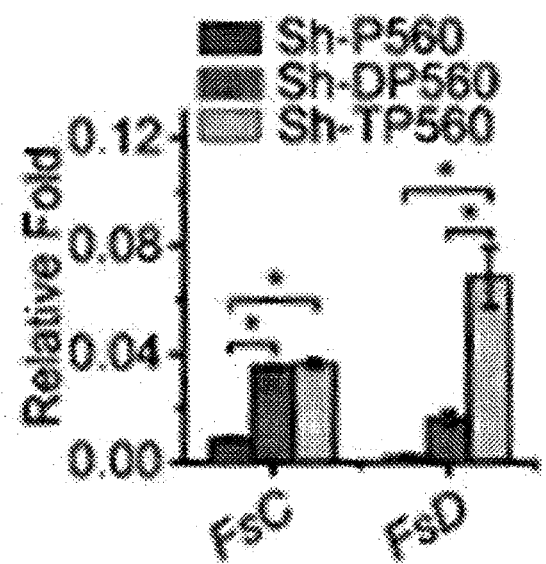
Figure 34:
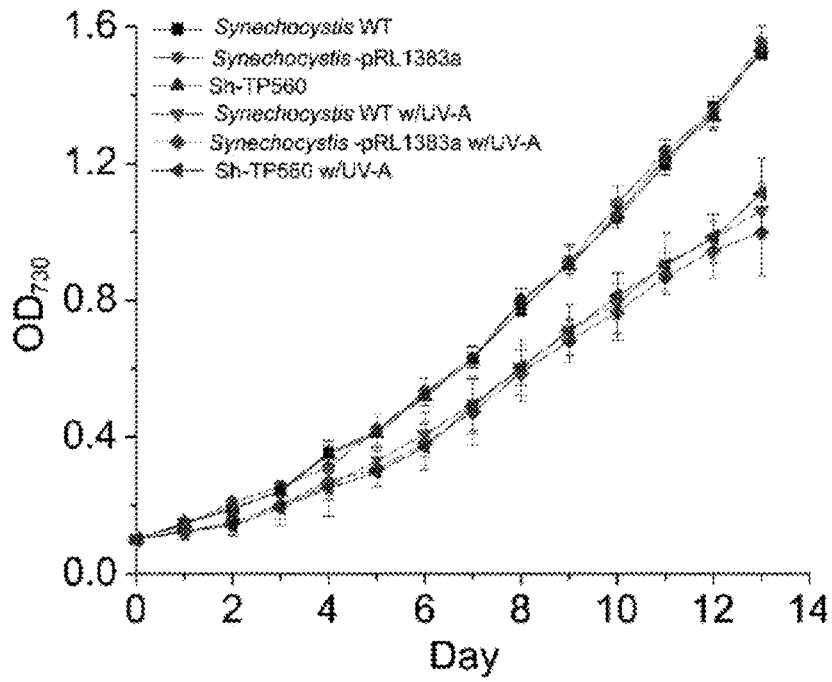
FIG. 34. Growth curves of wild type and engineered *Synechocystis* strains exposed to UV-A and white light. Data represent mean±standard deviation (n=3).

To further improve the shinorine productivity, the expression of FsC in Sh-P560 was enhanced, which can lead to the complete conversion of otherwise-accumulated 4-DG. Given its strongest strength among the tested promoters (FIGS. 28A-28B), Pcpc560 was selected and inserted upstream of FsC gene of the shinorine cluster in Sh-P560 (FIG. 32A). The new construct was then used to generate Sh-DP560 that was further validated by PCR and RT-PCR analysis (FIGS. 32B-32C). 4-DG disappeared from the methanolic extract of Sh-DP560 and the yield of shinorine was improved to 1.93±0.09 mg/g DW (FIG. 33A, Table 4). However, Sh-DP560 produced one new dominant compound along with shinorine, which had a retention time of 5.2 min in the HPLC analysis and was missing from Sh-Pori and Sh-P560 (FIGS. 28A and 33A). This compound was determined as MG based on its absorbance maximum at 310 nm and its expected molecular weight (FIG. 31). The disappeared 4-DG in Sh-DP560 indicated the improved expression of FsC by the newly inserted Pcpc560 but the accumulated MG suggested the relatively low transcription of FsD and/or the insufficient catalytic efficiency of its encoded NRPS. Indeed, the second Pcpc560 improved the transcription levels of FsC and FsD by 4 and 8 times, respectively, compared with Sh-P560 (FIG. 33B, Table 5). However, the level of FsD remained the lowest among all genes and was over 2 times lower than FsC. Improving the expression of FsD can likely divert more MG for the synthesis of shinorine. Accordingly, the third Pcpc560 promoter was inserted into the intergenic region of FsC and FsD and the production strain Sh-TP560 (FIGS. 32A-32C) was created. The qRT-PCR analysis revealed a 5-fold increase of FsD transcription in Sh-TP560, making it 2 times higher than FsC (FIG. 33B). Remarkably, all MG was converted to the final product in Sh-TP560 and the titer of shinorine was improved to 2.37±0.21 mg/g DW (FIG. 33A, Table 4). Importantly, the overproduction of shinorine had no effect on the growth of Sh-TP560 (FIG. 34). Compared with the commercially used red algae *P. umbilicalis*, Sh-TP560 possesses about 73% of its shinorine productivity but requires a significantly shorter growth period, suggesting the potential of Sh-TP560 to supply shinorine for commercial use. In addition, lack of any accumulation of any biosynthetic intermediate in Sh-TP560 makes it superior to other microbial hosts for the production of shinorine.

The Effect of Extracellular Serine on the Production of Shinorine in Sh-TP560

Figure 21A:
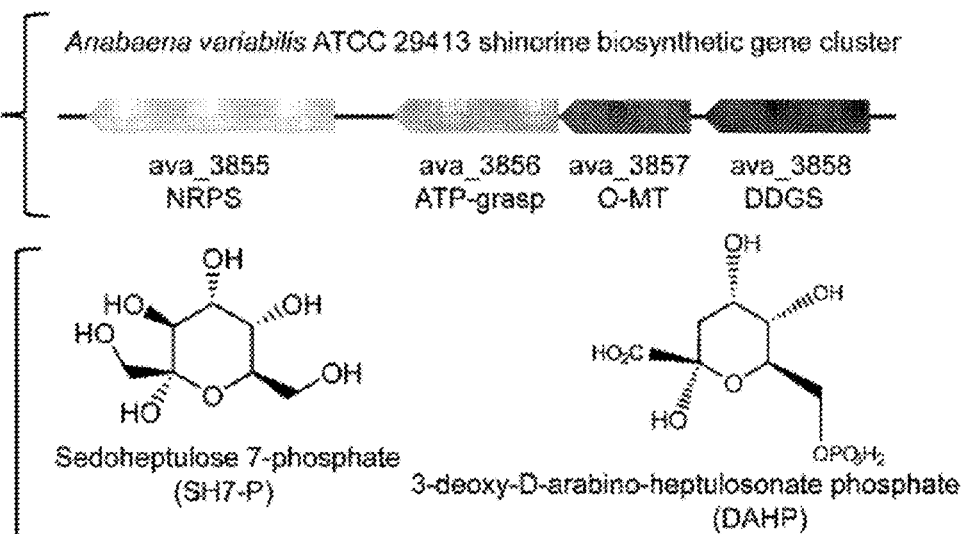
FIGS. 21A-21B. Biosynthesis pathway of shinorine. (A) The shinorine gene cluster in *Anabaena* consists of four genes encoding demethyl 4-deoxygadusol synthase, O-methyltransferase, ATP-grasp ligase, nonribosomal peptide synthetase (NRPS), respectively; (B) The biosynthesis of shinorine in *Anabeana* and other organisms. Two routes to 4-DG are known.
Figure 21B:
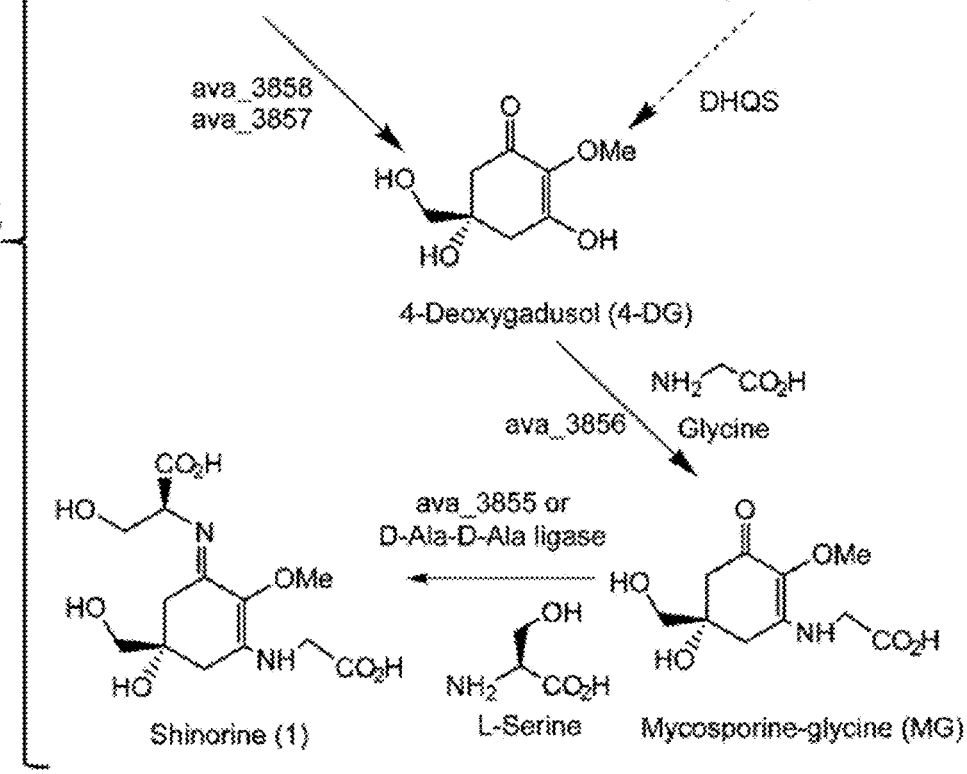

Increased precursor supply can improve the productivity of natural products in heterologous hosts. The shinorine biosynthesis requires SH-7P, glycine and serine as building blocks (FIGS. 21A-21B). The complete conversion of 4-DG into MG in Sh-DP560 and SH-TP560 suggested that shinorine biosynthesis is not limited by the cellular availability of glycine. On the other hand, the higher transcription level of FsD than FsC along with lack of any accumulation of MG in Sh-TP560 (FIG. 33B) led the examination of whether the availability of 1-serine might constrain the shinorine production. Therefore 1-serine was included at a final concentration of 0.5 mM in BG-11 medium to culture Sh-TP560 for 13 days. The same titers of shinorine were observed in serine-treated and serine-untreated Sh-TP560 (Table 4), suggesting 1-serine not to be a limiting factor of the shinorine production in Sh-TP560. When its concentration in BG-11 was higher than 0.5 mM, 1-serine inhibited the strain growth in a dose-dependent manner. Further improvement of shinorine production may be achieved by using stronger promoters, incorporating catalytically more active enzymes, and/or diverting additional metabolic flux toward the shinorine biosynthesis.

Protection of Sh-TP560 from UV rays by the Expressed Shinorine

Figure 35:
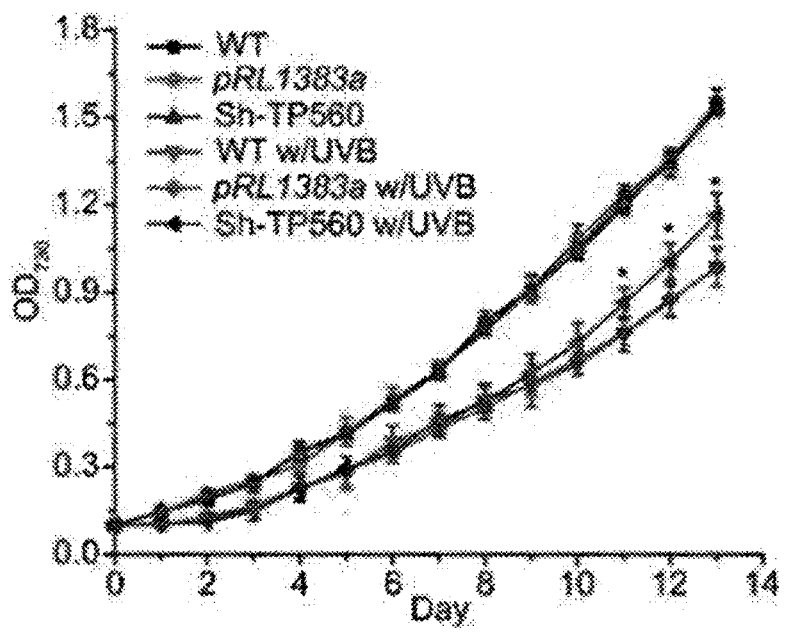
FIG. 35. Growth curves of WT and engineered *Synechocystis* strains under the treatment of UV rays and white lights for 13 days. Data represent mean±standard deviation (n=3). * indicates statistically significant difference (p<0.05, Student's t-test) of growth rates between Sh-TP560 and the two controls after UV-B exposure.

The primary biological function of MAAs is believed to protect organisms from the damages of UV radiation. To assess the photoprotective effect of shinorine on the growth of Sh-TP560, WT, *Synechocystis*-pRL1383a and Sh-TP560 were exposed to UV rays of 312 nm (UV-B) and 365 nm (UV-A) and white light for 5 hours per day for a total of 13 days. Compared with white light, UV rays reduced the growth of all strains (FIGS. 34 and 35). Remarkably, when exposed to UV-B, the cell densities ($OD_{730}$) of Sh-TP560 were similar to the two control strains within the first 10 days but were significantly higher from day 11 to 13 (FIG. 35). In contrast, no growth differences were observed when these strains were treated by UV-A (FIG. 34). Interestingly, UV rays had a minor effect on the production of shinorine in Sh-TP560 (Table 4). These results demonstrate that shinorine can protect its producer from the harmful effects of UV-B radiation.

As such, the current invention demonstrates the use of *Synechocystis* as the heterologous host to overproduce cyanobacterial natural product shinorine, a commercially valuable MAA. A useful strategy for improving the titer of shinorine in *Synechocystis* is provided, which integrated transcriptional and metabolic profiling with the transcriptional manipulation of biosynthetic genes. Sh-TP560 strain has shinorine productivity of 2.37±0.21 mg/g DW, marking it as a promising alternative of the red algae *P. umbilicalis* for the commercial supply of shinorine. Previous attempts to express cyanobacterial natural products, particularly polyketides and nonribosomal peptides, in *E. coli* or *Streptomyces* strains have resulted in limited success. These results indicate that *Synechocystis* is a new enabling host for probing the chemical potential of cyanobacterial species and producing cyanobacterial natural products and thereof. The photosynthetic nature of Synechocystis further makes the production of expressed compounds to be environmentally friendly and cost-effective. Also, the invention characterizes the photoprotective effects of shinorine in a heterologous host.

Materials and Methods

Extraction of Shinorine from Cyanobacterial Biomass

Anabaena, Fischerella, and wild type and engineered Synechocystis strains were grown in 600 ml of BG-11 medium at 26° C. with air bubbling. The culture media were centrifuged (4° C., 5,000 rpm for 10 min) to collect cell pellets after 13 days for Synechocystis strains and 21 days for filamentous strains. The pellets were then resuspended in 10 ml cooled methanol and lysed by sonication on ice with 2-s pulses. After centrifugation (4° C., 5,000 rpm for 30 min, the clear supernatants of lysates were collected and evaporated under reduced pressure. The dried residues were resuspended in water (1 ml) for HPLC and LC-MS analysis. Authentic shinorine was isolated from Helioguard 365 (Mibelle Biochemistry, USA) following the previous protocol.

Quantitative RT-PCR Analysis of Shinorine Biosynthetic Genes

Total RNA samples were isolated from engineered Synechocystis strains using ZR Fungal/Bacterial RNA MiniPrep kit (Zymo Research). The quantity and quality of the isolated RNAs were determined using Nanodrop. Synthesis of cDNAs was performed with random primers following the manufacturer's protocol (Thermo Scientific). The synthesized cDNAs were used as templates for qPCR to detect the transcription levels of shinorine biosynthetic genes and rnpB, while the isolated RNA samples themselves were used as the templates of PCR reactions to detect any residual genomic DNAs using primers listed in Table 6. The student's t-test analysis was applied to determine the difference between the samples, and a P-value <0.05 was considered to be statistically significant.

Reagents, Strains and Culture Conditions

Restriction enzymes, recombinant Taq DNA polymerase and Phusion DNA polymerase were purchased from Fisher Scientific or New England Labs. Spectinomycin and chloramphenicol were purchased from RPI Corp (USA). All other chemicals were from Fisher or Sigma-Aldrich. The GeneJET Plasmid Miniprep Kit, PCR Purification Kit and Gel Extraction Kit (Thermo Scientific) were used for molecular biology studies. All oligonucleotide primers used in this example were synthesized by Sigma-Aldrich and were listed in Table 6.

TABLE 6

Oligonucleotides used in Example 2.

| Primers | Sequence 5' to 3' | Function |
|---|---|---|
| Shi-Ori-F | CGTACGTACTACTTAATTGACAAATA (SEQ ID NO: 32) | Amplification of original gene cluster |
| Shi-Ori-R | GAGCTCCCCGACTTCTCAAAGGATAC (SEQ ID NO: 33) | |
| Shi-1211-F | CTCGAGGACGTCATGGGTACACCTCACG CTAC (SEQ ID NO: 34) | Cloning of gene cluster into pSL1211 |
| Shi-1211-R | CATATGCCCGACTTCTCAAAGGATAC (SEQ ID NO: 35) | |
| Ptrc-shi-F | CGTACGATTCTGAAATGAGCTGTTGACA A (SEQ ID NO: 36) | Amplification of Ptrc-shinorine gene cluster |
| Ptrc-shi-R | GAGCTCCCCGACTTCTCAAAGGATAC (SEQ ID NO: 37) | |
| PrnpB-AP-F | CTGCAGTTCAATGCGGTCCAATAC (SEQ ID NO: 38) | Amplification of PrnpB and fusion with APPT |
| PrnpB-AP-R | AGCCAAGTATGCTGCAACATTTTTTCTAG TGTGCCATTG (SEQ ID NO: 39) | |
| Pr-APPT-F | CAATGGCACACTAGAAAAAATGTTGCAG CATACTTGGCT (SEQ ID NO: 40) | Amplification of APPT and fusion with PrnpB |
| Pr-APPT-R | GCATGCTCAATAATGCCAGAATTTTG (SEQ ID NO: 41) | |
| PrnpB-F | CGTACGTTCAATGCGGTCCAATAC (SEQ ID NO: 42) | Amplification of PrnpB for the construction of pShi-PrnpB |
| PrnpB-R | ACGTCTTTTTCTAGTGTGCCATTG (SEQ ID NO: 43) | |
| P560-F | CGTACGCATTGAATTAATCTCCTAC (SEQ ID NO: 44) | Amplification of Pcpc560 for the construction of pShi-P560 |
| P560-R | GACGTCCACCTGTAGAGAAGAGTC (SEQ ID NO: 45) | |
| P560-FmysAB-F | CGTACGCATTGAATTAATCTC (SEQ ID NO: 46) | Amplification of Pcpc560-FsAB |
| P560-FmysAB-R | GAGCTCCTACAACCGCCGAATTAAAG (SEQ ID NO: 47) | |

TABLE 6-continued

Oligonucleotides used in Example 2.

| Primers | Sequence 5' to 3' | Function |
| --- | --- | --- |
| P560-CD-F | GAGCTCCATTGAATTAATCTCCTAC (SEQ ID NO: 48) | Amplification of Pcpc560 for fusion of P560-FsCD |
| P560-CD-R | CAGAAATAGATTGTGTCATCACCTGTAG AGAAGAGTC (SEQ ID NO: 49) | |
| P5-FmysCD-F | GACTCTTCTCTACAGGTGATGACACAATC TATTTCTG (SEQ ID NO: 50) | Amplification of FsCD for fusion of P560-FsCD |
| P5-FmysCD-R | CCGCTCGAGAGATTGTTCTTCCAATTCTT C (SEQ ID NO: 51) | |
| P560-C-F | GAGCTCCATTGAATTAATCTCCTAC (SEQ ID NO: 52) | Amplification of Pcpc560 for fusion of P560-FsC |
| P560-C-R | CAGAAATAGATTGTGTCATCACCTGTAG AGAAGAGTC (SEQ ID NO: 53) | |
| P5-FmysC-F | GACTCTTCTCTACAGGTGATGACACAATC TATTTCTG (SEQ ID NO: 54) | Amplification of FsC for fusion of P560-FsC |
| P5-FmysC-R | GGTACCCTAATCGCCACCAAACTC (SEQ ID NO: 55) | |
| P560-D-F | GTACCCATTGAATTAATCTCCTAC (SEQ ID NO: 56) | Amplification of Pcpc560 for fusion of P560-FsD |
| P560-D-R | CTAAAAAGTTTATTATTTCCATCACCTGT AGAGAAGAGTC (SEQ ID NO: 57) | |
| P5-FmysD-F | GACTCTTCTCTACAGGTGATGGAAATAAT AAACTTTTTAG (SEQ ID NO: 58) | Amplification of FsD for fusion of P560-FsD |
| P5-FmysD-R | GTCGACCCCGACTTCTCAAAGGATAC (SEQ ID NO: 59) | |
| Pori-FmysA-F | TGTGAATTAGTTGTAATG (SEQ ID NO: 60) | Colony PCR Pori-FsA |
| Pori-FmysA-R | CTACTTTAATCGCAATTC (SEQ ID NO: 61) | |
| FmysD-APPT-F | CAATTCACCCATAGTAGC (SEQ ID NO: 62) | Colony PCR FsD-APPT |
| FmysD-APPT-R | TAATCAAATTTAACTTGC (SEQ ID NO: 63) | |
| Ptrc-FmysA-F | CGTACGATTCTGAAATGAGCTGTTGACA A (SEQ ID NO: 64) | Colony PCR Ptrc-FsA |
| PrnpB-FmysA-F | CGTACGTTCAATGCGGTCCAATAC (SEQ ID NO: 65) | Colony PCR PrnpB-FsA |
| P560-FmysA-F | CGTACGCATTGAATTAATCTCCTAC (SEQ ID NO: 66) | Colony PCR Pcpc560-FsA |
| FmysA-R | GCTCATGCAGGTTTGGAG (SEQ ID NO: 67) | Colony PCR FsA reverse primer |
| DP560-FmysC-F | GAGCTCCATTGAATTAATCTCCTAC (SEQ ID NO: 68) | Colony PCR Pcpc560-FsC |
| DP560-FmysC-R | GTAAGCCTACCTACTGGA (SEQ ID NO: 69) | |
| TP560-FmysD-F | GGTACCCATTGAATTAATCTCCTAC (SEQ ID NO: 70) | Colony PCR Pcpc560-FsD |
| TP560-FmysD-R | GAGCGATGAATACCCATC (SEQ ID NO: 71) | |
| RT-FmysA-F | AGTAGTTGATGCGTTTGC (SEQ ID NO: 72) | RT-PCR FsA |
| RT-FmysA-R | CTACTTTAATCGCAATTC (SEQ ID NO: 73) | |
| RT-FmysB-F | GTGAACACACCACTACTG (SEQ ID NO: 74) | RT-PCR FsB |
| RT-FmysB-R | ACACTCTTGGCTTTAGTC (SEQ ID NO: 75) | |

TABLE 6-continued

Oligonucleotides used in Example 2.

| Primers | Sequence 5' to 3' | Function |
|---|---|---|
| RT-FmysC-F | CAAGATGGCACAATCTAC (SEQ ID NO: 76) | RT-PCR FsC |
| RT-FmysC-R | TCCAGTAGGTAGGCTTAC (SEQ ID NO: 77) | |
| RT-FmysD-F | AACATGTCCAACCCATAC (SEQ ID NO: 78) | RT-PCR FsD |
| RT-FmysD-R | GAGCGATGAATACCCATC (SEQ ID NO: 79) | |

E. coli DH5α and E. coli HB101 were used for routine molecular biology studies and triparental-mating conjugation, respectively. Both strains were maintained in LB medium supplemented with 50 µg/ml spectinomycin or 25 µg/ml chloramphenicol. Synechocystis, Fischerella, and Anabaena were purchased from UTEX and Anabaena sp. PCC 7120 was received. All cyanobacteria strains were grown in media bottles containing 300-600 ml BG-11 medium. Spectinomycin was added in a final concentration of 50 µg/ml to the cultures of engineered Synechocystis strains. All cultures were incubated at 26° C. with continuous air bubbling and under 16 h/8 h light/dark lighting cycle with illumination of 2000-2500 lux during lighting period. For plate growth, BG-11 medium was supplemented with 1.0% (wt/vol) agar and 0.3% (wt/vol) sodium thiosulfate. To determine the growth curves, Synechocystis strains were inoculated to 300 mL of BG-11 to reach an initial $OD_{730}$ of 0.1 and then grew under the above conditions. Measurements were taken daily by detecting the $OD_{730}$ on a Shimadzu UV-2700 UV-Vis spectrophotometer.

To test the effects of serine on the shinorine production, Sh-TP560 cells were first grown under the above conditions for 5 days to reach an optical density (OD730) of 0.4. Then, 0.5 mM L-serine was added into the cultures and shinorine was extracted from cell pellets after 8 days.

For UV radiation experiments, liquid cultures were grown in sterile plastic petri dishes (90 mm×15 mm) and exposed to UV and white lights for 5 hours per day. Light illumination was achieved through Spectronics ENB-260C 6W UV Lamp with the wavelength of 312 nm (UV-B) or 365 nm (UV-A) and LED lamp for the white light. The light intensity was 1.2 and 1.3 $W/m^{-2}$ for UV-B and UV-A, respectively. All cultures were shaken several times during the light exposure to avoid self-shading.

Bioinformatics Analysis of Shinorine Biosynthetic Gene Clusters in Cyanobacteria The protein sequences encoded by the shinorine biosynthetic genes in Anabaena (ava_3855-ava_3858) were used as queries to mine the genomes of subsection V cyanobacterial strains currently available in NCBI database (up to July, 2017) using BLAST program. Multiple sequence alignments and similarity scores were generated using Clustal Omega (see Worldwide Website: ebi.ac.uk/Tools/msa/clustalo/). PromoterHunter program (see Worldwide Website: phisite.org/main/index.php?nav=tools&nav_sel=hunter) was used to analyze the upstream and the intergenic regions of the shinorine biosynthetic gene cluster in Fischerella.

DNA Manipulation and Plasmid Construction gDNA was isolated according to methods described in Example 1.

PCR amplification of the shinorine gene cluster in Fischerella was carried out using the primers shown in Table 6. The cluster was cloned into pRL1383a vector to create pRL1383-Pori-Shi. The APPT gene was amplified from Anabaena sp. PCC7120 gDNA. The PrnpB promoter was amplified from Synechocystis gDNA. PrnpB and APPT were fused in the PCR reaction and then cloned into pRL1383-Pori-Shi to generate the pShiOri (FIG. 25A). Following the similar strategy, other shinorine expression constructs were prepared.

HPLC and LC-MS Analysis of Extracted Shinorine

HPLC and LC-MS analysis of extracted shinorine were conducted according to the methods described in Example 1.

REFERENCES

1. Balskus, E. P., and Walsh, C. T. (2010) The genetic and molecular basis for sunscreen biosynthesis in cyanobacteria, Science 329, 1653-1656.
2. Baran, P. S., Maimone, T. J., and Richter, J. M. (2007) Total synthesis of marine natural products without using protecting groups, Nature 446, 404-408.
3. Barry, S. M., Kers, J. A., Johnson, E. G., Song, L., Aston, P. R., Patel, B., Krasnoff, S. B., Crane, B. R., Gibson, D. M., and Loria, R. (2012) Cytochrome P450—catalyzed L-tryptophan nitration in thaxtomin phytotoxin biosynthesis, Nature chemical biology 8, 814-816.
4. Baumann, H. I., Keller, S., Wolter, F. E., Nicholson, G. J., Jung, G., Süssmuth, R. D., and Jüttner, F. (2007) Planktocyclin, a cyclooctapeptide protease inhibitor produced by the freshwater cyanobacterium Planktothrix rubescens, Journal of natural products 70, 1611-1615.
5. Beck, C., Knoop, H., Axmann, I. M., and Steuer, R. (2012) The diversity of cyanobacterial metabolism: genome analysis of multiple phototrophic microorganisms, BMC Genomics 13, 56.
6. Becker, K., Hartmann, A., Ganzera, M., Fuchs, D., and Gostner, J. M. (2016) Immunomodulatory Effects of the Mycosporine-Like Amino Acids Shinorine and Porphyra-334, Marine drugs 14, 119.
7. Beld, J., Sonnenschein, E. C., Vickery, C. R., Noel, J. P., and Burkart, M. D. (2014) The phosphopantetheinyl transferases: catalysis of a post-translational modification crucial for life, Natural product reports 31, 61-108.
8. Berla, B. M., Saha, R., Immethun, C. M., Maranas, C. D., Moon, T. S., and Pakrasi, H. (2013) Synthetic biology of cyanobacteria: unique challenges and opportunities, Frontiers in microbiology 4, 246.
9. Burja, A. M., Banaigs, B., Abou-Mansour, E., Burgess, J. G., and Wright, P. C. (2001) Marine cyanobacteria—a prolific source of natural products, Tetrahedron 57, 9347-9377.

10. Campbell, E. L., Cohen, M. F., and Meeks, J. C. (1997) A polyketide-synthase-like gene is involved in the synthesis of heterocyst glycolipids in Nostoc punctiforme strain ATCC 29133, Archives of microbiology 167, 251-258.

11. Carreto, J. I., and Carignan, M. O. (2011) Mycosporine-like amino acids: relevant secondary metabolites. Chemical and ecological aspects, Marine drugs 9, 387-446.

12. Conde, F. R., Churio, M. S., and Previtali, C. M. (2004) The deactivation pathways of the excited-states of the mycosporine-like amino acids shinorine and porphyra-334 in aqueous solution, Photochemical & Photobiological Sciences 3, 960-967.

13. Copp, J. N., and Neilan, B. A. (2006) The phosphopantetheinyl transferase superfamily: phylogenetic analysis and functional implications in cyanobacteria, Applied and environmental microbiology 72, 2298-2305.

14. Copp, J., Roberts, A., Marahiel, M., and Neilan, B. (2007) Characterization of PPTNs, a cyanobacterial phosphopantetheinyl transferase from Nodularia spumigena NSOR10, Journal of bacteriology 189, 3133-3139.

15. D'Agostino, P. M., Javalkote, V. S., Mazmouz, R., Pickford, R., Puranik, P. R., and Neilan, B. A. (2016) Comparative profiling and discovery of novel glycosylated mycosporine-like amino acids in two strains of the cyanobacterium Scytonema cf. crispum, Applied and environmental microbiology 82, 5951-5959.

16. De la Coba, F., Aguilera, J., De Galvez, M., Alvarez, M., Gallego, E., Figueroa, F., and Herrera, E. (2009) Prevention of the ultraviolet effects on clinical and histopathological changes, as well as the heat shock protein-70 expression in mouse skin by topical application of algal UV-absorbing compounds, Journal of dermatological science 55, 161-169.

17. Ding, Y., Rath, C. M., Bolduc, K. L., Hakansson, K., and Sherman, D. H. (2011) Chemoenzymatic synthesis of cryptophycin anticancer agents by an ester bond-forming non-ribosomal peptide synthetase module, J Am Chem Soc 133, 14492-14495.

18. Dittmann, E., Gugger, M., Sivonen, K., and Fewer, D. P. (2015) Natural product biosynthetic diversity and comparative genomics of the cyanobacteria, Trends in microbiology 23, 642-652.

19. Elhai, J., and Wolk, C. P. (1988) [83] Conjugal transfer of DNA to cyanobacteria, Methods in enzymology 167, 747-754.

20. Elovson, J., and Vagelos, P. R. (1968) Acyl carrier protein. X. Acyl carrier protein synthetase, The Journal of biological chemistry 243, 3603-3611.

21. Englund, E., Liang, F., and Lindberg, P. (2016) Evaluation of promoters and ribosome binding sites for biotechnological applications in the unicellular cyanobacterium Synechocystis sp. PCC 6803, Scientific reports 6, 36640.

22. Favre-Bonvin, J., Bernillon, J., Salin, N., and Arpin, N. (1987) Biosynthesis of mycosporines: mycosporine glutaminol in Trichothecium roseum, Phytochemistry 26, 2509-2514.

23. Gago-Ferrero, P., Diaz-Cruz, M. S., and Barcelo, D. (2012) An overview of UV-absorbing compounds (organic UV filters) in aquatic biota, Analytical and bioanalytical chemistry 404, 2597-2610.

24. Gao, Q., and Garcia-Pichel, F. (2011) An ATP-grasp ligase involved in the last biosynthetic step of the iminomycosporine shinorine in Nostoc punctiforme ATCC 29133, Journal of bacteriology 193, 5923-5928.

25. Garcia-Pichel, F., Wingard, C. E., and Castenholz, R. W. (1993) Evidence regarding the UV sunscreen role of a mycosporine-like compound in the cyanobacterium Gloeocapsa sp, Applied and Environmental Microbiology 59, 170-176.

26. George, N., Pick, H., Vogel, H., Johnsson, N., and Johnsson, K. (2004) Specific labeling of cell surface proteins with chemically diverse compounds, J Am Chem Soc 126, 8896-8897.

27. Gu, L., Wang, B., Kulkarni, A., Geders, T. W., Grindberg, R. V., Gerwick, L., Håkansson, K., Wipf, P., Smith, J. L., and Gerwick, W. H. (2009) Metamorphic enzyme assembly in polyketide diversification, Nature 459, 731-735.

28. Guerrero, F., Carbonell, V., Cossu, M., Correddu, D., and Jones, P. R. (2012) Ethylene synthesis and regulated expression of recombinant protein in Synechocystis sp. PCC 6803, PLoS One 7.

29. Häder, D.-P., Helbling, E., Williamson, C., and Worrest, R. (2011) Effects of UV radiation on aquatic ecosystems and interactions with climate change, Photochemical & Photobiological Sciences 10, 242-260.

30. Hartmann, A., Murauer, A., and Ganzera, M. (2017) Quantitative analysis of mycosporine-like amino acids in marine algae by capillary electrophoresis with diode-array detection, Journal of pharmaceutical and biomedical analysis 138, 153-157.

31. Hayashi, O, KATOH, T., and OKUWAKI, Y. (1994) Enhancement of antibody production in mice by dietary Spirulina platensis, Journal of nutritional science and vitaminology 40, 431-441.

32. Hopwood, D. A. (2009) Complex enzymes in microbial natural product biosynthesis, Part A: overview articles and peptides, Vol. 458, Academic Press.

33. Huang, H.-H., Camsund, D., Lindblad, P., and Heidorn, T. (2010) Design and characterization of molecular tools for a Synthetic Biology approach towards developing cyanobacterial biotechnology, Nucleic acids research 38, 2577-2593.

34. Jaki, B., Orjala, J., and Sticher, O. (1999) A novel extracellular diterpenoid with antibacterial activity from the cyanobacterium Nostoc commune, Journal of natural products 62, 502-503.

35. Jones, A. C., Ottilie, S., Eustáquio, A. S., Edwards, D. J., Gerwick, L., Moore, B. S., and Gerwick, W. H. (2012) Evaluation of Streptomyces coelicolor A3 (2) as a heterologous expression host for the cyanobacterial protein kinase C activator lyngbyatoxin A, FEBS Journal 279, 1243-1251.

36. Kanekiyo, K., Lee, J.-B., Hayashi, K., Takenaka, H., Hayakawa, Y., Endo, S., and Hayashi, T. (2005) Isolation of an Antiviral Polysaccharide, Nostoflan, from a Terrestrial Cyanobacterium, Nostoc f lagelliforme, Journal of natural products 68, 1037-1041.

37. Karentz, S., Cleaver, J. E., and Mitchell, D. L. (1991) DNA damage in the Antarctic, Nature 350, 28.

38. Katoch, M., Mazmouz, R., Chau, R., Pearson, L. A., Pickford, R., and Neilan, B. A. (2016) Heterologous Production of Cyanobacterial Mycosporine-Like Amino Acids Mycosporine-Ornithine and Mycosporine-Lysine in Escherichia coli, Applied and environmental microbiology 82, 6167-6173.

39. Kim, E. J., Lee, J. H., Choi, H., Pereira, A. R., Ban, Y. H., Yoo, Y. J., Kim, E., Park, J. W., Sherman, D. H., and Gerwick, W. H. (2012) Heterologous production of 4-O-demethylbarbamide, a marine cyanobacterial natural product, Organic letters 14, 5824-5827.

40. Koehn, F. E., and Carter, G. T. (2005) The evolving role of natural products in drug discovery, Nature reviews Drug discovery 4, 206-220.
41. Kumar, S., Stecher, G., and Tamura, K. (2016) MEGA7: Molecular Evolutionary Genetics Analysis version 7.0 for bigger datasets, Molecular biology and evolution, msw054.
42. Lai, M. C., and Lan, E. I. (2015) Advances in metabolic engineering of cyanobacteria for photosynthetic biochemical production, Metabolites 5, 636-658.
43. Lambalot, R. H., and Walsh, C. T. (1997) [27] Holo-[acyl-carrier-protein] synthase of *Escherichia coli*, Methods in enzymology 279, 254-262.
44. Lambalot, R. H., Gehring, A. M., Flugel, R. S., Zuber, P., LaCelle, M., Marahiel, M. A., Reid, R., Khosla, C., and Walsh, C. T. (1996) A new enzyme superfamily—the phosphopantetheinyl transferases, Chemistry & Biology 3, 923-936.
45. Lawrence, K. P., Long, P. F., and Young, A. R. (2017) Mycosporine-like Amino Acids for Skin Photoprotection, Current medicinal chemistry.
46. Leao, T., Castelão, G., Korobeynikov, A., Monroe, E. A., Podell, S., Glukhov, E., Allen, E. E., Gerwick, W. H., and Gerwick, L. (2017) Comparative genomics uncovers the prolific and distinctive metabolic potential of the cyanobacterial genus Moorea, Proceedings of the National Academy of Sciences 114, 3198-3203.
47. Li, B., Sher, D., Kelly, L., Shi, Y., Huang, K., Knerr, P. J., Joewono, I., Rusch, D., Chisholm, S. W., and Van Der Donk, W. A. (2010) Catalytic promiscuity in the biosynthesis of cyclic peptide secondary metabolites in planktonic marine cyanobacteria, Proceedings of the National Academy of Sciences 107, 10430-10435.
48. Lindberg, P., Park, S., and Melis, A. (2010) Engineering a platform for photosynthetic isoprene production in cyanobacteria, using *Synechocystis* as the model organism, Metabolic engineering 12, 70-79.
49. Liu, T., Mazmouz, R., Ongley, S. E., Chau, R., Pickford, R., Woodhouse, J. N., and Neilan, B. A. (2017) Directing the Heterologous Production of Specific Cyanobacterial Toxin Variants, 12, 2021-2029.
50. Llewellyn, C. A., and Airs, R. L. (2010) Distribution and abundance of MAAs in 33 species of microalgae across 13 classes, Mar Drugs 8, 1273-1291.
51. Luesch, H., Harrigan, G., Goetz, G., and Horgen, F. (2002) The cyanobacterial origin of potent anticancer agents originally isolated from sea hares, Current medicinal chemistry 9, 1791-1806.
52. Lüning, K., Titlyanov, E., and Titlyanova, T. (1997) Diurnal and circadian periodicity of mitosis and growth in marine macroalgae. III. The red alga Porphyra umbilicalis, European Journal of Phycology 32, 167-173.
53. Luo, Y., Enghiad, B., and Zhao, H. (2016) New tools for reconstruction and heterologous expression of natural product biosynthetic gene clusters, Natural product reports 33, 174-182.
54. Markley, A. L., Begemann, M. B., Clarke, R. E., Gordon, G. C., and Pfleger, B. F. (2014) Synthetic biology toolbox for controlling gene expression in the cyanobacterium *Synechococcus* sp. strain PCC 7002, ACS synthetic biology 4, 595-603.
55. Martins, A., Vieira, H., Gaspar, H., and Santos, S. (2014) Marketed marine natural products in the pharmaceutical and cosmeceutical industries: Tips for success, Marine drugs 12, 1066-1101.
56. Méjean, A., Mann, S., Vassiliadis, G. I., Lombard, B. r. r., Loew, D., and Ploux, O. (2009) In vitro reconstitution of the first steps of anatoxin-a biosynthesis in Oscillatoria PCC 6506: from free L-proline to acyl carrier protein bound dehydroproline, Biochemistry 49, 103-113.
57. Micallef, M. L., D'Agostino, P. M., Sharma, D., Viswanathan, R., and Moffitt, M. C.
(2015) Genome mining for natural product biosynthetic gene clusters in the Subsection V cyanobacteria, BMC genomics 16, 669.
58. Miranda, L. N., Hutchison, K., Grossman, A. R., and Brawley, S. H. (2013) Diversity and abundance of the bacterial community of the red macroalga Porphyra umbilicalis: did bacterial farmers produce macroalgae?, PLoS One 8, e58269.
59. Miyamoto, K. T., Komatsu, M., and Ikeda, H. (2014) Discovery of gene cluster for mycosporine-like amino acid biosynthesis from Actinomycetales microorganisms and production of a novel mycosporine-like amino acid by heterologous expression, Applied and environmental microbiology 80, 5028-5036.
60. Mo, S., Krunic, A., Chlipala, G., and Orjala, J. (2009) Antimicrobial ambiguine isonitriles from the cyanobacterium *Fischerella ambigua*, Journal of natural products 72, 894.
61. Mootz, H. D., Finking, R., and Marahiel, M. A. (2001) 4'-Phosphopantetheine transfer in primary and secondary metabolism of *Bacillus subtilis*, Journal of Biological Chemistry 276, 37289-37298.
62. Mushir, S., and Fatma, T. (2011) Ultraviolet radiation-absorbing mycosporine-like amino acids in Cyanobacterium Aulosira fertilissima: environmental perspective and characterization, Curr Res J Biol Sci 3, 165-171.
63. Ongley, S. E., Bian, X., Neilan, B. A., and Müller, R. (2013) Recent advances in the heterologous expression of microbial natural product biosynthetic pathways, Natural product reports 30, 1121-1138.
64. Ongley, S. E., Bian, X., Zhang, Y., Chau, R., Gerwick, W. H., Müller, R., and Neilan, B. A. (2013) High-titer heterologous production in *E. coli* of lyngbyatoxin, a protein kinase C activator from an uncultured marine cyanobacterium, ACS chemical biology 8, 1888-1893.
65. Oren, A., and Gunde-Cimerman, N. (2007) Mycosporines or mycosporine-like amino acids: UV protectants or multipurpose secondary metabolites?, FEMS Microbiology Letters 269, 1-10.
66. Pfeifer, B. A., Admiraal, S. J., Gramajo, H., Cane, D. E., and Khosla, C. (2001) Biosynthesis of complex polyketides in a metabolically engineered strain of E. coli, Science 291, 1790-1792.
67. Quadri, L. E. N., Weinreb, P. H., Lei, M., Nakano, M. M., Zuber, P., and Walsh, C. T. (1998) Characterization of Sfp, a *Bacillus subtilis* Phosphopantetheinyl Transferase for Peptidyl Carrier Protein Domains in Peptide Synthetases, Biochemistry 37, 1585-1595.
68. Rastogi, R. P., Sinha, R. P., Singh, S. P., and Häder, D.-P. (2010) Photoprotective compounds from marine organisms, Journal of industrial microbiology & biotechnology 37, 537-558.
69. Rippka, R., Deruelles, J., Waterbury, J. B., Herdman, M., and Stanier, R. Y. (1979) Generic assignments, strain histories and properties of pure cultures of cyanobacteria, Microbiology 111, 1-61.
70. Roberts, A. A., Copp, J. N., Marahiel, M. A., and Neilan, B. A. (2009) The *Synechocystis* sp. PCC6803 Sfp-Type Phosphopantetheinyl Transferase Does Not Possess Characteristic Broad-Range Activity, ChemBioChem 10, 1869-1877.

71. Sanchez-Quiles, D., and Tovar-Sanchez, A. (2014) Sunscreens as a source of hydrogen peroxide production in coastal waters, Environmental science & technology 48, 9037-9042.
72. Schmidt, E. W., Nelson, J. T., Rasko, D. A., Sudek, S., Eisen, J. A., Haygood, M. G., and Ravel, J. (2005) Patellamide A and C biosynthesis by a microcin-like pathway in Prochloron didemni, the cyanobacterial symbiont of Lissoclinum patella, Proc Natl Acad Sci U S A 102, 7315-7320.
73. Schneider, G. J., Turner, N. E., Richaud, C., Borbely, G., and Haselkorn, R. (1987) Purification and characterization of RNA polymerase from the cyanobacterium Anabaena 7120, The Journal of biological chemistry 262, 14633-14639.
74. Shi, Y., Yang, X., Garg, N., and van der Donk, W. A. (2011) Production of lantipeptides in Escherichia coli, J Am Chem Soc 133, 2338-2341.
75. Shih, P. M., Wu, D., Latifi, A., Axen, S. D., Fewer, D. P., Talla, E., Calteau, A., Cai, F., Tandeau de Marsac, N., Rippka, R., Herdman, M., Sivonen, K., Coursin, T., Laurent, T., Goodwin, L., Nolan, M., Davenport, K. W., Han, C. S., Rubin, E. M., Eisen, J. A., Woyke, T., Gugger, M., and Kerfeld, C. A. (2013) Improving the coverage of the cyanobacterial phylum using diversity-driven genome sequencing, Proc Natl Acad Sci U S A 110, 1053-1058.
76. Shinzato, C., Shoguchi, E., Kawashima, T., Hamada, M., Hisata, K., Tanaka, M., Fujie, M., Fujiwara, M., Koyanagi, R., Ikuta, T., Fujiyama, A., Miller, D. J., and Satoh, N. (2011) Using the Acropora digitifera genome to understand coral responses to environmental change, Nature 476, 320-323.
77. Singh, R. K., Tiwari, S. P., Rai, A. K., and Mohapatra, T. M. (2011) Cyanobacteria: an emerging source for drug discovery, The Journal of antibiotics 64, 401-412.
78. Singh, S. P., Klisch, M., Häder, D.-P., and Sinha, R. P. (2008) Role of various growth media on shinorine (mycosporine-like amino acid) concentration and photosynthetic yield in Anabaena variabilis PCC 7937, World Journal of Microbiology and Biotechnology 24, 3111.
79. Singh, S. P., Klisch, M., Sinha, R. P., and Häder, D.-P. (2010) Genome mining of mycosporine-like amino acid (MAA) synthesizing and non-synthesizing cyanobacteria: a bioinformatics study, Genomics 95, 120-128.
80. Tan, L. T. (2007) Bioactive natural products from marine cyanobacteria for drug discovery, Phytochemistry 68, 954-979.
81. Tang, Y., Frewert, S., Harmrolfs, K., Herrmann, J., Karmann, L., Kazmaier, U., Xia, L., Zhang, Y., and Muller, R. (2015) Heterologous expression of an orphan NRPS gene cluster from Paenibacillus larvae in Escherichia coli revealed production of sevadicin, Journal of biotechnology 194, 112-114.
82. Tianero, M. D. B., Donia, M. S., Young, T. S., Schultz, P. G., and Schmidt, E. W. (2011) Ribosomal route to small-molecule diversity, Journal of the American Chemical Society 134, 418-425.
83. Varman, A. M., Xiao, Y., Pakrasi, H. B., and Tang, Y. J. (2013) Metabolic engineering of Synechocystis sp. strain PCC 6803 for isobutanol production, Applied and environmental microbiology 79, 908-914.
84. Veetil, V. P., Angermayr, S. A., and Hellingwerf, K. J. (2017) Ethylene production with engineered Synechocystis sp PCC 6803 strains, Microbial cell factories 16, 34.
85. Videau, P., Wells, K. N., Singh, A. J., Gerwick, W. H., and Philmus, B. (2016) Assessment of Anabaena sp. strain PCC 7120 as a heterologous expression host for cyanobacterial natural products: production of lyngbyatoxin a, ACS synthetic biology 5, 978-988.
86. Walsh, T. A., Bevan, S. A., Gachotte, D. J., Larsen, C. M., Moskal, W. A., Merlo, P. A., Sidorenko, L. V., Hampton, R. E., Stoltz, V., Pareddy, D., Anthony, G. I., Bhaskar, P. B., Marri, P. R., Clark, L. M., Chen, W., Adu-Peasah, P. S., Wensing, S. T., Zirkle, R., and Metz, J. G. (2016) Canola engineered with a microalgal polyketide synthase-like system produces oil enriched in docosahexaenoic acid, Nat Biotechnol 34, 881-887.
87. Wang, W., Liu, X., and Lu, X. (2013) Engineering cyanobacteria to improve photosynthetic production of alka (e) nes, Biotechnology for biofuels 6, 1.
88. Wang, Y., Sun, T., Gao, X., Shi, M., Wu, L., Chen, L., and Zhang, W. (2016) Biosynthesis of platform chemical 3-hydroxypropionic acid (3-HP) directly from CO 2 in cyanobacterium Synechocystis sp. PCC 6803, Metabolic engineering 34, 60-70.
89. Weber, T., Blin, K., Duddela, S., Krug, D., Kim, H. U., Bruccoleri, R., Lee, S. Y., Fischbach, M. A., Müller, R., and Wohlleben, W. (2015) antiSMASH 3.0—a comprehensive resource for the genome mining of biosynthetic gene clusters, Nucleic acids research 43, W237-W243.
90. Whitehead, K., and Hedges, J. I. (2003) Electrospray ionization tandem mass spectrometric and electron impact mass spectrometric characterization of mycosporine-like amino acids, Rapid Commun Mass Spectrom 17, 2133-2138.
91. Xue, Y., Zhang, Y., Cheng, D., Daddy, S., and He, Q. (2014) Genetically engineering Synechocystis sp. Pasteur Culture Collection 6803 for the sustainable production of the plant secondary metabolite p-coumaric acid, Proceedings of the National Academy of Sciences 111, 9449-9454.
92. Yan, C., and Xu, X. (2008) Bifunctional enzyme FBPase/SBPase is essential for photoautotrophic growth in cyanobacterium Synechocystis sp. PCC 6803, Progress in Natural Science 18, 149-153.
93. Yang, G., Zhang, Y., Lee, N. K., Cozad, M. A., Kearney, S. E., Luesch, H., and Ding, Y. (2017) Cyanobacterial Sfp-type phosphopantetheinyl transferases functionalize carrier proteins of diverse biosynthetic pathways, Sci Rep 7, 11888.
94. Young, A. R., Claveau, J., and Rossi, A. B. (2017) Ultraviolet radiation and the skin: Photobiology and sunscreen photoprotection, Journal of the American Academy of Dermatology 76, S100-s109.
95. Yu, Y., You, L., Liu, D., Hollinshead, W., Tang, Y., and Zhang, F. (2013) Development of Synechocystis sp. PCC 6803 as a Phototrophic Cell Factory, Marine Drugs 11, 2894.
96. Zhang, H., Boghigian, B. A., Armando, J., and Pfeifer, B. A. (2011) Methods and options for the heterologous production of complex natural products, Natural product reports 28, 125-151.
97. Zhang, L., Li, L., and Wu, Q. (2007) Protective effects of mycosporine-like amino acids of Synechocystis sp. PCC 6803 and their partial characterization, Journal of photochemistry and photobiology. B, Biology 86, 240-245.
98. Zhou, J., Zhang, H., Meng, H., Zhu, Y., Bao, G., Zhang, Y., Li, Y., and Ma, Y. (2014) Discovery of a super-strong promoter enables efficient production of heterologous proteins in cyanobacteria, Scientific reports 4.
99. Ziemert, N., Ishida, K., Liaimer, A., Hertweck, C., and Dittmann, E. (2008) Ribosomal synthesis of tricyclic depsipeptides in bloom-forming cyanobacteria, Angew Chem Int Ed Engl 47, 7756-7759.Murray, M. G., and Thompson, W. F. (1980) Rapid isolation of high molecular weight plant DNA, Nucleic Acids Res 8, 4321-4326.

100. Fiore, M. F., Moon, D. H., Tsai, S. M., Lee, H., and Trevors, J. T. (2000) Miniprep DNA isolation from unicellular and filamentous cyanobacteria, J Microbiol Methods 39, 159-169.

101. Roberts, A. A., Copp, J. N., Marahiel, M. A., and Neilan, B. A. (2009) The *Synechocystis* sp. PCC6803 Sfp-type phosphopantetheinyl transferase does not possess characteristic broad-range activity, ChemBioChem 10, 1869-1877.

102. Micallef, M. L., D'Agostino, P. M., Sharma, D., Viswanathan, R., and Moffitt, M. C. (2015) Genome mining for natural product biosynthetic gene clusters in the subsection V cyanobacteria, BMC Genomics 16, 669.

We claim:

1. An expression construct comprising a promoter operably linked to a nucleic acid sequence encoding:
   (a) a *Fischerella* shinorine gene cluster comprising FsA, FsB, FsC, and FsD proteins; and
   (b) a phosphopantetheinyl transferase (PPT) from *Anabaena* sp. PCC7120 (APPT).

2. The expression construct of claim 1, wherein the promoter is a *Synechocystis* promoter.

3. The expression construct of claim 2, wherein the *Synechocystis* promoter is a PrnpB promoter or a Pcpc560 promoter.

4. The expression construct of claim 2, wherein the promoter is a synthetic promoter.

5. The expression construct of claim 4, wherein the synthetic promoter is a Ptrc promoter.

6. The expression construct of claim 1, wherein the promoter is positioned upstream relative to the nucleic acid sequence encoding the *Fischerella* shinorine gene cluster.

7. The expression construct of claim 1 further comprising a second promoter.

8. The expression construct of claim 7, wherein the second promoter is positioned between a nucleic acid sequence encoding FsB and a nucleic acid sequence encoding FsC.

9. The expression construct of claim 8, wherein the second promoter is a Pcpc560 promoter.

10. The expression construct of claim 7 further comprising a third promoter.

11. The expression construct of claim 10, wherein the third promoter is positioned between a nucleic acid sequence encoding FsC and a nucleic acid sequence encoding FsD.

12. The expression construct of claim 10, wherein the third promoter is a Pcpc560 promoter.

13. A recombinant cyanobacterial cell comprising the expression construct of claim 1.

14. The recombinant cyanobacterial cell of claim 13, wherein the cell does not comprise a native shinorine gene cluster.

15. The recombinant cyanobacterial cell of claim 13, wherein the cell is a *Synechocystis* cell.

16. The recombinant cyanobacterial cell of claim 13, wherein the expression construct is integrated into a chromosome of the cyanobacterial cell or is present in a self-replicating plasmid or module of the cyanobacterial cell.

17. A method for producing shinorine, the method comprising:
   (a) culturing the recombinant cyanobacterial cell of claim 13 under conditions permitting production of shinorine in the cell; and
   (b) isolating or recovering the shinorine from the recombinant cyanobacterial cell.

18. The method of claim 17, wherein the recombinant cyanobacterial cell is a *Synechocystis* cell.

19. The method of claim 17, wherein the expression construct of the recombinant cyanobacterial cell comprises three promoters.

20. The method of claim 19, wherein each of the three promoters is a Pcpc560 promoter.

* * * * *

```
                         SEQUENCE LISTING

<160> NUMBER OF SEQ ID NOS: 179

<210> SEQ ID NO 1
<211> LENGTH: 237
<212> TYPE: PRT
<213> ORGANISM: Unknown
<220> FEATURE:
<223> OTHER INFORMATION: Nostoc sp. PCC7120

<400> SEQUENCE: 1

Met Leu Gln His Thr Trp Leu Pro Lys Pro Asn Leu Thr Leu Leu
1               5                   10                  15

Ser Asp Glu Val His Leu Trp Arg Ile Pro Leu Asp Gln Pro Glu Ser
                20                  25                  30

Gln Leu Gln Asp Leu Ala Ala Thr Leu Ser Ser Asp Glu Leu Ala Arg
            35                  40                  45

Ala Asn Arg Phe Tyr Phe Pro Glu His Arg Arg Arg Phe Thr Ala Gly
        50                  55                  60

Arg Gly Ile Leu Arg Ser Ile Leu Gly Gly Tyr Leu Gly Val Glu Pro
65                  70                  75                  80

Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235

<210> SEQ ID NO 2
<211> LENGTH: 237
<212> TYPE: PRT
<213> ORGANISM: Anabaena variabilis

<400> SEQUENCE: 2

Met Leu Gln His Thr Trp Leu Pro Lys Pro Asn Leu Thr Leu Leu
1               5                   10                  15
```

```
Ser Asp Glu Val His Leu Trp Arg Ile Pro Leu Asp Arg Pro Glu Ser
            20                  25                  30

Gln Leu Gln His Leu Ala Ala Thr Leu Ser Ser Asp Glu Leu Ala Arg
        35                  40                  45

Ala Asn Arg Phe Tyr Phe Pro Glu His Arg Gln Arg Phe Thr Ala Gly
    50                  55                  60

Arg Gly Ile Leu Arg Ser Ile Leu Gly Leu Tyr Leu Gly Val Glu Pro
65                  70                  75                  80

Lys Gln Val Lys Phe Glu Tyr Glu Ser Arg Gly Lys Pro Val Leu Gly
                85                  90                  95

Asp Arg Phe Ala Asp Ser Gly Leu Leu Phe Asn Leu Ser His Ser Gln
            100                 105                 110

Asn Leu Gly Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Thr Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp Gln Tyr
225                 230                 235

<210> SEQ ID NO 3
<211> LENGTH: 220
<212> TYPE: PRT
<213> ORGANISM: Microcystis aeruginosa

<400> SEQUENCE: 3

Met Phe Ile Ser Thr Asp Glu Val His Leu Tyr Phe Ile Ser Leu Asp
1               5                   10                  15

Pro Ser Gly Asp Arg Leu Glu Thr Leu Ala Ser Leu Leu Ser Glu Asp
            20                  25                  30

Glu Ile Ile Arg Ala Asn Arg Tyr His Phe Pro Glu His Lys Arg Arg
        35                  40                  45

Phe Leu Val Ala Arg Gly Cys Leu Arg Glu Ile Leu Gly Ser Tyr Leu
    50                  55                  60

Ala Ile Ser Pro Glu Lys Ile Glu Phe Ile Tyr Ser Glu Arg Gly Lys
65                  70                  75                  80

Pro Ser Ile Asn Tyr Gln Leu Gln Phe Asn Leu Ser His Ser Glu Glu
                85                  90                  95

Met Ala Ile Cys Gly Leu Thr Leu Thr Ala Arg Ile Gly Val Asp Leu
            100                 105                 110

Glu Lys Met Arg Gln Met Lys Asp Leu Asp Ser Leu Thr Lys Arg Phe
        115                 120                 125

Phe Cys Ala Arg Glu His Glu Leu Val Glu Lys Ser Ala Glu Lys Glu
    130                 135                 140

Lys Leu Phe Phe Gln Leu Trp Thr Ala Lys Glu Ala Tyr Leu Lys Ala
```

```
                145                 150                 155                 160
        Val Gly Thr Gly Ile Ser Gly Gly Leu Asp Arg Val Glu Val Gly Leu
                        165                 170                 175

Asn Pro Leu Lys Leu Asp Asn Val Ala Gly Glu Trp Gln Leu Trp Thr
                        180                 185                 190

Ala Ala Ile Gly Asp Asn Tyr Arg Ala Thr Val Val Ile Glu Gly Ser
                        195                 200                 205

Asp Arg Val Ile Lys Thr Phe Gly Leu Ser Asp Leu
                        210                 215                 220

<210> SEQ ID NO 4
<211> LENGTH: 240
<212> TYPE: PRT
<213> ORGANISM: Unknown
<220> FEATURE:
<223> OTHER INFORMATION: Fischerella

<400> SEQUENCE: 4

Met Gly Ser Glu Thr Asn His Leu Trp Leu Thr Ala Pro Thr Asn Leu
1               5                   10                  15

Thr Leu Leu Pro Asp Asp Val His Val Trp Arg Ile Ser Leu Asp Arg
                20                  25                  30

Pro Glu Ser Glu Leu Gln Ala Leu Gln Thr Thr Leu Ser Ser Asp Glu
            35                  40                  45

Ile Ala Arg Ala Gln Arg Phe Tyr Phe Glu Gln His Arg Gln Arg Phe
    50                  55                  60

Val Ala Gly Arg Gly Ile Leu Arg Thr Ile Leu Gly Arg Tyr Leu Gly
65                  70                  75                  80

Val Glu Pro Gln Ala Val Glu Phe Thr Tyr Glu Leu Arg Gly Lys Pro
                85                  90                  95

Leu Leu Ala Asp Arg Phe Ala Asp Ser Gly Val Ser Phe Asn Leu Ser
            100                 105                 110

His Ser Gln Asp Leu Ala Leu Cys Gly Val Ser Arg Asn Arg Lys Ile
        115                 120                 125

Gly Ile Asp Val Glu Tyr Met Arg Ser Val Ser Asp Val Glu Ala Leu
    130                 135                 140

Ala Glu Arg Phe Phe Ala Pro Arg Glu Tyr Glu Val Val Arg Ser Leu
145                 150                 155                 160

Pro Ser Asn Gln Gln Gln Gln Val Phe Phe Arg Tyr Trp Thr Cys Lys
                165                 170                 175

Glu Ala Tyr Leu Lys Ala Ile Gly Val Gly Ile Val Gln Leu Glu Lys
            180                 185                 190

Val Glu Ile Ser Leu Thr Leu Glu Gln Pro Ala Lys Leu Ile Thr Asp
        195                 200                 205

Glu Glu Trp Ser Leu Ile Glu Leu Val Pro Gly Asp His Tyr Leu Gly
    210                 215                 220

Ala Val Ala Ile Ala Gly Gln Asn Leu Asp Leu Lys Tyr Trp Gln Tyr
225                 230                 235                 240

<210> SEQ ID NO 5
<211> LENGTH: 259
<212> TYPE: PRT
<213> ORGANISM: Synechococcus elongatus

<400> SEQUENCE: 5

Met Gln Arg Pro Asn Pro Ser Asp Ala Val Pro Val Pro Ser Ile Pro
1               5                   10                  15
```

Ser Cys Asp Arg Gly Pro Ile Pro Asn Pro Val Thr Trp Arg Thr Ser
            20                  25                  30

Pro Glu Pro Leu Phe Leu Ser Ala Gln Thr Val His Leu Trp Arg Cys
        35                  40                  45

Ser Leu Thr Arg Ser Leu Ser Ser Ala Glu Gln Ala Ile Val Ala Ala
 50                  55                  60

Asp Cys Asp Arg Ala Gln Ala Tyr Gly Ser Asn Arg Arg His Gln Phe
65                   70                  75                  80

Leu Cys Gly Arg Trp Trp Leu Arg Gln Leu Leu Ser Leu Tyr Leu Pro
                85                  90                  95

Glu Glu Pro Ala Asp Phe Arg Phe Gln Leu Ser Pro Thr Gly Lys Pro
            100                 105                 110

Glu Leu Pro Gln Ser Asn Leu Cys Phe Asn Leu Ser His Ser Gly Ser
        115                 120                 125

Thr Leu Leu Ile Ala Ile Ala Trp Gln Pro Val Gly Val Asp Val Glu
130                 135                 140

Gln Pro Arg Ser Arg Ser Trp Leu Ala Leu Ala Arg Arg Tyr Phe Pro
145                 150                 155                 160

Ser Ala Glu Leu Ala Ala Met Gln Gln Ser Thr Asp Cys Asp Arg Trp
                165                 170                 175

Gly Leu Ala Ser Trp Val Cys Lys Glu Ala Trp Ile Lys Ala Gln Gly
            180                 185                 190

Arg Thr Leu Ala Asn Ser Leu Arg His Leu Gln Cys Ala Trp Thr Ala
        195                 200                 205

Asn Gly Gln Pro Arg Leu Ser Gly Leu Gly Ser Glu Glu Ser Gln Val
    210                 215                 220

Gln Leu Leu Gln Val Asp Pro Gln Glu Gln Leu Trp Ala Ala Ile Ala
225                 230                 235                 240

Met Pro Ala Gly Trp Asn Tyr Gln Thr Trp Thr Ala Ala Ile Ile Arg
                245                 250                 255

Lys Asn His

<210> SEQ ID NO 6
<211> LENGTH: 246
<212> TYPE: PRT
<213> ORGANISM: Unknown
<220> FEATURE:
<223> OTHER INFORMATION: Synechocystis

<400> SEQUENCE: 6

Met Leu Pro Gln Pro Gln Ile Trp Leu Cys Pro Thr Asp Arg Pro Leu
1               5                   10                  15

Ile Pro Gly Tyr Gln Ala Leu Leu Ser Ser Glu Glu Met Ala Arg Gly
            20                  25                  30

Glu Arg Tyr Gln Arg Pro Gln Asp Lys Gln Arg Phe Leu Thr Met Arg
        35                  40                  45

Leu Ala Leu Arg Ile Leu Leu Ala Arg Gln Leu Asp Cys Leu Pro Gln
 50                  55                  60

Gln Leu Gln Phe Thr Tyr Gly Pro Gln Gly Lys Pro Glu Leu Val Asp
65                  70                  75                  80

Arg Glu Arg Arg Ser Pro Trp Phe Asn Val Ala His Ser Gly Asn Tyr
                85                  90                  95

Gly Leu Ile Gly Leu Ser Thr Glu Gly Glu Ile Gly Val Asp Leu Gln
            100                 105                 110

```
Ile Met Leu Pro Lys Pro His Tyr Leu Lys Leu Ala Lys Arg Phe Phe
            115                 120                 125

Ala Pro Gln Glu Val Gln Gln Leu Glu Ser Leu Glu Gly Glu Lys Arg
130                 135                 140

Thr Lys Leu Phe Tyr Gln Leu Trp Thr Ala Lys Glu Ala Phe Leu Lys
145                 150                 155                 160

Ala Thr Gly Lys Gly Ile Ser Gly Gly Leu Asn Gln Val Ile Pro Asp
                165                 170                 175

Glu Asn Leu Ala Lys Tyr Gln Tyr Leu Pro Asp Ser Gly Asp Thr Asn
            180                 185                 190

His Trp Arg Leu Ser Ser Gln Pro Leu Ala Asp Gln Gly Ser Asn
        195                 200                 205

Asp Asn Tyr Trp Met Ala Ile Ala Trp Cys Thr Asn Glu Val Asn Gln
    210                 215                 220

Val Glu Ser Asn Tyr Leu Pro Asn Ile Gln Pro Phe Gln Trp Pro Arg
225                 230                 235                 240

Asn Leu Asp Ser Leu Pro
                245

<210> SEQ ID NO 7
<211> LENGTH: 224
<212> TYPE: PRT
<213> ORGANISM: Bacillus subtilis

<400> SEQUENCE: 7

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 8
```

```
<211> LENGTH: 231
<212> TYPE: DNA
<213> ORGANISM: Unknown
<220> FEATURE:
<223> OTHER INFORMATION: Synechocystis
<220> FEATURE:
<221> NAME/KEY: CDS
<222> LOCATION: (1)..(231)

<400> SEQUENCE: 8 atg gat cag gaa att ttt gaa aaa gta aaa aaa atc gtc gtg gaa cag      48
Met Asp Gln Glu Ile Phe Glu Lys Val Lys Lys Ile Val Val Glu Gln
1               5                  10                  15 ttg gaa gtg gat cct gac aaa gtg acc ccc gat gcc acc ttt gcc gaa      96
Leu Glu Val Asp Pro Asp Lys Val Thr Pro Asp Ala Thr Phe Ala Glu
            20                  25                  30 gat tta ggg gct gat tcc ctc gat aca gtg gaa ttg gtc atg gcc ctg     144
Asp Leu Gly Ala Asp Ser Leu Asp Thr Val Glu Leu Val Met Ala Leu
        35                  40                  45 gaa gaa gag ttt gat att gaa att ccc gat gaa gtg gcg gaa acc att     192
Glu Glu Glu Phe Asp Ile Glu Ile Pro Asp Glu Val Ala Glu Thr Ile
    50                  55                  60 gat acc gtg ggc aaa gcc gtt gag cat atc gaa agt aaa                 231
Asp Thr Val Gly Lys Ala Val Glu His Ile Glu Ser Lys
65                  70                  75

<210> SEQ ID NO 9
<211> LENGTH: 77
<212> TYPE: PRT
<213> ORGANISM: Unknown
<220> FEATURE:
<223> OTHER INFORMATION: Synthetic Construct

<400> SEQUENCE: 9

Met Asp Gln Glu Ile Phe Glu Lys Val Lys Lys Ile Val Val Glu Gln
1               5                  10                  15

Leu Glu Val Asp Pro Asp Lys Val Thr Pro Asp Ala Thr Phe Ala Glu
            20                  25                  30

Asp Leu Gly Ala Asp Ser Leu Asp Thr Val Glu Leu Val Met Ala Leu
        35                  40                  45

Glu Glu Glu Phe Asp Ile Glu Ile Pro Asp Glu Val Ala Glu Thr Ile
    50                  55                  60

Asp Thr Val Gly Lys Ala Val Glu His Ile Glu Ser Lys
65                  70                  75

<210> SEQ ID NO 10
<211> LENGTH: 252
<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(252)

<400> SEQUENCE: 10 atg ggc caa tca gaa act ttt gaa aaa gtc aaa aaa att gtt atc gaa      48
Met Gly Gln Ser Glu Thr Phe Glu Lys Val Lys Lys Ile Val Ile Glu
1               5                  10                  15 caa cta agt gtg gag aac cct gac aca gta act cca gaa gct agt ttt      96
Gln Leu Ser Val Glu Asn Pro Asp Thr Val Thr Pro Glu Ala Ser Phe
            20                  25                  30 gcc aac gat tta cag gct gat tcc ctc gat aca gta gaa cta gta atg     144
Ala Asn Asp Leu Gln Ala Asp Ser Leu Asp Thr Val Glu Leu Val Met
```

```
                    35                  40                  45
gct ttg gaa gaa gaa ttt gat atc gaa att ccc gat gaa gcc gca gag      192
Ala Leu Glu Glu Glu Phe Asp Ile Glu Ile Pro Asp Glu Ala Ala Glu
 50                  55                  60 aaa att acc act gtt caa gaa gcg gtg gat tac atc aat aac caa gtt      240
Lys Ile Thr Thr Val Gln Glu Ala Val Asp Tyr Ile Asn Asn Gln Val
 65                  70                  75                  80 gcc gca tca gct                                                      252
Ala Ala Ser Ala <210> SEQ ID NO 11
<211> LENGTH: 84
<212> TYPE: PRT
<213> ORGANISM: Unknown
<220> FEATURE:
<223> OTHER INFORMATION: Synthetic Construct

<400> SEQUENCE: 11

Met Gly Gln Ser Glu Thr Phe Glu Lys Val Lys Lys Ile Val Ile Glu
 1               5                  10                  15

Gln Leu Ser Val Glu Asn Pro Asp Thr Val Thr Pro Glu Ala Ser Phe
                20                  25                  30

Ala Asn Asp Leu Gln Ala Asp Ser Leu Asp Thr Val Glu Leu Val Met
             35                  40                  45

Ala Leu Glu Glu Glu Phe Asp Ile Glu Ile Pro Asp Glu Ala Ala Glu
 50                  55                  60

Lys Ile Thr Thr Val Gln Glu Ala Val Asp Tyr Ile Asn Asn Gln Val
 65                  70                  75                  80

Ala Ala Ser Ala

<210> SEQ ID NO 12
<211> LENGTH: 264
<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(264)

<400> SEQUENCE: 12 atg ggt cta aaa caa aat tat agt gca gca gat att caa gct tgg atg      48
Met Gly Leu Lys Gln Asn Tyr Ser Ala Ala Asp Ile Gln Ala Trp Met
 1               5                  10                  15 ata tct aat cta gct gaa ttg ttg gga gta gat ggt gat gaa atc gat      96
Ile Ser Asn Leu Ala Glu Leu Leu Gly Val Asp Gly Asp Glu Ile Asp
                20                  25                  30 gct act gtc aat tta gaa agc tat ggt ttg gat tcg gca cag gca atg     144
Ala Thr Val Asn Leu Glu Ser Tyr Gly Leu Asp Ser Ala Gln Ala Met
             35                  40                  45 gta cta gtt agt aaa cta gag caa ttg ttg gga ttt caa cca tca cct     192
Val Leu Val Ser Lys Leu Glu Gln Leu Leu Gly Phe Gln Pro Ser Pro
 50                  55                  60 ttg ttg ttg tgg cat tac ccc act att gaa tcg ttg tct gaa cgt tta     240
Leu Leu Leu Trp His Tyr Pro Thr Ile Glu Ser Leu Ser Glu Arg Leu
 65                  70                  75                  80 gct gaa gaa ttg gaa gaa caa tct                                     264
Ala Glu Glu Leu Glu Glu Gln Ser
                85

<210> SEQ ID NO 13
```

```
<211> LENGTH: 88
<212> TYPE: PRT
<213> ORGANISM: Unknown
<220> FEATURE:
<223> OTHER INFORMATION: Synthetic Construct

<400> SEQUENCE: 13

Met Gly Leu Lys Gln Asn Tyr Ser Ala Ala Asp Ile Gln Ala Trp Met
1               5                   10                  15

Ile Ser Asn Leu Ala Glu Leu Leu Gly Val Asp Gly Asp Glu Ile Asp
                20                  25                  30

Ala Thr Val Asn Leu Glu Ser Tyr Gly Leu Asp Ser Ala Gln Ala Met
            35                  40                  45

Val Leu Val Ser Lys Leu Glu Gln Leu Leu Gly Phe Gln Pro Ser Pro
    50                  55                  60

Leu Leu Leu Trp His Tyr Pro Thr Ile Glu Ser Leu Ser Glu Arg Leu
65                  70                  75                  80

Ala Glu Glu Leu Glu Glu Gln Ser
                85

<210> SEQ ID NO 14
<211> LENGTH: 300
<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(300)

<400> SEQUENCE: 14 atg gaa caa tct aca act aat cac gcc cgc ccc caa att acc gct acc      48
Met Glu Gln Ser Thr Thr Asn His Ala Arg Pro Gln Ile Thr Ala Thr
1               5                   10                  15 tac ctt ccc ccc agc aat gaa att gaa gcc aga gtc acc caa gta atg      96
Tyr Leu Pro Pro Ser Asn Glu Ile Glu Ala Arg Val Thr Gln Val Met
                20                  25                  30 gag agt tta ttg gga atc gct cct att ggg gtt aat gat aac ttc ttt     144
Glu Ser Leu Leu Gly Ile Ala Pro Ile Gly Val Asn Asp Asn Phe Phe
            35                  40                  45 gag tta gga gga cat tcc ctg tta gca att caa gca gtt tca cag cta     192
Glu Leu Gly Gly His Ser Leu Leu Ala Ile Gln Ala Val Ser Gln Leu
    50                  55                  60 cgg gaa gaa ttt caa gta gaa tta ccc atg cga caa ttt tta ttt gag     240
Arg Glu Glu Phe Gln Val Glu Leu Pro Met Arg Gln Phe Leu Phe Glu
65                  70                  75                  80 tca ccc aca att ggg ggg ata gcc aaa att atc att gaa aat caa tcg     288
Ser Pro Thr Ile Gly Gly Ile Ala Lys Ile Ile Ile Glu Asn Gln Ser
                85                  90                  95 cct att act gat                                                     300
Pro Ile Thr Asp
            100

<210> SEQ ID NO 15
<211> LENGTH: 100
<212> TYPE: PRT
<213> ORGANISM: Unknown
<220> FEATURE:
<223> OTHER INFORMATION: Synthetic Construct

<400> SEQUENCE: 15

Met Glu Gln Ser Thr Thr Asn His Ala Arg Pro Gln Ile Thr Ala Thr
1               5                   10                  15
```

```
Tyr Leu Pro Pro Ser Asn Glu Ile Glu Ala Arg Val Thr Gln Val Met
            20                  25                  30

Glu Ser Leu Leu Gly Ile Ala Pro Ile Gly Val Asn Asp Asn Phe Phe
        35                  40                  45

Glu Leu Gly Gly His Ser Leu Leu Ala Ile Gln Ala Val Ser Gln Leu
    50                  55                  60

Arg Glu Glu Phe Gln Val Glu Leu Pro Met Arg Gln Phe Leu Phe Glu
65                  70                  75                  80

Ser Pro Thr Ile Gly Gly Ile Ala Lys Ile Ile Ile Glu Asn Gln Ser
                85                  90                  95

Pro Ile Thr Asp
            100

<210> SEQ ID NO 16
<211> LENGTH: 255
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(255)

<400> SEQUENCE: 16 atg gcc caa cgc cct atc att atc cct cgt aca aat act gaa cag cga    48
Met Ala Gln Arg Pro Ile Ile Ile Pro Arg Thr Asn Thr Glu Gln Arg
1               5                   10                  15 ata ggc gag att tgg aag aag gcg atg aag tgg gat tct gtc tcg ata    96
Ile Gly Glu Ile Trp Lys Lys Ala Met Lys Trp Asp Ser Val Ser Ile
            20                  25                  30 tgt gat gat ttc ttt gaa tct ggc gga aat tca ctt att gct gtg aga   144
Cys Asp Asp Phe Phe Glu Ser Gly Gly Asn Ser Leu Ile Ala Val Arg
        35                  40                  45 ata atc aac gct atc aac aaa gaa ttt cat tgt gcc ttg cct tta cat   192
Ile Ile Asn Ala Ile Asn Lys Glu Phe His Cys Ala Leu Pro Leu His
    50                  55                  60 gct ctt ttt gaa gct cca agc att gaa aag ctc gct cat aag gtt gat   240
Ala Leu Phe Glu Ala Pro Ser Ile Glu Lys Leu Ala His Lys Val Asp
65                  70                  75                  80 agt gat gaa gtt gaa                                                255
Ser Asp Glu Val Glu
                85

<210> SEQ ID NO 17
<211> LENGTH: 85
<212> TYPE: PRT
<213> ORGANISM: Unknown
<220> FEATURE:
<223> OTHER INFORMATION: Synthetic Construct

<400> SEQUENCE: 17

Met Ala Gln Arg Pro Ile Ile Ile Pro Arg Thr Asn Thr Glu Gln Arg
1               5                   10                  15

Ile Gly Glu Ile Trp Lys Lys Ala Met Lys Trp Asp Ser Val Ser Ile
            20                  25                  30

Cys Asp Asp Phe Phe Glu Ser Gly Gly Asn Ser Leu Ile Ala Val Arg
        35                  40                  45

Ile Ile Asn Ala Ile Asn Lys Glu Phe His Cys Ala Leu Pro Leu His
    50                  55                  60

Ala Leu Phe Glu Ala Pro Ser Ile Glu Lys Leu Ala His Lys Val Asp
```

Ser Asp Glu Val Glu
            85

<210> SEQ ID NO 18
<211> LENGTH: 372
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(372)

<400> SEQUENCE: 18

```
atg gct ttt cta gaa gat gtc cct cca aca gaa cgt cga gaa cac tta      48
Met Ala Phe Leu Glu Asp Val Pro Pro Thr Glu Arg Arg Glu His Leu
1               5                   10                  15 tta gaa tat ctt gga aaa gaa gta gca aaa atc tta gga ata aaa cat      96
Leu Glu Tyr Leu Gly Lys Glu Val Ala Lys Ile Leu Gly Ile Lys His
            20                  25                  30 ata ccc gac cca gaa caa gga ttt ata gaa atg gga att gac tct ttg     144
Ile Pro Asp Pro Glu Gln Gly Phe Ile Glu Met Gly Ile Asp Ser Leu
        35                  40                  45 ctt tcc att gaa ttc aaa aat cgt tta gaa aaa gga tta gaa att gct     192
Leu Ser Ile Glu Phe Lys Asn Arg Leu Glu Lys Gly Leu Glu Ile Ala
    50                  55                  60 tta cca tct act tta ata ttt gat ttt ccg aat att agc aaa tta aat     240
Leu Pro Ser Thr Leu Ile Phe Asp Phe Pro Asn Ile Ser Lys Leu Asn
65                  70                  75                  80 aat tat cta ttt gag caa att tat ggt tgg gaa gta aat act acc gtg     288
Asn Tyr Leu Phe Glu Gln Ile Tyr Gly Trp Glu Val Asn Thr Thr Val
                85                  90                  95 gag aca act gtt gat att gta gaa gtt aat gaa gat tta att ttg caa     336
Glu Thr Thr Val Asp Ile Val Glu Val Asn Glu Asp Leu Ile Leu Gln
            100                 105                 110 gaa ctg gca gat tta gaa gct ttt cta ggt aat tcc                     372
Glu Leu Ala Asp Leu Glu Ala Phe Leu Gly Asn Ser
        115                 120
```

<210> SEQ ID NO 19
<211> LENGTH: 124
<212> TYPE: PRT
<213> ORGANISM: Unknown
<220> FEATURE:
<223> OTHER INFORMATION: Synthetic Construct

<400> SEQUENCE: 19

Met Ala Phe Leu Glu Asp Val Pro Pro Thr Glu Arg Arg Glu His Leu
1               5                   10                  15

Leu Glu Tyr Leu Gly Lys Glu Val Ala Lys Ile Leu Gly Ile Lys His
            20                  25                  30

Ile Pro Asp Pro Glu Gln Gly Phe Ile Glu Met Gly Ile Asp Ser Leu
        35                  40                  45

Leu Ser Ile Glu Phe Lys Asn Arg Leu Glu Lys Gly Leu Glu Ile Ala
    50                  55                  60

Leu Pro Ser Thr Leu Ile Phe Asp Phe Pro Asn Ile Ser Lys Leu Asn
65                  70                  75                  80

Asn Tyr Leu Phe Glu Gln Ile Tyr Gly Trp Glu Val Asn Thr Thr Val
                85                  90                  95

Glu Thr Thr Val Asp Ile Val Glu Val Asn Glu Asp Leu Ile Leu Gln

```
                         100                 105                 110

Glu Leu Ala Asp Leu Glu Ala Phe Leu Gly Asn Ser
            115                 120

<210> SEQ ID NO 20
<211> LENGTH: 303
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(303)

<400> SEQUENCE: 20 atg gga tcg ctt ccc aaa cct gat ttt tct aac tta atc act cat gaa      48
Met Gly Ser Leu Pro Lys Pro Asp Phe Ser Asn Leu Ile Thr His Glu
1               5                   10                  15 gat ttt acg cct gca cgc aat gat tta gag aga aaa atc gcg cag att      96
Asp Phe Thr Pro Ala Arg Asn Asp Leu Glu Arg Lys Ile Ala Gln Ile
            20                  25                  30 tgg tca gaa att tta cag att tcg gaa att gat att aga gat aac ttt     144
Trp Ser Glu Ile Leu Gln Ile Ser Glu Ile Asp Ile Arg Asp Asn Phe
        35                  40                  45 ttt gaa gtt ggt ggt aat tcc ctt tta gca tta cat tta atg aat gcc     192
Phe Glu Val Gly Gly Asn Ser Leu Leu Ala Leu His Leu Met Asn Ala
    50                  55                  60 atc gaa caa aaa ttt ggt cga gag tta gca ctg tca act tta ctt act     240
Ile Glu Gln Lys Phe Gly Arg Glu Leu Ala Leu Ser Thr Leu Leu Thr
65                  70                  75                  80 aat aac tca att gaa aaa cta gca gaa att ctg caa aac ccc aca gat     288
Asn Asn Ser Ile Glu Lys Leu Ala Glu Ile Leu Gln Asn Pro Thr Asp
                85                  90                  95 gtt ttt ccc aat tca                                                  303
Val Phe Pro Asn Ser
            100

<210> SEQ ID NO 21
<211> LENGTH: 101
<212> TYPE: PRT
<213> ORGANISM: Unknown
<220> FEATURE:
<223> OTHER INFORMATION: Synthetic Construct

<400> SEQUENCE: 21

Met Gly Ser Leu Pro Lys Pro Asp Phe Ser Asn Leu Ile Thr His Glu
1               5                   10                  15

Asp Phe Thr Pro Ala Arg Asn Asp Leu Glu Arg Lys Ile Ala Gln Ile
            20                  25                  30

Trp Ser Glu Ile Leu Gln Ile Ser Glu Ile Asp Ile Arg Asp Asn Phe
        35                  40                  45

Phe Glu Val Gly Gly Asn Ser Leu Leu Ala Leu His Leu Met Asn Ala
    50                  55                  60

Ile Glu Gln Lys Phe Gly Arg Glu Leu Ala Leu Ser Thr Leu Leu Thr
65                  70                  75                  80

Asn Asn Ser Ile Glu Lys Leu Ala Glu Ile Leu Gln Asn Pro Thr Asp
                85                  90                  95

Val Phe Pro Asn Ser
            100

<210> SEQ ID NO 22
```

-continued

```
<211> LENGTH: 246
<212> TYPE: DNA
<213> ORGANISM: Lyngbya sp
<220> FEATURE:
<221> NAME/KEY: CDS
<222> LOCATION: (1)..(246)

<400> SEQUENCE: 22 atg gaa att ttt gaa cag gaa tgt cga aaa tta tta aaa tct cta ctg    48
Met Glu Ile Phe Glu Gln Glu Cys Arg Lys Leu Leu Lys Ser Leu Leu
1               5                   10                  15 ggt gtt caa cgt atg gag aga ttg cct ggt gac aca cca cta atg gag    96
Gly Val Gln Arg Met Glu Arg Leu Pro Gly Asp Thr Pro Leu Met Glu
            20                  25                  30 tca gga atg gat tca ctg gag ttg tta gaa ttt cgt gct ctt ata gaa   144
Ser Gly Met Asp Ser Leu Glu Leu Leu Glu Phe Arg Ala Leu Ile Glu
        35                  40                  45 aga aag ttt ggg att aag tta aag tct acc ttc ttt ttt agt tac aaa   192
Arg Lys Phe Gly Ile Lys Leu Lys Ser Thr Phe Phe Phe Ser Tyr Lys
50                  55                  60 act ctt ata gcg gta gca gag tat ctt tca gaa cgg gaa gat att aat   240
Thr Leu Ile Ala Val Ala Glu Tyr Leu Ser Glu Arg Glu Asp Ile Asn
65                  70                  75                  80 ttt agt                                                            246
Phe Ser

<210> SEQ ID NO 23
<211> LENGTH: 82
<212> TYPE: PRT
<213> ORGANISM: Lyngbya sp

<400> SEQUENCE: 23

Met Glu Ile Phe Glu Gln Glu Cys Arg Lys Leu Leu Lys Ser Leu Leu
1               5                   10                  15

Gly Val Gln Arg Met Glu Arg Leu Pro Gly Asp Thr Pro Leu Met Glu
            20                  25                  30

Ser Gly Met Asp Ser Leu Glu Leu Leu Glu Phe Arg Ala Leu Ile Glu
        35                  40                  45

Arg Lys Phe Gly Ile Lys Leu Lys Ser Thr Phe Phe Phe Ser Tyr Lys
    50                  55                  60

Thr Leu Ile Ala Val Ala Glu Tyr Leu Ser Glu Arg Glu Asp Ile Asn
65                  70                  75                  80

Phe Ser

<210> SEQ ID NO 24
<211> LENGTH: 261
<212> TYPE: DNA
<213> ORGANISM: Unknown
<220> FEATURE:
<223> OTHER INFORMATION: M. aeruginosa NIES843
<220> FEATURE:
<221> NAME/KEY: CDS
<222> LOCATION: (1)..(261)

<400> SEQUENCE: 24 atg gtg aca act gtt caa tct cct tgt acc gtt gaa gac att caa aac    48
Met Val Thr Thr Val Gln Ser Pro Cys Thr Val Glu Asp Ile Gln Asn
1               5                   10                  15 tgg ctc gtt gat cag ttt gct caa caa ctc gat gtt gac ctt gat gac    96
Trp Leu Val Asp Gln Phe Ala Gln Gln Leu Asp Val Asp Leu Asp Asp
            20                  25                  30 att gat att gaa gaa cct ttt gat aat tat gaa ctc gac tca cga aaa   144
```

```
Ile Asp Ile Glu Glu Pro Phe Asp Asn Tyr Glu Leu Asp Ser Arg Lys
         35                  40                  45 gcg tta gtt tta tta gga cgc tta gaa aaa tgg ctc gga aag gaa tta    192
Ala Leu Val Leu Leu Gly Arg Leu Glu Lys Trp Leu Gly Lys Glu Leu
 50                  55                  60 aat cct gtg gtc att ttt aac tat ccc acc att gct gaa tta gca acc    240
Asn Pro Val Val Ile Phe Asn Tyr Pro Thr Ile Ala Glu Leu Ala Thr
 65                  70                  75                  80 cga tta ggg gaa tta tat ctt                                        261
Arg Leu Gly Glu Leu Tyr Leu
                 85

<210> SEQ ID NO 25
<211> LENGTH: 87
<212> TYPE: PRT
<213> ORGANISM: Unknown
<220> FEATURE:
<223> OTHER INFORMATION: Synthetic Construct

<400> SEQUENCE: 25

Met Val Thr Thr Val Gln Ser Pro Cys Thr Val Glu Asp Ile Gln Asn
 1               5                  10                  15

Trp Leu Val Asp Gln Phe Ala Gln Gln Leu Asp Val Asp Leu Asp Asp
                 20                  25                  30

Ile Asp Ile Glu Glu Pro Phe Asp Asn Tyr Glu Leu Asp Ser Arg Lys
         35                  40                  45

Ala Leu Val Leu Leu Gly Arg Leu Glu Lys Trp Leu Gly Lys Glu Leu
 50                  55                  60

Asn Pro Val Val Ile Phe Asn Tyr Pro Thr Ile Ala Glu Leu Ala Thr
 65                  70                  75                  80

Arg Leu Gly Glu Leu Tyr Leu
                 85

<210> SEQ ID NO 26
<211> LENGTH: 285
<212> TYPE: DNA
<213> ORGANISM: Streptomyces coelicolor
<220> FEATURE:
<221> NAME/KEY: CDS
<222> LOCATION: (1)..(285)

<400> SEQUENCE: 26 atg gag cag cgg ctg gct ccg ctg tcc gcg gcc gag cgc gag cgg gca     48
Met Glu Gln Arg Leu Ala Pro Leu Ser Ala Ala Glu Arg Glu Arg Ala
 1               5                  10                  15 ctc acg gat ctc gtg cgc gtc cag gtc gcg gcg gtg ctc ggg cac tct     96
Leu Thr Asp Leu Val Arg Val Gln Val Ala Ala Val Leu Gly His Ser
                 20                  25                  30 gac ccc ggc gcg atc gag tcc ggc cgg gcc ttc cag gag ctg ggc ttc    144
Asp Pro Gly Ala Ile Glu Ser Gly Arg Ala Phe Gln Glu Leu Gly Phe
         35                  40                  45 gac tca ctg aca gcc gtc gaa ctt cgc aac cag ctg agc acc gcg agc    192
Asp Ser Leu Thr Ala Val Glu Leu Arg Asn Gln Leu Ser Thr Ala Ser
 50                  55                  60 gga ctg cgc ctg ccc acc acc ctc gtc ttc gac cac ccc tcc ccc gcc    240
Gly Leu Arg Leu Pro Thr Thr Leu Val Phe Asp His Pro Ser Pro Ala
 65                  70                  75                  80 gct ctc gcc gcc cac ctc tcg gcg gag ctg ttc ggc gag cag gag        285
Ala Leu Ala Ala His Leu Ser Ala Glu Leu Phe Gly Glu Gln Glu
                 85                  90                  95
```

<210> SEQ ID NO 27
<211> LENGTH: 95
<212> TYPE: PRT
<213> ORGANISM: Streptomyces coelicolor

<400> SEQUENCE: 27

```
Met Glu Gln Arg Leu Ala Pro Leu Ser Ala Ala Glu Arg Glu Arg Ala
1               5                   10                  15

Leu Thr Asp Leu Val Arg Val Gln Val Ala Ala Val Leu Gly His Ser
            20                  25                  30

Asp Pro Gly Ala Ile Glu Ser Gly Arg Ala Phe Gln Glu Leu Gly Phe
        35                  40                  45

Asp Ser Leu Thr Ala Val Glu Leu Arg Asn Gln Leu Ser Thr Ala Ser
    50                  55                  60

Gly Leu Arg Leu Pro Thr Thr Leu Val Phe Asp His Pro Ser Pro Ala
65                  70                  75                  80

Ala Leu Ala Ala His Leu Ser Ala Glu Leu Phe Gly Glu Gln Glu
                85                  90                  95
```

<210> SEQ ID NO 28
<211> LENGTH: 294
<212> TYPE: DNA
<213> ORGANISM: Streptomyces scabiei
<220> FEATURE:
<221> NAME/KEY: CDS
<222> LOCATION: (1)..(294)

<400> SEQUENCE: 28

```
atg gcc cgc cgg ctc gaa ccg ttg gac gaa ccc gcg cga cgc cgt ctg      48
Met Ala Arg Arg Leu Glu Pro Leu Asp Glu Pro Ala Arg Arg Arg Leu
1               5                   10                  15 ctg ctc gac ctg gtg tgc gac cac gcg gcc gcg gtc ctc ggc cac acc      96
Leu Leu Asp Leu Val Cys Asp His Ala Ala Ala Val Leu Gly His Thr
            20                  25                  30 ggc cgc cag gcc gtc ccg gcc gac cag gcg ttc tcc gcc gtc ggg ttc     144
Gly Arg Gln Ala Val Pro Ala Asp Gln Ala Phe Ser Ala Val Gly Phe
        35                  40                  45 gac tcg atg ctc gcc gtg tcc ttc cgt aac cgg ctg cgc acc gcg acc     192
Asp Ser Met Leu Ala Val Ser Phe Arg Asn Arg Leu Arg Thr Ala Thr
    50                  55                  60 ggc gtc ccc gtc gcc gcg acg gtg gtg ttc gac cat ccc acc ccc gcc     240
Gly Val Pro Val Ala Ala Thr Val Val Phe Asp His Pro Thr Pro Ala
65                  70                  75                  80 gcc ctc gcc gac cac ctg tac gac ggg ttg agc gcc cgt ccc gga ccg     288
Ala Leu Ala Asp His Leu Tyr Asp Gly Leu Ser Ala Arg Pro Gly Pro
                85                  90                  95 gcc gtt                                                              294
Ala Val
```

<210> SEQ ID NO 29
<211> LENGTH: 98
<212> TYPE: PRT
<213> ORGANISM: Streptomyces scabiei

<400> SEQUENCE: 29

```
Met Ala Arg Arg Leu Glu Pro Leu Asp Glu Pro Ala Arg Arg Arg Leu
1               5                   10                  15

Leu Leu Asp Leu Val Cys Asp His Ala Ala Ala Val Leu Gly His Thr
            20                  25                  30

Gly Arg Gln Ala Val Pro Ala Asp Gln Ala Phe Ser Ala Val Gly Phe
        35                  40                  45
```

```
Asp Ser Met Leu Ala Val Ser Phe Arg Asn Arg Leu Arg Thr Ala Thr
 50                  55                  60

Gly Val Pro Val Ala Ala Thr Val Val Phe Asp His Pro Thr Pro Ala
 65                  70                  75                  80

Ala Leu Ala Asp His Leu Tyr Asp Gly Leu Ser Ala Arg Pro Gly Pro
                 85                  90                  95

Ala Val
```

<210> SEQ ID NO 30
<211> LENGTH: 675
<212> TYPE: DNA
<213> ORGANISM: Bacillus subtilis
<220> FEATURE:
<221> NAME/KEY: CDS
<222> LOCATION: (1)..(675)

<400> SEQUENCE: 30

```
atg aaa att tat ggg att tac atg gat aga ccc ctg agc caa gaa gaa      48
Met Lys Ile Tyr Gly Ile Tyr Met Asp Arg Pro Leu Ser Gln Glu Glu
 1               5                  10                  15 aac gaa cgc ttt atg acc ttt att agc cct gaa aaa cgg gaa aaa tgt      96
Asn Glu Arg Phe Met Thr Phe Ile Ser Pro Glu Lys Arg Glu Lys Cys
                 20                  25                  30 cgc cgt ttt tat cat aaa gaa gat gcc cat cgt acc tta ttg ggt gat     144
Arg Arg Phe Tyr His Lys Glu Asp Ala His Arg Thr Leu Leu Gly Asp
             35                  40                  45 gtg ttg gtt cgg agt gtg att tct cgc caa tac caa ttg gat aaa agt     192
Val Leu Val Arg Ser Val Ile Ser Arg Gln Tyr Gln Leu Asp Lys Ser
 50                  55                  60 gat att cgg ttt tct act caa gaa tat ggt aaa ccc tgt att ccc gat     240
Asp Ile Arg Phe Ser Thr Gln Glu Tyr Gly Lys Pro Cys Ile Pro Asp
 65                  70                  75                  80 ttg ccc gat gcc cat ttt aat att agt cat tct ggt cgc tgg gtt att     288
Leu Pro Asp Ala His Phe Asn Ile Ser His Ser Gly Arg Trp Val Ile
                 85                  90                  95 ggt gct ttt gat agt caa ccc att ggt att gat att gaa aaa acc aaa     336
Gly Ala Phe Asp Ser Gln Pro Ile Gly Ile Asp Ile Glu Lys Thr Lys
                100                 105                 110 ccc att tct ttg gaa att gcc aaa cgc ttt ttc agt aaa acc gaa tac     384
Pro Ile Ser Leu Glu Ile Ala Lys Arg Phe Phe Ser Lys Thr Glu Tyr
             115                 120                 125 tct gat tta ttg gct aaa gat aaa gat gaa caa act gat tac ttt tac     432
Ser Asp Leu Leu Ala Lys Asp Lys Asp Glu Gln Thr Asp Tyr Phe Tyr
         130                 135                 140 cat ttg tgg agt atg aaa gaa tct ttt att aaa caa gaa ggt aaa ggt     480
His Leu Trp Ser Met Lys Glu Ser Phe Ile Lys Gln Glu Gly Lys Gly
145                 150                 155                 160 tta agt ttg ccc tta gat agt ttt tct gtg cgg ttg cat caa gat ggt     528
Leu Ser Leu Pro Leu Asp Ser Phe Ser Val Arg Leu His Gln Asp Gly
                165                 170                 175 caa gtt agt att gaa tta ccc gat agt cat tct ccc tgt tac att aaa     576
Gln Val Ser Ile Glu Leu Pro Asp Ser His Ser Pro Cys Tyr Ile Lys
                180                 185                 190 act tat gaa gtt gat ccc ggt tat aaa atg gct gtt tgt gca gca cac     624
Thr Tyr Glu Val Asp Pro Gly Tyr Lys Met Ala Val Cys Ala Ala His
            195                 200                 205 ccc gat ttt cca gaa gat att act atg gtt tcc tat gaa gaa ctg ttg     672
Pro Asp Phe Pro Glu Asp Ile Thr Met Val Ser Tyr Glu Glu Leu Leu
        210                 215                 220
```

<210> SEQ ID NO 31
<211> LENGTH: 224
<212> TYPE: PRT
<213> ORGANISM: Bacillus subtilis

<400> SEQUENCE: 31

```
Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
cgtacgtact acttaattga caaata                                          26

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
gagctccccg acttctcaaa ggatac                                          26

<210> SEQ ID NO 34
<211> LENGTH: 32

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ctcgaggacg tcatgggtac acctcacgct ac                              32

<210> SEQ ID NO 35
<211> LENGTH: 26
<212> TYPE: DNA
<213> ORGANISM: Artificial Sequence
<220> FEATURE:
<223> OTHER INFORMATION: primer

<400> SEQUENCE: 35
catatgcccg acttctcaaa ggatac                                     26

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
cgtacgattc tgaaatgagc tgttgacaa                                  29

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
gagctccccg acttctcaaa ggatac                                     26

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
ctgcagttca atgcggtcca atac                                       24

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
agccaagtat gctgcaacat tttttctagt gtgccattg                       39

<210> SEQ ID NO 40
<211> LENGTH: 39
<212> TYPE: DNA
<213> ORGANISM: Artificial Sequence
<220> FEATURE:
<223> OTHER INFORMATION: primer

<400> SEQUENCE: 40
caatggcaca ctagaaaaaa tgttgcagca tacttggct     39

<210> SEQ ID NO 41
<211> LENGTH: 26
<212> TYPE: DNA
<213> ORGANISM: Artificial Sequence
<220> FEATURE:
<223> OTHER INFORMATION: primer

<400> SEQUENCE: 41
gcatgctcaa taatgccaga attttg     26

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
cgtacgttca atgcggtcca atac     24

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
acgtcttttt ctagtgtgcc attg     24

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
cgtacgcatt gaattaatct cctac     25

<210> SEQ ID NO 45
<211> LENGTH: 24
<212> TYPE: DNA
<213> ORGANISM: Artificial Sequence
<220> FEATURE:
<223> OTHER INFORMATION: primer

<400> SEQUENCE: 45
gacgtccacc tgtagagaag agtc     24

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
cgtacgcatt gaattaatct c     21

<210> SEQ ID NO 47
<211> LENGTH: 26
<212> TYPE: DNA
<213> ORGANISM: Artificial Sequence
<220> FEATURE:
<223> OTHER INFORMATION: primer

<400> SEQUENCE: 47
gagctcctac aaccgccgaa ttaaag                        26

<210> SEQ ID NO 48
<211> LENGTH: 25
<212> TYPE: DNA
<213> ORGANISM: Artificial Sequence
<220> FEATURE:
<223> OTHER INFORMATION: primer

<400> SEQUENCE: 48
gagctccatt gaattaatct cctac                         25

<210> SEQ ID NO 49
<211> LENGTH: 37
<212> TYPE: DNA
<213> ORGANISM: Artificial Sequence
<220> FEATURE:
<223> OTHER INFORMATION: primer

<400> SEQUENCE: 49
cagaaataga ttgtgtcatc acctgtagag aagagtc             37

<210> SEQ ID NO 50
<211> LENGTH: 37
<212> TYPE: DNA
<213> ORGANISM: Artificial Sequence
<220> FEATURE:
<223> OTHER INFORMATION: primer

<400> SEQUENCE: 50
gactcttctc tacaggtgat gacacaatct atttctg             37

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ccgctcgaga gattgttctt ccaattcttc                     30

<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
gagctccatt gaattaatct cctac                         25

<210> SEQ ID NO 53
<211> LENGTH: 37
<212> TYPE: DNA
<213> ORGANISM: Artificial Sequence
<220> FEATURE:
<223> OTHER INFORMATION: primer

<400> SEQUENCE: 53
cagaaataga ttgtgtcatc acctgtagag aagagtc             37

<210> SEQ ID NO 54
<211> LENGTH: 37
<212> TYPE: DNA
<213> ORGANISM: Artificial Sequence
<220> FEATURE:
<223> OTHER INFORMATION: primer

<400> SEQUENCE: 54
gactcttctc tacaggtgat gacacaatct atttctg                                37

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ggtaccctaa tcgccaccaa actc                                              24

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
gtacccattg aattaatctc ctac                                              24

<210> SEQ ID NO 57
<211> LENGTH: 40
<212> TYPE: DNA
<213> ORGANISM: Artificial Sequence
<220> FEATURE:
<223> OTHER INFORMATION: primer

<400> SEQUENCE: 57
ctaaaaagtt tattatttcc atcacctgta gagaagagtc                             40

<210> SEQ ID NO 58
<211> LENGTH: 40
<212> TYPE: DNA
<213> ORGANISM: Artificial Sequence
<220> FEATURE:
<223> OTHER INFORMATION: primer

<400> SEQUENCE: 58
gactcttctc tacaggtgat ggaaataata aacttttag                              40

<210> SEQ ID NO 59
<211> LENGTH: 26
<212> TYPE: DNA
<213> ORGANISM: Artificial Sequence
<220> FEATURE:
<223> OTHER INFORMATION: primer

<400> SEQUENCE: 59
gtcgaccccg acttctcaaa ggatac                                            26

<210> SEQ ID NO 60
<211> LENGTH: 18
<212> TYPE: DNA
<213> ORGANISM: Artificial Sequence
<220> FEATURE:
<223> OTHER INFORMATION: primer

```
<400> SEQUENCE: 60
tgtgaattag ttgtaatg                                                    18

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
ctactttaat cgcaattc                                                    18

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
caattcaccc atagtagc                                                    18

<210> SEQ ID NO 63
<211> LENGTH: 18
<212> TYPE: DNA
<213> ORGANISM: Artificial Sequence
<220> FEATURE:
<223> OTHER INFORMATION: primer

<400> SEQUENCE: 63
taatcaaatt taacttgc                                                    18

<210> SEQ ID NO 64
<211> LENGTH: 29
<212> TYPE: DNA
<213> ORGANISM: Artificial Sequence
<220> FEATURE:
<223> OTHER INFORMATION: primer

<400> SEQUENCE: 64
cgtacgattc tgaaatgagc tgttgacaa                                        29

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
cgtacgttca atgcggtcca atac                                             24

<210> SEQ ID NO 66
<211> LENGTH: 25
<212> TYPE: DNA
<213> ORGANISM: Artificial Sequence
<220> FEATURE:
<223> OTHER INFORMATION: primer

<400> SEQUENCE: 66
cgtacgcatt gaattaatct cctac                                            25

<210> SEQ ID NO 67
```

<211> LENGTH: 18
<212> TYPE: DNA
<213> ORGANISM: Artificial Sequence
<220> FEATURE:
<223> OTHER INFORMATION: primer

<400> SEQUENCE: 67
gctcatgcag gtttggag                                                    18

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gagctccatt gaattaatct cctac                                            25

<210> SEQ ID NO 69
<211> LENGTH: 18
<212> TYPE: DNA
<213> ORGANISM: Artificial Sequence
<220> FEATURE:
<223> OTHER INFORMATION: primer

<400> SEQUENCE: 69
gtaagcctac ctactgga                                                    18

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
ggtacccatt gaattaatct cctac                                            25

<210> SEQ ID NO 71
<211> LENGTH: 18
<212> TYPE: DNA
<213> ORGANISM: Artificial Sequence
<220> FEATURE:
<223> OTHER INFORMATION: primer

<400> SEQUENCE: 71
gagcgatgaa tacccatc                                                    18

<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
agtagttgat gcgtttgc                                                    18

<210> SEQ ID NO 73
<211> LENGTH: 18
<212> TYPE: DNA
<213> ORGANISM: Artificial Sequence
<220> FEATURE:
<223> OTHER INFORMATION: primer

<400> SEQUENCE: 73
ctactttaat cgcaattc                                          18

<210> SEQ ID NO 74
<211> LENGTH: 18
<212> TYPE: DNA
<213> ORGANISM: Artificial Sequence
<220> FEATURE:
<223> OTHER INFORMATION: primer

<400> SEQUENCE: 74
gtgaacacac cactactg                                          18

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
acactcttgg ctttagtc                                          18

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
caagatggca caatctac                                          18

<210> SEQ ID NO 77
<211> LENGTH: 18
<212> TYPE: DNA
<213> ORGANISM: Artificial Sequence
<220> FEATURE:
<223> OTHER INFORMATION: primer

<400> SEQUENCE: 77
tccagtaggt aggcttac                                          18

<210> SEQ ID NO 78
<211> LENGTH: 18
<212> TYPE: DNA
<213> ORGANISM: Artificial Sequence
<220> FEATURE:
<223> OTHER INFORMATION: primer

<400> SEQUENCE: 78
aacatgtcca acccatac                                          18

<210> SEQ ID NO 79
<211> LENGTH: 18
<212> TYPE: DNA
<213> ORGANISM: Artificial Sequence
<220> FEATURE:
<223> OTHER INFORMATION: primer

<400> SEQUENCE: 79
gagcgatgaa tacccatc                                          18

<210> SEQ ID NO 80
<211> LENGTH: 208
<212> TYPE: DNA

<213> ORGANISM: Unknown
<220> FEATURE:
<223> OTHER INFORMATION: Synechocystis PCC6803

<400> SEQUENCE: 80

```
ttcaatgcgg tccaatacct ccctgccca actgggtaag ctcgcggctc cactgagtaa      60
tacagacaag gctaaacagg caatttttt cattggtcaa ctcctagcac caatttccca     120
agactacgga gggggcaatg aagtttcaat taattggggt cacaaaccac agcggcctat    180
ggctctaatc aatggcacac tagaaaaa                                       208
```

<210> SEQ ID NO 81
<211> LENGTH: 30
<212> TYPE: DNA
<213> ORGANISM: Artificial Sequence
<220> FEATURE:
<223> OTHER INFORMATION: hybrid promoter

<400> SEQUENCE: 81

```
ttgacaatta atcatccggc tcgtataatg                                      30
```

<210> SEQ ID NO 82
<211> LENGTH: 560
<212> TYPE: DNA
<213> ORGANISM: Unknown
<220> FEATURE:
<223> OTHER INFORMATION: Synechocystis PCC6803

<400> SEQUENCE: 82

```
ttgaattaat ctcctacttg actttatgag ttgggatttt cttaaacaca attccccgg      60
ataaactgag ggagtccaaa gtaatgaccc tagagttatt gttactgatc tccattaact    120
ttcgttaact acccggggat ttatgagaga tattacctaa ataaatccag ggagaaacac    180
ggaggcagcg acaagggcca ccgggatgct caaacagctc agcgcctagg cttgaatgct    240
tttgcaatcc cacagttaac tttatacaac ggtgatggga cttatgtctg ttacatcttg    300
ttaattttat tcctgctttt ttgttaagta atgttgcagg ggattctcag attgtcctgg    360
attgggaagg gaagacaacc agtttcgttc agcttatgtt ttagggctaa aattatgcaa    420
ttgatgttcg gtgcgaactt ttctcgtttt tttagtttcc agtggggtag ggaagactgt    480
tgcctaggga accacagcct actttccttt ttgagctttt tatcccacca ttttgatatt    540
cagggactct tctctacagg                                                560
```

<210> SEQ ID NO 83
<211> LENGTH: 17733
<212> TYPE: DNA
<213> ORGANISM: Artificial Sequence
<220> FEATURE:
<223> OTHER INFORMATION: sequence of plasmid Sh-Pori

<400> SEQUENCE: 83

```
ctcgcgagaa ttaattcaga taaaaaaat ccttagcttt cgctaaggat gatttctagc      60
gatgaccctg ctgattggtt cgctgaccat ttccgggtgc gggacggcgt taccagaaac    120
tcagaaggtt cgtccaacca aaccgactct gacggcagtt tacagagag atgataggt     180
ctgcttcagt aagccagatg ctacacaatt aggcttgtac gggtactcga cctgcatccc    240
ttaacttact tattaaataa tttatagcta ttgaaaagag ataagaattg ttcaaagcta    300
atattgtttta aatcgtcaat tcctgcatgt tttaaggaat tgttaaattg attttttgta    360
aatatttct tgtattcttt gttaaaataa aaaagggggac ctctagggtc cccaattaat    420
```

```
tagtaatata atctattaaa ggtcattcaa aaggtcatcc accggatcag cttagtaaag      480
ccctcgctag atttaatgc ggatgttgcg attacttcgc caactattgc gataacaaga       540
aaaagccagc ctttcatgat atatctccca atttgtgtag ggcttattat gcacgcttaa      600
aaataataaa agcagacttg acctgatagt ttggctgtga gcaattatgt gcttagtgca      660
tctaacgctt gagttaagcc gcgccgcgaa gcggcgtcgg cttgaacgaa ttgttagaca      720
ttatttgccg actaccttgg tgatctcgcc tttcacgtag tggacaaatt cttccaactg      780
atctgcgcgc gaggccaagc gatcttcttc ttgtccaaga taagcctgtc tagcttcaag      840
tatgacgggc tgatactggg ccggcaggcg ctccattgcc cagtcggcag cgacatcctt      900
cggcgcgatt ttgccggtta ctgcgctgta ccaaatgcgg gacaacgtaa gcactacatt      960
tcgctcatcg ccagcccagt cgggcggcga gttccatagc gttaaggttt catttagcgc     1020
ctcaaataga tcctgttcag gaaccggatc aaagagttcc tccgccgctg gacctaccaa     1080
ggcaacgcta tgttctcttg cttttgtcag caagatagcc agatcaatgt cgatcgtggc     1140
tggctcgaag atacctgcaa gaatgtcatt gcgctgccat tctccaaatt gcagttcgcg     1200
cttagctgga taacgccacg gaatgatgtc gtcgtgcaca acaatggtga cttctacagc     1260
gcggagaatc tcgctctctc caggggaagc cgaagtttcc aaaaggtcgt tgatcaaagc     1320
tcgccgcgtt gtttcatcaa gccttacggt caccgtaacc agcaaatcaa tatcactgtg     1380
tggcttcagg ccgccatcca ctgcggagcc gtacaaatgt acggccagca acgtcggttc     1440
gagatggcgc tcgatgacgc caactacctc tgatagttga gtcgatactt cggcgatcac     1500
cgcttccctc atgatgttta actttgtttt agggcgactg ccctgctgcg taacatcgtt     1560
gctgctccat aacatcaaac atcgaccac ggcgtaacgc gcttgctgct tggatgcccg      1620
aggcatagac tgtaccccaa aaaaacagtc ataacaagcc atgaaaaccg ccactgcgcc     1680
gttaccaccg ctgcgttcgg tcaaggttct ggaccagttg cgtgagcgca tacgctactt     1740
gcattacagc ttacgaaccg aacaggctta tgtccactgg gttcgtgcct tcatccgttt     1800
ccacggtgtg cgtcacccgg caaccttggg cagcagcgaa gtcgaggcat ttctgtcctg     1860
gctggcgaac gagcgcaagg tttcggtctc cacgcatcgt caggcattgg cggccttgct     1920
gttcttctac ggcaaggtgc tgtgcacgga tctgccctgg cttcaggaga tcggaagacc     1980
tcggccgtcg cggcgcttgc cggtggtgct gaccccggat gaagtggttc gcatcctcgg     2040
ttttctggaa ggcgagcatc gtttgttcgc ccagcttctg tatggaacgg gcggatcagt     2100
gagggtttgc aactgcgggt caaggatctg gatttcgatc acggcacgat catcgtgcgg     2160
gagggcaagg gctccaagga tcgggccttg atgttacccg agagcttggc acccagcctg     2220
cgcgagcagg ggaattgatc cggtggatga cctttgaat gacctttaat agattatatt      2280
actaattaat tggggaccct agaggtcccc ttttttattt tctgaacggt ctggttatag     2340
gtacattgag caactgactg aaatgcctca aatgttctt tacgatgcca ttgggatata      2400
tcaacggtgg tatatccagt gattttttc tccattttag cttccttagc tcctgaaaat      2460
ctcgataact caaaaaatac gcccggtagt gatcttattt cattatggtg aaagttggaa     2520
cctcttacga gcggccgcat acgatttagg tgacactata ggatccctgc cggcggtcc      2580 ggcgcgcccg ggctcgagtg cacgtacgta ctacttaatt gacaaatatg catcacacca     2640
tagacatata gttcccgtat tttctcagaa aataacaata ttcagtaatt aaaaattcta     2700
aacagcaaat ccagagatat tttggctcta tcgatatttt ttcgtcagaa cttgtctgat     2760
```

```
ctgcaaaatt ttttagggt tcacatatca tatttagtac attgagaaat catatcttat    2820
ttttatttaa tttttcttta gtaataaatt atcctaatat atattttggt agatattttc    2880
tctattagag ttaagctaaa ttttgttaag gatactcatt aattaatttg tgttccacag    2940
agttaagtta aacacttatc tcttgatgtt gctttgaaaa ctgacaaagt aactgcgatt    3000
gatttggctt tcagcttgaa taacatttcc agcctttta ggtatggcag agtatcactt    3060
ttgcacacaaa tataaggttc tagataaatg ttaaaaaaca gcgaactgaa tatcaatcag    3120
ggctgtaatc ttcagtggaa gctaggagac aagcagagaa agttttccac actaaaagtc    3180
ctgcaaatca tagcagttga agatcagcta taatcgcaaa agttaataat tttcattgcc    3240
attaacatca gttgaatctt ggtatcttgt taccttcaaa tattgcatgt atactaaaaa    3300
cggcttagag atttacttgt tttgaagagt tcaaatcttt tttaggcaat gtttataact    3360
aatttaggtg aaactccggc tattagtcgt tcatagtata gactaacaat gcatcgttgt    3420
cagaaacaga tgttgttttt tagtggtctt tatttgattg taattaggta ttgaatcaag    3480
ttttcgaggc tatcttatga ttcgtttatg tatagtagaa acctaaaaga tagcttgaaa    3540
atagtgaatt ttcattgttg attaatatcc aaccaaact aggatgagat agtagtttat    3600
ctacttattc ttgtttgtga attagttgta atgtggagta aaaaagcaat caacattcaa    3660
cgtggatatt gttcagatcc attccccgca ttcatacgta aaggacaaaa ataatgggta    3720
cacctcacgc tacttttgca gctactgaga cagcatttca tgtgacgggc tacgaaaaga    3780
tagattttag cctggtttat gtgaatggtg tattcaacat caaaaacaca gaaattgctg    3840
atagttatca gaagtttgga cgctgcttga ctgttgttga tcataatgtc taccgtttgt    3900
atggagacca aattaagtca tattttcgtt actacgacat agacttaact gtgtttccaa    3960
ttactattac tgaacctggc aaaaccatgt caacttttga acaagtagtt gatgcgtttg    4020
ccgattttgg cttaattcgt aaagaaccag ttttagtagt tggtggtggt ttagttactg    4080
atgttgtagg ttttgcttgt gcagcttatc gtcgcagtac taactatatt cgcattccca    4140
cgactttgat tggtttgata gatgctggaa ttgcgattaa agtagcagtc aatcataaaa    4200
agctgaaaaa tcgcttgggt gcttaccatg caccgcagaa agtcattcta gacttttcct    4260
ttctcaagac actaccaaca gcccaagtcc ggaatggaat ggcggagtta gtgaaaattg    4320
ctgtggtagc aaatgcagaa gttttttaatt ggctgtatga gtacggagaa gatttactgc    4380
atacacactt tggctatctc aacggtacag aggaactgca agaaattgct cacaaagtta    4440
actacgaagc aattaaaacc atgctggagt tagaaactcc aaacctgcat gagctagact    4500
tagatcgcgt cattgcttat ggtcacactt ggagtccgac actagaatta gcaccgcggg    4560
ttcctctgta tcatggtcat gctgtcaaca tcgatatggc gctatcagca actattgctg    4620
aacgacgggg atatattact gtagcagaac gcgatcgcat tcttggattg atgagtcgtc    4680
taggtttagc ccttgatcat ccccttctag atagcgattt gttatggtac gctacccagt    4740
ctatcaccca gacaagagac gggaaacaac gcgccgccat gccaaaacct attggtgagt    4800
gtttctttgt caatgaccta acccgtgaag aattgcatca agctttgatt gcacacaagg    4860
atgtatgtgc aacatatccc cgtggtggag atggggattga agcctatatc agtgcagaac    4920
aatctgagat ggtaggagtt tagaatcgtg actagcattg ttgaaaagaa cacagctaga    4980
cccgtaactc cccacggtat cttggttgaa cagctacaaa aaactctggc tttggcagaa    5040
tcaggaaata cacctgaaac tgttgtgact gcactacgac aggcgtatca attagcggcg    5100
ggtttagaac cttatattag tgaacacacc actactgaat ctgacgcctt agcagcactg    5160
```

-continued

```
gtacaaaaaa ctaccaaaga agactggaca aaacgtttca ctgatggtga aacagtgcgt    5220
caactagaac aggaaatgct ttctggacac gtcgagggac aaaccctgaa aatgtttgtt    5280
cacatgacta aagccaagag tgttttggaa gtaggaatgt tcaccgggta ttctgctttg    5340
gcaatggcag aggcattacc tgatgatgga cgagtggtag catgtgaagt agactcttat    5400
gttgctagct ttgctcaaac ttgttttcca aactcgcccc acggtcataa aattactgtg    5460
gaagttgcac cagccttgga aactctgcaa aaacttgcag cagcaggtga atcatttgat    5520
ttgatattca tcgatgctga caagaaagag tatgtgcagt atttccagat catcttggat    5580
aataatctac ttgcatctaa cggcattatt tgtgtagata acactttaat gcagggacag    5640
gtttatctgc caccagaaca acgtacagct aatggtgaag cgatcgctca atttaaccaa    5700
atcattaccc aagatccgcg tgtagaacaa gttatactac cgcttcgtga tggtgtgact    5760
ttaattcggc ggttgtagaa ggatgggggtt tgggtggtac tgatgggttt ttttgaggg    5820 cgaattatat gacacaatct atttctgtgg cttctgttgg acaaacaact cagtcggtga    5880
gcctgggact tcgcatatct gcgttgtgga aaagtttagc tacacttgca ctgctgttgt    5940
tagtattgcc aatcaatgct gcgattgtgt tggtatcgct gttattgggt agtcaatcgc    6000
aagcgatcgc caccgaaccc aaaaacatct tgattagtgg cggtaaaatg actaaggcgt    6060
tacaattagc ccgtagtttt cacgccgccg gacatcgagt ggttttagta gaaactcaca    6120
aatactggtt aacgggacac cgatttttcca aagcagtaag tcgtttctac actctaccaa    6180
cgccccaatc tgatcctgaa gcatacaccc aagccctatt agatattgtt caaaagaaa     6240 atatcgatgt ctatgtaccc gtgtgcagtc cggttgctag ttactacgac tctttagcta    6300
aacccgtact gtcgaagtac tgcgaggttt tcactgtga cgcagatgtc acccaaatgt     6360
tggatgataa atacgctttt gctgagaaag cgcggagttt ggggttatct gttcccaagt    6420
ctttcaaaat tactgacccg gaacaggtga gcaactttga ttttctcaa gaaaagcgta     6480 aatacatcct caaaagcatt ccttatgact ctgttcgtcg cttagattta accaaacttc    6540
cttgtgagac tcccgaagca acagcagatt ttgtcaacag cttacccatc agttcccaaa    6600
agccatggat tatgcaagaa ttcattcctg gaaaagaatt ttgcacccac agcactgtcc    6660
gcaatgggga gttgagaatg cattgctgtt gtgaatcttc ggcatttcaa gttaactatg    6720
agaatgtcga tcatccccaa atttggaat gggtgcgaca ctttgtcaaa gcattaggta    6780
tcactggaca ggtatctttt gattttatcg aagcacaaga tggcacaatc tacgccattg    6840
aatgtaatcc gcgtacccat tctgccatca ctatgttcta caatcatccg gatgtggcaa    6900
atgcttattt gagtgaaatt ccacaagtag aaccaattca acctctgatt aatagtaagc    6960
ctacctactg gacttatcac gaaatttggc gattgacagg aattcgttct ttctcacagt    7020
tgcaaacttg gttgaaaaac ttttttggtg gaaaagatgc gatttacagt ttgagtgatc    7080 ctctacccttt tttaacagtt catcactggc aaattccttt attattgcta caaaatttgc    7140
aacagctaaa aggttggatc aggatagatt ttaatattgg gaaattggtt gagtttggtg    7200
gcgattagat tcagttatca gttatcagtt atcagttagt agctgttcac tgataattta    7260
tagatattga atatatataa gactcatatt tgatttctga aatacacgta gggtgcgtga    7320
tagctacgcc ataacacacc ctactggcgc gtcaagccta aaatgttgca ataaatctct    7380
gattctatct ctgtgttctc tctcttgaaa agctttgatc ggaggaaacc tccgctcaaa    7440
cttttcgctg cttcctctgc ggtttattaa tgcactattt taaggctgtc gcgcccttg     7500
```

```
ttaaagtcaa attttttat caaaccgcag aggcgcagag gaatcagaga gaaggaaata      7560
attcttaatt gaattgtatt aagttataaa tcactatatt ttatcaaaga tggaaataat      7620
aaacttttta gatgattctc tggaaattga agaacagaag aaaaattggg aaagacaggt      7680
aggagatatt tctgatcttt ctctgctgag tttagaagaa cagcaaaaaa tattatttat      7740
atggaatcag acagaaagta attatgattt gtcgatttgt ctacatgagt tatttgcagc      7800
acaggtagag aaaacaccag atgcaaaagc tctcaagttt gctgatcaag aattgagtta      7860
tcatcagtta aattgtcggg cgaatcaact cgctcactat ttgcaatctt tgggaattgt      7920
aactgaagat ttagttggga tttgtgtgga acgttcccta gaaatggttg tggggttatt      7980
gggtattttg aaagcgggtg cggcttatgt tccaattgat cctggatatc cccaagaacg      8040
tttaggatat atgttggcgg attcccaggt gtcggtgttg ttgactcaaa gtcatttagt      8100
cgatagttta ccaacatgtc caacccatac tatttgcttg gatactgact gggatctgat      8160
ttctcaatat agcgatcgca atctccaaaa tacaacgaca ccagaaaatc tcgcttatgt      8220
aatttacact tctggttcta ctggtaaacc taaaggagcg atgaataccc atcgcggtat      8280
ttgcaatcgt ctgttatgga tgcaagatgc ttatcaactc actcaacaag atcgggttct      8340
gcaaaaaact ccctttagtt ttgatgtctc tgtctgggaa ttcttttggc cgttgattac      8400
cggggcgcgg ctgattatag cacaaccagg tggacacaag atagttctt atctaattaa      8460 tacaattatc aagaagaaa ttaccacatt acattttgtt ccttcgatgt tgcaggtatt      8520
tttgcaagct aaaggagtgg aaaattgtca gtcattaaaa cgggtaatta ctagtggtga      8580
agctttacct gtgagtctgc aagaacggtt ttttgaacgt ttgggatgtg aactgcacaa      8640
tctttatggt cctacagaag cagcgatcga tgttacgttt tggcagtgtc aacctcaaag      8700
tcaatatcaa acagtaccga ttggtcgtcc catcgctaat actcaaatat atatattaga      8760
tcaacatttg caacctgtgc ctgtgggtgt tgtgggtgaa cttttatattg gtggtgtggg      8820 agttgccaga ggttactggc gtcgtccaga attaactaca gaaagatttg tatctaatcc      8880
ctttgcaacg ggacaaatgt ataaaactgg tgacttggcg cgctatttac ctgatggtaa      8940
tatcgagtat gttggcagaa ttgacgatca agttaaaatt cgcggttttc ggattgagtt      9000
gggagaaatt gagagtacgc tgacgcaaca ttcccagatt agtcaagctg tggttgtcgc      9060
ccagacagat aatttgaata ataagcattt aattgcttat attgttcccc agggagaacc      9120
acccacacca acccaactgc ggaatttcct tcagggtaag ctacctgaat tcatggttcc      9180
ctcagctttt gtctgcttaa attcctttcc tctcactcct agtggaaaaa tagacaggcg      9240
atcgcttccc aaacctgatt tttctaactt aatcactcat gaagatttta cgcctgcacg      9300
caatgattta gagagaaaaa tcgcgcagat ttggtcagaa attttacaga tttcggaaat      9360
tgatattaga gataactttt ttgaagttgg tggtaattcc cttttagcat tacatttaat      9420
gaatgccatc gaacaaaaat ttggtcgaga gttagcactg tcaactttac ttactaataa      9480
ctcaattgaa aaactagcag aaattctgca aaacccaca gatgttttc ccaattcacc      9540 catagtagca attcagccca aaggtacaaa acgtcctttt ttctgcatcc atccagccgg      9600
cggacatgta ctttgctatt ttagtttggc gcattattta ggcactgacc agccatttta      9660
cggtttacaa gcacagggtt tttatggtga agaagaacca ctaactacag ttgtagaaat      9720
ggctaggctt tatgctcaag ctatacaaac aattcaaccc acagggccat atcaaattgg      9780
tggttggtcg tttggtggtg tagttgccta tgaaacggct caacaactac accaacaagg      9840
aaaagaagtt tcattactag caattttaga ttcctacgtg ccaattctgt tagataaaaa      9900
```

```
taaaaaaatt gatgatgttt atttagttgg tgtactatcc cgtgtatttg gcggaatgtt    9960
tggtcaagat aatctgattt cactagcgga aatcgaaaat ttaagtgtgg aagaaagttt   10020
aaattacatc atcgaaaaag cacgccaagc caaaattttt ccgccaggag tggaacgtca   10080
caacaatcgc cgcattttag atgttttagt cggaacttta aaagccactt attcttatga   10140
acgttgtccc tatcctggca aagttactat ttttagagcc agagaaaaac atatcatggc   10200
tcctgatcct actttagttt gggtagaatt attttcagtt ttggctgcgg aggaaattga   10260
aattcataat gtccccggta atcactattc atttgtttta gaacctcacg tccaagcttt   10320
ggctgaaagt ttgcagaaat gtttgtgctg atacaagatc cccgacttct ttgaggatgc   10380
agctggcgaa taggggggtca aacccctcgt gcgcccacaa attggttgta gagacgcgcc   10440
atggcgcgtc tctacatctg gtggaatgac gaaaaatctc ggtgaggggt gtcacccctg   10500
attcgccagc tgtatccttt gagaagtcgg ggagctcggt acccctagag tcgacctgca   10560
gttcaatgcg gtccaatacc tcccctgccc aactgggtaa gctcgcggct ccactgagta   10620
atacagacaa ggctaaacag gcaaatttt tcattggtca actcctagca ccaatttccc   10680
aagactacgg aggggggcaat gaagtttcaa ttaattgggg tcacaaacca cagcggccta   10740
tggctctaat caatggcaca ctagaaaaaa tgttgcagca tacttggcta ccaaaacccc   10800
caaatttaac cttattgtca gatgaagttc atctctggcg cattccctt gaccaaccag   10860
aatcacagct acaggattta gccgctacct tatctagtga cgaattagcc cgtgcaaaca   10920
gatttttattt tcccgaacat cgccggcgtt ttactgctgg tcgtggtatt ctccgcagta   10980
tcttgggggg ctatttgggt gtggaaccag ggcaagttaa atttgattat gaatcccgtg   11040
gtaaaccaat attaggcgat cgctttgccg agagtggttt attatttaac ttgtcacact   11100
cccagaactt ggccttgtgt gcagtcaatt acacgcgcca aatcggcatc gatttagaat   11160
atctccgccc cacatctgat ttagaatccc ttgccaaaag gttctttta ccgcgagaat   11220
atgaattatt gcgatcgcta cccgatgagc aaaaacaaaa aatttctt cgttactgga   11280
cttgtaaaga ggcttatctt aaagcaacgg gtgacggcat cgctaaatta gaggaaattg   11340
aaatagcact aactcccaca gaaccagcta agttacagac agctccagcg tggagtctcc   11400
tagagctagt gccagatgat aattgtgttg ctgctgttgc cgtggcgggt tttggctggc   11460
agccaaaatt ctggcattat tgagcatgca agcttctccc tatagtgagt cgtattagcg   11520
gccgcatcga atataacttc gtataatgta tgctatacga agttattagc gatgaggaca   11580
tgaggttgcc ccgtattcag tgtcgctgat ttgtattgtc tgaagttgtt tttacgttaa   11640
gttgatgcag atcaattaat acgatacctg cgtcataatt gattatttga cgtggtttga   11700
tggcctccac gcacgttgtg atatgtagat gataatcatt atcactttac gggtcctttc   11760
cggtgatccg acaggttacg gggcggcgac ctcgcgggtt ttcgctattt atgaaaattt   11820
tccggtttaa ggcgtttccg ttcttcttcg tcataactta atgtttttat ttaaaatacc   11880
ctctgaaaag aaaggaaacg acaggtgctg aaagcgaggc ttttggcct ctgtcgtttc   11940
ctttctctgt ttttgtccgt ggaatgaaca atggaagtcc tcgtctcgcc ctcgaattag   12000
cccgcctaat gagcgggctt tttttgaatt aattctcgcg agctggcacg acaggtttcc   12060
cgactggaaa gcgggcagtg agcgcaacgc aattaatgta agttagcgcg aattgcaagc   12120
tggccgacgc gctgggctac gtcttgctgg cgttcgggag cagaagagca tacatctgga   12180
agcaaagcca ggaaagcggc ctatggagct gtgcggcagc gctcagtagg caattttca   12240
```

| | |
|---|---|
| aaatattgtt aagccttttc tgagcatggt atttttcatg gtattaccaa ttagcaggaa | 12300 |
| aataagccat tgaatataaa agataaaaat gtcttgttta caatagagtg ggggggggtca | 12360 |
| gcctgccgcc ttgggccggg tgatgtcgta cttgcccgcc gcgaactcgg ttaccgtcca | 12420 |
| gcccagcgcg accagctccg gcaacgcctc gcgcacccgc ttgcggcgct tgcgcatggt | 12480 |
| cgaaccactg gcctctgacg gccagacata gccgcacaag gtatctatgg aagccttgcc | 12540 |
| ggttttgccg gggtcgatcc agccacacag ccgctggtgc agcaggcggg cggtttcgct | 12600 |
| gtccagcgcc cgcacctcgt ccatgctgat gcgcacatgc tggccgccac ccatgacggc | 12660 |
| ctgcgcgatc aagggttca gggccacgta caggcgcccg tccgcctcgt cgctggcgta | 12720 |
| ctccgacagc agccgaaacc cctgccgctt gcggccattc tgggcgatga tggataccct | 12780 |
| ccaaaggcgc tcgatgcagt cctgtatgtg cttgagcgcc ccaccactat cgacctctgc | 12840 |
| cccgatttcc tttgccagcg cccgatagct acctttgacc acatggcatt cagcggtgac | 12900 |
| ggcctcccac ttgggttcca ggaacagccg gagctgccgt ccgccttcgg tcttgggttc | 12960 |
| cgggccaagc actaggccat taggcccagc catggccacc agcccttgca ggatgcgcag | 13020 |
| atcatcagcg cccagcggct ccgggccgct gaactcgatc cgcttgccgt cgccgtagtc | 13080 |
| atacgtcacg tccagcttgc tgcgcttgcg ctcgccccgc ttgagggcac ggaacaggcc | 13140 |
| gggggccaga cagtgcgccg ggtcgtgccg gacgtggctg aggctgtgct tgttcttagg | 13200 |
| cttcaccacg gggcaccccc ttgctcttgc gctgcctctc cagcacgcg ggcttgagca | 13260 |
| ccccgccgtc atgccgcctg aaccaccgat cagcgaacgg tgcgccatag ttggccttgc | 13320 |
| tcacaccgaa gcggacgaag aaccggcgct ggtcgtcgtc cacacccat cctcggcct | 13380 |
| cggcgctggt catgctcgac aggtaggact gccagcggat gttatcgacc agtaccgagc | 13440 |
| tgccccggct ggcctgctgc tggtcgcctg cgcccatcat ggccgcgccc ttgctggcat | 13500 |
| ggtgcaggaa cacgatagag cacccggtat cggcggcgat ggcctccatg cgaccgatga | 13560 |
| cctgggccat ggggccgctg gcgttttctt cctcgatgtg gaaccggcgc agcgtgtcca | 13620 |
| gcaccatcag gcggcggccc tcggcggcgc gcttgaggcc gtcgaaccac tccggggcca | 13680 |
| tgatgttggg caggctgccg atcagcggct ggatcagcag gccgtcagcc acggcttgcc | 13740 |
| gttcctcggc gctgaggtgc gccccaaggg cgtgcaggcg gtgatgaatg gcggtgggcg | 13800 |
| ggtcttcggc gggcaggtag atcaccgggc cggtgggcag ttcgcccacc tccagcagat | 13860 |
| ccggcccgcc tgcaatctgt gcggccagtt gcagggccag catggattta ccggcaccac | 13920 |
| cgggcgacac cagcgccccg accgtaccgg ccaccatgtt gggcaaaacg tagtccagcg | 13980 |
| gtggcggcgc tgctgcgaac gcctccagaa tattgatagg cttatgggta gccattgatt | 14040 |
| gcctcctttg caggcagttg gtggttaggc gctggcgggg tcactacccc cgccctgcgc | 14100 |
| cgctctgagt tcttccaggc actcgcgcag cgcctcgtat tcgtcgtcgg tcagccagaa | 14160 |
| cttgcgctga cgcatcccctt tggccttcat gcgctcggca tatcgcgctt ggcgtacagc | 14220 |
| gtcagggctg gccagcaggt cgccggtctg cttgtccttt tggtctttca tatcagtcac | 14280 |
| cgagaaactt gccggggccg aaaggcttgt cttcgcggaa caaggacaag gtgcagccgt | 14340 |
| caaggttaag gctggccata tcagcgactg aaaagcggcc agcctcggcc ttgtttgacg | 14400 |
| tataaccaaa gccaccgggc aaccaatagc ccttgtcact tttgatcagg tagaccgacc | 14460 |
| ctgaagcgct tttttcgtat tccataaaac cccttctgt gcgtgagtac tcatagtata | 14520 |
| acaggcgtga gtaccaacgc aagcactaca tgctgaaatc tggcccgccc ctgtccatgc | 14580 |
| ctcgctggcg gggtgccggt gcccgtgcca gctcggcccg cgcaagctgg acgctgggca | 14640 |

```
gacccatgac cttgctgacg gtgcgctcga tgtaatccgc ttcgtggccg ggcttgcgct    14700
ctgccagcgc tgggctggcc tcggccatgg ccttgccgat ttcctcggca ctgcggcccc    14760
ggctggccag cttctgcgcg gcgataaagt cgcacttgct gaggtcatga ccgaagcgct    14820
tgaccagccc ggccatctcg ctgcggtact cgtccagcgc cgtgcgccgg tggcggctaa    14880
gctgccgctc gggcagttcg aggctggcca gcctgcgggc cttctcctgc tgccgctggg    14940
cctgctcgat ctgctggcca gcctgctgca ccagcgccgg ccagcggtg gcggtcttgc     15000 ccttggattc acgcagcagc acccacggct gataaccggc gcgggtggtg tgcttgtcct    15060
tgcggttggt gaagcccgcc aagcggccat agtggcggct gtcggcgctg gccgggtcgg    15120
cgtcgtactc gctggccagc gtccgggcaa tctgcccccg aagttcaccg cctgcggcgt    15180
cggccacctt gacccatgcc tgatagttct tcgggctggt ttccactacc agggcaggct    15240
cccggccctc ggctttcatg tcatccaggt caaactcgct gaggtcgtcc accagcacca    15300
gaccatgccg ctcctgctcg gcgggcctga tatacacgtc attgccctgg gcattcatcc    15360
gcttgagcca tggcgtgttc tggagcactt cggcggctga ccattcccgg ttcatcatct    15420
ggccggtggg tgcgtccctg acgccgatat cgaagcgctc acagcccatg gccttgagct    15480
gtcggcctat ggcctgcaaa gtcctgtcgt tcttcatcgg gccaccaagc gcagccagat    15540
cgagccgtcc tcggttgtca gtggcgtcag gtcgagcaag agcaacgatg cgatcagcag    15600
caccaccgta ggcatcatgg aagccagcat cacggttagc catagcttcc agtgccaccc    15660
ccgcgacgcg ctccgggcgc tctgcgcggc gctgctcacc tcggcggcta cctcccgcaa    15720
ctctttggcc agctccaccc atgccgcccc tgtctggcgc tgggctttca gccactccgc    15780
cgcctgcgcc tcgctggcct gcttggtctg gctcatgacc tgccgggctt cgtcggccag    15840
tgtcgccatg ctctgggcca gcggttcgat ctgctccgct aactcgttga tgcctctgga    15900
tttcttcact ctgtcgattg cgttcatggt ctattgcctc ccggtattcc tgtaagtcga    15960
tgatctgggc gttggcggtg tcgatgttca gggccacgtc tgcccggtcg gtgcggatgc    16020
cccggccttc catctccacc acgttcggcc ccaggtgaac accgggcagg cgctcgatgc    16080
cctgcgcctc aagtgttctg tggtcaatgc gggcgtcgtg ccagcccgc tctaatgccc     16140 ggttggcatg gtcggcccat gcctcgcggg tctgctcaag ccatgccttg ggcttgagcg    16200
cttcggtctt ctgtgcccg cccttctccg gggtcttgcc gttgtaccgc ttgaaccact     16260
gagcggcggg ccgctcgatg ccgtcattga tccgctcgga gatcatcagg tggcagtgcg    16320
ggttctcgcc gccaccggca tggatggcca gcgtatacgg caggcgctcg gcaccggtca    16380
ggtgctgggc gaactcggac gccagcgcct tctgctggtc gagggtcagc tcgaccggca    16440
gggcaaattc gacctccttg aacagccgcc cattggcgcg ttcatacagg tcggcagcat    16500
cccagtagtc ggcgggccgc tcgacgaact ccggcatgtg cccggattcg gcgtgcaaga    16560
cttcatccat gtcgcgggca tacttgcctt cgcgctggat gtagtcggcc ttggccctgg    16620
ccgattggcc gcccgacctg ctgccggttt cgccgtaag gtgataaatc gccatgctgc     16680
ctcgctgttg cttttgcttt tcggctccat gcaatggccc tcggagagcg caccgcccga    16740
agggtggccg ttaggccagt ttctcgaaga gaaaccggta agtgcgccct cccctacaaa    16800
gtagggtcgg gattgccgcc gctgtgcctc catgatagcc tacgagacag cacattaaca    16860
atggggtgtc aagatggtta aggggagcaa caaggcggcg gatcggctgg ccaagctcga    16920
agaacaacga gcgcgaatca atgccgaaat tcagcgggag cgggcaaggg aacagcagca    16980
```

-continued

| | |
|---|---|
| agagcgcaag aacgaaacaa ggcgcaaggt gctggtgggg gccatgattt tggccaaggt | 17040 |
| gaacagcagc gagtggccgg aggatcggct catggcggca atggatgcgt accttgaacg | 17100 |
| cgaccacgac cgcgccttgt tcggtctgcc gccacgccag aaggatgagc cgggctgaat | 17160 |
| gatcgaccga gacaggccct gcggggctgc acacgcgccc ccaccettcg ggtagggga | 17220 |
| aaggccgcta aagcggctaa aagcgctcca gcgtatttct gcggggtttg gtgtggggtt | 17280 |
| tagcgggctt tgcccgcctt tccccctgcc gcgcagcggt ggggcggtgt gtagcctagc | 17340 |
| gcagcgaata gaccagctat ccggcctctg gccgggcata ttgggcaagg gcagcagcgc | 17400 |
| cccacaaggg cgctgataac cgcgcctagt ggattattct tagataatca tggatggatt | 17460 |
| tttccaacac cccgccagcc cccgcccctg ctgggtttgc aggtttgggg gcgtgacagt | 17520 |
| tattgcaggg gttcgtgaca gttattgcag ggggcgtga cagttattgc aggggttcgt | 17580 |
| gacagttagt acgggagtga cgggcactgg ctggcaatgt ctagcaacgg caggcatttc | 17640 |
| ggctgagggt aaaagaactt tccgctaagc gatagactgt atgtaaacac agtattgcaa | 17700 |
| ggacgcggaa catgcctcat gtggcggcca gga | 17733 |

<210> SEQ ID NO 84
<211> LENGTH: 16842
<212> TYPE: DNA
<213> ORGANISM: Artificial Sequence
<220> FEATURE:
<223> OTHER INFORMATION: sequence of plasmid Sh-PrnpB

<400> SEQUENCE: 84

| | |
|---|---|
| ctcgcgagaa ttaattcaga taaaaaaaat ccttagcttt cgctaaggat gatttctagc | 60 |
| gatgaccctg ctgattggtt cgctgaccat ttccgggtgc gggacggcgt taccagaaac | 120 |
| tcagaaggtt cgtccaacca aaccgactct gacggcagtt tacgagagag atgatagggt | 180 |
| ctgcttcagt aagccagatg ctacacaatt aggcttgtac gggtactcga cctgcatccc | 240 |
| ttaacttact tattaaataa tttatagcta ttgaaaagag ataagaattg ttcaaagcta | 300 |
| atattgttta aatcgtcaat tcctgcatgt tttaaggaat tgttaaattg attttttgta | 360 |
| aatattttct tgtattcttt gttaaaataa aaaaggggac tctagggtc cccaattaat | 420 |
| tagtaatata atctattaaa ggtcattcaa aaggtcatcc accggatcag cttagtaaag | 480 |
| ccctcgctag atttttaatgc ggatgttgcg attacttcgc caactattgc gataacaaga | 540 |
| aaaagccagc ctttcatgat atatctccca atttgtgtag ggcttattat gcacgcttaa | 600 |
| aaataataaa agcagacttg acctgatagt ttggctgtga gcaattatgt gcttagtgca | 660 |
| tctaacgctt gagttaagcc gcgccgcgaa gcggcgtcgg cttgaacgaa ttgttagaca | 720 |
| ttatttgccg actaccttgg tgatctcgcc tttcacgtag tggacaaatt cttccaactg | 780 |
| atctgcgcgc gaggccaagc gatcttcttc ttgtccaaga taagcctgtc tagcttcaag | 840 |
| tatgacgggc tgatactggg ccggcaggcg ctccattgcc cagtcggcag cgacatcctt | 900 |
| cggcgcgatt ttgccggtta ctgcgctgta ccaaatgcgg gacaacgtaa gcactacatt | 960 |
| tcgctcatcg ccagcccagt cgggcggcga gttccatagc gttaaggttt catttagcgc | 1020 |
| ctcaaataga tcctgttcag gaaccggatc aaagagttcc tccgccgctg gacctaccaa | 1080 |
| ggcaacgcta tgttctcttg cttttgtcag caagatagcc agatcaatgt cgatcgtggc | 1140 |
| tggctcgaag atacctgcaa gaatgtcatt gcgctgccat tctccaaatt gcagttcgcg | 1200 |
| cttagctgga taacgccacg gaatgatgtc gtcgtgcaca acaatggtga cttctacagc | 1260 |
| gcggagaatc tcgctctctc caggggaagc cgaagtttcc aaaaggtcgt tgatcaaagc | 1320 |

```
tcgccgcgtt gtttcatcaa gccttacggt caccgtaacc agcaaatcaa tatcactgtg    1380
tggcttcagg ccgccatcca ctgcggagcc gtacaaatgt acggccagca acgtcggttc    1440
gagatggcgc tcgatgacgc caactacctc tgatagttga gtcgatactt cggcgatcac    1500
cgcttccctc atgatgttta actttgtttt agggcgactg ccctgctgcg taacatcgtt    1560
gctgctccat aacatcaaac atcgacccac ggcgtaacgc gcttgctgct tggatgcccg    1620
aggcatagac tgtaccccaa aaaacagtc ataacaagcc atgaaaaccg ccactgcgcc    1680
gttaccaccg ctgcgttcgg tcaaggttct ggaccagttg cgtgagcgca tacgctactt    1740
gcattacagc ttacgaaccg aacaggctta tgtccactgg gttcgtgcct tcatccgttt    1800
ccacggtgtg cgtcacccgg caaccttggg cagcagcgaa gtcgaggcat ttctgtcctg    1860
gctggcgaac gagcgcaagg tttcggtctc cacgcatcgt caggcattgg cggccttgct    1920
gttcttctac ggcaaggtgc tgtgcacgga tctgccctgg cttcaggaga tcggaagacc    1980
tcggccgtcg cggcgcttgc cggtggtgct gaccccggat gaagtggttc gcatcctcgg    2040
ttttctggaa ggcgagcatc gtttgttcgc ccagcttctg tatggaacgg gcggatcagt    2100
gagggtttgc aactgcgggt caaggatctg gatttcgatc acggcacgat catcgtgcgg    2160
gagggcaagg gctccaagga tcgggccttg atgttacccg agagcttggc acccagcctg    2220
cgcgagcagg ggaattgatc cggtggatga ccttttgaat gacctttaat agattatatt    2280
actaattaat tggggaccct agaggtcccc ttttttattt tctgaacggt ctggttatag    2340
gtacattgag caactgactg aaatgcctca aaatgttctt tacgatgcca ttgggatata    2400
tcaacggtgg tatatccagt gattttttc tccattttag cttccttagc tcctgaaaat    2460
ctcgataact caaaaaatac gcccggtagt gatcttattt cattatggtg aaagttggaa    2520
cctcttacga gcggccgcat acgatttagg tgacactata ggatccctgc cggccggtcc    2580
ggcgcgcccg ggctcgagtg cacgtacgtt caatgcggtc caatacctcc cctgcccaac    2640
tgggtaagct cgcggctcca ctgagtaata cagacaaggc taaacaggca aatttttca    2700 ttggtcaact cctagcacca atttcccaag actacggagg gggcaatgaa gtttcaatta    2760
attggggtca caaccacag cggcctatgg ctctaatcaa tggcacacta gaaaagacg    2820 tcatgggtac acctcacgct acttttgcag ctactgagac agcatttcat gtgacgggct    2880
acgaaaagat agatttagc ctggtttatg tgaatggtgt attcaacatc aaaaacacag    2940
aaattgctga tagttatcag aagtttggac gctgcttgac tgttgttgat cataatgtct    3000
accgtttgta tggagaccaa attaagtcat attttcgtta ctacgacata gacttaactg    3060
tgtttccaat tactattact gaacctggca aaaccatgtc aacttttgaa caagtagttg    3120
atgcgtttgc cgattttggc ttaattcgta agaaccagt tttagtagtt ggtggtggtt    3180
tagttactga tgttgtaggt tttgcttgtg cagcttatcg tcgcagtact aactatattc    3240
gcattcccac gactttgatt ggtttgatag atgctgaat tgcgattaaa gtagcagtca    3300
atcataaaaa gctgaaaaat cgcttgggtg cttaccatgc accgcagaaa gtcattctag    3360
acttttcctt tctcaagaca ctaccaacag cccaagtccg gaatggaatg gcggagttag    3420
tgaaaattgc tgtggtagca aatgcagaag tttttaattg gctgtatgag tacggagaag    3480
atttactgca tacacacttt ggctatctca acggtacaga ggaactgcaa gaaattgctc    3540
acaaagttaa ctacgaagca attaaaacca tgctggagtt agaaactcca aacctgcatg    3600
agctagactt agatcgcgtc attgcttatg gtcacacttg gagtccgaca ctagaattag    3660
```

```
caccgcgggt tcctctgtat catggtcatg ctgtcaacat cgatatggcg ctatcagcaa      3720
ctattgctga acgacgggga tatattactg tagcagaacg cgatcgcatt cttggattga      3780
tgagtcgtct aggtttagcc cttgatcatc cccttctaga tagcgatttg ttatggtacg      3840
ctacccagtc tatcacccag acaagagacg ggaaacaacg cgccgccatg ccaaaaccta      3900
ttggtgagtg tttctttgtc aatgacctaa cccgtgaaga attgcatcaa gctttgattg      3960
cacacaagga tgtatgtgca acatatcccc gtggtggaga tgggattgaa gcctatatca      4020
gtgcagaaca atctgagatg gtaggagttt agaatcgtga ctagcattgt tgaaaagaac      4080
acagctagac ccgtaactcc ccacggtatc ttggttgaac agctacaaaa aactctggct      4140
ttggcagaat caggaaatac acctgaaact gttgtgactg cactacgaca ggcgtatcaa      4200
ttagcggcgg gtttagaacc ttatattagt gaacacacca ctactgaatc tgacgcctta      4260
gcagcactgg tacaaaaaac taccaaagaa gactggacaa aacgtttcac tgatggtgaa      4320
acagtgcgtc aactagaaca ggaaatgctt tctggacacg tcgagggaca aaccctgaaa      4380
atgtttgttc acatgactaa agccaagagt gttttggaag taggaatgtt caccgggtat      4440
tctgctttgg caatggcaga ggcattacct gatgatggac gagtggtagc atgtgaagta      4500
gactcttatg ttgctagctt tgctcaaact tgtttccaaa actcgcccca cggtcataaa      4560
attactgtgg aagttgcacc agccttggaa actctgcaaa aacttgcagc agcaggtgaa      4620
tcatttgatt tgatattcat cgatgctgac aagaaagagt atgtgcagta tttccagatc      4680
atcttggata taatctact gcatctaac ggcattattt gtgtagataa cactttaatg      4740
cagggacagg tttatctgcc accagaacaa cgtacagcta atggtgaagc gatcgctcaa      4800
tttaaccaaa tcattaccca agatccgcgt gtagaacaag ttatactacc gcttcgtgat      4860 ggtgtgacttt aattcggcg gttgtagaag gatgggttt gggtggtact gatgggtttt      4920
ttttgagggc gaattatatg acacaatcta tttctgtggc ttctgttgga caaacaactc      4980
agtcggtgag cctgggactt cgcatatctg cgttgtggaa aagtttagct acacttgcac      5040
tgctgttgtt agtattgcca atcaatgctg cgattgtgtt ggtatcgctg ttattgggta      5100
gtcaatcgca agcgatcgcc accgaaccca aaaacatctt gattagtggc ggtaaaatga      5160
ctaaggcgtt acaattagcc cgtagttttc acgccgccgg acatcgagtg gttttagtag      5220
aaactcacaa atactggtta acgggacacc gattttccaa agcagtaagt cgttctaca      5280 ctctaccaac gccccaatct gatcctgaag catacaccca agcccctatta gatattgttc      5340 aaaaagaaaa tatcgatgtc tatgtacccg tgtgcagtcc ggttgctagt tactacgact      5400
ctttagctaa acccgtactg tcgaagtact gcgaggtttt tcactgtgac gcagatgtca      5460
cccaaatgtt ggatgataaa tacgcttttg ctgagaaagc gcggagtttg gggttatctg      5520
ttcccaagtc tttcaaaatt actgacccgg aacaggtgag caactttgat ttttctcaag      5580
aaaagcgtaa atacatcctc aaaagcattc cttatgactc tgttcgtcgc ttagatttaa      5640
ccaaacttcc ttgtgagact cccgaagcaa cagcagattt tgtcaacagc ttacccatca      5700
gttcccaaaa gccatggatt atgcaagaat tcattcctgg aaaagaattt tgcacccaca      5760
gcactgtccg caatggggag ttgagaatgc attgctgttg tgaatcttcg gcatttcaag      5820
ttaactatga gaatgtcgat catccccaaa ttttggaatg ggtgcgacac tttgtcaaag      5880
cattaggtat cactgacag gtatctttttg attttatcga agcacaagat ggcacaatct      5940
acgccattga atgtaatccg cgtacccatt ctgccatcac tatgttctac aatcatccgg      6000
atgtggcaaa tgcttatttg agtgaaattc cacaagtaga accaattcaa cctctgatta      6060
```

```
atagtaagcc tacctactgg acttatcacg aaatttggcg attgacagga attcgttctt    6120
tctcacagtt gcaaacttgg ttgaaaaact tttttggtgg aaaagatgcg atttacagtt    6180
tgagtgatcc tctaccttt ttaacagttc atcactggca aattccttta ttattgctac    6240
aaaatttgca acagctaaaa ggttggatca ggatagattt taatattggg aaattggttg    6300
agtttggtgg cgattagatt cagttatcag ttatcagtta tcagttagta gctgttcact    6360
gataatttat agatattgaa tatatataag actcatattt gatttctgaa atacacgtag    6420
ggtgcgtgat agctacgcca taacacaccc tactggcgcg tcaagcctaa atgttgcaa     6480
taaatctctg attctatctc tgtgttctct ctcttgaaaa gctttgatcg gaggaaacct    6540
ccgctcaaac ttttcgctgc ttcctctgcg gtttattaat gcactatttt aaggctgtcg    6600
cgcccttgt taaagtcaaa ttttttttatc aaaccgcaga ggcgcagagg aatcagagag    6660
aaggaaataa ttcttaattg aattgtatta agttataaat cactatattt tatcaaagat    6720
ggaaataata aacttttag atgattctct ggaaattgaa gaacagaaga aaaattggga     6780
aagacaggta ggagatattt ctgatctttc tctgctgagt ttagaagaac agcaaaaaat    6840
attatttata tggaatcaga cagaaagtaa ttatgatttg tcgatttgtc tacatgagtt    6900
atttgcagca caggtagaga aaacaccaga tgcaaaagct ctcaagtttg ctgatcaaga    6960
attgagttat catcagttaa attgtcgggc gaatcaactc gctcactatt tgcaatcttt    7020
gggaattgta actgaagatt tagttgggat ttgtgtggaa cgttccctag aaatggttgt    7080
ggggttattg ggtattttga aagcgggtgc ggcttatgtt ccaattgatc ctggatatcc    7140
ccaagaacgt ttaggatata tgttggcgga ttcccaggtg tcggtgttgt tgactcaaag    7200
tcatttagtc gatagtttac caacatgtcc aacccatact atttgcttgg atactgactg    7260
ggatctgatt tctcaatata gcgatcgcaa tctccaaaat acaacgacac cagaaaatct    7320
cgcttatgta atttacactt ctggttctac tggtaaacct aaaggagcga tgaatacccca   7380
tcgcggtatt tgcaatcgtc tgttatggat gcaagatgct tatcaactca ctcaacaaga    7440
tcgggttctg caaaaaactc cctttagttt tgatgtctct gtctgggaat tcttttggcc    7500
gttgattacc ggggcgcggc tgattatagc acaaccaggg ggacacaagg atagttctta    7560
tctaattaat acaattatcc aagaagaaat taccacatta cattttgttc cttcgatgtt    7620
gcaggtattt ttgcaagcta aaggagtgga aaattgtcag tcattaaaac gggtaattac    7680
tagtggtgaa gctttacctg tgagtctgca agaacggttt tttgaacgtt tgggatgtga    7740
actgcacaat ctttatggtc ctacagaagc agcgatcgat gttacgtttt ggcagtgtca    7800
acctcaaagt caatatcaaa cagtaccgat tggtcgtccc atcgctaata ctcaaatata    7860
tatattagat caacatttgc aacctgtgcc tgtgggtgtt gtgggtgaac tttatattgg    7920
tggtgtggga gttgccagag gttactggcg tcgtccagaa ttaactacag aaagatttgt    7980
atctaatccc tttgcaacgg gacaaatgta taaaactggt gacttggcgc gctatttacc    8040
tgatggtaat atcgagtatg ttggcagaat tgacgatcaa gttaaaattc gcggttttcg    8100
gattgagttg ggagaaattg agagtacgct gacgcaacat tcccagatta gtcaagctgt    8160
ggttgtcgcc cagacagata atttgaataa taagcattta attgcttata ttgttccccca   8220
gggagaacca cccacaccaa cccaactgcg gaatttcctt cagggtaagc tacctgaatt    8280
catggttccc tcagcttttg tctgcttaaa ttcctttcct ctcactccta gtggaaaaat    8340
agacaggcga tcgcttccca aacctgattt ttctaactta atcactcatg aagattttac    8400
```

```
gcctgcacgc aatgatttag agagaaaaat cgcgcagatt tggtcagaaa ttttacagat      8460
ttcggaaatt gatattagag ataactttttt tgaagttggt ggtaattccc ttttagcatt     8520
acatttaatg aatgccatcg aacaaaaatt tggtcgagag ttagcactgt caacttact      8580 tactaataac tcaattgaaa aactagcaga aattctgcaa acccacag atgttttcc        8640 caattcaccc atagtagcaa ttcagcccaa aggtacaaaa cgtcctttt tctgcatcca     8700 tccagccggc ggacatgtac tttgctattt tagtttggcg cattatttag gcactgacca    8760
gccattttac ggtttacaag cacagggttt ttatggtgaa gaagaaccac taactacagt    8820
tgtagaaatg gctaggcttt atgctcaagc tatacaaaca attcaaccca cagggccata    8880
tcaaattggt ggttggtcgt ttggtggtgt agttgcctat gaaacggctc aacaactaca    8940
ccaacaagga aaagaagttt cattactagc aatttttagat tcctacgtgc caattctgtt   9000
agataaaaat aaaaaaattg atgatgttta tttagttggt gtactatccc gtgtatttgg    9060
cggaatgttt ggtcaagata atctgatttc actagcggaa atcgaaaatt taagtgtgga    9120
agaaagttta aattacatca tcgaaaaagc acgccaagcc aaaattttttc cgccaggagt   9180 ggaacgtcac aacaatcgcc gcatttttaga tgttttagtc ggaactttaa aagccactta   9240
ttcttatgaa cgttgtccct atcctggcaa agttactatt tttagagcca gagaaaaaca   9300
tatcatggct cctgatccta ctttagtttg ggtagaatta ttttcagttt tggctgcgga   9360
ggaaattgaa attcataatg tccccggtaa tcactattca ttttgtttag aacctcacgt    9420
ccaagctttg gctgaaagtt tgcagaaatg tttgtgctga tacaagatcc ccgacttctt    9480
tgaggatgca gctggcgaat aggggtcaa accctcgtg cgcccacaaa ttggttgtag      9540
agacgcgcca tggcgcgtct ctacatctgg tggaatgacg aaaaatctcg gtgagggtg    9600 tcaccctga ttcgccagct gtatccttg agaagtcggg gagctcggta cccctagagt     9660
cgacctgcag ttcaatgcgg tccaatacct cccctgccca actgggtaag ctcgcggctc    9720
cactgagtaa tacagacaag gctaaacagg caaatttttt cattggtcaa ctcctagcac    9780
caatttccca agactacgga gggggcaatg aagtttcaat taattggggt cacaaaccac    9840
agcggcctat ggctctaatc aatggcacac tagaaaaaat gttgcagcat acttggctac    9900
caaaaccccc aaatttaacc ttattgtcag atgaagttca tctctggcgc attccccttg    9960
accaaccaga atcacagcta caggatttag ccgctacctt atctagtgac gaattagccc   10020
gtgcaaacag atttttattt cccgaacatc gccggcgttt tactgctggt cgtggtattc   10080
tccgcagtat cttgggggggc tatttggggtg tggaaccagg gcaagttaaa tttgattatg  10140
aatcccgtgg taaaccaata ttaggcgatc gctttgccga gagtggttta ttatttaact  10200
tgtcacactc ccagaacttg gccttgtgtg cagtcaatta cacgcgccaa atcggcatcg    10260
atttagaata tctccgcccc acatctgatt tagaatccct tgccaaaagg ttcttttttac  10320 cgcgagaata tgaattattg cgatcgctac ccgatgagca aaaacaaaaa attttctttc    10380
gttactggac ttgtaaagag gcttatctta aagcaacggg tgacggcatc gctaaattag    10440
aggaaattga aatagcacta actcccacag aaccagctaa gttacagaca gctccagcgt    10500
ggagtctcct agagctagtg ccagatgata attgtgttgc tgctgttgcc gtggcgggtt    10560
ttggctggca gccaaaattc tggcattatt gagcatgcaa gcttctccct atagtgagtc    10620
gtattagcgg ccgcatcgaa tataacttcg tataatgtat gctatacgaa gttattagcg    10680
atgaggacat gaggttgccc cgtattcagt gtcgctgatt tgtattgtct gaagttgttt    10740
ttacgttaag ttgatgcaga tcaattaata cgatacctgc gtcataattg attatttgac    10800
```

```
gtggtttgat ggcctccacg cacgttgtga tatgtagatg ataatcatta tcactttacg   10860
ggtcctttcc ggtgatccga caggttacgg ggcggcgacc tcgcgggttt tcgctattta   10920
tgaaaatttt ccggtttaag gcgtttccgt tcttcttcgt cataacttaa tgtttttatt   10980 taaaatacccc tctgaaaaga aaggaaacga caggtgctga aagcgaggct ttttggcctc   11040
tgtcgtttcc tttctctgtt tttgtccgtg gaatgaacaa tggaagtcct cgtctcgccc   11100
tcgaattagc ccgcctaatg agcgggcttt ttttgaatta attctcgcga gctggcacga   11160
caggtttccc gactggaaag cgggcagtga gcgcaacgca attaatgtaa gttagcgcga   11220
attgcaagct ggccgacgcg ctgggctacg tcttgctggc gttcgggagc agaagagcat   11280
acatctggaa gcaaagccag gaaagcggcc tatggagctg tgcggcagcg ctcagtaggc   11340 aattttttcaa aatattgtta agccttttct gagcatggta tttttcatgg tattaccaat   11400
tagcaggaaa ataagccatt gaatataaaa gataaaaatg tcttgtttac aatagagtgg   11460 gggggggtcag cctgccgcct tgggccgggt gatgtcgtac ttgcccgccg cgaactcggt   11520
taccgtccag cccagcgcga ccagctccgg caacgcctcg cgcacccgct tgcggcgctt   11580
gcgcatggtc gaaccactgg cctctgacgg ccagacatag ccgcacaagg tatctatgga   11640
agccttgccg gttttgccgg ggtcgatcca gccacacagc cgctggtgca gcaggcgggc   11700
ggtttcgctg tccagcgccc gcacctcgtc catgctgatg cgcacatgct ggccgccacc   11760
catgacggcc tgcgcgatca aggggttcag ggccacgtac aggcgcccgt ccgcctcgtc   11820
gctggcgtac tccgacagca gccgaaaccc ctgccgcttg cggccattct gggcgatgat   11880 ggatacctttc caaaggcgct cgatgcagtc ctgtatgtgc ttgagcgccc caccactatc   11940
gacctctgcc ccgatttcct ttgccagcgc ccgatagcta cctttgacca catggcattc   12000
agcggtgacg gcctcccact tgggttccag gaacagccgg agctgccgtc cgccttcggt   12060
cttgggttcc gggccaagca ctaggccatt aggcccagcc atggccacca gcccttgcag   12120
gatgcgcaga tcatcagcgc ccagcggctc cgggccgctg aactcgatcc gcttgccgtc   12180
gccgtagtca tacgtcacgt ccagcttgct gcgcttgcgc tcgccccgct tgagggcacg   12240
gaacaggccg ggggccagac agtgcgccgg gtcgtgccgg acgtggctga ggctgtgctt   12300
gttcttaggc ttcaccacgg ggcaccccct tgctcttgcg ctgcctctcc agcacggcgg   12360
gcttgagcac cccgccgtca tgccgcctga accaccgatc agcgaacggt gcgccatagt   12420
tggccttgct cacaccgaag cggacgaaga accggcgctg gtcgtcgtcc acacccatt   12480 cctcggcctc ggcgctggtc atgctcgaca ggtaggactg ccagcggatg ttatcgacca   12540
gtaccgagct gccccggctg gcctgctgct ggtcgcctgc gcccatcatg gccgcgccct   12600
tgctggcatg gtgcaggaac acgatagagc accggtatc ggcggcgatg gcctccatgc   12660
gaccgatgac ctgggccatg gggccgctgg cgttttcttc ctcgatgtgg aaccggcgca   12720
gcgtgtccag caccatcagg cggcggccct cggcggcgcg cttgaggccg tcgaaccact   12780
ccggggccat gatgttgggc aggctgccga tcagcggctg atcagcagg ccgtcagcca   12840 cggcttgccg ttcctcggcg ctgaggtgcg ccccaagggc gtgcaggcgg tgatgaatgg   12900 cggtgggcg gtcttcggcg ggcaggtaga tcaccgggcc ggtgggcagt tcgcccacct   12960
ccagcagatc cggcccgcct gcaatctgtg cggccagttg cagggccagc atggatttac   13020
cggcaccacc gggcgacacc agcgcccga ccgtaccggc caccatgttg ggcaaaacgt   13080
agtccagcgg tggcggcgct gctgcgaacg cctccagaat attgataggc ttatgggtag   13140
```

```
ccattgattg cctcctttgc aggcagttgg tggttaggcg ctggcggggt cactaccccc    13200
gccctgcgcc gctctgagtt cttccaggca ctcgcgcagc gcctcgtatt cgtcgtcggt    13260
cagccagaac ttgcgctgac gcatcccttt ggccttcatg cgctcggcat atcgcgcttg    13320
gcgtacagcg tcagggctgg ccagcaggtc gccggtctgc ttgtcctttt ggtctttcat    13380
atcagtcacc gagaaacttg ccggggccga aaggcttgtc ttcgcggaac aaggacaagg    13440
tgcagccgtc aaggttaagg ctggccatat cagcgactga aaagcggcca gcctcggcct    13500
tgtttgacgt ataaccaaag ccaccgggca accaatagcc cttgtcactt ttgatcaggt    13560
agaccgaccc tgaagcgctt ttttcgtatt ccataaaacc cccttctgtg cgtgagtact    13620
catagtataa caggcgtgag taccaacgca agcactacat gctgaaatct ggcccgcccc    13680
tgtccatgcc tcgctggcgg ggtgccggtg cccgtgccag ctcggcccgc gcaagctgga    13740
cgctgggcag acccatgacc ttgctgacgg tgcgctcgat gtaatccgct tcgtggccgg    13800
gcttgcgctc tgccagcgct gggctggcct cggccatggc cttgccgatt tcctcggcac    13860
tgcggccccg gctggccagc ttctgcgcgg cgataaagtc gcacttgctg aggtcatgac    13920
cgaagcgctt gaccagcccg gccatctcgc tgccggtactc gtccagcgcc gtgcgccggt    13980
ggcggctaag ctgccgctcg ggcagttcga ggctggccag cctgcgggcc ttctcctgct    14040
gccgctgggc ctgctcgatc tgctggccag cctgctgcac cagcgccggg ccagcggtgg    14100
cggtcttgcc cttggattca cgcagcagca cccacggctg ataaccggcg cgggtggtgt    14160
gcttgtcctt gcggttggtg aagcccgcca agcggccata gtggcggctg tcggcgctgg    14220
ccgggtcggc gtcgtactcg ctggccagcg tccgggcaat ctgcccccga agttcaccgc    14280
ctgcggcgtc ggccaccttg acccatgcct gatagttctt cgggctggtt tccactacca    14340
gggcaggctc ccggccctcg gctttcatgt catccaggtc aaactcgctg aggtcgtcca    14400
ccagcaccag accatgccgc tcctgctcgg cgggcctgat atacacgtca ttgccctggg    14460
cattcatccg cttgagccat ggcgtgttct ggagcacttc ggcggctgac cattcccggt    14520
tcatcatctg gccggtgggt gcgtccctga cgccgatatc gaagcgctca cagcccatgg    14580
ccttgagctg tcggcctatg gcctgcaaag tcctgtcgtt cttcatcggg ccaccaagcg    14640
cagccagatc gagccgtcct cggttgtcag tggcgtcagg tcgagcaaga gcaacgatgc    14700
gatcagcagc accaccgtag gcatcatgga agccagcatc acggttagcc atagcttcca    14760
gtgccacccc cgcgacgcgc tccgggcgct ctgcgcggcg ctgctcacct cggcggctac    14820
ctcccgcaac tctttggcca gctccaccca tgccgcccct gtctggcgct gggctttcag    14880
ccactccgcc gcctgcgcct cgctggcctg cttggtctgg ctcatgacct gccgggcttc    14940
gtcggccagt gtcgccatgc tctgggccag cggttcgatc tgctccgcta actcgttgat    15000
gcctctggat ttcttcactc tgtcgattgc gttcatggtc tattgcctcc cggtattcct    15060
gtaagtcgat gatctgggcg ttggcggtgt cgatgttcag ggccacgtct gcccggtcgg    15120
tgcggatgcc ccggccttcc atctccacca cgttcggccc caggtgaaca ccgggcaggc    15180
gctcgatgcc ctgcgcctca agtgttctgt ggtcaatgcg ggcgtcgtgg ccagcccgct    15240
ctaatgcccg gttggcatgg tcggcccatg cctcgcgggt ctgctcaagc catgccttgg    15300
gcttgagcgc ttcggtcttc tgtgccccgc ccttctccgg ggtcttgccg ttgtaccgct    15360
tgaaccactg agcggcgggc cgctcgatgc cgtcattgat ccgctcggag atcatcaggt    15420
ggcagtgcgg gttctcgccg ccaccggcat ggatggccag cgtatacggc aggcgctcgg    15480
caccggtcag gtgctgggcg aactcggacg ccagcgcctt ctgctggtcg agggtcagct    15540
```

```
cgaccggcag ggcaaattcg acctccttga acagccgccc attggcgcgt tcatacaggt    15600
cggcagcatc ccagtagtcg gcgggccgct cgacgaactc cggcatgtgc ccggattcgg    15660
cgtgcaagac ttcatccatg tcgcgggcat acttgccttc gcgctggatg tagtcggcct    15720
tggccctggc cgattggccg cccgacctgc tgccggtttt cgccgtaagg tgataaatcg    15780
ccatgctgcc tcgctgttgc ttttgctttt cggctccatg caatggccct cggagagcgc    15840
accgcccgaa gggtggccgt taggccagtt tctcgaagag aaaccggtaa gtgcgccctc    15900
ccctacaaag tagggtcggg attgccgccg ctgtgcctcc atgatagcct acgagacagc    15960
acattaacaa tggggtgtca agatggttaa ggggagcaac aaggcggcgg atcggctggc    16020
caagctcgaa gaacaacgag cgcgaatcaa tgccgaaatt cagcgggagc gggcaaggga    16080
acagcagcaa gagcgcaaga acgaaacaag gcgcaaggtg ctggtggggg ccatgatttt    16140
ggccaaggtg aacagcagcg agtggccgga ggatcggctc atggcggcaa tggatgcgta    16200
ccttgaacgc gaccacgacc gcgccttgtt cggtctgccg ccacgccaga aggatgagcc    16260
gggctgaatg atcgaccgag acaggccctg cggggctgca cacgcgcccc cacccttcgg    16320 gtaggggaa aggccgctaa agcggctaaa agcgctccag cgtatttctg cggggtttgg     16380
tgtggggttt agcgggcttt gcccgccttt cccctgccg cgcagcggtg gggcggtgtg     16440
tagcctagcg cagcgaatag accagctatc cggcctctgg ccgggcatat tgggcaaggg    16500
cagcagcgcc ccacaagggc gctgataacc gcgcctagtg gattattctt agataatcat    16560
ggatggattt ttccaacacc ccgccagccc ccgcccctgc tgggtttgca ggtttggggg    16620
cgtgacagtt attgcagggg ttcgtgacag ttattgcagg gggcgtgac agttattgca     16680 ggggttcgtg acagttagta cgggagtgac gggcactggc tggcaatgtc tagcaacggc    16740
aggcatttcg gctgaggta aaagaacttt ccgctaagcg atagactgta tgtaaacaca     16800
gtattgcaag gacgcggaac atgcctcatg tggcggccag ga                       16842
```

<210> SEQ ID NO 85
<211> LENGTH: 16985
<212> TYPE: DNA
<213> ORGANISM: Artificial Sequence
<220> FEATURE:
<223> OTHER INFORMATION: sequence of plasmid Sh-Ptrc

<400> SEQUENCE: 85

```
ctcgcgagaa ttaattcaga taaaaaaat ccttagcttt cgctaaggat gatttctagc      60
gatgaccctg ctgattggtt cgctgaccat ttccgggtgc gggacggcgt taccagaaac    120
tcagaaggtt cgtccaacca aaccgactct gacggcagtt tacgagagag atgatagggt    180
ctgcttcagt aagccagatg ctacacaatt aggcttgtac gggtactcga cctgcatccc    240
ttaacttact tattaaataa tttatagcta ttgaaaagag ataagaattg ttcaaagcta    300
atattgttta atcgtcaat tcctgcatgt tttaaggaat tgttaaattg atttttttgta    360 aatattttct tgtattcttt gttaaaataa aaaggggac ctctagggtc cccaattaat     420
tagtaatata atctattaaa ggtcattcaa aaggtcatcc accggatcag cttagtaaag    480
ccctcgctag attttaatgc ggatgttgcg attacttcgc caactattgc gataacaaga    540
aaaagccagc ctttcatgat atatctccca atttgtgtag ggcttattat gcacgcttaa    600
aaataataaa agcagacttg acctgatagt ttggctgtga gcaattatgt gcttagtgca    660
tctaacgctt gagttaagcc gcgccgcgaa gcggcgtcgg cttgaacgaa ttgttagaca    720
```

```
ttatttgccg actaccttgg tgatctcgcc tttcacgtag tggacaaatt cttccaactg    780
atctgcgcgc gaggccaagc gatcttcttc ttgtccaaga taagcctgtc tagcttcaag    840
tatgacgggc tgatactggg ccggcaggcg ctccattgcc cagtcggcag cgacatcctt    900
cggcgcgatt ttgccggtta ctgcgctgta ccaaatgcgg gacaacgtaa gcactacatt    960
tcgctcatcg ccagcccagt cgggcggcga gttccatagc gttaaggttt catttagcgc   1020
ctcaaataga tcctgttcag gaaccggatc aaagagttcc tccgccgctg gacctaccaa   1080
ggcaacgcta tgttctcttg cttttgtcag caagatagcc agatcaatgt cgatcgtggc   1140
tggctcgaag atacctgcaa gaatgtcatt gcgctgccat tctccaaatt gcagttcgcg   1200
cttagctgga taacgccacg gaatgatgtc gtcgtgcaca acaatggtga cttctacagc   1260
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgaccac ggcgtaacgc gcttgctgct tggatgcccg   1620
aggcatagac tgtaccccaa aaaaacagtc ataacaagcc atgaaaaccg ccactgcgcc   1680
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga ccttttgaat gacctttaat agattatatt   2280
actaattaat tggggaccct agaggtcccc tttttatttt tctgaacggt ctggttatag   2340
gtacattgag caactgactg aaatgcctca aaatgttctt tacgatgcca ttgggatata   2400
tcaacggtgg tatatccagt gattttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgat tctgaaatga gctgttgaca attaatcatc   2640
cggctcgtat aatgtgtgga attgtgagcg ataacaatt tcacacagga aacagcgccg   2700
ctgagaaaaa gcgaagcggc actgctcttt aacaatttat cagacaatct gtgtgggcac   2760
tcgaccggaa ttatcgatta actttattat taaaaattaa agaggtatat attaatgtat   2820
cgattaaata aggaggaata aaccatgggg ggttctcatc atcatcatca tcatggtatg   2880
gctagcatga ctggtggaca gcaaatgggt cgggatctgt acgacgatga cgataaggat   2940
cgatggatcc gacctcgagg acgtcatggg tacacctcac gctacttttg cagctactga   3000
gacagcattt catgtgacgg gctacgaaaa gatagatttt agcctggttt atgtgaatgg   3060
tgtattcaac atcaaaaaca cagaaattgc tgatagttat cagaagtttg gacgctgctt   3120
```

```
gactgttgtt gatcataatg tctaccgttt gtatggagac caaattaagt catatttcg    3180
ttactacgac atagacttaa ctgtgtttcc aattactatt actgaacctg gcaaaaccat    3240
gtcaacttt  gaacaagtag ttgatgcgtt tgccgatttt ggcttaattc gtaaagaacc    3300
agttttagta gttggtggtg gtttagttac tgatgttgta ggttttgctt gtgcagctta    3360
tcgtcgcagt actaactata ttcgcattcc cacgactttg attggtttga tagatgctgg    3420
aattgcgatt aaagtagcag tcaatcataa aaagctgaaa aatcgcttgg gtgcttacca    3480
tgcaccgcag aaagtcattc tagactttc ctttctcaag acactaccaa cagcccaagt    3540
ccggaatgga atggcggagt tagtgaaaat tgctgtggta gcaaatgcag aagttttaa    3600
ttggctgtat gagtacggag aagatttact gcatacacac tttggctatc tcaacggtac    3660
agaggaactg caagaaattg ctcacaaagt taactacgaa gcaattaaaa ccatgctgga    3720
gttagaaact ccaaacctgc atgagctaga cttagatcgc gtcattgctt atggtcacac    3780
ttggagtccg acactagaat tagcaccgcg ggttcctctg tatcatggtc atgctgtcaa    3840
catcgatatg gcgctatcag caactattgc tgaacgacgg ggatatatta ctgtagcaga    3900
acgcgatcgc attcttggat tgatgagtcg tctaggttta gcccttgatc atccccttct    3960
agatagcgat ttgttatggt acgctaccca gtctatcacc cagacaagag acgggaaaca    4020
acgcgccgcc atgccaaaac ctattggtga gtgtttcttt gtcaatgacc taacccgtga    4080
agaattgcat caagctttga ttgcacacaa ggatgtatgt gcaacatatc cccgtggtgg    4140
agatgggatt gaagcctata tcagtgcaga acaatctgag atggtaggag tttagaatcg    4200
tgactagcat tgttgaaaag aacacagcta gacccgtaac tccccacggt atcttggttg    4260
aacagctaca aaaaactctg gctttggcag aatcaggaaa tacacctgaa actgttgtga    4320
ctgcactacg acaggcgtat caattagcgg cgggtttaga accttatatt agtgaacaca    4380
ccactactga atctgacgcc ttagcagcac tggtacaaaa aactaccaaa gaagactgga    4440
caaaacgttt cactgatggt gaaacagtgc gtcaactaga acaggaaatg ctttctggac    4500
acgtcgaggg acaaaccctg aaaatgtttt tcacatgac taaagccaag agtgttttgg    4560
aagtaggaat gttcaccggg tattctgctt tggcaatggc agaggcatta cctgatgatg    4620
gacgagtggt agcatgtgaa gtagactctt atgttgctag ctttgctcaa acttgtttcc    4680
aaaactcgcc ccacggtcat aaaattactg tggaagttgc accagccttg gaaactctgc    4740
aaaaacttgc agcagcaggt gaatcatttg atttgatatt catcgatgct gacaagaaag    4800
agtatgtgca gtatttccag atcatcttgg ataataatct acttgcatct aacggcatta    4860
tttgtgtaga taacactta  atgcagggac aggtttatct gccaccagaa caacgtacag    4920
ctaatggtga agcgatcgct caatttaacc aaatcattac ccaagatccg cgtgtagaac    4980
aagttatact accgcttcgt gatggtgtga ctttaattcg gcggttgtag aaggatgggg    5040
tttgggtggt actgatgggt ttttttgag ggcgaattat atgacacaat ctatttctgt    5100
ggcttctgtt ggacaaacaa ctcagtcggt gagcctggga cttcgcatat ctgcgttgtg    5160
gaaaagttta gctacacttg cactgctgtt gttagtattg ccaatcaatg ctgcgattgt    5220
gttggtatcg ctgttattgg gtagtcaatc gcaagcgatc gccaccgaac ccaaaaacat    5280
cttgattagt ggcggtaaaa tgactaaggc gttacaatta gcccgtagtt tcacgccgc    5340
cggacatcga gtggttttag tagaaactca caaatactgg ttaacgggac accgattttc    5400
caaagcagta agtcgtttct acactctacc aacgccccaa tctgatcctg aagcatacac    5460
```

```
ccaagcccta ttagatattg ttcaaaaaga aaatatcgat gtctatgtac ccgtgtgcag    5520
tccggttgct agttactacg actctttagc taaacccgta ctgtcgaagt actgcgaggt    5580
ttttcactgt gacgcagatg tcacccaaat gttggatgat aaatacgctt ttgctgagaa    5640
agcgcggagt ttggggttat ctgttcccaa gtctttcaaa attactgacc cggaacaggt    5700
gagcaacttt gattttctc aagaaaagcg taaatacatc ctcaaaagca ttccttatga    5760
ctctgttcgt cgcttagatt taaccaaact tccttgtgag actcccgaag caacagcaga    5820
ttttgtcaac agcttaccca tcagttccca aaagccatgg attatgcaag aattcattcc    5880
tggaaaagaa ttttgcaccc acagcactgt ccgcaatggg gagttgagaa tgcattgctg    5940
ttgtgaatct tcggcatttc aagttaacta tgagaatgtc gatcatcccc aaattttgga    6000
atgggtgcga cactttgtca aagcattagg tatcactgga caggtatctt ttgattttat    6060
cgaagcacaa gatggcacaa tctacgccat tgaatgtaat ccgcgtaccc attctgccat    6120
cactatgttc tacaatcatc cggatgtggc aaatgcttat ttgagtgaaa ttccacaagt    6180
agaaccaatt caacctctga ttaatagtaa gcctacctac tggacttatc acgaaatttg    6240
gcgattgaca ggaattcgtt ctttctcaca gttgcaaact tggttgaaaa acttttttgg    6300
tggaaaagat gcgatttaca gtttgagtga tcctctacct tttttaacag ttcatcactg    6360
gcaaattcct ttattattgc tacaaaattt gcaacagcta aaaggttgga tcaggataga    6420
ttttaatatt gggaaattgg ttgagtttgg tggcgattag attcagttat cagttatcag    6480
ttatcagtta gtagctgttc actgataatt tatagatatt gaatatatat aagactcata    6540
tttgatttct gaaatacacg tagggtgcgt gatagctacg ccataacaca ccctactggc    6600
gcgtcaagcc taaatgttg caataaatct ctgattctat ctctgtgttc tctctcttga    6660
aaagctttga tcggaggaaa cctccgctca aacttttcgc tgcttcctct gcggtttatt    6720
aatgcactat tttaaggctg tcgcgcccct tgttaaagtc aaatttttt atcaaaccgc    6780 agaggcgcag aggaatcaga gagaaggaaa taattcttaa ttgaattgta ttaagttata    6840
aatcactata ttttatcaaa gatggaaata ataaactttt tagatgattc tctggaaatt    6900
gaagaacaga gaaaaattg ggaaagacag gtaggagata tttctgatct ttctctgctg    6960
agtttagaag aacagcaaaa aatattattt atatggaatc agacagaaag taattatgat    7020
ttgtcgattt gtctacatga gttatttgca gcacaggtag agaaaacacc agatgcaaaa    7080
gctctcaagt ttgctgatca agaattgagt tatcatcagt taaattgtcg ggcgaatcaa    7140
ctcgctcact atttgcaatc tttgggaatt gtaactgaag atttagttgg gatttgtgtg    7200
gaacgttccc tagaaatggt tgtgggggtta ttgggtattt tgaaagcggg tgcggcttat    7260
gttccaattg atcctggata tccccaagaa cgtttaggat atatgttggc ggattcccag    7320
gtgtcggtgt tgttgactca aagtcattta gtcgatagtt taccaacatg tccaacccat    7380
actatttgct tggatactga ctgggatctg atttctcaat atagcgatcg caatctccaa    7440
aatacaacga caccagaaaa tctcgcttat gtaatttaca cttctggttc tactggtaaa    7500
cctaaaggag cgatgaatac ccatcgcggt atttgcaatc gtctgttatg gatgcaagat    7560
gcttatcaac tcactcaaca agatcgggtt ctgcaaaaaa ctcccttag ttttgatgtc    7620 tctgtctggg aattcttttg ccgttgatt accggggcgc ggctgattat agcacaacca    7680
ggtggacaca aggatagttc ttatctaatt aatacaatta tccaagaaga aattaccaca    7740
ttacattttg ttccttcgat gttgcaggta ttttttgcaag ctaaaggagt ggaaaattgt    7800
cagtcattaa aacgggtaat tactagtggt gaagctttac ctgtgagtct gcaagaacgg    7860
```

```
tttttttgaac gtttgggatg tgaactgcac aatctttatg gtcctacaga agcagcgatc   7920
gatgttacgt tttggcagtg tcaacctcaa agtcaatatc aaacagtacc gattggtcgt   7980
cccatcgcta atactcaaat atatatatta gatcaacatt tgcaacctgt gcctgtgggt   8040
gttgtgggtg aactttatat tggtggtgtg ggagttgcca gaggttactg gcgtcgtcca   8100
gaattaacta cagaaagatt tgtatctaat ccctttgcaa cgggacaaat gtataaaact   8160
ggtgacttgg cgcgctattt acctgatggt aatatcgagt atgttggcag aattgacgat   8220
caagttaaaa ttcgcggttt tcggattgag ttgggagaaa ttgagagtac gctgacgcaa   8280
cattcccaga ttagtcaagc tgtggttgtc gcccagacag ataatttgaa taataagcat   8340
ttaattgctt atattgttcc ccagggagaa ccacccacac caacccaact gcggaatttc   8400
cttcagggta agctacctga attcatggtt ccctcagctt ttgtctgctt aaattccttt   8460
cctctcactc ctagtggaaa aatagacagg cgatcgcttc ccaaacctga ttttctaac    8520
ttaatcactc atgaagattt tacgcctgca cgcaatgatt tagagagaaa aatcgcgcag   8580
atttggtcag aaattttaca gatttcggaa attgatatta gagataactt ttttgaagtt   8640
ggtggtaatt ccctttagc attacattta atgaatgcca tcgaacaaaa atttggtcga    8700
gagttagcac tgtcaacttt acttactaat aactcaattg aaaaactagc agaaattctg   8760
caaaacccca cagatgtttt tcccaattca cccatagtag caattcagcc caaaggtaca   8820
aaacgtcctt ttttctgcat ccatccagcc ggcggacatg tactttgcta ttttagtttg   8880
gcgcattatt taggcactga ccagccattt tacggtttac aagcacaggg tttttatggt   8940
gaagaagaac cactaactac agttgtagaa atggctaggc tttatgctca agctatacaa   9000
acaattcaac ccacagggcc atatcaaatt ggtggttggt cgtttggtgg tgtagttgcc   9060
tatgaaacgg ctcaacaact acaccaacaa ggaaaagaag tttcattact agcaatttta   9120
gattcctacg tgccaattct gttagataaa aataaaaaaa ttgatgatgt ttatttagtt   9180
ggtgtactat cccgtgtatt tggcggaatg tttggtcaag ataatctgat ttcactagcg   9240
gaaatcgaaa atttaagtgt ggaagaaagt ttaaattaca tcatcgaaaa agcacgccaa   9300
gccaaaattt ttccgccagg agtggaacgt cacaacaatc gccgcatttt agatgtttta   9360
gtcggaactt taaaagccac ttattcttat gaacgttgtc cctatcctgg caaagttact   9420
attttagag ccagagaaaa acatatcatg gctcctgatc ctactttagt ttgggtagaa    9480
ttattttcag ttttggctgc ggaggaaatt gaaattcata atgtccccgg taatcactat   9540
tcatttgttt tagaacctca cgtccaagct ttggctgaaa gtttgcagaa atgtttgtgc   9600
tgatacaaga tccccgactt ctttgaggat gcagctggcg aatagggggt caaacccctc   9660
gtgcgcccac aaattggttg tagagacgcg ccatggcgcg tctctacatc tggtggaatg   9720
acgaaaaatc tcggtgaggg gtgtcacccc tgattcgcca gctgtatcct tgagaagtc    9780
ggggagctcg gtaccctag agtcgacctg cagttcaatg cggtccaata cctcccctgc    9840
ccaactgggt aagctcgcgg ctccactgag taatacagac aaggctaaac aggcaaattt   9900
tttcattggt caactcctag caccaatttc ccaagactac ggaggggca atgaagtttc    9960
aattaattgg ggtcacaaac cacagcggcc tatggctcta atcaatgcca cactagaaaa   10020
aatgttgcag catacttggc taccaaaacc cccaaattta accttattgt cagatgaagt   10080
tcatctctgg cgcattcccc ttgaccaacc agaatcacag ctacaggatt tagccgctac   10140
cttatctagt gacgaattag cccgtgcaaa cagatttat tttcccgaac atcgccggcg     10200
```

```
ttttactgct ggtcgtggta ttctccgcag tatcttgggg ggctatttgg gtgtggaacc   10260
agggcaagtt aaatttgatt atgaatcccg tggtaaacca atattaggcg atcgctttgc   10320
cgagagtggt ttattattta acttgtcaca ctcccagaac ttggccttgt gtgcagtcaa   10380
ttacacgcgc caaatcggca tcgatttaga atatctccgc cccacatctg atttagaatc   10440
ccttgccaaa aggttctttt taccgcgaga atatgaatta ttgcgatcgc tacccgatga   10500
gcaaaaacaa aaaattttct ttcgttactg gacttgtaaa gaggcttatc ttaaagcaac   10560
gggtgacggc atcgctaaat tagaggaaat tgaaatagca ctaactccca cagaaccagc   10620
taagttacag acagctccag cgtggagtct cctagagcta gtgccagatg ataattgtgt   10680
tgctgctgtt gccgtggcgg gttttggctg gcagccaaaa ttctggcatt attgagcatg   10740
caagcttctc cctatagtga gtcgtattag cggccgcatc gaatataact tcgtataatg   10800
tatgctatac gaagttatta gcgatgagga catgaggttg ccccgtattc agtgtcgctg   10860
atttgtattg tctgaagttg tttttacgtt aagttgatgc agatcaatta atacgatacc   10920
tgcgtcataa ttgattattt gacgtggttt gatggcctcc acgcacgttg tgatatgtag   10980
atgataatca ttatcacttt acgggtcctt tccggtgatc cgacaggtta cggggcggcg   11040
acctcgcggg ttttcgctat ttatgaaaat tttccggttt aaggcgtttc cgttcttctt   11100
cgtcataact taatgttttt atttaaaata ccctctgaaa agaaaggaaa cgacaggtgc   11160
tgaaagcgag gcttttttggc ctctgtcgtt tcctttctct gtttttgtcc gtggaatgaa   11220
caatggaagt cctcgtctcg ccctcgaatt agcccgccta atgagcgggc ttttttttgaa   11280 ttaattctcg cgagctggca cgacaggttt cccgactgga aagcgggcag tgagcgcaac   11340
gcaattaatg taagttagcg cgaattgcaa gctggccgac gcgctgggct acgtcttgct   11400
ggcgttcggg agcagaagag catacatctg gaagcaaagc caggaaagcg gcctatgagg   11460
ctgtgcggca gcgctcagta ggcaattttt caaaatattg ttaagccttt tctgagcatg   11520
gtatttttca tggtattacc aattagcagg aaaataagcc attgaatata aaagataaaa   11580
atgtcttgtt tacaatagag tggggggggt cagcctgccg ccttgggccg ggtgatgtcg   11640
tacttgcccg ccgcgaactc ggttaccgtc cagcccagcg cgaccagctc cggcaacgcc   11700
tcgcgcaccc gcttgcggcg cttgcgcatg gtcgaaccac tggcctctga cggccagaca   11760
tagccgcaca aggtatctat ggaagccttg ccggttttgc cggggtcgat ccagccacac   11820
agccgctggt gcagcaggcg gcggtttcg ctgtccagcg cccgcacctc gtccatgctg   11880
atgcgcacat gctggccgcc acccatgacg gcctgcgcga tcaagggggtt cagggccacg   11940 tacaggcgcc cgtccgcctc gtcgctggcg tactccgaca gcagccgaaa cccctgccgc   12000
ttgcggccat tctgggcgat gatggatacc ttccaaaggc gctcgatgca gtcctgtatg   12060
tgcttgagcg ccccaccact atcgacctct gccccgattt cctttgccag cgcccgatag   12120
ctacctttga ccacatggca ttcagcggta acggcctccc acttgggttc caggaacagc   12180
cggagctgcc gtccgccttc ggtcttgggt tccgggccaa gcactaggcc attaggccca   12240
gccatggcca ccagcccttg caggatgcgc agatcatcag cgcccagcgg ctccgggccg   12300
ctgaactcga tccgcttgcc gtcgccgtag tcatacgtca cgtccagctt gctgcgcttg   12360
cgctcgcccc gcttgagggc acggaacagg ccggggggcca gacagtgcgc cgggtcgtgc   12420
cggacgtggc tgaggctgtg cttgttctta ggcttcacca cggggcaccc ccttgctctt   12480
gcgctgcctc tccagcacgg cgggcttgag caccccgccg tcatgccgcc tgaaccaccg   12540
atcagcgaac ggtgcgccat agttggcctt gctcacaccg aagcggacga agaaccggcg   12600
```

```
ctggtcgtcg tccacacccc attcctcggc ctcggcgctg gtcatgctcg acaggtagga    12660
ctgccagcgg atgttatcga ccagtaccga gctgccccgg ctggcctgct gctggtcgcc    12720
tgcgcccatc atggccgcgc ccttgctggc atggtgcagg aacacgatag agcacccggt    12780
atcggcggcg atggcctcca tgcgaccgat gacctgggcc atggggccgc tggcgttttc    12840
ttcctcgatg tggaaccggc gcagcgtgtc cagcaccatc aggcggcggc cctcggcggc    12900
gcgcttgagg ccgtcgaacc actccggggc catgatgttg ggcaggctgc cgatcagcgg    12960
ctggatcagc aggccgtcag ccacggcttg ccgttcctcg gcgctgaggt gcgcccaag     13020 ggcgtgcagg cggtgatgaa tggcggtggg cgggtcttcg gcgggcaggt agatcaccg     13080 gccggtgggc agttcgccca cctccagcag atccggcccg cctgcaatct gtgcggccag    13140 tgcagggcc agcatggatt taccggcacc accgggcgac accagcgccc cgaccgtacc     13200
ggccaccatg ttgggcaaaa cgtagtccag cggtggcggc gctgctgcga acgcctccag    13260
aatattgata ggcttatggg tagccattga ttgcctcctt tgcaggcagt tggtggttag    13320
gcgctggcgg ggtcactacc cccgccctgc gccgctctga gttcttccag gcactcgcgc    13380
agcgcctcgt attcgtcgtc ggtcagccag aacttgcgct gacgcatccc tttggccttc    13440
atgcgctcgg catatcgcgc ttggcgtaca gcgtcagggc tggccagcag gtcgccggtc    13500
tgcttgtcct tttggtcttt catatcagtc accgagaaac ttgccggggc cgaaaggctt    13560
gtcttcgcgg aacaaggaca aggtgcagcc gtcaaggtta aggctggcca tatcagcgac    13620
tgaaaagcgg ccagcctcgg ccttgtttga cgtataacca aagccaccgg gcaaccaata    13680
gcccttgtca cttttgatca ggtagaccga ccctgaagcg ctttttttcgt attccataaa    13740 accccttct gtgcgtgagt actcatagta taacaggcgt gagtaccaac gcaagcacta     13800
catgctgaaa tctggcccgc ccctgtccat gcctcgctgg cggggtgccg gtgcccgtgc    13860
cagctcggcc cgcgcaagct ggacgctggg cagacccatg accttgctga cggtgcgctc    13920
gatgtaatcc gcttcgtggc cgggcttgcg ctctgccagc gctgggctgg cctcggccat    13980
ggccttgccg atttcctcgg cactgcggcc ccggctggcc agcttctgcg cggcgataaa    14040
gtcgcacttg ctgaggtcat gaccgaagcg cttgaccagc ccggccatct cgctgcgta    14100 ctcgtccagc gccgtgcgcc ggtggcggct aagctgccgc tcgggcagtt cgaggctggc    14160
cagcctgcgg gccttctcct gctgccgctg ggcctgctcg atctgctggc cagcctgctg    14220
caccagcgcc gggccagcgg tggcggtctt gcccttggat tcacgcagca gcacccacgg    14280
ctgataaccg gcgcgggtgg tgtgcttgtc cttgcggttg gtgaagcccg ccaagcggcc    14340
atagtggcgg ctgtcggcgc tggccgggtc ggcgtcgtac tcgctggcca gcgtccgggc    14400
aatctgcccc cgaagttcac cgcctgcggc gtcgccacc ttgacccatg cctgatagtt     14460
cttcgggctg gtttccacta ccagggcagg ctcccggccc tcggctttca tgtcatccag    14520
gtcaaactcg ctgaggtcgt ccaccagcac cagaccatgc cgctcctgct cggcgggcct    14580
gatatacacg tcattgccct gggcattcat ccgcttgagc catggcgtgt tctggagcac    14640
ttcggcggct gaccattccc ggttcatcat ctggccggtg ggtgcgtccc tgacgccgat    14700
atcgaagcgc tcacagccca tggccttgag ctgtcggcct atggcctgca aagtcctgtc    14760
gttcttcatc gggccaccaa gcgcagccag atcgagccgt cctcggttgt cagtggcgtc    14820
aggtcgagca agagcaacga tgcgatcagc agcaccaccg taggcatcat ggaagccagc    14880
atcacggtta gccatagctt ccagtgccac ccccgcgacg cgctccgggc gctctgcgcg    14940
```

```
gcgctgctca cctcggcggc tacctcccgc aactctttgg ccagctccac ccatgccgcc  15000
cctgtctggc gctgggcttt cagccactcc gccgcctgcg cctcgctggc ctgcttggtc  15060
tggctcatga cctgccgggc ttcgtcggcc agtgtcgcca tgctctgggc cagcggttcg  15120
atctgctccg ctaactcgtt gatgcctctg gatttcttca ctctgtcgat tgcgttcatg  15180
gtctattgcc tcccggtatt cctgtaagtc gatgatctgg gcgttggcgg tgtcgatgtt  15240
cagggccacg tctgcccggt cggtgcggat gccccggcct ccatctccca ccacgttcgg  15300
ccccaggtga acaccgggca ggcgctcgat gccctgcgcc tcaagtgttc tgtggtcaat  15360
gcgggcgtcg tggccagccc gctctaatgc ccggttggca tggtcggccc atgcctcgcg  15420
ggtctgctca agccatgcct tgggcttgag cgcttcggtc ttctgtgccc cgcccttctc  15480
cggggtcttg ccgttgtacc gcttgaacca ctgagcggcg ggccgctcga tgccgtcatt  15540
gatccgctcg gagatcatca ggtggcagtg cgggttctcg ccgccaccgg catggatggc  15600
cagcgtatac ggcaggcgct cggcaccggt caggtgctgg gcgaactcgg acgccagcgc  15660
cttctgctgg tcgagggtca gctcgaccgg cagggcaaat tcgacctcct tgaacagccg  15720
cccattggcg cgttcataca ggtcggcagc atcccagtag tcggcgggcc gctcgacgaa  15780
ctccggcatg tgcccggatt cggcgtgcaa gacttcatcc atgtcgcggg catacttgcc  15840
ttcgcgctgg atgtagtcgg ccttggcccT ggccgattgg ccgcccgacc tgctgccggt  15900
tttcgccgta aggtgataaa tcgccatgct gcctcgctgt tgcttttgct tttcggctcc  15960
atgcaatggc cctcggagag cgcaccgccc gaagggtggc cgttaggcca gtttctcgaa  16020
gagaaaccgg taagtgcgcc ctcccctaca aagtagggtc gggattgccg ccgctgtgcc  16080
tccatgatag cctacgagac agcacattaa caatgggtg tcaagatggt taaggggagc  16140
aacaaggcgg cggatcggct ggccaagctc gaagaacaac gagcgcgaat caatgccgaa  16200
attcagcggg agcgggcaag ggaacagcag caagagcgca agaacgaaac aaggcgcaag  16260
gtgctggtgg gggccatgat tttggccaag gtgaacagca gcgagtggcc ggaggatcgg  16320
ctcatggcgg caatggatgc gtaccttgaa cgcgaccacg accgcgcctt gttcggtctg  16380
ccgccacgcc agaaggatga gccgggctga atgatcgacc gagacaggcc ctgcggggct  16440
gcacacgcgc ccccacccct cgggtagggg gaaaggccgc taaagcggct aaaagcgctc  16500
cagcgtattt ctgcgggtt tggtgtgggg tttagcgggc tttgcccgcc tttcccctg    16560
ccgcgcagcg gtgggcggt gtgtagccta gcgcagcgaa tagaccagct atccggcctc  16620
tggccgggca tattgggcaa gggcagcagc gccccacaag ggcgctgata accgcgccta  16680
gtggattatt cttagataat catggatgga tttttccaac accccgccag ccccgcccc   16740
tgctgggttt gcaggtttgg gggcgtgaca gttattgcag gggttcgtga cagttattgc  16800
agggggcgt gacagttatt gcaggggttc gtgacagtta gtacgggagt gacgggcact  16860
ggctggcaat gtctagcaac ggcaggcatt tcggctgagg gtaaaagaac tttccgctaa  16920
gcgatagact gtatgtaaac acagtattgc aaggacgcgg aacatgcctc atgtggcggc  16980
cagga                                                               16985
```

<210> SEQ ID NO 86
<211> LENGTH: 17198
<212> TYPE: DNA
<213> ORGANISM: Artificial Sequence
<220> FEATURE:
<223> OTHER INFORMATION: sequence of plasmid Sh-P560

<400> SEQUENCE: 86

-continued

```
ctcgcgagaa ttaattcaga taaaaaaaat ccttagcttt cgctaaggat gatttctagc      60
gatgaccctg ctgattggtt cgctgaccat ttccgggtgc gggacggcgt taccagaaac     120
tcagaaggtt cgtccaacca aaccgactct gacggcagtt tacgagagag atgatagggt     180
ctgcttcagt aagccagatg ctacacaatt aggcttgtac gggtactcga cctgcatccc     240
ttaacttact tattaaataa tttatagcta ttgaaaagag ataagaattg ttcaaagcta     300
atattgttta aatcgtcaat tcctgcatgt tttaaggaat tgttaaattg attttttgta     360
aatattttct tgtattcttt gttaaaataa aaaggggac ctctagggtc cccaattaat      420
tagtaatata atctattaaa ggtcattcaa aaggtcatcc accggatcag cttagtaaag     480
ccctcgctag attttaatgc ggatgttgcg attacttcgc caactattgc gataacaaga     540
aaaagccagc ctttcatgat atatctccca atttgtgtag ggcttattat gcacgcttaa    600
aaataataaa agcagacttg acctgatagt ttggctgtga gcaattatgt gcttagtgca    660
tctaacgctt gagttaagcc gcgccgcgaa gcggcgtcgg cttgaacgaa ttgttagaca    720
ttatttgccg actaccttgg tgatctcgcc tttcacgtag tggacaaatt cttccaactg    780
atctgcgcgc gaggccaagc gatcttcttc ttgtccaaga taagcctgtc tagcttcaag    840
tatgacgggc tgatactggg ccggcaggcg ctccattgcc cagtcggcag cgacatcctt    900
cggcgcgatt ttgccggtta ctgcgctgta ccaaatgcgg gacaacgtaa gcactacatt    960
tcgctcatcg ccagcccagt cgggcggcga gttccatagc gttaaggttt catttagcgc   1020
ctcaaataga tcctgttcag gaaccggatc aaagagttcc tccgccgctg gacctaccaa   1080
ggcaacgcta tgttctcttg cttttgtcag caagatagcc agatcaatgt cgatcgtggc   1140
tggctcgaag atacctgcaa gaatgtcatt gcgctgccat tctccaaatt gcagttcgcg   1200
cttagctgga taacgccacg gaatgatgtc gtcgtgcaca acaatggtga cttctacagc   1260
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgacccac ggcgtaacgc gcttgctgct ggatgcccg    1620
aggcatagac tgtaccccaa aaaacagtc ataacaagcc atgaaaaccg ccactgcgcc    1680
gttaccaccg ctgcgttcgg tcaaggttct ggaccagttg cgtgagcgca tacgctactt    1740
gcattacagc ttacgaaccg aacaggctta tgtccactgg gttcgtgcct tcatccgttt    1800
ccacggtgtg cgtcacccgg caaccttggg cagcagcgaa gtcgaggcat ttctgtcctg    1860
gctggcgaac gagcgcaagg tttcggtctc cacgcatcgt caggcattgg cggccttgct    1920
gttcttctac ggcaaggtgc tgtgcacgga tctgccctgg cttcaggaga tcggaagacc    1980
tcggccgtcg cggcgcttgc cggtggtgct gaccccggat gaagtggttc gcatcctcgg    2040
ttttctggaa ggcgagcatc gtttgttcgc ccagcttctg tatggaacgg gcggatcagt    2100
gagggtttgc aactgcgggt caaggatctg gatttcgatc acggcacgat catcgtgcgg    2160
gagggcaagg gctccaagga tcgggccttg atgttacccg agagcttggc acccagcctg    2220
cgcgagcagg ggaattgatc cggtggatga ccttttgaat gacctttaat agattatatt    2280
actaattaat tggggaccct agaggtcccc tttttatttt tctgaacggt ctggttatag    2340
```

```
gtacattgag caactgactg aaatgcctca aaatgttctt tacgatgcca ttgggatata    2400
tcaacggtgg tatatccagt gattttttc tccattttag cttccttagc tcctgaaaat    2460
ctcgataact caaaaaatac gcccggtagt gatcttattt cattatggtg aaagttggaa    2520
cctcttacga gcggccgcat acgattiagg tgacactata ggatccctgc cggccggtcc    2580
ggcgcgcccg ggctcgagtg cacgtacgca ttgaattaat ctcctacttg actttatgag    2640
ttgggatttt cttaaacaca attccccegg ataaactgag ggagtccaaa gtaatgaccc    2700
tagagttatt gttactgatc tccattaact ttcgttaact acccggggat ttatgagaga    2760
tattacctaa ataaatccag ggagaaacac ggaggcagcg acaagggcca ccggatgct     2820 caaacagctc agcgcctagg cttgaatgct tttgcaatcc cacagttaac tttatacaac    2880
ggtgatggga cttatgtctg ttacatcttg ttaattttat tcctgctttt tgttaagta     2940 atgttgcagg ggattctcag attgtcctgg attgggaagg gaagacaacc agtttcgttc    3000
agcttatgtt ttagggctaa aattatgcaa ttgatgttcg gtgcgaactt ttctcgtttt    3060 tttagttttcc agtggggtag ggaagactgt tgcctaggga accacagcct actttccttt   3120
ttgagctttt tatcccacca ttttgatatt cagggactct tctctacagg tggacgtcat    3180
gggtacacct cacgctactt tgcagctac tgagacagca tttcatgtga cgggctacga      3240
aaagatagat tttagcctgg tttatgtgaa tggtgtattc aacatcaaaa acacagaaat    3300
tgctgatagt tatcagaagt ttggacgctg cttgactgtt gttgatcata atgtctaccg    3360
tttgtatgga gaccaaatta agtcatattt tcgttactac gacatagact taactgtgtt    3420
tccaattact attactgaac ctggcaaaac catgtcaact tttgaacaag tagttgatgc    3480
gtttgccgat tttggcttaa ttcgtaaaga accagttta gtagttggtg gtggtttagt     3540
tactgatgtt gtaggttttg cttgtgcagc ttatcgtcgc agtactaact atattcgcat    3600
tcccacgact ttgattggtt tgatagatgc tggaattgcg attaaagtag cagtcaatca    3660
taaaaagctg aaaaatcgct tgggtgctta ccatgcaccg cagaaagtca ttctagactt    3720
ttcctttctc aagacactac caacagccca gtccggaat ggaatggcgg agttagtgaa     3780
aattgctgtg gtagcaaatg cagaagtttt taattggctg tatgagtacg gagaagattt    3840
actgcataca cactttggct atctcaacgg tacagaggaa ctgcaagaaa ttgctcacaa    3900
agttaactac gaagcaatta aaaccatgct ggagttagaa actccaaacc tgcatgagct    3960
agacttagat cgcgtcattg cttatggtca cacttggagt ccgacactag aattagcacc    4020
gcgggttcct ctgtatcatg gtcatgctgt caacatcgat atggcgctat cagcaactat    4080
tgctgaacga cggggatata ttactgtagc agaacgcgat cgcattcttg gattgatgag    4140
tcgtctaggt ttagcccttg atcatcccct tctagatagc gatttgttat ggtacgctac    4200
ccagtctatc acccagacaa gagacgggaa acaacgcgcc gccatgccaa aacctattgg    4260
tgagtgtttc tttgtcaatg acctaacccg tgaagaattg catcaagctt tgattgcaca    4320
caaggatgta tgtgcaacat atcccgtgg tggagatggg attgaagcct atatcagtgc     4380
agaacaatct gagatggtag gagtttagaa tcgtgactag cattgttgaa aagaacacag    4440
ctagacccgt aactccccac ggtatcttgg ttgaacagct acaaaaaact ctggctttgg    4500
cagaatcagg aaatacacct gaaactgttg tgactgcact acgacaggcg tatcaattag    4560
cggcgggttt agaaccttat attagtgaac acaccactac tgaatctgac gccttagcag    4620
cactggtaca aaaaactacc aaagaagact ggacaaaacg tttcactgat ggtgaaacag    4680
tgcgtcaact agaacaggaa atgctttctg gacacgtcga gggacaaacc ctgaaaatgt    4740
```

```
ttgttcacat gactaaagcc aagagtgttt tggaagtagg aatgttcacc gggtattctg    4800
ctttggcaat ggcagaggca ttacctgatg atggacgagt ggtagcatgt gaagtagact    4860
cttatgttgc tagctttgct caaacttgtt tccaaaactc gccccacggt cataaaatta    4920
ctgtggaagt tgcaccagcc ttggaaactc tgcaaaaact tgcagcagca ggtgaatcat    4980
ttgatttgat attcatcgat gctgacaaga aagagtatgt gcagtatttc cagatcatct    5040
tggataataa tctacttgca tctaacggca ttatttgtgt agataacact ttaatgcagg    5100
gacaggttta tctgccacca gaacaacgta cagctaatgg tgaagcgatc gctcaattta    5160
accaaatcat tacccaagat ccgcgtgtag aacaagttat actaccgctt cgtgatggtg    5220
tgactttaat tcggcggttg tagaaggatg gggtttgggt ggtactgatg ggtttttttt    5280
gagggcgaat tatatgacac aatctatttc tgtggcttct gttggacaaa caactcagtc    5340
ggtgagcctg ggacttcgca tatctgcgtt gtggaaaagt ttagctacac ttgcactgct    5400
gttgttagta ttgccaatca atgctgcgat tgtgttggta tcgctgttat tgggtagtca    5460
atcgcaagcg atcgccaccg aacccaaaaa catcttgatt agtggcggta aaatgactaa    5520
ggcgttacaa ttagcccgta gttttcacgc cgccggacat cgagtggttt tagtagaaac    5580
tcacaaatac tggttaacgg acaccgattt tccaaagca gtaagtcgtt tctacactct    5640
accaacgccc caatctgatc ctgaagcata cacccaagcc ctattagata ttgttcaaaa    5700
agaaaatatc gatgtctatg tacccgtgtg cagtccggtt gctagttact acgactcttt    5760
agctaaaccc gtactgtcga agtactgcga ggttttttcac tgtgacgcag atgtcaccca    5820
aatgttggat gataaatacg cttttgctga gaaagcgcgg agtttggggt tatctgttcc    5880
caagtctttc aaaattactg acccggaaca ggtgagcaac tttgatttt ctcaagaaaa    5940 gcgtaaatac atcctcaaaa gcattcctta tgactctgtt cgtcgcttag atttaaccaa    6000
acttccttgt gagactcccg aagcaacagc agattttgtc aacagcttac ccatcagttc    6060
ccaaaagcca tggattatgc aagaattcat tcctggaaaa gaattttgca cccacagcac    6120
tgtccgcaat ggggagttga gaatgcattg ctgttgtgaa tcttcggcat ttcaagttaa    6180
ctatgagaat gtcgatcatc cccaaatttt ggaatgggtg cgacactttg tcaaagcatt    6240
aggtatcact ggacaggtat cttttgattt tatcgaagca caagatggca caatctacgc    6300
cattgaatgt aatccgcgta cccattctgc catcactatg ttctacaatc atccggatgt    6360
ggcaaatgct tatttgagtg aaattccaca agtagaacca attcaacctc tgattaatag    6420
taagcctacc tactggactt atcacgaaat ttggcgattg acaggaattc gttctttctc    6480
acagttgcaa acttggttga aaaactttt tggtggaaaa gatgcgattt acagtttgag    6540
tgatcctcta ccttttttaa cagttcatca ctggcaaatt cctttattat tgctacaaaa    6600
tttgcaacag ctaaaaggtt ggatcaggat agattttaat attgggaaat tggttgagtt    6660
tggtggcgat tagattcagt tatcagttat cagttatcag ttagtagctg ttcactgata    6720
atttatagat attgaatata tataagactc atatttgatt tctgaaatac acgtagggtg    6780
cgtgatagct acgccataac acaccctact ggcgcgtcaa gcctaaaatg ttgcaataaa    6840
tctctgattc tatctctgtg ttctctctct tgaaaagctt tgatcggagg aaacctccgc    6900
tcaaactttt cgctgcttcc tctgcggttt attaatgcac tattttaagg ctgtcgcgcc    6960
ctttgttaaa gtcaaatttt tttatcaaac cgcagaggcg cagaggaatc agagagaagg    7020
aaataattct taattgaatt gtattaagtt ataaatcact atattttatc aaagatggaa    7080
```

```
ataataaact ttttagatga ttctctggaa attgaagaac agaagaaaaa ttgggaaaga    7140
caggtaggag atatttctga tctttctctg ctgagtttag aagaacagca aaaaatatta    7200
tttatatgga atcagacaga aagtaattat gatttgtcga tttgtctaca tgagttattt    7260
gcagcacagg tagagaaaac accagatgca aaagctctca agtttgctga tcaagaattg    7320
agttatcatc agttaaattg tcgggcgaat caactcgctc actatttgca atctttggga    7380
attgtaactg aagatttagt tgggatttgt gtggaacgtt ccctagaaat ggttgtgggg    7440
ttattgggta ttttgaaagc gggtgcggct tatgttccaa ttgatcctgg atatccccaa    7500
gaacgtttag gatatatgtt ggcggattcc caggtgtcgg tgttgttgac tcaaagtcat    7560
ttagtcgata gtttaccaac atgtccaacc catactattt gcttggatac tgactgggat    7620
ctgatttctc aatatagcga tcgcaatctc caaaatacaa cgacaccaga aaatctcgct    7680
tatgtaattt acacttctgg ttctactggt aaacctaaag gagcgatgaa tacccatcgc    7740
ggtatttgca atcgtctgtt atggatgcaa gatgcttatc aactcactca acaagatcgg    7800
gttctgcaaa aaactcccct tagttttgat gtctctgtct gggaattctt ttggccgttg    7860
attaccgggg cgcggctgat tatagcacaa ccaggtggac acaaggatag ttcttatcta    7920
attaatacaa ttatccaaga agaaattacc acattacatt ttgttccttc gatgttgcag    7980
gtatttttgc aagctaaagg agtggaaaat tgtcagtcat taaaacgggt aattactagt    8040
ggtgaagctt tacctgtgag tctgcaagaa cggttttttg aacgtttggg atgtgaactg    8100
cacaatcttt atggtcctac agaagcagcg atcgatgtta cgttttggca gtgtcaacct    8160
caaagtcaat atcaaacagt accgattggt cgtcccatcg ctaatactca aatatatata    8220
ttagatcaac atttgcaacc tgtgcctgtg ggtgttgtgg gtgaacttta tattggtggt    8280
gtgggagttg ccagaggtta ctggcgtcgt ccagaattaa ctacagaaag atttgtatct    8340
aatccctttg caacgggaca aatgtataaa actggtgact tggcgcgcta tttacctgat    8400
ggtaatatcg agtatgttgg cagaattgac gatcaagtta aaattcgcgg ttttcggatt    8460
gagttgggag aaattgagag tacgctgacg caacattccc agattagtca agctgtggtt    8520
gtcgcccaga cagataattt gaataataag catttaattg cttatattgt tccccaggga    8580
gaaccaccca caccaaccca actgcggaat tccttcagg gtaagctacc tgaattcatg    8640
gttccctcag cttttgtctg cttaaattcc tttcctctca ctcctagtgg aaaaatagac    8700
aggcgatcgc ttcccaaacc tgatttttct aacttaatca ctcatgaaga ttttacgcct    8760
gcacgcaatg atttagagag aaaaatcgcg cagatttggt cagaaatttt acagatttcg    8820
gaaattgata ttagagataa ctttttttgaa gttggtggta attccctttt agcattacat    8880
ttaatgaatg ccatcgaaca aaaatttggt cgagagttag cactgtcaac tttacttact    8940
aataactcaa ttgaaaaact agcagaaatt ctgcaaaacc ccacagatgt ttttcccaat    9000
tcacccatag tagcaattca gcccaaaggt acaaaacgtc ctttttttctg catccatcca    9060 gccggcggac atgtactttg ctattttagt ttggcgcatt atttaggcac tgaccagcca    9120
ttttacggtt tacaagcaca gggtttttat ggtgaagaag aaccactaac tacagttgta    9180
gaaatggcta ggctttatgc tcaagctata caaacaattc aacccacagg gccatatcaa    9240
attggtggtt ggtcgtttgg tggtgtagtt gcctatgaaa cggctcaaca actacaccaa    9300
caaggaaaag aagtttcatt actagcaatt ttagattcct acgtgccaat tctgttagat    9360
aaaaataaaa aaattgatga tgtttattta gttggtgtac tatcccgtgt atttggcgga    9420
atgtttggtc aagataatct gatttcacta gcggaaatcg aaaaatttaag tgtggaagaa    9480
```

```
agtttaaatt acatcatcga aaaagcacgc caagccaaaa ttttccgcc aggagtggaa      9540
cgtcacaaca atcgccgcat tttagatgtt ttagtcggaa ctttaaaagc cacttattct    9600
tatgaacgtt gtccctatcc tggcaaagtt actatttta gagccagaga aaaacatatc     9660
atggctcctg atcctacttt agtttgggta gaattatttt cagttttggc tgcggaggaa    9720
attgaaattc ataatgtccc cggtaatcac tattcatttg ttttagaacc tcacgtccaa    9780
gctttggctg aaagtttgca gaaatgtttg tgctgataca agatcccga cttctttgag    9840
gatgcagctg gcgaataggg ggtcaaaccc ctcgtgcgcc cacaaattgg ttgtagagac    9900
gcgccatggc gcgtctctac atctggtgga atgacgaaaa atctcggtga ggggtgtcac    9960
ccctgattcg ccagctgtat cctttgagaa gtcggggagc tcggtacccc tagagtcgac   10020
ctgcagttca atgcggtcca atacctcccc tgcccaactg ggtaagctcg cggctccact   10080
gagtaataca gacaaggcta acaggcaaa tttttcatt ggtcaactcc tagcaccaat     10140
ttcccaagac tacggagggg gcaatgaagt ttcaattaat tggggtcaca aaccacagcg   10200
gcctatggct ctaatcaatg gcacactaga aaaaatgttg cagcatactt ggctaccaaa   10260
acccccaaat ttaaccttat tgtcagatga agttcatctc tggcgcattc cccttgacca   10320
accagaatca cagctacagg atttagccgc taccttatct agtgacgaat tagcccgtgc   10380
aaacagattt tattttcccg aacatcgccg gcgttttact gctggtcgtg gtattctccg   10440
cagtatcttg gggggctatt tgggtgtgga accagggcaa gttaaatttg attatgaatc   10500
ccgtggtaaa ccaatattag gcgatcgctt tgccgagagt ggtttattat ttaacttgtc   10560
acactcccag aacttggcct tgtgtgcagt caattacacg cgccaaatcg gcatcgattt   10620
agaatatctc cgccccacat ctgatttaga atcccttgcc aaaaggttct ttttaccgcg   10680
agaatatgaa ttattgcgat cgctacccga tgagcaaaaa caaaaaattt tctttcgtta   10740
ctggacttgt aaagaggctt atcttaaagc aacgggtgac ggcatcgcta aattagagga   10800
aattgaaata gcactaactc ccacagaacc agctaagtta cagacagctc cagcgtggag   10860
tctcctagag ctagtgccag atgataattg tgttgctgct gttgccgtgg cgggttttgg   10920
ctggcagcca aaattctggc attattgagc atgcaagctt ctccctatag tgagtcgtat   10980
tagcggccgc atcgaatata acttcgtata atgtatgcta tacgaagtta ttagcgatga   11040
ggacatgagg ttgccccgta ttcagtgtcg ctgatttgta ttgtctgaag ttgttttttac  11100
gttaagttga tgcagatcaa ttaatacgat acctgcgtca taattgatta tttgacgtgg   11160
tttgatggcc tccacgcacg ttgtgatatg tagatgataa tcattatcac tttacgggtc   11220
ctttccggtg atccgacagg ttacggggcg gcgacctcgc gggttttcgc tatttatgaa   11280
aattttccgg tttaaggcgt ttccgttctt cttcgtcata acttaatgtt tttatttaaa   11340
ataccctctg aaaagaaagg aaacgacagg tgctgaaagc gaggcttttt ggcctctgtc   11400
gtttcctttc tctgtttttg tccgtggaat gaacaatgga agtcctcgtc tcgccctcga   11460
attagcccgc ctaatgagcg ggcttttttt gaattaattc tcgcgagctg gcacgacagg   11520
tttcccgact ggaaagcggg cagtgagcgc aacgcaatta atgtaagtta gcgcgaattg   11580
caagctggcc gacgcgctgg gctacgtctt gctggcgttc gggagcagaa gagcatacat   11640
ctggaagcaa agccaggaaa gcggcctatg gagctgtgcg gcagcgctca gtaggcaatt   11700
tttcaaaata ttgttaagcc ttttctgagc atggtatttt tcatggtatt accaattagc   11760
aggaaaataa gccattgaat ataaaagata aaaatgtctt gtttacaata gagtgggggg   11820
```

```
ggtcagcctg ccgccttggg ccgggtgatg tcgtacttgc ccgccgcgaa ctcggttacc   11880
gtccagccca gcgcgaccag ctccggcaac gcctcgcgca cccgcttgcg gcgcttgcgc   11940
atggtcgaac cactggcctc tgacggccag acatagccgc acaaggtatc tatggaagcc   12000
ttgccggttt tgccggggtc gatccagcca cacagccgct ggtgcagcag gcgggcggtt   12060
tcgctgtcca gcgcccgcac ctcgtccatg ctgatgcgca catgctggcc gccacccatg   12120
acggcctgcg cgatcaaggg gttcagggcc acgtacaggc gcccgtccgc ctcgtcgctg   12180
gcgtactccg acagcagccg aaacccctgc cgcttgcggc cattctgggc gatgatggat   12240
accttccaaa ggcgctcgat gcagtcctgt atgtgcttga gcgccccacc actatcgacc   12300 tctgcccga tttcctttgc cagcgcccga tagctacctt tgaccacatg gcattcagcg   12360
gtgacggcct cccacttggg ttccaggaac agccggagct gccgtccgcc ttcggtcttg   12420
ggttccgggc caagcactag gccattaggc ccagccatgg ccaccagccc ttgcaggatg   12480
cgcagatcat cagcgcccag cggctccggg ccgctgaact cgatccgctt gccgtcgccg   12540
tagtcatacg tcacgtccag cttgctgcgc ttgcgctcgc cccgcttgag ggcacggaac   12600
aggccggggg ccagacagtg cgccgggtcg tgccggacgt ggctgaggct gtgcttgttc   12660
ttaggcttca ccacggggca ccccctttgct cttgcgctgc ctctccagca cggcgggctt   12720
gagcaccccg ccgtcatgcc gcctgaacca ccgatcagcg aacggtgcgc catagttggc   12780
cttgctcaca ccgaagcgga cgaagaaccg gcgctggtcg tcgtccacac cccattcctc   12840
ggcctcggcg ctggtcatgc tcgacaggta ggactgccag cggatgttat cgaccagtac   12900
cgagctgccc cggctggcct gctgctggtc gcctgcgccc atcatggccg cgcccttgct   12960
ggcatggtgc aggaacacga tagagcaccc ggtatcggcg gcgatggcct ccatgcgacc   13020
gatgacctgg gccatgggc cgctggcgtt ttcttcctcg atgtggaacc ggcgcagcgt   13080
gtccagcacc atcaggcggc ggccctcggc ggcgcgcttg aggccgtcga accactccgg   13140
ggccatgatg ttgggcaggc tgccgatcag cggctggatc agcaggccgt cagccacggc   13200
ttgccgttcc tcggcgctga ggtgcgcccc aagggcgtgc aggcggtgat gaatggcggt   13260
gggcgggtct tcggcgggca ggtagatcac cgggccggtg ggcagttcgc ccacctccag   13320
cagatccggc ccgcctgcaa tctgtgcggc cagttgcagg gccagcatgg atttaccggc   13380
accaccgggc gacaccagcg ccccgaccgt accggccacc atgttgggca aaacgtagtc   13440
cagcggtggc ggcgctgctg cgaacgcctc cagaatattg ataggcttat gggtagccat   13500
tgattgcctc ctttgcaggc agttggtggt taggcgctgg cggggtcact accccgccc   13560 tgcgccgctc tgagttcttc caggcactcg cgcagcgcct cgtattcgtc gtcggtcagc   13620
cagaacttgc gctgacgcat ccctttggcc ttcatgcgct cggcatatcg cgcttggcgt   13680
acagcgtcag ggctggccag caggtcgccg gtctgcttgt cctttggtc tttcatatca   13740 gtcaccgaga aacttgccgg ggccgaaagg cttgtcttcg cggaacaagg acaaggtgca   13800
gccgtcaagg ttaaggctgg ccatatcagc gactgaaaag cggccagcct cggccttgtt   13860
tgacgtataa ccaaagccac cgggcaacca atagcccttg tcacttttga tcaggtagac   13920
cgaccctgaa gcgcttttt cgtattccat aaaaccccct tctgtgcgtg agtactcata   13980
gtataacagg cgtgagtacc aacgcaagca ctacatgctg aaatctggcc cgcccctgtc   14040
catgcctcgc tggcggggtg ccggtgcccg tgccagctcg gcccgcgcaa gctggacgct   14100 gggcagacc atgaccttgc tgacggtgcg ctcgatgtaa tccgcttcgt ggccgggctt   14160
gcgctctgcc agcgctgggc tggcctcggc catggccttg ccgatttcct cggcactgcg   14220
```

```
gccccggctg gccagcttct gcgcggcgat aaagtcgcac ttgctgaggt catgaccgaa   14280
gcgcttgacc agcccggcca tctcgctgcg gtactcgtcc agcgccgtgc gccggtggcg   14340
gctaagctgc cgctcgggca gttcgaggct ggccagcctg cgggccttct cctgctgccg   14400
ctgggcctgc tcgatctgct ggccagcctg ctgcaccagc gccgggccag cggtggcggt   14460
cttgcccttg gattcacgca gcagcaccca cggctgataa ccggcgcggg tggtgtgctt   14520
gtccttgcgg ttggtgaagc ccgccaagcg gccatagtgg cggctgtcgg cgctggccgg   14580
gtcggcgtcg tactcgctgg ccagcgtccg ggcaatctgc ccccgaagtt caccgcctgc   14640
ggcgtcggcc accttgaccc atgcctgata gttcttcggg ctggtttcca ctaccagggc   14700
aggctcccgg ccctcggctt tcatgtcatc caggtcaaac tcgctgaggt cgtccaccag   14760
caccagacca tgccgctcct gctcggcggg cctgatatac acgtcattgc cctgggcatt   14820
catccgcttg agccatggcg tgttctggag cacttcggcg gctgaccatt cccggttcat   14880
catctggccg tgggtgcgt ccctgacgcc gatatcgaag cgctcacagc ccatggcctt   14940
gagctgtcgg cctatggcct gcaaagtcct gtcgttcttc atcgggccac caagcgcagc   15000
cagatcgagc cgtcctcggt tgtcagtggc gtcaggtcga gcaagagcaa cgatgcgatc   15060
agcagcacca ccgtaggcat catggaagcc agcatcacgg ttagccatag cttccagtgc   15120 caccccccgcg acgcgctccg ggcgctctgc gcggcgctgc tcacctcggc ggctacctcc   15180
cgcaactctt tggccagctc cacccatgcc gccctgtct ggcgctgggc tttcagccac   15240
tccgccgcct gcgcctcgct ggcctgcttg gtctggctca tgacctgccg gcttcgtcg   15300 gccagtgtcg ccatgctctg ggccagcggt tcgatctgct ccgctaactc gttgatgcct   15360
ctggatttct tcactctgtc gattgcgttc atggtctatt gcctcccggt attcctgtaa   15420
gtcgatgatc tgggcgttgg cggtgtcgat gttcagggcc acgtctgccc ggtcggtgcg   15480
gatgccccgg ccttccatct ccaccacgtt cggcccagg tgaacaccgg gcaggcgctc   15540
gatgccctgc gcctcaagtg ttctgtggtc aatgcgggcg tcgtggccag cccgctctaa   15600
tgcccggttg gcatggtcgg cccatgcctc gcgggtctgc tcaagccatg ccttgggctt   15660
gagcgcttcg gtcttctgtg ccccgccctt ctccggggtc ttgccgttgt accgcttgaa   15720
ccactgagcg gcgggccgct cgatgccgtc attgatccgc tcggagatca tcaggtggca   15780
gtgcgggttc tcgccgccac cggcatggat ggccagcgta tacggcaggc gctcggcacc   15840
ggtcaggtgc tgggcgaact cggacgccag cgccttctgc tggtcgaggg tcagctcgac   15900
cggcagggca aattcgacct ccttgaacag ccgcccattg gcgcgttcat acaggtcggc   15960
agcatcccag tagtcggcgg gccgctcgac gaactccggc atgtgcccgg attcggcgtg   16020
caagacttca tccatgtcgc gggcatactt gccttcgcgc tggatgtagt cggccttggc   16080
cctggccgat tggccgcccg acctgctgcc ggttttcgcc gtaaggtgat aaatcgccat   16140
gctgcctcgc tgttgctttt gcttttcggc tccatgcaat ggccctcgga gagcgcaccg   16200
cccgaagggt ggccgttagg ccagtttctc gaagagaaac cggtaagtgc gccctcccct   16260
acaaagtagg gtcgggattg ccgccgctgt gcctccatga tagcctacga gacagcacat   16320
taacaatggg gtgtcaagat ggttaagggg agcaacaagg cggcggatcg gctggccaag   16380
ctcgaagaac aacgagcgcg aatcaatgcc gaaattcagc gggagcgggc aagggaacag   16440
cagcaagagc gcaagaacga aacaaggcgc aaggtgctgg tggggccat gattttggcc   16500 aaggtgaaca gcagcgagtg gccggaggat cggctcatgg cggcaatgga tgcgtacctt   16560
```

| | |
|---|---:|
| gaacgcgacc acgaccgcgc cttgttcggt ctgccgccac gccagaagga tgagccgggc | 16620 |
| tgaatgatcg accgagacag gccctgcggg gctgcacacg cgcccccacc cttcgggtag | 16680 |
| ggggaaaggc cgctaaagcg gctaaaagcg ctccagcgta tttctgcggg gtttggtgtg | 16740 |
| gggtttagcg ggctttgccc gccttccc ctgccgcgca gcggtggggc ggtgtgtagc | 16800 |
| ctagcgcagc gaatagacca gctatccggc ctctggccgg gcatattggg caagggcagc | 16860 |
| agcgccccac aagggcgctg ataaccgcgc ctagtggatt attcttagat aatcatggat | 16920 |
| ggattttttcc aacaccccgc cagccccgc ccctgctggg tttgcaggtt tgggggcgtg | 16980 |
| acagttattg caggggttcg tgacagttat tgcagggggg cgtgacagtt attgcagggg | 17040 |
| ttcgtgacag ttagtacggg agtgacgggc actggctggc aatgtctagc aacggcaggc | 17100 |
| atttcggctg agggtaaaag aactttccgc taagcgatag actgtatgta aacacagtat | 17160 |
| tgcaaggacg cggaacatgc ctcatgtggc ggccagga | 17198 |

<210> SEQ ID NO 87
<211> LENGTH: 17712
<212> TYPE: DNA
<213> ORGANISM: Artificial Sequence
<220> FEATURE:
<223> OTHER INFORMATION: sequence of plasmid Sh-DP560

<400> SEQUENCE: 87

| | |
|---|---:|
| ctcgcgagaa ttaattcaga taaaaaaaat ccttagcttt cgctaaggat gatttctagc | 60 |
| gatgaccctg ctgattggtt cgctgaccat ttccgggtgc gggacggcgt taccagaaac | 120 |
| tcagaaggtt cgtccaacca aaccgactct gacggcagtt tacgagagag atgatagggt | 180 |
| ctgcttcagt aagccagatg ctacacaatt aggcttgtac gggtactcga cctgcatccc | 240 |
| ttaacttact tattaaataa tttatagcta ttgaaaagag ataagaattg ttcaaagcta | 300 |
| atattgtttta aatcgtcaat tcctgcatgt tttaaggaat tgttaaattg attttttgta | 360 |
| aatattttct tgtattcttt gttaaaaataa aaagggggac ctctagggtc cccaattaat | 420 |
| tagtaatata atctattaaa ggtcattcaa aaggtcatcc accggatcag cttagtaaag | 480 |
| ccctcgctag attttaatgc ggatgttgcg attacttcgc caactattgc gataacaaga | 540 |
| aaaagccagc ctttcatgat atatctccca atttgtgtag ggcttattat gcacgcttaa | 600 |
| aaataataaa agcagacttg acctgatagt ttggctgtga gcaattatgt gcttagtgca | 660 |
| tctaacgctt gagttaagcc gcgccgcgaa gcggcgtcgg cttgaacgaa ttgttagaca | 720 |
| ttatttgccg actaccttgg tgatctcgcc tttcacgtag tggacaaatt cttccaactg | 780 |
| atctgcgcgc gaggccaagc gatcttcttc ttgtccaaga taagcctgtc tagcttcaag | 840 |
| tatgacgggc tgatactggg ccggcaggcg ctccattgcc cagtcggcag cgacatcctt | 900 |
| cggcgcgatt ttgccggtta ctgcgctgta ccaaatgcgg gacaacgtaa gcactacatt | 960 |
| tcgctcatcg ccagcccagt cgggcggcga gttccatagc gttaaggttt catttagcgc | 1020 |
| ctcaaataga tcctgttcag gaaccggatc aaagagttcc tccgccgctg gacctaccaa | 1080 |
| ggcaacgcta tgttctcttg cttttgtcag caagatagcc agatcaatgt cgatcgtggc | 1140 |
| tggctcgaag atacctgcaa gaatgtcatt gcgctgccat tctccaaatt gcagttcgcg | 1200 |
| cttagctgga taacgccacg gaatgatgtc gtcgtgcaca caatggtgac ttctacagc | 1260 |
| gcggagaatc tcgctctctc caggggaagc cgaagtttcc aaaaggtcgt tgatcaaagc | 1320 |
| tcgccgcgtt gtttcatcaa gccttacggt caccgtaacc agcaaatcaa tatcactgtg | 1380 |
| tggcttcagg ccgccatcca ctgcggagcc gtacaaatgt acggccagca acgtcggttc | 1440 |

-continued

| | |
|---|---|
| gagatggcgc tcgatgacgc caactacctc tgatagttga gtcgatactt cggcgatcac | 1500 |
| cgcttccctc atgatgttta actttgtttt agggcgactg ccctgctgcg taacatcgtt | 1560 |
| gctgctccat aacatcaaac atcgacccac ggcgtaacgc gcttgctgct tggatgcccg | 1620 |
| aggcatagac tgtaccccaa aaaaacagtc ataacaagcc atgaaaaccg ccactgcgcc | 1680 |
| gttaccaccg ctgcgttcgg tcaaggttct ggaccagttg cgtgagcgca tacgctactt | 1740 |
| gcattacagc ttacgaaccg aacaggctta tgtccactgg gttcgtgcct tcatccgttt | 1800 |
| ccacggtgtg cgtcacccgg caaccttggg cagcagcgaa gtcgaggcat ttctgtcctg | 1860 |
| gctggcgaac gagcgcaagg tttcggtctc cacgcatcgt caggcattgg cggccttgct | 1920 |
| gttcttctac ggcaaggtgc tgtgcacgga tctgccctgg cttcaggaga tcggaagacc | 1980 |
| tcggccgtcg cggcgcttgc cggtggtgct gaccccggat gaagtggttc gcatcctcgg | 2040 |
| ttttctggaa ggcgagcatc gtttgttcgc ccagcttctg tatggaacgg gcggatcagt | 2100 |
| gagggtttgc aactgcgggt caaggatctg gatttcgatc acggcacgat catcgtgcgg | 2160 |
| gagggcaagg gctccaagga tcgggccttg atgttacccg agagcttggc acccagcctg | 2220 |
| cgcgagcagg ggaattgatc cggtggatga ccttttgaat gacctttaat agattatatt | 2280 |
| actaattaat tggggaccct agaggtcccc tttttatttt tctgaacggt ctggttatag | 2340 |
| gtacattgag caactgactg aaatgcctca aaatgttctt tacgatgcca ttgggatata | 2400 |
| tcaacggtgg tatatccagt gatttttttc tccattttag cttccttagc tcctgaaaat | 2460 |
| ctcgataact caaaaaatac gcccggtagt gatcttattt cattatggtg aaagttggaa | 2520 |
| cctcttacga gcggccgcat acgatttagg tgacactata ggatccctgc cggccggtcc | 2580 |
| ggcgcgcccg ggctcgagtg cacgtacgca ttgaattaat ctcctacttg actttatgag | 2640 |
| ttgggatttt cttaaacaca attcccccgg ataaactgag ggagtccaaa gtaatgaccc | 2700 |
| tagagttatt gttactgatc tccattaact ttcgttaact acccggggat ttatgagaga | 2760 |
| tattacctaa ataaatccag ggagaaacac ggaggcagcg acaagggcca ccgggatgct | 2820 |
| caaacagctc agcgcctagg cttgaatgct tttgcaatcc cacagttaac tttatacaac | 2880 |
| ggtgatggga cttatgtctg ttacatcttg ttaattttat tcctgctttt ttgttaagta | 2940 |
| atgttgcagg ggattctcag attgtcctgg attgggaagg gaagacaacc agtttcgttc | 3000 |
| agcttatgtt ttagggctaa aattatgcaa ttgatgttcg gtgcgaactt ttctcgtttt | 3060 |
| tttagtttcc agtggggtag ggaagactgt tgcctaggga accacagcct actttccttt | 3120 |
| ttgagctttt tatcccacca ttttgatatt cagggactct tctctacagg tggacgtcat | 3180 |
| gggtacacct cacgctactt ttgcagctac tgagacagca tttcatgtga cgggctacga | 3240 |
| aaagatagat tttagcctgg tttatgtgaa tggtgtattc aacatcaaaa acacagaaat | 3300 |
| tgctgatagt tatcagaagt ttggacgctg cttgactgtt gttgatcata atgtctaccg | 3360 |
| tttgtatgga gaccaaatta agtcatattt tcgttactac gacatagact taactgtgtt | 3420 |
| tccaattact attactgaac ctggcaaaac catgtcaact tttgaacaag tagttgatgc | 3480 |
| gtttgccgat tttggcttaa ttcgtaaaga accagttta gtagtggtg gtggtttagt | 3540 |
| tactgatgtt gtaggttttg cttgtgcagc ttatcgtcgc agtactaact atattcgcat | 3600 |
| tcccacgact ttgattggtt tgatagatgc tggaattgcg attaaagtag cagtcaatca | 3660 |
| taaaaagctg aaaaatcgct tgggtgctta ccatgcaccg cagaaagtca ttctagactt | 3720 |
| ttcctttctc aagacactac caacagccca agtccggaat ggaatggcgg agttagtgaa | 3780 |

```
aattgctgtg gtagcaaatg cagaagtttt taattggctg tatgagtacg gagaagattt    3840
actgcataca cactttggct atctcaacgg tacagaggaa ctgcaagaaa ttgctcacaa    3900
agttaactac gaagcaatta aaaccatgct ggagttagaa actccaaacc tgcatgagct    3960
agacttagat cgcgtcattg cttatggtca cacttggagt ccgacactag aattagcacc    4020
gcgggttcct ctgtatcatg gtcatgctgt caacatcgat atggcgctat cagcaactat    4080
tgctgaacga cggggatata ttactgtagc agaacgcgat cgcattcttg gattgatgag    4140
tcgtctaggt ttagcccttg atcatcccct tctagatagc gatttgttat ggtacgctac    4200
ccagtctatc acccagacaa gagacgggaa acaacgcgcc gccatgccaa aacctattgg    4260
tgagtgtttc tttgtcaatg acctaacccg tgaagaattg catcaagctt tgattgcaca    4320
caaggatgta tgtgcaacat atccccgtgg tggagatggg attgaagcct atatcagtgc    4380
agaacaatct gagatggtag gagtttagaa tcgtgactag cattgttgaa aagaacacag    4440
ctagacccgt aactcccccac ggtatcttgg ttgaacagct acaaaaaact ctggctttgg    4500
cagaatcagg aaatacacct gaaactgttg tgactgcact acgacaggcg tatcaattag    4560
cggcgggttt agaaccttat attagtgaac acaccactac tgaatctgac gccttagcag    4620
cactggtaca aaaaactacc aaagaagact ggacaaaacg tttcactgat ggtgaaacag    4680
tgcgtcaact agaacaggaa atgctttctg acacgtcga gggacaaacc ctgaaaatgt    4740
ttgttcacat gactaaagcc aagagtgttt tggaagtagg aatgttcacc gggtattctg    4800
ctttggcaat ggcagaggca ttacctgatg atggacgagt ggtagcatgt gaagtagact    4860
cttatgttgc tagctttgct caaacttgtt tccaaaactc gccccacggt cataaaatta    4920
ctgtggaagt tgcaccagcc ttggaaactc tgcaaaaact tgcagcagca ggtgaatcat    4980
ttgatttgat attcatcgat gctgacaaga aagagtatgt gcagtatttc cagatcatct    5040
tggataataa tctacttgca tctaacggca ttatttgtgt agataacact ttaatgcagg    5100
gacaggttta tctgccacca gaacaacgta cagctaatgg tgaagcgatc gctcaattta    5160
accaaatcat tacccaagat ccgcgtgtag aacaagttat actaccgctt cgtgatggtg    5220
tgactttaat tcggcggttg taggagctcc attgaattaa tctcctactt gactttatga    5280
gttgggattt tcttaaacac aattcccccg gataaactga gggagtccaa agtaatgacc    5340
ctagagttat tgttactgat ctccattaac tttcgttaac tacccgggga tttatgagag    5400
atattaccta aataaatcca gggagaaaca cggaggcagc gacaagggcc accgggatgc    5460
tcaaacagct cagcgcctag gcttgaatgc ttttgcaatc ccacagttaa ctttatacaa    5520
cggtgatggg acttatgtct gttacatctt gttaatttta ttcctgcttt tttgttaagt    5580
aatgttgcag gggattctca gattgtcctg gattgggaag ggaagacaac cagtttcgtt    5640
cagcttatgt tttagggcta aaattatgca attgatgttc ggtgcgaact tttctcgttt    5700
ttttagtttc cagtggggta gggaagactg ttgcctaggg aaccacagcc tactttcctt    5760
tttgagcttt ttatcccacc attttgatat tcagggactc ttctctacag gtgatgacac    5820
aatctatttc tgtggcttct gttggacaaa caactcagtc ggtgagcctg ggacttcgca    5880
tatctgcgtt gtggaaaagt ttagctacac ttgcactgct gttgttagta ttgccaatca    5940
atgctgcgat tgtgttggta tcgctgttat tgggtagtca atcgcaagcg atcgccaccg    6000
aacccaaaaa catcttgatt agtggcggta aaatgactaa ggcgttacaa ttagcccgta    6060
gttttcacgc cgccggacat cgagtggttt tagtagaaac tcacaaatac tggttaacgg    6120
gacaccgatt ttccaaagca gtaagtcgtt tctacactct accaacgccc caatctgatc    6180
```

```
ctgaagcata cacccaagcc ctattagata ttgttcaaaa agaaaatatc gatgtctatg    6240
tacccgtgtg cagtccggtt gctagttact acgactcttt agctaaaccc gtactgtcga    6300
agtactgcga ggttttttcac tgtgacgcag atgtcaccca aatgttggat gataaatacg   6360
cttttgctga gaaagcgcgg agtttggggt tatctgttcc caagtctttc aaaattactg    6420 accccggaaca ggtgagcaac tttgattttt ctcaagaaaa gcgtaaatac atcctcaaaa   6480
gcattcctta tgactctgtt cgtcgcttag atttaaccaa acttccttgt gagactcccg    6540
aagcaacagc agattttgtc aacagcttac ccatcagttc ccaaaagcca tggattatgc    6600
aagaattcat tcctggaaaa gaattttgca cccacagcac tgtccgcaat ggggagttga    6660
gaatgcattg ctgttgtgaa tcttcggcat ttcaagttaa ctatgagaat gtcgatcatc    6720
cccaaatttt ggaatgggtg cgacactttg tcaaagcatt aggtatcact ggacaggtat    6780
cttttgattt tatcgaagca caagatggca caatctacgc cattgaatgt aatccgcgta    6840
cccattctgc catcactatg ttctacaatc atccggatgt ggcaaatgct tatttgagtg    6900
aaattccaca gtagaaccca attcaacctc tgattaatag taagcctacc tactggactt    6960
atcacgaaat ttggcgattg acaggaattc gttctttctc acagttgcaa acttggttga    7020
aaaacttttt tggtggaaaa gatgcgattt acagtttgag tgatcctcta ccttttttaa    7080
cagttcatca ctggcaaatt cctttattat tgctacaaaa tttgcaacag ctaaaaggtt    7140
ggatcaggat agattttaat attgggaaat tggttgagtt tggtggcgat tagattcagt    7200
tatcagttat cagttatcag ttagtagctg ttcactgata attttatagat attgaatata    7260 tataagactc atatttgatt tctgaaatac acgtagggtg cgtgatagct acgccataac    7320
acaccctact ggcgcgtcaa gcctaaaatg ttgcaataaa tctctgattc tatctctgtg    7380
ttctctctct tgaaaagctt tgatcggagg aaacctccgc tcaaactttt cgctgcttcc    7440
tctgcggttt attaatgcac tattttaagg ctgtcgcgcc ctttgttaaa gtcaaatttt    7500
tttatcaaac cgcagaggcg cagaggaatc agagagaagg aaataattct taattgaatt    7560
gtattaagtt ataaatcact atattttatc aaagatggaa ataataaact ttttagatga    7620
ttctctggaa attgaagaac agaagaaaaa ttgggaaaga caggtaggag atatttctga    7680
tcttctctcg ctgagtttag aagaacagca aaaatatta tttatatgga atcagacaga    7740
aagtaattat gatttgtcga tttgtctaca tgagttattt gcagcacagg tagagaaaac    7800
accagatgca aaagctctca gtttgctga tcaagaattg agttatcatc agttaaattg    7860
tcgggcgaat caactcgctc actatttgca atctttggga attgtaactg aagatttagt    7920
tgggatttgt gtggaacgtt ccctagaaat ggttgtgggg ttattgggta ttttgaaagc    7980
gggtgcggct tatgttccaa ttgatcctgg atatccccaa gaacgtttag gatatatgtt    8040
ggcggattcc caggtgtcgg tgttgttgac tcaaagtcat ttagtcgata gtttaccaac    8100
atgtccaacc catactattt gcttggatac tgactgggat ctgatttctc aatatagcga    8160
tcgcaatctc caaaatacaa cgacaccaga aaatctcgct tatgtaattt acacttctgg    8220
ttctactggt aaacctaaag gagcgatgaa tacccatcgc ggtatttgca atcgtctgtt    8280
atggatgcaa gatgcttatc aactcactca acaagatcgg gttctgcaaa aaactcccctt   8340 tagttttgat gtctctgtct gggaattctt ttggccgttg attaccgggg cgcggctgat    8400
tatagcacaa ccaggtggac acaaggatag ttcttatcta attaatacaa ttatccaaga    8460
agaaattacc acattacatt tgttccttc gatgttgcag gtattttgc aagctaaagg     8520
```

-continued

```
agtggaaaat tgtcagtcat taaaacgggt aattactagt ggtgaagctt tacctgtgag    8580
tctgcaagaa cggttttttg aacgtttggg atgtgaactg cacaatcttt atggtcctac    8640
agaagcagcg atcgatgtta cgttttggca gtgtcaacct caaagtcaat atcaaacagt    8700
accgattggt cgtcccatcg ctaatactca aatatatata ttagatcaac atttgcaacc    8760
tgtgcctgtg ggtgttgtgg gtgaacttta tattggtggt gtgggagttg ccagaggtta    8820
ctggcgtcgt ccagaattaa ctacagaaag atttgtatct aatccctttg caacgggaca    8880
aatgtataaa actggtgact ggcgcgcta tttacctgat ggtaatatcg agtatgttgg    8940
cagaattgac gatcaagtta aaattcgcgg ttttcggatt gagttgggag aaattgagag    9000
tacgctgacg caacattccc agattagtca agctgtggtt gtcgcccaga cagataattt    9060
gaataataag catttaattg cttatattgt tccccaggga gaaccaccca caccaaccca    9120
actgcggaat ttccttcagg gtaagctacc tgaattcatg gttccctcag cttttgtctg    9180
cttaaattcc tttcctctca ctcctagtgg aaaaatagac aggcgatcgc ttcccaaacc    9240 tgattttct aacttaatca ctcatgaaga ttttacgcct gcacgcaatg atttagagag    9300
aaaaatcgcg cagatttggt cagaaatttt acagatttcg gaaattgata ttagagataa    9360
cttttttgaa gttggtggta attcccttt agcattacat ttaatgaatg ccatcgaaca    9420
aaaatttggt cgagagttag cactgtcaac tttacttact aataactcaa ttgaaaaact    9480
agcagaaatt ctgcaaaacc ccacagatgt ttttcccaat tcacccatag tagcaattca    9540
gcccaaaggt acaaaacgtc cttttttctg catccatcca gccggcggac atgtactttg    9600
ctattttagt ttggcgcatt atttaggcac tgaccagcca ttttacggtt tacaagcaca    9660 gggttttat ggtgaagaag aaccactaac tacagttgta gaaatggcta ggctttatgc    9720
tcaagctata caaacaattc aacccacagg gccatatcaa attggtggtt ggtcgtttgg    9780
tggtgtagtt gcctatgaaa cggctcaaca actacaccaa caaggaaaag aagtttcatt    9840
actagcaatt ttagattcct acgtgccaat tctgttagat aaaaataaaa aaattgatga    9900
tgtttattta gttggtgtac tatcccgtgt atttggcgga atgtttggtc aagataatct    9960
gatttcacta gcggaaatcg aaaatttaag tgtggaagaa agtttaaatt acatcatcga   10020
aaaagcacgc caagccaaaa ttttttccgcc aggagtggaa cgtcacaaca atcgccgcat   10080
tttagatgtt ttagtcggaa cttttaaaagc cacttattct tatgaacgtt gtccctatcc   10140
tggcaaagtt actatttta gagccagaga aaaacatatc atggctcctg atcctacttt   10200
agtttgggta gaattatttt cagttttggc tgcggaggaa attgaaattc ataatgtccc   10260
cggtaatcac tattcatttg ttttagaacc tcacgtccaa gctttggctg aaagtttgca   10320
gaaatgtttg tgctgataca agatccccga cttctttgag gatgcagctg gcgaataggg   10380
ggtcaaaccc ctcgtgcgcc cacaaattgg ttgtagagac gcgccatggc gcgtctctac   10440
atctggtgga atgacgaaaa atctcggtga ggggtgtcac ccctgattcg ccagctgtat   10500
cctttgagaa gtcgggggta cccctagagt cgacctgcag ttcaatgcgg tccaatacct   10560
cccctgccca actgggtaag ctcgcggctc cactgagtaa tacagacaag gctaaacagg   10620
caaatttttt cattggtcaa ctcctagcac caatttccca agactacgga gggggcaatg   10680
aagtttcaat taattggggt cacaaaccac agcggcctat ggctctaatc aatggcacac   10740
tagaaaaaat gttgcagcat acttggctac caaaaccccc aaatttaacc ttattgtcag   10800
atgaagttca tctctggcgc attccccttg accaaccaga atcacagcta caggatttag   10860
ccgctacctt atctagtgac gaattagccc gtgcaaacag atttatttt cccgaacatc   10920
```

```
gccggcgttt tactgctggt cgtggtattc tccgcagtat cttggggggc tatttgggtg   10980
tggaaccagg gcaagttaaa tttgattatg aatcccgtgg taaaccaata ttaggcgatc   11040
gctttgccga gagtggttta ttatttaact tgtcacactc ccagaacttg gccttgtgtg   11100
cagtcaatta cacgcgccaa atcggcatcg atttagaata tctccgcccc acatctgatt   11160
tagaatccct tgccaaaagg ttcttttttac cgcgagaata tgaattattg cgatcgctac   11220
ccgatgagca aaaacaaaaa attttctttc gttactggac ttgtaaagag gcttatctta   11280
aagcaacggg tgacggcatc gctaaattag aggaaattga aatagcacta actcccacag   11340
aaccagctaa gttacagaca gctccagcgt ggagtctcct agagctagtg ccagatgata   11400
attgtgttgc tgctgttgcc gtggcgggtt ttggctggca gccaaaattc tggcattatt   11460
gagcatgcaa gcttctccct atagtgagtc gtattagcgg ccgcatcgaa tataacttcg   11520
tataatgtat gctatacgaa gttattagcg atgaggacat gaggttgccc cgtattcagt   11580
gtcgctgatt tgtattgtct gaagttgttt ttacgttaag ttgatgcaga tcaattaata   11640
cgatacctgc gtcataattg attatttgac gtggtttgat ggcctccacg cacgttgtga   11700
tatgtagatg ataatcatta tcactttacg ggtccttttcc ggtgatccga caggttacgg   11760
ggcggcgacc tcgcgggttt tcgctattta tgaaaatttt ccggtttaag gcgtttccgt   11820
tcttcttcgt cataacttaa tgttttttatt taaaataccc tctgaaaaga aggaaacga   11880 caggtgctga aagcgaggct ttttggcctc tgtcgtttcc tttctctgtt tttgtccgtg   11940
gaatgaacaa tggaagtcct cgtctcgccc tcgaattagc ccgcctaatg agcgggcttt   12000
ttttgaatta attctcgcga gctggcacga caggtttccc gactggaaag cgggcagtga   12060
gcgcaacgca attaatgtaa gttagcgcga attgcaagct ggccgacgcg ctgggctacg   12120
tcttgctggc gttcgggagc agaagagcat acatctggaa gcaaagccag gaaagcggcc   12180
tatggagctg tgcggcagcg ctcagtaggc aattttttcaa aatattgtta agccttttct   12240
gagcatggta tttttcatgg tattaccaat tagcaggaaa ataagccatt gaatataaaa   12300
gataaaaatg tcttgtttac aatagagtgg ggggggtcag cctgccgcct tgggccgggt   12360
gatgtcgtac ttgcccgccg cgaactcggt taccgtccag cccagcgcga ccagctccgg   12420
caacgcctcg cgcacccgct tgcggcgctt gcgcatggtc gaaccactgg cctctgacgg   12480
ccagacatag ccgcacaagg tatctatgga agccttgccg gttttgccgg ggtcgatcca   12540
gccacacagc cgctggtgca gcaggcgggc ggtttcgctg tccagcgccc gcacctcgtc   12600
catgctgatg cgcacatgct ggccgccacc catgacggcc tgcgcgatca aggggttcag   12660
ggccacgtac aggcgcccgt ccgcctcgtc gctggcgtac tccgacagca gccgaaaccc   12720
ctgccgcttg cggccattct gggcgatgat ggataccttc caaaggcgct cgatgcagtc   12780
ctgtatgtgc ttgagcgccc caccactatc gacctctgcc ccgatttcct tgccagcgc   12840 ccgatagcta cctttgacca catggcattc agcggtgacg gcctcccact gggttccag   12900 gaacagccgg agctgccgtc cgccttcggt cttgggttcc gggccaagca ctaggccatt   12960
aggcccagcc atggccacca gcccttgcag gatgcgcaga tcatcagcgc ccagcggctc   13020
cgggccgctg aactcgatcc gcttgccgtc gccgtagtca tacgtcacgt ccagcttgct   13080
gcgcttgcgc tcgccccgct tgagggcacg gaacaggccg ggggccagac agtgcgccgg   13140
gtcgtgccgg acgtggctga ggctgtgctt gttcttaggc ttcaccacgg ggcaccccct   13200
tgctcttgcg ctgcctctcc agcacggcgg gcttgagcac ccgcccgtca tgccgcctga   13260
```

```
accaccgatc agcgaacggt gcgccatagt tggccttgct cacaccgaag cggacgaaga    13320
accggcgctg gtcgtcgtcc acaccccatt cctcggcctc ggcgctggtc atgctcgaca    13380
ggtaggactg ccagcggatg ttatcgacca gtaccgagct gccccggctg gcctgctgct    13440
ggtcgcctgc gcccatcatg gccgcgccct tgctggcatg gtgcaggaac acgatagagc    13500
acccggtatc ggcggcgatg gcctccatgc gaccgatgac ctgggccatg gggccgctgg    13560
cgttttcttc ctcgatgtgg aaccggcgca gcgtgtccag caccatcagg cggcggccct    13620
cggcggcgcg cttgaggccg tcgaaccact ccggggccat gatgttgggc aggctgccga    13680
tcagcggctg gatcagcagg ccgtcagcca cggcttgccg ttcctcggcg ctgaggtgcg    13740
ccccaagggc gtgcaggcgg tgatgaatgg cggtgggcgg gtcttcggcg gcaggtaga    13800 tcaccgggcc ggtgggcagt tcgcccacct ccagcagatc cggcccgcct gcaatctgtg    13860
cggccagttg cagggccagc atggatttac cggcaccacc gggcgacacc agcgccccga    13920
ccgtaccggc caccatgttg ggcaaaacgt agtccagcgg tggcggcgct gctgcgaacg    13980
cctccagaat attgataggc ttatgggtag ccattgattg cctcctttgc aggcagttgg    14040
tggttaggcg ctggcggggt cactacccccc gccctgcgcc gctctgagtt cttccaggca    14100
ctcgcgcagc gcctcgtatt cgtcgtcggt cagccagaac ttgcgctgac gcatcccttt    14160
ggccttcatg cgctcggcat atcgcgcttg gcgtacagcg tcagggctgg ccagcaggtc    14220
gccggtctgc ttgtcctttt ggtctttcat atcagtcacc gagaaacttg ccggggccga    14280
aaggcttgtc ttcgcggaac aaggacaagg tgcagccgtc aaggttaagg ctggccatat    14340
cagcgactga aaagcggcca gcctcggcct tgtttgacgt ataaccaaag ccaccgggca    14400
accaatagcc cttgtcactt ttgatcaggt agaccgaccc tgaagcgctt ttttcgtatt    14460
ccataaaacc cccttctgtg cgtgagtact catagtataa caggcgtgag taccaacgca    14520
agcactacat gctgaaatct ggcccgcccc tgtccatgcc tcgctggcgg ggtgccggtg    14580
cccgtgccag ctcggcccgc gcaagctgga cgctgggcag acccatgacc ttgctgacgg    14640
tgcgctcgat gtaatccgct tcgtggccgg gcttgcgctc tgccagcgct gggctggcct    14700
cggccatggc cttgccgatt tcctcggcac tgccggcccg gctggccagc ttctgcgcgg    14760
cgataaagtc gcacttgctg aggtcatgac cgaagcgctt gaccagcccg gccatctcgc    14820
tgcggtactc gtccagcgcc gtgcgccggt ggcggctaag ctgccgctcg ggcagttcga    14880
ggctggccag cctgcgggcc ttctcctgct gccgctgggc ctgctcgatc tgctggccag    14940
cctgctgcac cagcgccggg ccagcggtgg cggtcttgcc cttggattca cgcagcagca    15000
cccacggctg ataaccggcg cgggtggtgt gcttgtcctt gcggttggtg aagcccgcca    15060
agcggccata gtggcggctg tcggcgctgg ccgggtcggc gtcgtactcg ctggccagcg    15120
tccgggcaat ctgcccccga agttcaccgc ctgcggcgtc ggccaccttg acccatgcct    15180
gatagttctt cgggctggtt tccactacca gggcaggctc ccggcccctcg gctttcatgt    15240 catccaggtc aaactcgctg aggtcgtcca ccagcaccag accatgccgc tcctgctcgg    15300
cgggcctgat atacacgtca ttgccctggg cattcatccg cttgagccat ggcgtgttct    15360
ggagcacttc ggcggctgac cattcccggt tcatcatctg gccggtgggt gcgtccctga    15420
cgccgatatc gaagcgctca cagcccatgg ccttgagctg tcggcctatg gcctgcaaag    15480
tcctgtcgtt cttcatcggg ccaccaagcg cagccagatc gagccgtcct cggttgtcag    15540
tggcgtcagg tcgagcaaga gcaacgatgc gatcagcagc accaccgtag gcatcatgga    15600
agccagcatc acggttagcc atagcttcca gtgccacccc cgcgacgcgc tccgggcgct    15660
```

```
ctgcgcggcg ctgctcacct cggcggctac ctcccgcaac tctttggcca gctccaccca    15720
tgccgcccct gtctggcgct gggctttcag ccactccgcc gcctgcgcct cgctggcctg    15780
cttggtctgg ctcatgacct gccgggcttc gtcggccagt gtcgccatgc tctgggccag    15840
cggttcgatc tgctccgcta actcgttgat gcctctggat tcttcactc tgtcgattgc     15900 gttcatggtc tattgcctcc cggtattcct gtaagtcgat gatctgggcg ttggcggtgt    15960
cgatgttcag ggccacgtct gcccggtcgg tgcggatgcc ccggccttcc atctccacca    16020
cgttcggccc caggtgaaca ccgggcaggc gctcgatgcc ctgcgcctca gtgttctgt     16080 ggtcaatgcg ggcgtcgtgg ccagcccgct ctaatgcccg gttggcatgg tcggcccatg    16140
cctcgcgggt ctgctcaagc catgccttgg gcttgagcgc ttcggtcttc tgtgccccgc    16200
ccttctccgg ggtcttgccg ttgtaccgct tgaaccactg agcggcgggc cgctcgatgc    16260
cgtcattgat ccgctcggag atcatcaggt ggcagtgcgg gttctcgccg ccaccggcat    16320
ggatggccag cgtatacggc aggcgctcgg caccggtcag gtgctgggcg aactcggacg    16380
ccagcgcctt ctgctggtcg agggtcagct cgaccggcag ggcaaattcg acctccttga    16440
acagccgccc attggcgcgt tcatacaggt cggcagcatc ccagtagtcg gcgggccgct    16500
cgacgaactc cggcatgtgc ccggattcgg cgtgcaagac ttcatccatg tcgcgggcat    16560
acttgccttc gcgctggatg tagtcggcct tggccctggc cgattggccg cccgacctgc    16620
tgccggtttt cgccgtaagg tgataaatcg ccatgctgcc tcgctgttgc ttttgctttt    16680
cggctccatg caatggccct cggagagcgc accgccgaa  gggtggccgt taggccagtt    16740
tctcgaagag aaaccggtaa gtgcgccctc ccctacaaag tagggtcggg attgccgccg    16800
ctgtgcctcc atgatagcct acgagacagc acattaacaa tggggtgtca agatggttaa    16860
ggggagcaac aaggcggcgg atcggctggc caagctcgaa gaacaacgag cgcgaatcaa    16920
tgccgaaatt cagcgggagc gggcaaggga acagcagcaa gagcgcaaga acgaaacaag    16980
gcgcaaggtg ctggtggggg ccatgatttt ggccaaggtg aacagcagcg agtggccgga    17040
ggatcggctc atggcggcaa tggatgcgta ccttgaacgc gaccacgacc gcgccttgtt    17100
cggtctgccg ccacgccaga aggatgagcc gggctgaatg atcgaccgag acaggccctg    17160
cggggctgca cacgcgcccc caccccttcgg gtaggggaa aggccgctaa agcggctaaa    17220
agcgctccag cgtatttctg cggggtttgg tgtggggttt agcgggcttt gcccgccttt    17280
ccccctgccg cgcagcggtg gggcggtgtg tagcctagcg cagcgaatag accagctatc    17340
cggcctctgg ccgggcatat tgggcaaggg cagcagcgcc ccacaagggc gctgataacc    17400
gcgcctagtg gattattctt agataatcat ggatggattt ttccaacacc ccgccagccc    17460
ccgcccctgc tgggtttgca ggtttggggg cgtgacagtt attgcagggg ttcgtgacag    17520
ttattgcagg ggggcgtgac agttattgca ggggttcgtg acagttagta cgggagtgac    17580
gggcactggc tggcaatgtc tagcaacggc aggcatttcg gctgagggta aaagaacttt    17640
ccgctaagcg atagactgta tgtaaacaca gtattgcaag gacgcggaac atgcctcatg    17700
tggcggccag ga                                                       17712
```

<210> SEQ ID NO 88
<211> LENGTH: 17869
<212> TYPE: DNA
<213> ORGANISM: Artificial Sequence
<220> FEATURE:
<223> OTHER INFORMATION: sequence of plasmid Sh-TP560

<400> SEQUENCE: 88

```
ctcgcgagaa ttaattcaga taaaaaaaat ccttagcttt cgctaaggat gatttctagc      60
gatgaccctg ctgattggtt cgctgaccat ttccgggtgc gggacggcgt taccagaaac     120
tcagaaggtt cgtccaacca aaccgactct gacggcagtt tacgagagag atgatagggt     180
ctgcttcagt aagccagatg ctacacaatt aggcttgtac gggtactcga cctgcatccc     240
ttaacttact tattaaataa tttatagcta ttgaaaagag ataagaattg ttcaaagcta     300
atattgttta aatcgtcaat tcctgcatgt tttaaggaat tgttaaattg atttttttgta    360
aatattttct tgtattcttt gttaaaataa aaaaggggac ctctagggtc cccaattaat     420
tagtaatata atctattaaa ggtcattcaa aaggtcatcc accggatcag cttagtaaag     480
ccctcgctag attttaatgc ggatgttgcg attacttcgc caactattgc gataacaaga     540
aaaagccagc ctttcatgat atatctccca atttgtgtag ggcttattat gcacgcttaa     600
aaataataaa agcagacttg acctgatagt ttggctgtga caattatgt gcttagtgca      660
tctaacgctt gagttaagcc gcgccgcgaa gcggcgtcgg cttgaacgaa ttgttagaca     720
ttatttgccg actaccttgg tgatctcgcc tttcacgtag tggacaaatt cttccaactg     780
atctgcgcgc gaggccaagc gatcttcttc ttgtccaaga taagcctgtc tagcttcaag     840
tatgacgggc tgatactggg ccggcaggcg ctccattgcc cagtcggcag cgacatcctt     900
cggcgcgatt ttgccggtta ctgcgctgta ccaaatgcgg gacaacgtaa gcactacatt     960
tcgctcatcg ccagcccagt cgggcggcga gttccatagc gttaaggttt catttagcgc    1020
ctcaaataga tcctgttcag gaaccggatc aaagagttcc tccgccgctg gacctaccaa    1080
ggcaacgcta tgttctcttg cttttgtcag caagatagcc agatcaatgt cgatcgtggc    1140
tggctcgaag atacctgcaa gaatgtcatt gcgctgccat tctccaaatt gcagttcgcg    1200
cttagctgga taacgccacg gaatgatgtc gtcgtgcaca acaatggtga cttctacagc    1260
gcggagaatc tcgctctctc caggggaagc cgaagtttcc aaaaggtcgt tgatcaaagc    1320
tcgccgcgtt gtttcatcaa gccttacggt caccgtaacc agcaaatcaa tatcactgtg    1380
tggcttcagg ccgccatcca ctgcggagcc gtacaaatgt acggccagca acgtcggttc    1440
gagatggcgc tcgatgacgc caactacctc tgatagttga gtcgatactt cggcgatcac    1500
cgcttccctc atgatgttta actttgtttt agggcgactg ccctgctgcg taacatcgtt    1560
gctgctccat aacatcaaac atcgacccac ggcgtaacgc gcttgctgct ggatgcccg     1620
aggcatagac tgtaccccaa aaaaacagtc ataacaagcc atgaaaaccg ccactgcgcc    1680
gttaccaccg ctgcgttcgg tcaaggttct ggaccagttg cgtgagcgca tacgctactt    1740
gcattacagc ttacgaaccg aacaggctta tgtccactgg gttcgtgcct tcatccgttt    1800
ccacggtgtg cgtcacccgg caaccttggg cagcagcgaa gtcgaggcat ttctgtcctg    1860
gctggcgaac gagcgcaagg tttcggtctc cacgcatcgt caggcattgg cggccttgct    1920
gttcttctac ggcaaggtgc tgtgcacgga tctgccctgg cttcaggaga tcggaagacc    1980
tcggccgtcg cggcgcttgc cggtggtgct gaccccggat gaagtggttc gcatcctcgg    2040
ttttctggaa ggcgagcatc gtttgttcgc ccagcttctg tatggaacgg gcggatcagt    2100
gagggtttgc aactgcgggt caaggatctg gatttcgatc acggcacgat catcgtgcgg    2160
gagggcaagg gctccaagga tcgggccttg atgttacccg agagcttggc acccagcctg    2220
cgcgagcagg ggaattgatc cggtggatga ccttttgaat gacctttaat agattatatt    2280
actaattaat tggggaccct agaggtcccc ttttttattt tctgaacggt ctggttatag    2340
```

```
gtacattgag caactgactg aaatgcctca aaatgttctt tacgatgcca ttgggatata   2400
tcaacggtgg tatatccagt gattttttc tccattttag cttccttagc tcctgaaaat    2460
ctcgataact caaaaaatac gcccggtagt gatcttattt cattatggtg aaagttggaa   2520
cctcttacga gcggccgcat acgattagg tgacactata ggatccctgc cggccggtcc    2580
ggcgcgcccg ggctcgagtg cacgtacgca ttgaattaat ctcctacttg actttatgag   2640
ttgggatttt cttaaacaca attccccgg ataaactgag ggagtccaaa gtaatgaccc    2700
tagagttatt gttactgatc tccattaact ttcgttaact acccggggat ttatgagaga   2760
tattacctaa ataaatccag ggagaaacac ggaggcagcg acaagggcca ccgggatgct   2820
caaacagctc agcgcctagg cttgaatgct tttgcaatcc cacagttaac tttatacaac   2880
ggtgatggga cttatgtctg ttacatcttg ttaatttat tcctgctttt tgttaagta    2940 atgttgcagg ggattctcag attgtcctgg attgggaagg gaagacaacc agtttcgttc   3000
agcttatgtt ttagggctaa aattatgcaa ttgatgttcg gtgcgaactt ttctcgtttt   3060
tttagtttcc agtggggtag ggaagactgt tgcctaggga accacagcct actttccttt   3120
ttgagctttt tatcccacca ttttgatatt cagggactct tctctacagg tggacgtcat   3180
gggtacacct cacgctactt tgcagctac tgagacagca tttcatgtga cgggctacga    3240
aaagatagat tttagcctgg tttatgtgaa tggtgtattc aacatcaaaa acacagaaat   3300
tgctgatagt tatcagaagt ttggacgctg cttgactgtt gttgatcata atgtctaccg   3360
tttgtatgga gaccaaatta agtcatattt tcgttactac gacatagact taactgtgtt   3420
tccaattact attactgaac ctggcaaaac catgtcaact tttgaacaag tagttgatgc   3480
gtttgccgat tttggcttaa ttcgtaaaga accagtttta gtagttggtg gtggtttagt   3540
tactgatgtt gtaggttttg cttgtgcagc ttatcgtcgc agtactaact atattcgcat   3600
tcccacgact ttgattggtt tgatagatgc tggaattgcg attaaagtag cagtcaatca   3660
taaaaagctg aaaaatcgct tgggtgctta ccatgcaccg cagaaagtca ttctagactt   3720
ttcctttctc aagacactac caacagccca agtccggaat ggaatggcgg agttagtgaa   3780
aattgctgtg gtagcaaatg cagaagtttt taattggctg tatgagtacg gagaagattt   3840
actgcataca cactttggct atctcaacgg tacagaggaa ctgcaagaaa ttgctcacaa   3900
agttaactac gaagcaatta aaaccatgct ggagttagaa actccaaacc tgcatgagct   3960
agacttagat cgcgtcattg cttatggtca cacttggagt ccgacactag aattagcacc   4020
gcgggttcct ctgtatcatg gtcatgctgt caacatcgat atggcgctat cagcaactat   4080
tgctgaacga cggggatata ttactgtagc agaacgcgat cgcattcttg gattgatgag   4140
tcgtctaggt ttagcccttg atcatcccct tctagatagc gatttgttat ggtacgctac   4200
ccagtctatc acccagacaa gagacgggaa acaacgcgcc gccatgccaa aacctattgg   4260
tgagtgtttc tttgtcaatg acctaacccg tgaagaattg catcaagctt tgattgcaca   4320
caaggatgta tgtgcaacat atccccgtgg tggagatggg attgaagcct atatcagtgc   4380
agaacaatct gagatggtag gagtttagaa tcgtgactag cattgttgaa aagaacacag   4440
ctagacccgt aactccccac ggtatcttgg ttgaacagct acaaaaaact ctggctttgg   4500
cagaatcagg aaatacacct gaaactgttg tgactgcact acgacaggcg tatcaattag   4560
cggcgggttt agaaccttat attagtgaac acaccactac tgaatctgac gccttagcag   4620
cactggtaca aaaaactacc aaagaagact ggacaaaacg tttcactgat ggtgaaacag   4680
```

```
tgcgtcaact agaacaggaa atgctttctg gacacgtcga gggacaaacc ctgaaaatgt    4740
ttgttcacat gactaaagcc aagagtgttt tggaagtagg aatgttcacc gggtattctg    4800 cttttggcaat ggcagaggca ttacctgatg atggacgagt ggtagcatgt gaagtagact    4860
cttatgttgc tagctttgct caaacttgtt tccaaaactc gccccacggt cataaaatta    4920
ctgtggaagt tgcaccagcc ttggaaactc tgcaaaaact tgcagcagca ggtgaatcat    4980
ttgatttgat attcatcgat gctgacaaga aagagtatgt gcagtatttc cagatcatct    5040
tggataataa tctacttgca tctaacggca ttatttgtgt agataacact ttaatgcagg    5100
gacaggttta tctgccacca gaacaacgta cagctaatgg tgaagcgatc gctcaattta    5160
accaaatcat tacccaagat ccgcgtgtag aacaagttat actaccgctt cgtgatggtg    5220
tgactttaat tcggcggttg taggagctcc attgaattaa tctcctactt gactttatga    5280
gttgggattt tcttaaacac aattcccccg gataaactga gggagtccaa agtaatgacc    5340
ctagagttat tgttactgat ctccattaac tttcgttaac tacccgggga tttatgagag    5400
atattaccta aataaatcca gggagaaaca cggaggcagc gacaagggcc accgggatgc    5460
tcaaacagct cagcgcctag gcttgaatgc ttttgcaatc ccacagttaa ctttatacaa    5520
cggtgatggg acttatgtct gttacatctt gttaatttta ttcctgcttt tttgttaagt    5580
aatgttgcag gggattctca gattgtcctg gattgggaag ggaagacaac cagtttcgtt    5640
cagcttatgt tttagggcta aaattatgca attgatgttc ggtgcgaact tttctcgttt    5700
ttttagtttc cagtgggta gggaagactg ttgcctaggg aaccacagcc tactttcctt    5760
tttgagcttt ttatcccacc attttgatat tcagggactc ttctctacag gtgatgacac    5820
aatctatttc tgtggcttct gttggacaaa caactcagtc ggtgagcctg ggacttcgca    5880
tatctgcgtt gtggaaaagt ttagctacac ttgcactgct gttgttagta ttgccaatca    5940
atgctgcgat tgtgttggta tcgctgttat tgggtagtca atcgcaagcg atcgccaccg    6000
aacccaaaaa catcttgatt agtggcggta aaatgactaa ggcgttacaa ttagcccgta    6060
gttttcacgc cgccggacat cgagtggttt tagtagaaac tcacaaatac tggttaacgg    6120
gacaccgatt ttccaaagca gtaagtcgtt tctacactct accaacgccc caatctgatc    6180
ctgaagcata cacccaagcc ctattagata ttgttcaaaa agaaaatatc gatgtctatg    6240
tacccgtgtg cagtccggtt gctagttact acgactcttt agctaaaccc gtactgtcga    6300
agtactgcga ggttttttcac tgtgacgcag atgtcaccca aatgttggat gataaatacg    6360
cttttgctga gaaagcgcgg agtttggggt tatctgttcc caagtctttc aaaattactg    6420
acccggaaca ggtgagcaac tttgattttt ctcaagaaaa gcgtaaatac atcctcaaaa    6480
gcattcctta tgactctgtt cgtcgcttag atttaaccaa acttccttgt gagactcccg    6540
aagcaacagc agattttgtc aacagcttac ccatcagttc ccaaaagcca tggattatgc    6600
aagaattcat tcctggaaaa gattttgtgca cccacagcac tgtccgcaat ggggagttga    6660
gaatgcattg ctgttgtgaa tcttcggcat ttcaagttaa ctatgagaat gtcgatcatc    6720
cccaaatttt ggaatgggtg cgacactttg tcaaagcatt aggtatcact ggacaggtat    6780
cttttgattt tatcgaagca caagatggca caatctacgc cattgaatgt aatccgcgta    6840
cccattctgc catcactatg ttctacaatc atccggatgt ggcaaatgct tatttgagtg    6900
aaattccaca agtagaacca attcaacctc tgattaatag taagcctacc tactggactt    6960
atcacgaaat ttggcgattg acaggaattc gttcttctc acagttgcaa acttggttga    7020 aaaactttt tggtggaaaa gatgcgattt acagtttgag tgatcctcta ccttttttaa    7080
```

| | |
|---|---|
| cagttcatca ctggcaaatt cctttattat tgctacaaaa tttgcaacag ctaaaaggtt | 7140 |
| ggatcaggat agattttaat attgggaaat tggttgagtt tggtggcgat tagggtaccc | 7200 |
| attgaattaa tctcctactt gactttatga gttgggattt tcttaaacac aattcccccg | 7260 |
| gataaactga gggagtccaa agtaatgacc ctagagttat tgttactgat ctccattaac | 7320 |
| tttcgttaac tacccgggga tttatgagag atattaccta aataaatcca gggagaaaca | 7380 |
| cggaggcagc gacaagggcc accgggatgc tcaaacagct cagcgcctag gcttgaatgc | 7440 |
| ttttgcaatc ccacagttaa ctttatacaa cggtgatggg acttatgtct gttacatctt | 7500 |
| gttaatttta ttcctgcttt tttgttaagt aatgttgcag gggattctca gattgtcctg | 7560 |
| gattgggaag ggaagacaac cagtttcgtt cagcttatgt tttagggcta aaattatgca | 7620 |
| attgatgttc ggtgcgaact tttctcgttt ttttagtttc cagtggggta gggaagactg | 7680 |
| ttgcctaggg aaccacagcc tactttcctt tttgagcttt ttatcccacc attttgatat | 7740 |
| tcagggactc ttctctacag gtgatggaaa taataaactt tttagatgat tctctggaaa | 7800 |
| ttgaagaaca gaagaaaaat tgggaaagac aggtaggaga tatttctgat ctttctctgc | 7860 |
| tgagtttaga agaacagcaa aaaatattat ttatatggaa tcagacagaa agtaattatg | 7920 |
| atttgtcgat ttgtctacat gagttatttg cagcacaggt agagaaaaca ccagatgcaa | 7980 |
| aagctctcaa gtttgctgat caagaattga gttatcatca gttaaattgt cgggcgaatc | 8040 |
| aactcgctca ctatttgcaa tctttgggaa ttgtaactga agatttagtt gggatttgtg | 8100 |
| tggaacgttc cctagaaatg gttgtggggt tattgggtat tttgaaagcg ggtgcggctt | 8160 |
| atgttccaat tgatcctgga tatccccaag aacgtttagg atatatgttg gcggattccc | 8220 |
| aggtgtcggt gttgttgact caaagtcatt tagtcgatag tttaccaaca tgtccaaccc | 8280 |
| atactatttg cttggatact gactgggatc tgatttctca atatagcgat cgcaatctcc | 8340 |
| aaaatacaac gacaccagaa aatctcgctt atgtaattta cacttctggt tctactggta | 8400 |
| aacctaaagg agcgatgaat acccatcgcg gtatttgcaa tcgtctgtta tggatgcaag | 8460 |
| atgcttatca actcactcaa caagatcggg ttctgcaaaa aactcccttt agttttgatg | 8520 |
| tctctgtctg ggaattcttt tggccgttga ttaccggggc gcggctgatt atagcacaac | 8580 |
| caggtggaca caaggatagt tcttatctaa ttaatacaat tatccaagaa gaaattacca | 8640 |
| cattacattt tgttccttcg atgttgcagg tattttgca agctaaagga gtggaaaatt | 8700 |
| gtcagtcatt aaaacgggta attactagtg gtgaagcttt acctgtgagt ctgcaagaac | 8760 |
| ggtttttga cgtttggga tgtgaactgc acaatctttt tggtcctaca gaagcagcga | 8820 |
| tcgatgttac gttttggcag tgtcaacctc aaagtcaata tcaaacagta ccgattggtc | 8880 |
| gtcccatcgc taatactcaa atatatatat tagatcaaca tttgcaacct gtgcctgtgg | 8940 |
| gtgttgtggg tgaactttat attggtggtg tgggagttgc cagaggttac tggcgtcgtc | 9000 |
| cagaattaac tacagaaaga tttgtatcta atccctttgc aacgggacaa atgtataaaa | 9060 |
| ctggtgactt ggcgcgctat ttacctgatg gtaatatcga gtatgttggc agaattgacg | 9120 |
| atcaagttaa aattcgcggt tttcggattg agttgggaga aattgagagt acgctgacgc | 9180 |
| aacattccca gattagtcaa gctgtggttg tcgcccagac agataaatttg aataataagc | 9240 |
| atttaattgc ttatattgtt ccccagggag aaccacccac accaacccaa ctgcggaatt | 9300 |
| tccttcaggg taagctacct gaattcatgg ttccctcagc ttttgtctgc ttaaattcct | 9360 |
| ttcctctcac tcctagtgga aaaatagaca ggcgatcgct tcccaaacct gattttctcta | 9420 |

```
acttaatcac tcatgaagat tttacgcctg cacgcaatga tttagagaga aaaatcgcgc    9480
agatttggtc agaaatttta cagatttcgg aaattgatat tagagataac tttttttgaag   9540 ttggtggtaa ttccctttta gcattacatt taatgaatgc catcgaacaa aaatttggtc    9600
gagagttagc actgtcaact ttacttacta ataactcaat tgaaaaacta gcagaaattc    9660
tgcaaaaccc cacagatgtt tttcccaatt cacccatagt agcaattcag cccaaaggta    9720
caaaacgtcc ttttttctgc atccatccag ccggcggaca tgtactttgc tattttagtt    9780
tggcgcatta tttaggcact gaccagccat tttacggttt acaagcacag ggtttttatg    9840
gtgaagaaga accactaact acagttgtag aaatggctag gctttatgct caagctatac    9900
aaacaattca acccacaggg ccatatcaaa ttggtggttg gtcgtttggt ggtgtagttg    9960
cctatgaaac ggctcaacaa ctacaccaac aaggaaaaga agtttcatta ctagcaattt    10020
tagattccta cgtgccaatt ctgttagata aaaataaaaa aattgatgat gtttatttag    10080
ttggtgtact atcccgtgta tttggcggaa tgtttggtca agataatctg atttcactag    10140
cggaaatcga aaatttaagt gtggaagaaa gtttaaatta catcatcgaa aaagcacgcc    10200
aagccaaaat ttttccgcca ggagtggaac gtcacaacaa tcgccgcatt ttagatgttt    10260
tagtcggaac tttaaaagcc acttattctt atgaacgttg tccctatcct ggcaaagtta    10320 ctattttttag agccagagaa aaacatatca tggctcctga tcctacttta gtttgggtag    10380
aattattttc agttttggct gcggaggaaa ttgaaattca taatgtcccc ggtaatcact    10440
attcatttgt tttagaacct cacgtccaag ctttggctga agtttgcag aaatgtttgt    10500 gctgatacaa gatccccgac ttctttgagg atgcagctgg cgaatagggg gtcaaacccc    10560
tcgtgcgccc acaaattggt tgtagagacg cgccatggcg cgtctctaca tctggtggaa    10620
tgacgaaaaa tctcggtgag gggtgtcacc cctgattcgc cagctgtatc ctttgagaag    10680
tcggggtcga cctgcagttc aatgcggtcc aatacctccc ctgcccaact gggtaagctc    10740
gcggctccac tgagtaatac agacaaggct aaacaggcaa attttttcat tggtcaactc    10800
ctagcaccaa tttcccaaga ctacggaggg ggcaatgaag tttcaattaa ttggggtcac    10860
aaaccacagc ggcctatggc tctaatcaat ggcacactag aaaaaatgtt gcagcatact    10920
tggctaccaa accccaaa tttaaccta ttgtcagatg aagttcatct ctggcgcatt    10980 cccctgacc aaccagaatc acagctcag gatttagccg ctaccttatc tagtgacgaa    11040
ttagcccgtg caaacagatt ttatttccc gaacatcgcc ggcgtttac tgctggtcgt    11100 ggtattctcc gcagtatctt gggggggctat ttggtgtgg aaccaggca agttaaattt    11160 gattatgaat cccgtggtaa accaatatta ggcgatcgct ttgccgagag tggtttatta    11220
tttaacttgt cacactccca gaacttggcc ttgtgtgcag tcaattacac gcgccaaatc    11280
ggcatcgatt tagaatatct ccgccccaca tctgatttag aatcccttgc caaaaggttc    11340
tttttaccgc gagaatatga attattgcga tcgctacccg atgagcaaaa acaaaaaatt    11400
ttctttcgtt actggacttg taaagaggct tatcttaaag caacgggtga cggcatcgct    11460
aaattagagg aaattgaaat agcactaact cccacagaac cagctaagtt acagacagct    11520
ccagcgtgga gtctcctaga gctagtgcca gatgataatt gtgttgctgc tgttgccgtg    11580
gcgggttttg gctggcagcc aaaattctgg cattattgag catgcaagct tctccctata    11640
gtgagtcgta ttagcggccg catcgaatat aacttcgtat aatgtatgct atacgaagtt    11700
attagcgatg aggacatgag gttgcccgcgt attcagtgtc gctgatttgt attgtctgaa    11760
gttgttttta cgttaagttg atgcagatca attaatacga tacctgcgtc ataattgatt    11820
```

```
atttgacgtg gtttgatggc ctccacgcac gttgtgatat gtagatgata atcattatca    11880
ctttacgggt cctttccggt gatccgacag gttacggggc ggcgacctcg cgggttttcg    11940
ctatttatga aaattttccg gtttaaggcg tttccgttct tcttcgtcat aacttaatgt    12000
ttttatttaa aataccctct gaaaagaaag gaaacgacag gtgctgaaag cgaggctttt    12060
tggcctctgt cgtttccttt ctctgttttt gtccgtggaa tgaacaatgg aagtcctcgt    12120
ctcgccctcg aattagcccg cctaatgagc gggcttttt tgaattaatt ctcgcgagct    12180
ggcacgacag gtttcccgac tggaaagcgg gcagtgagcg caacgcaatt aatgtaagtt    12240
agcgcgaatt gcaagctggc cgacgcgctg ggctacgtct tgctggcgtt cgggagcaga    12300
agagcataca tctggaagca aagccaggaa agcggcctat ggagctgtgc ggcagcgctc    12360
agtaggcaat ttttcaaaat attgttaagc cttttctgag catggtattt ttcatggtat    12420
taccaattag caggaaaata agccattgaa tataaaagat aaaaatgtct tgtttacaat    12480
agagtggggg gggtcagcct gccgccttgg gccgggtgat gtcgtacttg cccgccgcga    12540
actcggttac cgtccagccc agcgcgacca gctccggcaa cgcctcgcgc accgcttgc    12600
ggcgcttgcg catggtcgaa ccactggcct ctgacggcca gacatagccg cacaaggtat    12660
ctatggaagc cttgccggtt ttgccggggt cgatccagcc acacagccgc tggtgcagca    12720
ggcgggcggt ttcgctgtcc agcgcccgca cctcgtccat gctgatgcgc acatgctggc    12780
cgccacccat gacggcctgc gcgatcaagg ggttcagggc cacgtacagg cgcccgtccg    12840
cctcgtcgct ggcgtactcc gacagcagcc gaaaccccctg ccgcttgcgg ccattctggg    12900
cgatgatgga taccttccaa aggcgctcga tgcagtcctg tatgtgcttg agcgccccac    12960
cactatcgac ctctgccccg atttcctttg ccagcgcccg atagctacct ttgaccacat    13020
ggcattcagc ggtgacggcc tcccacttgg gttccaggaa cagccggagc tgccgtccgc    13080
cttcggtctt gggttccggg ccaagcacta ggccattagg cccagccatg gccaccagcc    13140
cttgcaggat gcgcagatca tcagcgccca gcggctccgg gccgctgaac tcgatccgct    13200
tgccgtcgcc gtagtcatac gtcacgtcca gcttgctgcg cttgcgctcg ccccgcttga    13260
gggcacggaa caggccgggg gccagacagt gcgccgggtc gtgccggacg tggctgaggc    13320
tgtgcttgtt cttaggcttc accacggggc accccccttgc tcttgcgctg cctctccagc    13380
acggcgggct tgagcacccc gccgtcatgc cgcctgaacc accgatcagc gaacggtgcg    13440
ccatagttgg ccttgctcac accgaagcgg acgaagaacc ggcgctggtc gtcgtccaca    13500
ccccattcct cggcctcggc gctggtcatg ctcgacaggt aggactgcca gcggatgtta    13560
tcgaccagta ccgagctgcc ccggctggcc tgctgctggt cgcctgcgcc catcatggcc    13620
gcgcccttgc tggcatggtg caggaacacg atagagcacc cggtatcggc ggcgatggc    13680
tccatgcgac cgatgacctg ggccatgggg ccgctggcgt tttcttcctc gatgtggaac    13740
cggcgcagcg tgtccagcac catcaggcgg cggccctcgg cggcgcgctt gaggccgtcg    13800
aaccactccg gggccatgat gttgggcagg ctgccgatca gcggctggat cagcaggccg    13860
tcagccacgg cttgccgttc ctcggcgctg aggtgcgccc caagggcgtg caggcggtga    13920
tgaatggcgg tgggcgggtc ttcggcgggc aggtagatca ccgggccggt gggcagttcg    13980
cccacctcca gcagatccgg cccgcctgca atctgtgcgg ccagttgcag ggccagcatg    14040
gatttaccgg caccaccggg cgacaccagc gccccgaccg taccggccac catgttgggc    14100
aaaacgtagt ccagcggtgg cggcgctgct gcgaacgcct ccagaatatt gataggctta    14160
```

```
tgggtagcca ttgattgcct cctttgcagg cagttggtgg ttaggcgctg gcggggtcac   14220 taccccccgcc ctgcgccgct ctgagttctt ccaggcactc gcgcagcgcc tcgtattcgt   14280
cgtcggtcag ccagaacttg cgctgacgca tcccttttggc cttcatgcgc tcggcatatc   14340
gcgcttggcg tacagcgtca gggctggcca gcaggtcgcc ggtctgcttg tccttttggt   14400
ctttcatatc agtcaccgag aaacttgccg gggccgaaag gcttgtcttc gcggaacaag   14460
gacaaggtgc agccgtcaag gttaaggctg gccatatcag cgactgaaaa gcggccagcc   14520
tcggccttgt ttgacgtata accaaagcca ccgggcaacc aatagccctt gtcacttttg   14580
atcaggtaga ccgaccctga agcgcttttt tcgtattcca taaaacccccc ttctgtgcgt   14640 gagtactcat agtataacag gcgtgagtac caacgcaagc actacatgct gaaatctggc   14700
ccgcccctgt ccatgcctcg ctggcggggt gccggtgccc gtgccagctc ggcccgcgca   14760
agctggacgc tgggcagacc catgaccttg ctgacggtgc gctcgatgta atccgcttcg   14820
tggccgggct tgcgctctgc cagcgctggg ctggcctcgg ccatggcctt gccgatttcc   14880
tcggcactgc ggccccggct ggccagcttc tgcgcggcga taaagtcgca cttgctgagg   14940
tcatgaccga agcgcttgac cagcccggcc atctcgctgc ggtactcgtc cagcgccgtg   15000
cgccggtggc ggctaagctg ccgctcgggc agttcgaggc tggccagcct gcgggccttc   15060
tcctgctgcc gctgggcctg ctcgatctgc tggccagcct gctgcaccag cgccgggcca   15120
gcggtggcgg tcttgccctt ggattcacgc agcagcaccc acggctgata accgcgcgcg   15180
gtggtgtgct tgtccttgcg gttggtgaag cccgccaagc ggccatagtg gcggctgtcg   15240
gcgctggccg ggtcggcgtc gtactcgctg ccagcgtcc gggcaatctg cccccgaagt   15300
tcaccgcctg cggcgtcggc caccttgacc catgcctgat agttcttcgg gctggtttcc   15360
actaccaggg caggctcccg gccctcggct ttcatgtcat ccaggtcaaa ctcgctgagg   15420
tcgtccacca gcaccagacc atgccgctcc tgctcggcgg gcctgatata cacgtcattg   15480
ccctgggcat tcatccgctt gagccatggc gtgttctgga gcacttcggc ggctgaccat   15540
tcccggttca tcatctggcc ggtgggtgcg tccctgacgc cgatatcgaa gcgctcacag   15600
cccatggcct tgagctgtcg gcctatggcc tgcaaagtcc tgtcgttctt catcgggcca   15660
ccaagcgcag ccagatcgag ccgtcctcgg ttgtcagtgg cgtcaggtcg agcaagagca   15720
acgatgcgat cagcagcacc accgtaggca tcatggaagc cagcatcacg gttagccata   15780
gcttccagtg ccaccccgc gacgcgctcc gggcgctctg cgcggcgctg ctcacctcgg   15840 cggctaccctc ccgcaactct ttggccagct ccacccatgc cgcccctgtc tggcgctggg   15900 cttttcagcca ctccgccgcc tgcgcctcgc tggcctgctt ggtctggctc atgacctgcc   15960
gggcttcgtc ggccagtgtc gccatgctct gggccagcgg ttcgatctgc tccgctaact   16020
cgttgatgcc tctggatttc ttcactctgt cgattgcgtt catggtctat tgcctcccgg   16080
tattcctgta agtcgatgat ctgggcgttg gcggtgtcga tgttcagggc cacgtctgcc   16140
cggtcggtgc ggatgccccg gccttccatc tccaccacgt tcggcccag gtgaacaccg   16200 ggcaggcgct cgatgccctg cgcctcaagt gttctgtggt caatgcgggc gtcgtggcca   16260
gcccgctcta atgcccggtt ggcatggtcg gccatgcct cgcgggtctg ctcaagccat   16320
gccttgggct tgagcgcttc ggtcttctgt gccccgccct tctccggggt cttgccgttg   16380
taccgcttga accactgagc ggcgggccgc tcgatgccgt cattgatccg ctcggagatc   16440
atcaggtggc agtgcgggtt ctcgccgcca ccggcatgga tggccagcgt ataccggcagg   16500 cgctcggcac cggtcaggtg ctgggcgaac tcggacgcca gcgccttctg ctggtcgagg   16560
```

-continued

```
gtcagctcga ccggcagggc aaattcgacc tccttgaaca gccgcccatt ggcgcgttca    16620
tacaggtcgg cagcatccca gtagtcggcg ggccgctcga cgaactccgg catgtgcccg    16680
gattcggcgt gcaagacttc atccatgtcg cgggcatact tgccttcgcg ctggatgtag    16740
tcggccttgg ccctggccga ttggccgccc gacctgctgc cggttttcgc cgtaaggtga    16800
taaatcgcca tgctgcctcg ctgttgcttt tgcttttcgg ctccatgcaa tggccctcgg    16860
agagcgcacc gcccgaaggg tggccgttag gccagtttct cgaagagaaa ccggtaagtg    16920
cgccctcccc tacaaagtag ggtcgggatt gccgccgctg tgcctccatg atagcctacg    16980
agacagcaca ttaacaatgg ggtgtcaaga tggttaaggg gagcaacaag gcggcggatc    17040
ggctggccaa gctcgaagaa caacgagcgc gaatcaatgc cgaaattcag cgggagcggg    17100
caagggaaca gcagcaagag cgcaagaacg aaacaaggcg caaggtgctg gtgggggcca    17160
tgattttggc caaggtgaac agcagcgagt ggccggagga tcggctcatg gcggcaatgg    17220
atgcgtacct tgaacgcgac cacgaccgcg ccttgttcgg tctgccgcca cgccagaagg    17280
atgagccggg ctgaatgatc gaccgagaca ggccctgcgg ggctgcacac gcgcccccac    17340
ccttcgggta gggggaaagg ccgctaaagc ggctaaaagc gctccagcgt atttctgcgg    17400
ggtttggtgt ggggtttagc gggctttgcc cgccttcccc cctgccgcgc agcggtgggg    17460
cggtgtgtag cctagcgcag cgaatagacc agctatccgg cctctggccg ggcatattgg    17520
gcaagggcag cagcgcccca caagggcgct gataaccgcg cctagtggat tattcttaga    17580
taatcatgga tggattttc caacaccccg ccagccccg cccctgctgg gtttgcaggt    17640 ttggggcgt gacagttatt gcaggggttc gtgacagtta ttgcagggg gcgtgacagt    17700 tattgcaggg gttcgtgaca gttagtacgg gagtgacggg cactggctgg caatgtctag    17760
caacggcagg catttcggct gagggtaaaa gaactttccg ctaagcgata gactgtatgt    17820
aaacacagta ttgcaaggac gcggaacatg cctcatgtgg cggccagga    17869
```

<210> SEQ ID NO 89
<211> LENGTH: 27
<212> TYPE: DNA
<213> ORGANISM: Artificial Sequence
<220> FEATURE:
<223> OTHER INFORMATION: Sfp-FW Primer

<400> SEQUENCE: 89
catgccatgg aaatttatgg gatttac    27

<210> SEQ ID NO 90
<211> LENGTH: 28
<212> TYPE: DNA
<213> ORGANISM: Artificial Sequence
<220> FEATURE:
<223> OTHER INFORMATION: Sfp-Rv Primer

<400> SEQUENCE: 90
ccgctcgagc tacaacagtt cttcatag    28

<210> SEQ ID NO 91
<211> LENGTH: 26
<212> TYPE: DNA
<213> ORGANISM: Artificial Sequence
<220> FEATURE:
<223> OTHER INFORMATION: MPPT-Fw Primer

<400> SEQUENCE: 91
catgccatgg ttatatctac cgatga                                    26

<210> SEQ ID NO 92
<211> LENGTH: 25
<212> TYPE: DNA
<213> ORGANISM: Artificial Sequence
<220> FEATURE:
<223> OTHER INFORMATION: MPPT-Rv Primer

<400> SEQUENCE: 92
ccgctcgagt agatcagaaa ggcca                                     25

<210> SEQ ID NO 93
<211> LENGTH: 26
<212> TYPE: DNA
<213> ORGANISM: Artificial Sequence
<220> FEATURE:
<223> OTHER INFORMATION: SPPT-Fw Primer

<400> SEQUENCE: 93
catgccatgg tcccccagcc ccaaat                                    26

<210> SEQ ID NO 94
<211> LENGTH: 25
<212> TYPE: DNA
<213> ORGANISM: Artificial Sequence
<220> FEATURE:
<223> OTHER INFORMATION: SPPT-Rv Primer

<400> SEQUENCE: 94
ccgctcgagg ggcaatgaat caagg                                     25

<210> SEQ ID NO 95
<211> LENGTH: 26
<212> TYPE: DNA
<213> ORGANISM: Artificial Sequence
<220> FEATURE:
<223> OTHER INFORMATION: SePPT-Fw Primer

<400> SEQUENCE: 95
catgccatgg aacgccccaa ccctag                                    26

<210> SEQ ID NO 96
<211> LENGTH: 28
<212> TYPE: DNA
<213> ORGANISM: Artificial Sequence
<220> FEATURE:
<223> OTHER INFORMATION: SePPT-Rv Primer

<400> SEQUENCE: 96
ccgctcgaga tgattttcc ggattatg                                   28

<210> SEQ ID NO 97
<211> LENGTH: 25
<212> TYPE: DNA
<213> ORGANISM: Artificial Sequence
<220> FEATURE:
<223> OTHER INFORMATION: APPT-Fw Primer

<400> SEQUENCE: 97
catgccatgg tgcagcatac ttggc                                     25

<210> SEQ ID NO 98
<211> LENGTH: 26
<212> TYPE: DNA
<213> ORGANISM: Artificial Sequence

```
<220> FEATURE:
<223> OTHER INFORMATION: APPT-Rv Primer

<400> SEQUENCE: 98
ccgctcgaga taatgccaga attttg                                          26

<210> SEQ ID NO 99
<211> LENGTH: 28
<212> TYPE: DNA
<213> ORGANISM: Artificial Sequence
<220> FEATURE:
<223> OTHER INFORMATION: AvPPT-Fw Primer

<400> SEQUENCE: 99
catgccatgg tgcagcatac ttggctac                                        28

<210> SEQ ID NO 100
<211> LENGTH: 28
<212> TYPE: DNA
<213> ORGANISM: Artificial Sequence
<220> FEATURE:
<223> OTHER INFORMATION: AvPPT-Rv Primer

<400> SEQUENCE: 100
ccgctcgaga tactgccaga attttggc                                        28

<210> SEQ ID NO 101
<211> LENGTH: 26
<212> TYPE: DNA
<213> ORGANISM: Artificial Sequence
<220> FEATURE:
<223> OTHER INFORMATION: FPPT-Fw Primer

<400> SEQUENCE: 101
catgccatgg ggtctgagac taatca                                          26

<210> SEQ ID NO 102
<211> LENGTH: 27
<212> TYPE: DNA
<213> ORGANISM: Artificial Sequence
<220> FEATURE:
<223> OTHER INFORMATION: FPPT-Rv Primer

<400> SEQUENCE: 102
ccgctcgaga tactgccagt actttaa                                         27

<210> SEQ ID NO 103
<211> LENGTH: 26
<212> TYPE: DNA
<213> ORGANISM: Artificial Sequence
<220> FEATURE:
<223> OTHER INFORMATION: SFACP-Fw Primer

<400> SEQUENCE: 103
catgccatgg atcaggaaat ttttga                                          26

<210> SEQ ID NO 104
<211> LENGTH: 27
<212> TYPE: DNA
<213> ORGANISM: Artificial Sequence
<220> FEATURE:
<223> OTHER INFORMATION: SFACP-Rv Primer

<400> SEQUENCE: 104
ccgctcgagt ttactttcga tatgctc                                         27
```

<210> SEQ ID NO 105
<211> LENGTH: 23
<212> TYPE: DNA
<213> ORGANISM: Artificial Sequence
<220> FEATURE:
<223> OTHER INFORMATION: AFACP-Fw Primer

<400> SEQUENCE: 105
ggaattccat atgagccaat cag                                    23

<210> SEQ ID NO 106
<211> LENGTH: 27
<212> TYPE: DNA
<213> ORGANISM: Artificial Sequence
<220> FEATURE:
<223> OTHER INFORMATION: AFACP-Rv Primer

<400> SEQUENCE: 106
ccgctcgaga gctgatgcgg caacttg                                27

<210> SEQ ID NO 107
<211> LENGTH: 29
<212> TYPE: DNA
<213> ORGANISM: Artificial Sequence
<220> FEATURE:
<223> OTHER INFORMATION: APACP-Fw Primer

<400> SEQUENCE: 107
catgccatgg gtctaaaaca aaattatag                              29

<210> SEQ ID NO 108
<211> LENGTH: 30
<212> TYPE: DNA
<213> ORGANISM: Artificial Sequence
<220> FEATURE:
<223> OTHER INFORMATION: APACP-Rv Primer

<400> SEQUENCE: 108
ccgctcgaga gattgttctt ccaattcttc                             30

<210> SEQ ID NO 109
<211> LENGTH: 28
<212> TYPE: DNA
<213> ORGANISM: Artificial Sequence
<220> FEATURE:
<223> OTHER INFORMATION: APNPCP-Fw Primer

<400> SEQUENCE: 109
catgccatgg aacaatctac aactaatc                               28

<210> SEQ ID NO 110
<211> LENGTH: 27
<212> TYPE: DNA
<213> ORGANISM: Artificial Sequence
<220> FEATURE:
<223> OTHER INFORMATION: APNPCP-Rv Primer

<400> SEQUENCE: 110
ccgctcgaga tcagtaatag gcgattg                                27

<210> SEQ ID NO 111
<211> LENGTH: 30
<212> TYPE: DNA
<213> ORGANISM: Artificial Sequence
<220> FEATURE:
<223> OTHER INFORMATION: FNPCP-Fw Primer

```
<400> SEQUENCE: 111
catgccatgg cccaacgccc tatcattatc                                    30

<210> SEQ ID NO 112
<211> LENGTH: 27
<212> TYPE: DNA
<213> ORGANISM: Artificial Sequence
<220> FEATURE:
<223> OTHER INFORMATION: FNPCP-Rv Primer

<400> SEQUENCE: 112
ccgctcgagt tcaacttcat cactatc                                       27

<210> SEQ ID NO 113
<211> LENGTH: 28
<212> TYPE: DNA
<213> ORGANISM: Artificial Sequence
<220> FEATURE:
<223> OTHER INFORMATION: FisPCP-Fw Primer

<400> SEQUENCE: 113
catgccatgg gatcgcttcc caaacctg                                      28

<210> SEQ ID NO 114
<211> LENGTH: 27
<212> TYPE: DNA
<213> ORGANISM: Artificial Sequence
<220> FEATURE:
<223> OTHER INFORMATION: FisPCP-Rv Primer

<400> SEQUENCE: 114
ccgctcgagt gaattgggaa aaacatc                                       27

<210> SEQ ID NO 115
<211> LENGTH: 27
<212> TYPE: DNA
<213> ORGANISM: Artificial Sequence
<220> FEATURE:
<223> OTHER INFORMATION: FNsACP-Fw Primer

<400> SEQUENCE: 115
catgccatgg cttttctaga agatgtc                                       27

<210> SEQ ID NO 116
<211> LENGTH: 27
<212> TYPE: DNA
<213> ORGANISM: Artificial Sequence
<220> FEATURE:
<223> OTHER INFORMATION: FNsACP-Rv Primer

<400> SEQUENCE: 116
ccgctcgagg gaattaccta gaaaagc                                       27

<210> SEQ ID NO 117
<211> LENGTH: 28
<212> TYPE: DNA
<213> ORGANISM: Artificial Sequence
<220> FEATURE:
<223> OTHER INFORMATION: AprACP-Fw Primer

<400> SEQUENCE: 117
catgccatgg aaattttga acaggaat                                       28

<210> SEQ ID NO 118
```

```
<211> LENGTH: 27
<212> TYPE: DNA
<213> ORGANISM: Artificial Sequence
<220> FEATURE:
<223> OTHER INFORMATION: AprACP-Rv Primer

<400> SEQUENCE: 118
ccgctcgaga ctaaaattaa tatcttc                                          27

<210> SEQ ID NO 119
<211> LENGTH: 26
<212> TYPE: DNA
<213> ORGANISM: Artificial Sequence
<220> FEATURE:
<223> OTHER INFORMATION: MACP-Fw Primer

<400> SEQUENCE: 119
catgccatgg tgacaactgt tcaatc                                           26

<210> SEQ ID NO 120
<211> LENGTH: 25
<212> TYPE: DNA
<213> ORGANISM: Artificial Sequence
<220> FEATURE:
<223> OTHER INFORMATION: MACP-Rv Primer

<400> SEQUENCE: 120
ccgctcgaga agatataatt cccct                                            25

<210> SEQ ID NO 121
<211> LENGTH: 25
<212> TYPE: DNA
<213> ORGANISM: Artificial Sequence
<220> FEATURE:
<223> OTHER INFORMATION: ScACP-Fw Primer

<400> SEQUENCE: 121
catgccatgg agcagcggct ggctc                                            25

<210> SEQ ID NO 122
<211> LENGTH: 25
<212> TYPE: DNA
<213> ORGANISM: Artificial Sequence
<220> FEATURE:
<223> OTHER INFORMATION: ScACP-Rv Primer

<400> SEQUENCE: 122
ccgctcgagc tcctgctcgc cgaac                                            25

<210> SEQ ID NO 123
<211> LENGTH: 24
<212> TYPE: DNA
<213> ORGANISM: Artificial Sequence
<220> FEATURE:
<223> OTHER INFORMATION: SSPCP-Fw Primer

<400> SEQUENCE: 123
catgccatgg aggagatcct cgcc                                             24

<210> SEQ ID NO 124
<211> LENGTH: 26
<212> TYPE: DNA
<213> ORGANISM: Artificial Sequence
<220> FEATURE:
<223> OTHER INFORMATION: SSPCP-Rv Primer

<400> SEQUENCE: 124
```
ccgctcgagg gtacgcccgg ccaggc                                    26

<210> SEQ ID NO 125
<211> LENGTH: 27
<212> TYPE: DNA
<213> ORGANISM: Artificial Sequence
<220> FEATURE:
<223> OTHER INFORMATION: Ptrc-F Primer

<400> SEQUENCE: 125
ggatccattc tgaaatgagc tgttgac                                   27

<210> SEQ ID NO 126
<211> LENGTH: 26
<212> TYPE: DNA
<213> ORGANISM: Artificial Sequence
<220> FEATURE:
<223> OTHER INFORMATION: SHI-F Primer

<400> SEQUENCE: 126
ctcgagatgg gtacacctca cgctac                                    26

<210> SEQ ID NO 127
<211> LENGTH: 24
<212> TYPE: DNA
<213> ORGANISM: Artificial Sequence
<220> FEATURE:
<223> OTHER INFORMATION: SHI-R Primer

<400> SEQUENCE: 127
agatcttcag cacaaacatt tctg                                      24

<210> SEQ ID NO 128
<211> LENGTH: 24
<212> TYPE: DNA
<213> ORGANISM: Artificial Sequence
<220> FEATURE:
<223> OTHER INFORMATION: PRNPB-F Primer

<400> SEQUENCE: 128
agatctttca atgcggtcca atac                                      24

<210> SEQ ID NO 129
<211> LENGTH: 40
<212> TYPE: DNA
<213> ORGANISM: Artificial Sequence
<220> FEATURE:
<223> OTHER INFORMATION: PRNPB-R Primer

<400> SEQUENCE: 129
gttgatgcct accatcatat gttttttctag tgtgccattg                    40

<210> SEQ ID NO 130
<211> LENGTH: 40
<212> TYPE: DNA
<213> ORGANISM: Artificial Sequence
<220> FEATURE:
<223> OTHER INFORMATION: FPPT-F Primer

<400> SEQUENCE: 130
tggcacacta gaaaaacata tgatggtagg catcaactat                     40

<210> SEQ ID NO 131
<211> LENGTH: 26
<212> TYPE: DNA

```
<213> ORGANISM: Artificial Sequence
<220> FEATURE:
<223> OTHER INFORMATION: FPPT-R Primer

<400> SEQUENCE: 131
gagctctcac tctggccacc gccaac                                          26

<210> SEQ ID NO 132
<211> LENGTH: 40
<212> TYPE: DNA
<213> ORGANISM: Artificial Sequence
<220> FEATURE:
<223> OTHER INFORMATION: APPT-F Primer

<400> SEQUENCE: 132
tggcacacta gaaaaacata tgatgttgca gcatacttgg                           40

<210> SEQ ID NO 133
<211> LENGTH: 27
<212> TYPE: DNA
<213> ORGANISM: Artificial Sequence
<220> FEATURE:
<223> OTHER INFORMATION: APPT-R Primer

<400> SEQUENCE: 133
gagctcataa tgccagaatt ttggctg                                         27

<210> SEQ ID NO 134
<211> LENGTH: 27
<212> TYPE: DNA
<213> ORGANISM: Artificial Sequence
<220> FEATURE:
<223> OTHER INFORMATION: SPPT-Up-F Primer

<400> SEQUENCE: 134
ccaagcttcc tggcagtagt gttggtg                                         27

<210> SEQ ID NO 135
<211> LENGTH: 40
<212> TYPE: DNA
<213> ORGANISM: Artificial Sequence
<220> FEATURE:
<223> OTHER INFORMATION: SPPT-Up-R Primer

<400> SEQUENCE: 135
ggtaacgaaa actagtcgta cgaggtcagt ttaaacagcg                           40

<210> SEQ ID NO 136
<211> LENGTH: 40
<212> TYPE: DNA
<213> ORGANISM: Artificial Sequence
<220> FEATURE:
<223> OTHER INFORMATION: SPPT-Dn-F Primer

<400> SEQUENCE: 136
aaactgacct cgtacgacta gttttcgtta ccttgggccg                           40

<210> SEQ ID NO 137
<211> LENGTH: 26
<212> TYPE: DNA
<213> ORGANISM: Artificial Sequence
<220> FEATURE:
<223> OTHER INFORMATION: SPPT-Dn-R Primer

<400> SEQUENCE: 137
gtgaattcgg gctacaccgt cgctac                                          26
```

<210> SEQ ID NO 138
<211> LENGTH: 35
<212> TYPE: DNA
<213> ORGANISM: Artificial Sequence
<220> FEATURE:
<223> OTHER INFORMATION: Syn-APPT-F Primer

<400> SEQUENCE: 138
taaagaggta tatattaatg ttgcagcata cttgg                      35

<210> SEQ ID NO 139
<211> LENGTH: 86
<212> TYPE: DNA
<213> ORGANISM: Artificial Sequence
<220> FEATURE:
<223> OTHER INFORMATION: Syn-APPT-R Primer

<400> SEQUENCE: 139
catagctgtt tcctgtgtca aaaaccccct caagacccgt ttagaggccc caaggggtta      60
tgctagtcaa taatgccaga attttg                                          86

<210> SEQ ID NO 140
<211> LENGTH: 36
<212> TYPE: DNA
<213> ORGANISM: Artificial Sequence
<220> FEATURE:
<223> OTHER INFORMATION: Syn-MPPT-F Primer

<400> SEQUENCE: 140
taaagaggta tatattaatg tttatatcta ccgatg                     36

<210> SEQ ID NO 141
<211> LENGTH: 84
<212> TYPE: DNA
<213> ORGANISM: Artificial Sequence
<220> FEATURE:
<223> OTHER INFORMATION: Syn-MPPT-R Primer

<400> SEQUENCE: 141
catagctgtt tcctgtgtca aaaaccccct caagacccgt ttagaggccc caaggggtta      60
tgctagtcat agatcagaaa ggcc                                            84

<210> SEQ ID NO 142
<211> LENGTH: 38
<212> TYPE: DNA
<213> ORGANISM: Artificial Sequence
<220> FEATURE:
<223> OTHER INFORMATION: Syn-SFP-F Primer

<400> SEQUENCE: 142
taaagaggta tatattaatg aaaatttatg ggatttac                   38

<210> SEQ ID NO 143
<211> LENGTH: 85
<212> TYPE: DNA
<213> ORGANISM: Artificial Sequence
<220> FEATURE:
<223> OTHER INFORMATION: Syn-SFP-R Primer

<400> SEQUENCE: 143
catagctgtt tcctgtgtca aaaaccccct caagacccgt ttagaggccc caaggggtta      60
tgctagctac aacagttctt catag                                           85

<210> SEQ ID NO 144
<211> LENGTH: 27
<212> TYPE: DNA
<213> ORGANISM: Artificial Sequence
<220> FEATURE:
<223> OTHER INFORMATION: Ptrc-F Primer

<400> SEQUENCE: 144
ctcgtacgat tctgaaatga gctgttg                                27

<210> SEQ ID NO 145
<211> LENGTH: 35
<212> TYPE: DNA
<213> ORGANISM: Artificial Sequence
<220> FEATURE:
<223> OTHER INFORMATION: Ptrc-APPT-R Primer

<400> SEQUENCE: 145
ccaagtatgc tgcaacatta atatatacct cttta                       35

<210> SEQ ID NO 146
<211> LENGTH: 36
<212> TYPE: DNA
<213> ORGANISM: Artificial Sequence
<220> FEATURE:
<223> OTHER INFORMATION: Ptrc-MPPT-R Primer

<400> SEQUENCE: 146
catcggtaga tataaacatt aatatatacc tcttta                      36

<210> SEQ ID NO 147
<211> LENGTH: 38
<212> TYPE: DNA
<213> ORGANISM: Artificial Sequence
<220> FEATURE:
<223> OTHER INFORMATION: Ptrc-SFP-R Primer

<400> SEQUENCE: 147
gtaaatccca taaattttca ttaatatata cctctttta                   38

<210> SEQ ID NO 148
<211> LENGTH: 36
<212> TYPE: DNA
<213> ORGANISM: Artificial Sequence
<220> FEATURE:
<223> OTHER INFORMATION: Kana-F Primer

<400> SEQUENCE: 148
gtcttgaggg gttttttgac acaggaaaca gctatg                      36

<210> SEQ ID NO 149
<211> LENGTH: 26
<212> TYPE: DNA
<213> ORGANISM: Artificial Sequence
<220> FEATURE:
<223> OTHER INFORMATION: Kana-R Primer

<400> SEQUENCE: 149
aaactagtaa acgacggcca gtgaat                                 26

<210> SEQ ID NO 150
<211> LENGTH: 19
<212> TYPE: DNA
<213> ORGANISM: Artificial Sequence
<220> FEATURE:
<223> OTHER INFORMATION: RT-rnpB-F Primer

```
<400> SEQUENCE: 150
cgtgaggaca gtgccacag                                                   19

<210> SEQ ID NO 151
<211> LENGTH: 19
<212> TYPE: DNA
<213> ORGANISM: Artificial Sequence
<220> FEATURE:
<223> OTHER INFORMATION: RT-rnpB-R Primer

<400> SEQUENCE: 151
cgctcttacc gcacctttg                                                   19

<210> SEQ ID NO 152
<211> LENGTH: 18
<212> TYPE: DNA
<213> ORGANISM: Artificial Sequence
<220> FEATURE:
<223> OTHER INFORMATION: RT-SPPT-F Primer

<400> SEQUENCE: 152
tttgattggc ttaagtac                                                    18

<210> SEQ ID NO 153
<211> LENGTH: 18
<212> TYPE: DNA
<213> ORGANISM: Artificial Sequence
<220> FEATURE:
<223> OTHER INFORMATION: RT-SPPT-R Primer

<400> SEQUENCE: 153
aatgcttcct tcgctgtc                                                    18

<210> SEQ ID NO 154
<211> LENGTH: 18
<212> TYPE: DNA
<213> ORGANISM: Artificial Sequence
<220> FEATURE:
<223> OTHER INFORMATION: RT-APPT-F Primer

<400> SEQUENCE: 154
atctagtgac gaattagc                                                    18

<210> SEQ ID NO 155
<211> LENGTH: 17
<212> TYPE: DNA
<213> ORGANISM: Artificial Sequence
<220> FEATURE:
<223> OTHER INFORMATION: RT-APPT-R Primer

<400> SEQUENCE: 155
aataaaccac tctcggc                                                     17

<210> SEQ ID NO 156
<211> LENGTH: 18
<212> TYPE: DNA
<213> ORGANISM: Artificial Sequence
<220> FEATURE:
<223> OTHER INFORMATION: RT-MPPT-F Primer

<400> SEQUENCE: 156
gtattaacta tcaattgc                                                    18

<210> SEQ ID NO 157
```

```
<211> LENGTH: 18
<212> TYPE: DNA
<213> ORGANISM: Artificial Sequence
<220> FEATURE:
<223> OTHER INFORMATION: RT-MPPT-R Primer

<400> SEQUENCE: 157
aagctatcta aatctttc                                                    18

<210> SEQ ID NO 158
<211> LENGTH: 18
<212> TYPE: DNA
<213> ORGANISM: Artificial Sequence
<220> FEATURE:
<223> OTHER INFORMATION: RT-Sfp-F Primer

<400> SEQUENCE: 158
tagtcattct ggtcgctg                                                    18

<210> SEQ ID NO 159
<211> LENGTH: 18
<212> TYPE: DNA
<213> ORGANISM: Artificial Sequence
<220> FEATURE:
<223> OTHER INFORMATION: RT-Sfp-R Primer

<400> SEQUENCE: 159
ataaatcaga gtattcgg                                                    18

<210> SEQ ID NO 160
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 160
ttgacagcta gctcagtcct aggtataatg ctagc                                 35

<210> SEQ ID NO 161
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 161
ttgacggcta gctcagtcct aggtacagtg ctagc                                 35

<210> SEQ ID NO 162
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 162
tttacagcta gctcagtcct aggtattatg ctagc                                 35

<210> SEQ ID NO 163
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 163
```
ttgacagcta gctcagtcct aggtactgtg ctagc                                35

<210> SEQ ID NO 164
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 164
ctgatagcta gctcagtcct agggattatg ctagc                                35

<210> SEQ ID NO 165
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 165
ttgacagcta gctcagtcct aggtattgtg ctagc                                35

<210> SEQ ID NO 166
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 166
tttacggcta gctcagtcct aggtactatg ctagc                                35

<210> SEQ ID NO 167
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 167
tttacggcta gctcagtcct aggtatagtg ctagc                                35

<210> SEQ ID NO 168
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 168
tttacggcta gctcagccct aggtattatg ctagc                                35

<210> SEQ ID NO 169
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 169
ctgacagcta gctcagtcct aggtataatg ctagc                                35

<210> SEQ ID NO 170
<211> LENGTH: 35
<212> TYPE: DNA

```
<213> ORGANISM: Artificial Sequence
<220> FEATURE:
<223> OTHER INFORMATION: Exemplary promoter from J23 library

<400> SEQUENCE: 170
tttacagcta gctcagtcct agggactgtg ctagc                              35

<210> SEQ ID NO 171
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 171
tttacggcta gctcagtcct aggtacaatg ctagc                              35

<210> SEQ ID NO 172
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 172
ttgacggcta gctcagtcct aggtatagtg ctagc                              35

<210> SEQ ID NO 173
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 173
ctgatagcta gctcagtcct agggattatg ctagc                              35

<210> SEQ ID NO 174
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 174
ctgatggcta gctcagtcct agggattatg ctagc                              35

<210> SEQ ID NO 175
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 175
tttatggcta gctcagtcct aggtacaatg ctagc                              35

<210> SEQ ID NO 176
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 176
tttatagcta gctcagccct tggtacaatg ctagc                              35
```

```
<210> SEQ ID NO 177
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 177
ttgacagcta gctcagtcct agggactatg ctagc                              35

<210> SEQ ID NO 178
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 178
ttgacagcta gctcagtcct agggattgtg ctagc                              35

<210> SEQ ID NO 179
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 179
ttgacggcta gctcagtcct aggtattgtg ctagc                              35
```